US009381205B2

(12) United States Patent
Damelin et al.

(10) Patent No.: US 9,381,205 B2
(45) Date of Patent: Jul. 5, 2016

(54) ANTI-EFNA4 ANTIBODY-DRUG CONJUGATES

(71) Applicants: Pfizer, Inc., New York, NY (US); Stem CentRx, Inc., South San Francisco, CA (US)

(72) Inventors: Marc Isaac Damelin, Park Ridge, NJ (US); Kiran Manohar Khandke, Nanuet, NY (US); Puja Sapra, River Edge, NJ (US); Alexander John Bankovich, San Francisco, CA (US); Scott J. Dylla, Emerald Hills, CA (US)

(73) Assignees: Pfizer, Inc., New York, NY (US); Stemcentrx, Inc., South San Francisco, CA (US)

( * ) Notice: Subject to any disclaimer, the term of this patent is extended or adjusted under 35 U.S.C. 154(b) by 0 days.

(21) Appl. No.: 14/525,442

(22) Filed: Oct. 28, 2014

(65) Prior Publication Data

US 2015/0125472 A1    May 7, 2015

Related U.S. Application Data

(60) Provisional application No. 61/899,800, filed on Nov. 4, 2013.

(51) Int. Cl.
| | | |
|---|---|---|
| *A61K 39/395* | (2006.01) | |
| *A61K 31/704* | (2006.01) | |
| *A61K 47/48* | (2006.01) | |
| *C07K 16/30* | (2006.01) | |

(52) U.S. Cl.
CPC ............ *A61K 31/704* (2013.01); *A61K 47/484* (2013.01); *A61K 47/48561* (2013.01); *A61K 47/48569* (2013.01); *C07K 16/30* (2013.01); *C07K 2317/24* (2013.01); *C07K 2317/34* (2013.01); *C07K 2317/565* (2013.01); *C07K 2317/76* (2013.01); *C07K 2317/77* (2013.01)

(58) Field of Classification Search
None
See application file for complete search history.

(56) References Cited

U.S. PATENT DOCUMENTS

| 4,671,958 A | 6/1987 | Rodwell et al. |
|---|---|---|
| 4,939,244 A | 7/1990 | Lee |
| 4,970,198 A | 11/1990 | Lee et al. |
| 4,977,143 A | 12/1990 | McGahren et al. |
| 4,978,748 A | 12/1990 | Ellestad et al. |
| 4,996,305 A | 2/1991 | McGahren et al. |
| 5,024,948 A | 6/1991 | Rothstein et al. |
| 5,037,651 A | 8/1991 | Lee |
| 5,053,394 A | 10/1991 | Ellestad et al. |
| 5,079,233 A | 1/1992 | Lee |
| 5,108,912 A | 4/1992 | Lee et al. |
| 5,112,946 A | 5/1992 | Maione |
| 5,336,603 A | 8/1994 | Capon et al. |
| 5,349,053 A | 9/1994 | Landolfi |
| 5,359,046 A | 10/1994 | Capon et al. |
| 5,447,851 A | 9/1995 | Beutler et al. |
| 5,516,658 A | 5/1996 | Beckmann et al. |
| 5,606,040 A | 2/1997 | McGahren et al. |
| 5,622,929 A | 4/1997 | Willner et al. |
| 5,648,095 A | 7/1997 | Illum et al. |
| 5,663,149 A | 9/1997 | Pettit et al. |
| 5,712,374 A | 1/1998 | Kuntsmann et al. |
| 5,714,586 A | 2/1998 | Kuntsmann et al. |
| 5,738,844 A | 4/1998 | Beckmann et al. |
| 5,739,116 A | 4/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,877,296 A | 3/1999 | Hamann et al. |
| 5,952,329 A | 9/1999 | Cincotta et al. |
| 5,969,110 A | 10/1999 | Beckmann et al. |
| 5,994,076 A | 11/1999 | Chenchik et al. |
| 6,015,562 A | 1/2000 | Hinmann et al. |
| 6,024,938 A | 2/2000 | Corbo et al. |
| 6,274,117 B1 | 8/2001 | Beckmann et al. |
| 6,309,633 B1 | 10/2001 | Ekwuribe et al. |
| 6,461,603 B2 | 10/2002 | Bentley et al. |
| 6,927,203 B1 | 8/2005 | Kinch et al. |
| 6,949,366 B2 | 9/2005 | Beckmann et al. |
| 7,341,997 B2 | 3/2008 | Bartlett et al. |
| 7,422,739 B2 | 9/2008 | Anderson et al. |
| 7,604,799 B2 | 10/2009 | Kinch et al. |
| 7,659,374 B2 | 2/2010 | Wu et al. |
| 7,807,459 B2 | 10/2010 | Tsang et al. |
| 7,897,570 B2 | 3/2011 | Bartlett et al. |
| 8,003,098 B2 | 8/2011 | Nakatsuru et al. |
| 8,222,253 B2 | 7/2012 | Wang et al. |
| 8,273,862 B2 | 9/2012 | Moran et al. |
| 8,461,119 B2 | 6/2013 | Pasquale et al. |
| 8,865,873 B2 | 10/2014 | Liu et al. |

(Continued)

FOREIGN PATENT DOCUMENTS

| EP | 0307434 | 3/1989 |
|---|---|---|
| EP | 0367166 | 5/1990 |

(Continued)

OTHER PUBLICATIONS

George et al. (Circulation. 1998; 97: 900-906).*
Brown et al (J. Immunol. May 1996; 156(9):3285-3291.*
Vajdos et al (J. Mol. Biol. Jul. 5, 2002;320(2); 415-428).*
Office action dated Aug. 13, 2015 issued in Chinese application (No. 201180065609.1).
Office action dated Oct. 12, 2015 issued in European application (No. 11801934.8).
Office action dated Oct. 6, 2015 issued in Mexican Appln. (No. MX/a/2013/006569).
Office action dated Jun. 26, 2015 issued in Russian application (No. 2013128444).

(Continued)

*Primary Examiner* — Sheela J Huff
(74) *Attorney, Agent, or Firm* — Womble Carlyle Sandridge & Rice, LLP

(57) ABSTRACT

The present invention provides for anti-EFNA4 antibody-drug conjugates and methods for preparing and using the same.

27 Claims, 20 Drawing Sheets

(56) References Cited

U.S. PATENT DOCUMENTS

| | | | |
|---|---|---|---|
| 2002/0197262 A1 | 12/2002 | Hasan et al. | |
| 2003/0032995 A1 | 2/2003 | Handy et al. | |
| 2004/0043928 A1 | 3/2004 | Kekuda et al. | |
| 2005/0013819 A1 | 1/2005 | Kinch et al. | |
| 2005/0153923 A1 | 7/2005 | Kinch | |
| 2007/0292904 A1 | 12/2007 | Roifman et al. | |
| 2008/0003210 A1 | 1/2008 | Bruckheimer et al. | |
| 2009/0155255 A1 | 6/2009 | Glaser et al. | |
| 2009/0304721 A1* | 12/2009 | Kinch | A61K 47/48415 424/183.1 |
| 2010/0113415 A1 | 5/2010 | Rajapakse et al. | |
| 2010/0184119 A1 | 7/2010 | Bright et al. | |
| 2010/0273160 A1 | 10/2010 | Donahoe et al. | |
| 2011/0020221 A1 | 1/2011 | Berman et al. | |
| 2011/0280892 A1 | 11/2011 | Kinch et al. | |
| 2012/0083454 A1 | 4/2012 | Vescovi et al. | |
| 2013/0061340 A1 | 3/2013 | Dylla et al. | |
| 2013/0061342 A1 | 3/2013 | Dylla et al. | |
| 2013/0260385 A1 | 10/2013 | Dylla et al. | |
| 2015/0030636 A1 | 1/2015 | Dylla et al. | |

FOREIGN PATENT DOCUMENTS

| | | |
|---|---|---|
| EP | 1852441 | 11/2007 |
| EP | 2338898 | 6/2011 |
| EP | 2446895 | 5/2012 |
| JP | 2003-532365 | 11/2003 |
| JP | 2010-501596 | 1/2010 |
| WO | WO 88/07089 | 9/1988 |
| WO | WO 91/06570 | 5/1991 |
| WO | WO 95/06065 A1 | 3/1995 |
| WO | WO 96/04388 | 2/1996 |
| WO | WO 98/01548 A1 | 1/1998 |
| WO | WO 99/52541 A2 | 10/1999 |
| WO | WO 01/11086 A2 | 2/2001 |
| WO | WO 03/004057 A1 | 1/2003 |
| WO | WO 03/038098 A2 | 5/2003 |
| WO | WO 03/040304 A2 | 5/2003 |
| WO | WO 03/064589 A2 | 8/2003 |
| WO | WO 03/075957 | 9/2003 |
| WO | WO 03/092623 A2 | 11/2003 |
| WO | WO 03/093320 A2 | 11/2003 |
| WO | WO 2004/029218 A2 | 4/2004 |
| WO | WO 2004/048938 A2 | 6/2004 |
| WO | WO 2005/048917 A2 | 6/2005 |
| WO | WO 2006/020935 A2 | 2/2006 |
| WO | WO 2006/031653 A2 | 3/2006 |
| WO | WO 2006/047298 A2 | 5/2006 |
| WO | WO 2007/098124 A2 | 8/2007 |
| WO | WO 2007/106744 A2 | 9/2007 |
| WO | WO 2007/146968 A1 | 12/2007 |
| WO | WO 2008/071447 A2 | 6/2008 |
| WO | WO 2008/147765 A1 | 12/2008 |
| WO | WO 2009/052830 | 4/2009 |
| WO | WO 2010/111180 A1 | 9/2010 |
| WO | WO 2010/141974 A1 | 12/2010 |
| WO | WO 2012/031280 | 3/2012 |
| WO | WO 2012/042021 A1 | 4/2012 |
| WO | WO 2012/059882 A2 | 5/2012 |
| WO | WO 2012/0118547 | 9/2012 |
| WO | WO 2012/131527 A1 | 10/2012 |
| WO | WO 2013/072813 A2 | 5/2013 |
| WO | WO 2013/088304 A1 | 6/2013 |
| WO | WO 2013/119964 | 8/2013 |
| WO | WO 2013/126810 A1 | 8/2013 |
| WO | WO 2014/105810 | 7/2014 |
| WO | WO 2015/031698 | 3/2015 |

OTHER PUBLICATIONS

Abdou et al, "Ephrin A4 expression in osteosarcoma, impact on prognosis, and patient outcome", *Indian Journal of Cancer* (2010) 47(1):46-52.

Al-Hajj et al, "Self-renewal and solid tumor stem cells", *Oncogene* (2004) 23:7274-7282.

Alonso et al, "Expression profile of Eph receptors and ephrin ligands in healthy human B lymphocytes and chronic lymphocytic leukemia B-cells", *Leukemia Research* (2009) 33(3):395-406.

Ashkenazi et al, "Protection against endotoxic shock by a tumor necrosis factor receptor immunoadhesin", *Proceedings of the National Academy of Sciences USA* (1991) 88(23):10535-10539.

Bakker et al, "Receptor scintigraphy with a radioiodinated somatostatin analogue: radiolabeling, purification, biologic activity, and in vivo application in animals", *Journal of Nuclear Medicine* (1990) 31(9):1501-1509.

Battle et al, "β-Catenin and TCF Mediate Cell Positioning in the Intestinal Epithelium by Controlling the Expression of EphB/EphrinB", *Cell* (2002) 111(2):251-263.

Boger et al, "CC-1065 and the duocarmycins: Unraveling the keys to a new class of naturally derived DNA alkylating agents", *Proc Natl Acad Sci USA* (1995) 92:3642-3649.

Boghaert et al "Antibody-targeted chemotherapy with the calicheamicin conjugate hu3S193-N-Acetly gamma calicheamicin dimethyl hydrazide targets Lewis Y and eliminates Lewis Y positive human carcinoma cells and xenografts", *Clinical Cancer Research* (2004) 10:4538-4549 [XP002368435].

Chattopadhyay et al, "Purification and stabilization of $^{99m}$Tc-d,1-HMPAO: Role of organic extractants", *Nuclear Medicine and Biology* (2001) 28:741-744.

Chothia, C. et al "Canonical structures for the hypervariable regions of immunoglobulins." *J. Mol. Biol.* (1987) 196:901-917.

Chothia, C. et al "Conformations of immunoglobulin hypervariable regions." *Nature* (Dec. 28, 1989) 342:877-883.

Curtis et al "The genomic and transcriptomic architecture of 2,000 breast tumours reveals novel subgroups." *Nature* (2012) 486(7403):346-352.

Dalerba, P. et al "Phenotypic characterization of human colorectal cancer stem cells." *Proc Natl Acad Sci U S A.* (Jun. 12, 2007) 104(24):10158-63. Epub Jun. 4, 2007.

De Nardo, GI et al "Comparison of 1,4,7,10-tetraazacyclododecane-N,N',N",N'''-tetraacetic acid (DOTA)-peptide-ChL6, a novel immunoconjugate with catabolizable linker, to 2-iminothiolane-2-[p(bromoacetamido)benzyl]-DOTA-ChL6 in breast cancer xenografts." *Clin Cancer Res.* (Oct. 1998) 4(10):2483-90.

Dewanjee et al, "Noninvasive imaging of c-myc oncogene messenger RNA with indium-111-antisense probes in a mammary tumor-bearing mouse", *Journal of Nuclear Medicine* (1994) 35(6):1054-1063.

Dijoseph et al, "Antibody-targeted chemotherapy with CMC-544: a CD22-targeted immunoconjugate of calicheamicin for the treatment of B-lymphoid malignancies", *Blood* (2004) 103(5):1807-1814.

Dylla et al, "Colorectal Cancer Stem Cells Are Enriched in Xenogeneic Tumors Following Chemotherapy", *PLoS One* (2008) 3(6):e2428.

Eph Nomenclature Committee "Unified Nomenclature for Eph Family Receptors and Their Ligands, the Ephrins" *Cell* (Aug. 8, 1997) 90(3):403-4.

Fuhrmann, S et al "Abstract 5625: In vitro and in vivo pharmacology of MEDI-565 (MT111), a novel CEA/CD3-bispecific single-chain BiTE antibody in development for the treatment of gastrointestinal adenocarcinomas" AACR (2010).

Garnett, "Targeted drug conjugates: principles and progress", *Advanced Drug Delivery Reviews* (2001) 53(2):171-216.

GenBank NM_0044282; *Homo sapiens* ephrin-A1 (EFNA1), transcript variant 1, mRNA; NCBI Reference Sequence: NM_004428.2, 2013.

GenBank NM_005227; *Homo sapiens* ephrin-A4 (EFNA4), transcript variant 1, mRNA NCBI Reference Sequence: NM_005227.2, 2013.

GenBank NM_182689; *Homo sapiens* ephrin-A4 (EFNA4), transcript variant 2, mRNA NCBI Reference Sequence: NM_182689.1, 2013.

GenBank NM_182690; *Homo sapiens* ephrin-A4 (EFNA4), transcript variant 3, mRNA NCBI Reference Sequence: NM_182690.2, 2013.

GenBank NP_001101162; ephrin-A4 precursor [Rattus norvegicus] NCBI Reference Sequence: NP_001101162.1, 2013.

GenBank NP_005218; ephrin-A4 isoform a precursor [*Homo sapiens*] NCBI Reference Sequence: NP_005218.1, 2013.

(56) References Cited

OTHER PUBLICATIONS

GenBank NP_031936; ephrin-A4 precursor [Mus musculus] NCBI Reference Sequence: NP_031936.2, 2013.
GenBank NP_872631; ephrin-A4 isoform b precursor [Homo sapiens] NCBI Reference Sequence: NP_872631.1, 2013.
GenBank NP_872632; ephrin-A4 isoform c precursor [Homo sapiens] NCBI Reference Sequence: N_872632.2, 2013.
GenBank XP_001152916; Predicted: ephrin A4 isoform 1 [Pan troglodytes] NCBI Reference Sequence: XP_001152916.1, 2006.
GenBank XP_001152971; Predicted: ephrin-A4 isoform 2 [Pan troglodytes] NCBI Reference Sequence: XP_001152971.,1 2012.
GenBank XP_001153095; Predicted: ephrin-A4 isoform 3 [Pan troglodytes] NCBI Reference Sequence: XP_001153095.1, 2012.
GenBank XP_524893; Predicted: ephrin-A4 isoform 4 [Pan troglodytes] NCBI Reference Sequence: XP_524893.1, 2012.
Gentle et al, "Direct Production of Proteins with N-Terminal Cysteine for Site-Specific Conjugation", *Bioconjugate Chem.* (2004) 15:658-663.
Guenther et al "Giant cell tumors of the bone: molecular profiling and expression analysis of Ephrin A1 receptor, Claudin 7, CD52, FGFR3 and AMFR." *Pathology—Research and Practice* (2005) 201:649-663.
Hafner et al, "Differential Gene Expression of Eph Receptors and Ephrins in Benign Human Tissues and Cancers", *Clinical Chemistry* (2004) 50(3):490-499.
Hamann et al: "Gemtuzumab ozogamicin, a Potent and Selective Anti-cd33 Antibody-Calicheamicin Conjugate for Treatment of Acute Myeloid Leukemia", *Bioconjugate Chemistry* (2002) 13(1):47-58 [XP009080679].
Hamann et al "An Anti-cd33 Antibody-Calicheamicin Conjugate for Treatment of Acute Myeloid Leukemia. Choice of Linker", *Bioconjugate Chemistry* (2002) 13(1):40-46.
Hinman et al, "Preparation and Characterization of Monoclonal Antibody Conjugates of the Calicheamicins: A Novel and Potent Family of Antitumor Antibiotics", *Cancer Research* (1993) 53(14):3336-3343.
Hoey et al, "DLL4 Blockade Inhibits Tumor Growth and Reduces Tumor-Initiating Cell Frequency", *Cell Stem Cell* (2009) 5(2):168-177.
Holen et al. "Signaling through ephrin-A ligand leads to activation of Srcfamily kinases, Akt phosphorylation, and inhibition of antigen receptor-induced apoptosis." *J Leukoc Biol.* (Oct. 2008) 84(4):1183-91.
Holliger et al, "Engineered antibody fragments and the rise of single domains", *Nature Biotechnology* (2005) 23(9):1126-1136.
Hoves et al, "The JAM-assay: optimized conditions to determine death-receptor-mediated apoptosis", *Methods* (2003) 31(2):127-134.
Huff, Carol Ann et al "Strategies to eliminate cancer stem cells: Clinical implications" *Eur J Cancer* (2006) 42(9):1293-1297.
Jones et al, "Sensitive determination of cell number using the CyQUANT® cell proliferation assay", *Journal of Immunological Methods* (2001) 254:85-98.
Junutula et al, "Site-specific conjugation of a cytotoxic drug to an antibody improves the therapeutic index", *Nature Biotechnology* (2008) 26(8):925-932.
Kearney et al, "A New Mouse Myeloma Cell Line That Has Lost Immunoglobulin Expression But Permits the Construction of Antibody-Secreting Hybrid Cell Lines", *The Journal of Immunology* (1979) 123(4):1548-1550.
Koopman et al, "Annexin V for Flow Cytometric Detection of Phosphatidylserine Expression on B Cells Undergoing Apoptosis", *Blood* (1994) 84(5):1415-1420.
Krenning et al, "Localisation of endocrine-related tumours with radioiodinated analogue of somatostatin", *The Lancet* (1989) 1(8632):242-244.
Liu et al "LY2875358, a Neutralizing and Internalizing Anti-MET Bivalent Antibody, Inhibits HGF-Dependent and HGF-Independent MET Activation and Tumor Growth" *Clin. Cancer Res.*(2014) 20(23): 6059-6070.

Mac Callum et al, "Antibody-antigen Interactions: Contact Analysis and Binding Site Topography", *J Mol Biol* (1996) 262(5):732-745.
Merlos-Suárez et al, "The Intestinal Stem Cell Signature Identifies Colorectal Cancer Stem Cells and Predicts Disease Relapse", *Cell Stem Cell* (2011) 8(5):511-524.
Merrill et al "Cell mixing at a neural crest-mesoderm boundary and deficient ephrin-Eph signaling in the pathogenesis of craniosynostosis." *Hum Mol Genet* (2006) 15(8):1319-1328.
Mosch et al, "Eph Receptors and Ephrin Ligands: Important Players in Angiogenesis and Tumor Angiogenesis", *Journal of Oncology* (2010) vol. 2010, Article ID 135285, 12 pages.
Nicolaou et al, "Synthetic calicheamicin mimics with novel initiation mechanisms: DNA cleavage, cytotoxicity, and apoptosis", *Chemistry & Biology* (1994) 1(1):57-66.
Orsulic et al, "Expression of Eph receptors and ephrins is differentially regulated by E-cadherin", *Journal of Cell Science* (2000) 113(Pt 10):1793-1802.
Pasquale, "Eph receptors and ephrins in cancer: bidirectional signalling and beyond", *Nature Reviews: Cancer* (2010) 10(3):165-180.
Peng et al, "Detection of B lymphoma cells undergoing apoptosis by Annexin-V assay", *Chinese Medical Sciences Journal* (2002) 17(1):17-21.
Peterson et al, "Enzymatic Cleavage of Peptide-Linked Radiolabels from Immunoconjugates", *Bioconjugate Chemistry* (1999) 10(4):553-557.
Pettit et al, "Specific Activities of Dolastatin 10 and Peptide Derivatives against Cryptococcus neoformans", *Antimicrobial Agents and Chemotherapy* (1998) 42(11):2961-2965.
Prokop et al, "Induction of apoptosis by enediyne antibiotic calicheamicin thetall proceeds through a caspase-mediated mitochondrial amplification loop in an entirely Bax-dependent manner.", *Oncogene* (2003) 22(57):9107-9120.
Remillard et al, "Antimitotic Activity of the Potent Tumor Inhibitor Maytansine", *Science* (1975) 189:1002-1005.
Sagiuchi et al, "Transient seizure activity demonstrated by Tc-99m HMPAO SPECT and diffusion-weighted MR imaging", *Annals of Nuclear Medicine* (2001) 15(3):267-270.
Siegel et al, "Calicheamicin Derivatives Conjugated to Monoclonal Antibodies: Determination of Loading Values and Distributions by Infrared and UV Matrix-Assisted Laser Desorption/Ionization Mass Spectrometry and Electrospray Ionization Mass Spectrometry", *Analytical Chemistry* (1997) 69(14):2716-2726.
Stancovski et al "Mechanistic aspects of the opposing effects of monoclonal antibodies to the ERBB2 receptor on tumor growth" *PNAS* (1991) 88:8691-8695.
Stuehmer W. et al: "Murine EAG1 ion channel protein targeted antibody SEQ ID No. 2", Database UniProt [Online] IBIS (Jun. 15, 2006), XP002672640, Database accession No. AEG89626.
Surawska et al, "The role of ephrins and Eph receptors in cancer", *Cytokine & Growth Factor Reviews* (2004) 15:419-433.
Tanaka et al, "N-terminal glycine-specific protein conjugation catalyzed by microbial transglutaminase", *FEBS Letters* (2005) 579:2092-2096.
Tsuchiya M. et al.: "Novel cell having fucose transporter function inhibited, useful for producing antibodies that can be used for treating diseases such as tumors.", Database UniProt [Online] IBIS; Aug. 24, 2006, XP002672641, Database accession No. AEI67098.
Vié, H et al "Human fusion proteins between interleukin 2 and IgM heavy chain are cytotoxic for cells expressing the interleukin 2 receptor." *Proc Natl Acad Sci* USA (1992);89(23):11337-41.
Weinstein et al. "The Cancer Genome Atlas Pan-Cancer analysis project" *Nature Genetics* (2013) 45:1113-1120.
Yang Jun-Jie et al "[Preparation and analysis of monoclonal antibody against EphA4 peptide]." *Zhong Nan Da Xue Xue Bao Yi Xue Ban.* (Oct. 2005) 30(5):529-32.—Abstract only.
Yasuhara et al, "Comparison of Comet Assay, Electron Microscopy, and Flow Cytometry for Detection of Apoptosis", *The Journal of Histochemistry & Cytochemistry*(2003) 51(7):873-885.
Yoo et al, "Technetium-99m labeling and biodistribution of anti-TAC disulfide-stabilized Fv fragment", *Journal of Nuclear Medicine* (1997) 38(2):294-300.

(56) References Cited

OTHER PUBLICATIONS

Zantek et al, "E-Cadherin Regulates the Function of the EphA2 Receptor Tyrosine Kinase", *Cell Growth & Differentiation* (1999) 10(9):629-638.

Zein et al, "Calicheamicin $\gamma_1^I$: An Antitumor Antibiotic That Cleaves Double-Stranded DNA Site Specifically", *Science* (1988) 240(4856):1198-1201.

Zheng, XX et al "Administration of noncytolytic IL-10/Fc in murine models of lipopolysaccharide-induced septic shock and allogeneic islet transplantation."*J Immunol.* (1995)154(10):5590-600.

Zhou et al "Tumour-initiating cells: challenges and opportunities for anticancer drug discovery." *Nat Rev Drug Discov.* (2009) 8(10):806-23.

Zimmermann et al, "A Triglycine Linker Improves Tumor Uptake and Biodistributions of 67-Cu-Labeled Anti-Neuroblastoma Mab chCE7 F(ab')$_2$ Fragments", *Nuclear Medicine & Biology* (1999) 26(8):943-950.

International Search Report dated Jul. 16, 2012 issued in PCT/2011/063831.

Written Opinion dated Jul. 16, 2012 issued in PCT/2011/063831.

International Search Report dated Feb. 10, 2015 issued in PCT/US2014/062544.

Written Opinion dated Feb. 10, 2015 issued in PCT/US2014/062544.

Official Action dated May 16, 2014 issued in Chinese application (No. 201180065609.1).

Official Action dated Jan. 23, 2015 issued in Chinese application (No. 201180065609.1).

Official Action Issued in Colombian application (No. 13-216.891) received Dec. 30, 2014.

Official Action dated Sep. 29, 2014 issued in European application (No. 11801934.8).

Official Action dated Nov. 13, 2013 issued in New Zeland application (No. 611428).

Official Action dated Mar. 3, 2015 issued in New Zeland application (No. 611428).

Official Actiondated Mar. 3, 2015 issued in New Zealand application (No. 705008).

Office Action dated Sep. 9, 2014 issued in U.S. Appl. No. 13/992,599.

Office Action dated Jan. 26, 2015 issued in U.S. Appl. No. 13/992,599.

Cul et al "EFNA1 ligand and its receptor EphA2: potential biomarkers for hepatocellular carcinoma" *International Journal of Cancer*, 2010, 126.4: 940-949.

Official Action dated Mar. 11, 2015 issued in Australian application (No. 2011360938).

Office action dated Dec. 8, 2015 issued in Japanese application (No. 2013-543326).

Office Action dated Oct. 27, 2015 issued in Russian application (No. 2013128444).

Offica action dated Apr. 21, 2014 issued in Saudi Arabian application (No. 11330037).

Offica action dated Apr. 9, 2015 issued in Saudi Arabian application (No. 11330037).

Official Action dated Nov. 26, 2015 issued in ROC (Taiwan) Patent Appln. No. 100145222.

Herbertson et al., "Phase I Biodistribution and Pharmacokinetic Study of Lewis Y-Targeting Immunoconjugate CMD-193 in Patients with Advanced Epithelial Cancers", *Clin. Cancer Res.*, 2009, 15(21):6709-6715.

\* cited by examiner

```
huEFNA4 iso b NP_872631.1  MRLLPLLRTVLWAAFLGSPLRGGSSLRHVVYWNSSNPRLLRGDAVVELGL
huEFNA4 iso c NP_872632.2  MRLLPLLRTVLWAAFLGSPLRGGSSLRHVVYWNSSNPRLLRGDAVVELGL
huEFNA4 iso a NP_005218.1  MRLLPLLRTVLWAAFLGSPLRGGSSLRHVVYWNSSNPRLLRGDAVVELGL huEFNA4 iso b NP_872631.1  NDYLDIVCPHYEGPGPPEGPETFALYMVDWPGYESCQAEGPRAYKRWVCS
huEFNA4 iso c NP_872632.2  NDYLDIVCPHYEGPGPPEGPETFALYMVDWPGYESCQAEGPRAYKRWVCS
huEFNA4 iso a NP_005218.1  NDYLDIVCPHYEGPGPPEGPETFALYMVDWPGYESCQAEGPRAYKRWVCS huEFNA4 iso b NP_872631.1  LPFGHVQFSEKIQRFTPFSLGFEFLPGETYYYISVPTPESSGQCLRLQVS
huEFNA4 iso c NP_872632.2  LPFGHVQFSEKIQRFTPFSLGFEFLPGETYYYISVPTPESSGQCLRLQVS
huEFNA4 iso a NP_005218.1  LPFGHVQFSEKIQRFTPFSLGFEFLPGETYYYISVPTPESSGQCLRLQVS huEFNA4 iso b NP_872631.1  VCCKERR-ARVLPRSPGGGIPAACTGGANSDRQDGALMGEIRGSEVTLA
huEFNA4 iso c NP_872632.2  VCCKERN-LPSHPKEP-- -E-----SSQDPLEEEGSLLPALGVPIQTDK
huEFNA4 iso a NP_005218.1  VCCKERKSESAHPVGSPGESG----TSGWRGGDTPSPLCLLLLLLLLILR huEFNA4 iso b NP_872631.1  GACPLITG  (SEQ ID NO: 3)
huEFNA4 iso c NP_872632.2  MEH-----  (SEQ ID NO: 4)
huEFNA4 iso a NP_005218.1  LLRIL---  (SEQ ID NO: 2)
```

FIG. 1

| CLONE | ISOTYPE | VH | DH | JH | CDRH1 SEQ ID NOS: 65-76 | CDRH2 SEQ ID NOS: 77-88 | CDRH3 SEQ ID NOS: 89-100 | VL | JL | CDRL1 SEQ ID NOS: 101-112 | CDRL2 SEQ ID NOS: 113-124 | CDRL3 SEQ ID NOS: 125-136 |
|---|---|---|---|---|---|---|---|---|---|---|---|---|
| E2 | IgG1/K | VHJ558 | P1 | JH3 | GYTFTDYE | FDPETGNT | ARGYPAWFGY | IGKV1-110 | JK1 | QSLAHTNGNTY | KVSNMRFS | SQDTHVPPT |
| E5 | IgG1/K | IGHV2-6 | NONE | JH3 | GFSLTTYG | IWGGGST | ASDWAY | IGKV6-15 | JK2 | QNVGTN | SASYRYS | QQYKRYPYT |
| E8 | NOT DONE | VHJ558 | IGHD6-1 | JH4 | GYTFTNYW | IDPSDSYI | ARERLSHAMDY | IGVK9-128 | JK2 | QDIKSY | YATSLAD | LQHGESPYT |
| E15 | IgG1/K | IGHV5-6 | DSP2.9 | JH3 | GFTFSTYG | ISSGGTYT | TRHDPNDGYYFLFAY | IGKV6-b | JK5 | QSVGNN | YASNRYT | QQHYSSPLT |
| E22 | IgG2b/K | VHJ558 | DFL16.1e | JH4 | GYTFTGYY | IYPGNFNT | AREDGSPYYAMDY | IGKV1-110 | JK1 | QSLVHSNGNTF | RVSNRFS | FQATHVPWT |
| E31 | IgG1/K | VHJ558 | DFL16.1 | JH4 | GYTFTRDW | IHPYDSET | VTFIKTMVDTYYYAMDY | IGKV1-135 | JK1 | QSLLHSDGKTY | LVSNLDS | WQGTHFPQT |
| E47 | IgG1/K | IGHV1-26 | P1inv | JH2 | GYTFYFY | INPNNGGT | ARWGTHYFDY | IGKV21-7 | JK1 | QSVSSSSYTY | FASNLES | QHSWEIPPT |
| E60 | IgG2a/K | IGHV1-39 | DQ52a.2 | JH4 | GYSFTVYN | INPYYGGT | ARGGKTGTYYYVMDY | IGKV12-44 | JK5 | ENIDSY | AATLLAD | QHYSTLT |
| E73 | IgG1/K | IGHV3-6 | DSP2.13 | JH2 | GYSITSGYY | ISYDGRN | AREGYGDYPFDY | IGKV21-7 | JK1 | QSVSSSSYSY | YASNLES | QHSWEIPRT |
| E76 | IgG2b/K | J558.87.193 | DFL16.1e | JH4 | GYTFTGYY | IYPGNFNT | AREDGSPYYAMDY | IGKV1-110 | JK1 | QSLVHSNGNTF | RVSNRFS | FQATHVPWT |
| E91 | IgG2b/K | IGHV1-64 | P8inv | JH4 | GYTFTSYW | IHPNSDTI | ATPERRRAMDY | IGKV4-74 | JK4 | SSLSSSY | STSFLAS | QQYDSSPFT |
| E105 | IgG1/K | VH3660 | DSP2.2 | JH3 | GASITSGY | INYSGNT | ARSTMITTGAWFAY | IGKV6-32 | JK5 | QSVSKD | YASNRYT | QQDYSSPLT |

FIG. 2

EFFICACY OF VARIOUS ANTI-EFNA4-MTIs IN BR22 TNBC PDX

| DAY | VEHICLE | 3 mg/kg huE15-vc0101 | 10 mg/kg huE15-mc8261 | 3 mg/kg huE22-vc0101 | 10 mg/kg huE22-mc8261 | 3 mg/kg huE47-vc0101 | 10 mg/kg huE47-mc8261 |
|---|---|---|---|---|---|---|---|
| 0 | 195 ± 17 | 198 ± 16 | 198 ± 22 | 184 ± 24 | 184 ± 24 | 172 ± 17 | 184 ± 15 |
| 7 | 376 ± 43 | 313 ± 17 | 329 ± 52 | 317 ± 37 | 339 ± 36 | 259 ± 33 | 288 ± 21 |
| 14 | 564 ± 54 | 354 ± 39 | 664 ± 65 | 558 ± 83 | 781 ± 98 | 547 ± 56 | 735 ± 101 |
| 21 | 819 ± 97 | 299 ± 59 | 1061 ± 69 | 901 ± 175 | 1377 ± 125 | 839 ± 110 | 1270 ± 125 |
| 28 | GT | 478 ± 113 | 1739 ± 110 | 1537 ± 321 | 2257 ± 173 | 1618 ± 221 | 2442 ± 344 |
| 35 | GT | 1032 ± 216 | 2935 ± 341 | 2617 ± 414 | 3284 ± 261 | 2468 ± 271 | 3190 ± 265 |

FIG. 19

EFFICACY OF VARIOUS ANTI-EFNA4-MTIs IN BR31 TNBC PDX

| DAY | VEHICLE | 3 mg/kg CONTROL-AcBut-CM | 3 mg/kg huE22-vc0101 | 3 mg/kg huE47-vc0101 | 3 mg/kg huE15-vc0101 |
|---|---|---|---|---|---|
| 0 | 159 ± 10 | 148 ± 12 | 151 ± 13 | 142 ± 11 | 167 ± 17 |
| 7 | 269 ± 17 | 227 ± 23 | 188 ± 17 | 176 ± 18 | 174 ± 18 |
| 14 | 425 ± 32 | 133 ± 10 | 80 ± 8 | 84 ± 8 | 99 ± 10 |
| 21 | 668 ± 50 | 101 ± 21 | 67 ± 6 | 58 ± 10 | 44 ± 11 |
| 28 | 1088 ± 93 | 70 ± 17 | 44 ± 10 | 60 ± 13 | 33 ± 10 |
| 36 | GT | 105 ± 28 | 57 ± 13 | 79 ± 17 | 41 ± 13 |
| 44 | GT | 214 ± 76 | 87 ± 28 | 146 ± 32 | 91 ± 30 |
| 49 | GT | 234 ± 83 | 111 ± 37 | 205 ± 43 | 119 ± 36 |
| 56 | GT | 393 ± 103 | 151 ± 55 | 285 ± 57 | 169 ± 44 |
| 63 | GT | 680 ± 181 | 454 ± 138 | 637 ± 140 | 376 ± 98 |
| 71 | GT | 1169 ± 300 | 680 ± 206 | 857 ± 176 | 641 ± 178 |
| 78 | GT | 1300 ± 331 | 949 ± 215 | 1005 ± 256 | 837 ± 271 |
| 85 | GT | GT | 1005 ± 201 | GT | 1129 ± 374 |

FIG. 20

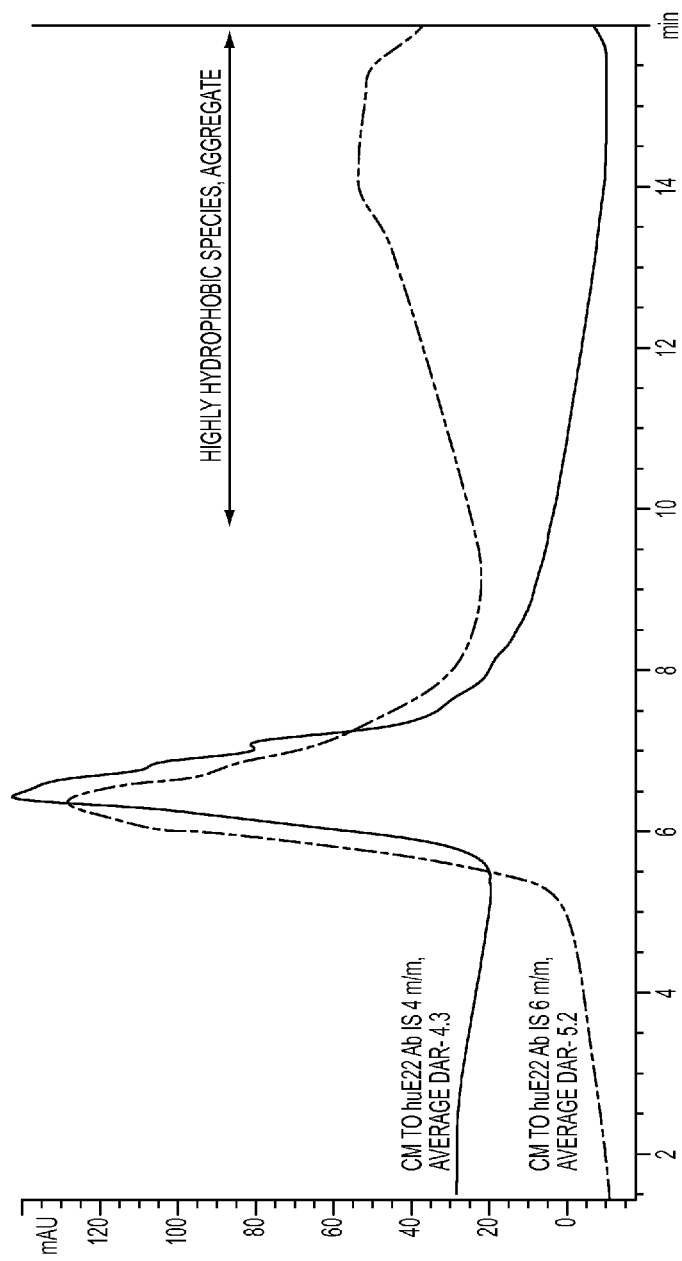

ANTI-EFNA4 ANTIBODY-DRUG CONJUGATES

RELATED APPLICATIONS

Priority is claimed to provisional U.S. Application No. 61/899,800, filed 4 Nov. 2013, which is incorporated by reference herein in its entirety.

SEQUENCE LISTING

This application is being filed electronically via EFS-Web and includes an electronically submitted sequence listing in .txt format. The .txt file contains a sequence listing entitled "PC72005_Sequence_Listing.txt" created on Nov. 1, 2013, and having a size of 56 KB. The sequence listing contained in this .txt file is part of the specification and which is incorporated herein by reference in its entirety.

FIELD OF THE INVENTION

The present invention relates to ephrin-A4 ligand (EFNA4) antibodies and antibody-drug conjugates. The present invention further relates to the methods of using such antibodies and antibody-drug conjugates for the treatment of cancer.

BACKGROUND

Ephrin receptors (EPH), the largest family of receptor tyrosine kinases, are type-I transmembrane proteins that bind with ephrin ligands (EFN). Receptors in the EPH subfamily typically have a single kinase domain and an extracellular region containing a Cys-rich domain and 2 fibronectin type III repeats. Based upon sequence analyses, ephrin ligands can be divided into two groups: ephrin-A ligands (EFNA) and three ephrin-B ligands (EFNB). EFNA ligands (i.e., EFNA1, EFNA2, EFNA3, EFNA4, EFNA5, EFNA6) are typically anchored to the cell surface via glycosyl phosphatidylinositol (GPI) linkages, although some non-GPI-anchored proteins are produced through alternative splicing of ephrin mRNAs, such as EFNA4. EFNB ligands (i.e. EFNB1, EFNB2, EFNB3) contain a transmembrane domain and a short cytoplasmic region with conserved tyrosine residues and a PDZ-binding motif. EFNA ligands preferentially bind with any of the nine different ephrin A receptors (EPHA) (i.e., EPHA1, EPHA2, EPHA3, EPHA4, EPHA5, EPHA6, EPHA7, EPHA8, EPHA9), whereas EFNB ligands preferentially bind with any of six different ephrin B receptors (EPHB) (i.e. EPHB 1, EPHB2, EPHB 3, EPHB4, EPHB 5, EPHB 6), although some cross-interactions have been reported.

EFN-EPH signaling can be bi-directional (impacting both the ligand- and receptor-expressing cells) and regulates a broad range of biological activities including neural development, cell patterning, angiogenesis, and cell motility and invasion. In the context of cancer, the expression of various EPHs and EFNs has been observed, and various functions have been reported (Hafner et al., Clinical Chemistry 50(3):490-499, 2004; Surawska et al., Cytokine & Growth Factor Reviews 15(6):419-433, 2004; Pasquale, E. B, Nature Reviews Cancer 10(3):165-180, 2010). Due to ligand-receptor binding promiscuity as well as functional overlap, it has been difficult to precisely define the roles of each EFN and EPH. While therapeutic targeting of the EPH receptors for the treatment of cancer has been explored targeting of EFN ligands has not been pursued to any great extent (Pasquale, E. B., Nature Reviews Cancer 10(3):165-180, 2010).

There remains a significant need for additional therapeutic options for cancers. To this end, the present invention provides novel antibody-drug conjugates that target EFNA4-positive cancers.

SUMMARY

The present invention provides EFNA4 antibody-drug conjugates and their use in detection, prophylaxis, and therapy of EFNA4 associated disorders. An EFNA4 antibody-drug conjugate of the invention is generally of the formula: Ab-(L-D), wherein Ab is an antibody, or antigen-binding fragment thereof, that binds to EFNA4, or an EFNA4-binding fragment thereof; and L-D is a linker-drug moiety, wherein L is a linker, and D is a drug. The Ab of the disclosed antibody-drug conjugate can be any EFNA4-binding antibody. In some aspects of the invention, the Ab is a chimeric, CDR-grafted, humanized, or a recombinant human antibody, or EFNA4-binding fragment thereof. In some aspects of the invention, the Ab is an internalizing antibody and/or a neutralizing antibody.

The present invention also provides EFNA4 antibody-drug conjugates and their use in detection, prophylaxis, and therapy of EFNA4 associated disorders. An EFNA4 antibody-drug conjugate of the invention is generally of the formula: Ab-(L-D), wherein Ab is an antibody, or antigen-binding fragment thereof, that binds to EFNA4, or an EFNA4-binding fragment thereof; and L-D is a linker-drug moiety, wherein L is a linker, and D is calicheamicin.

In particular aspects of the invention, the Ab is a huE22 or hu47 antibody, or an antibody that competes for binding to human EFNA4 with huE22 or huE47, and/or an antibody that binds to the same epitope as a huE22 or huE47 antibody. For example, the Ab may compete for binding to human EFNA4 with, and/or bind the same epitope as, an antibody comprising (a) a heavy chain variable region set forth as SEQ ID NO: 13 and a light chain variable region set forth as SEQ ID NO: 27; or (b) a heavy chain variable region set forth as SEQ ID NO: 39 and a light chain variable region set forth as SEQ ID NO: 53.

Among Abs that compete for binding to human EFNA4 with huE22, and/or bind to the same epitope as huE22, representative Abs useful for preparing EFNA4 antibody-drug conjugates of the invention include antibodies comprising at least one heavy chain variable region and at least one light chain variable region, wherein the at least one heavy chain variable region comprises three CDRs defined by SEQ ID NOs: 15, 19, and 23. Additional Abs include antibodies comprising at least one heavy chain variable region and at least one light chain variable region, wherein the at least one light chain variable region comprises three CDRs defined as SEQ ID NOs: 29, 33, and 35. Additional Abs include antibodies comprising (a) a heavy chain variable region comprising three CDRs set forth as SEQ ID NOs: 15, 19, and 23; and (b) a light chain variable region comprising three CDRs set forth as SEQ ID NOs: 29, 33, and 35.

In other EFNA4 antibody-drug conjugates of the invention, the Ab comprises a heavy chain variable region having an amino acid sequence that is at least 90% identical to SEQ ID NO: 13 and a light chain variable having an amino acid sequence that is at least 90% identical to SEQ ID NO: 27, for example, a heavy chain variable region set forth as SEQ ID NO: 13 and a light chain variable region set forth as SEQ ID NO: 27.

Among Abs that compete for binding to human EFNA4 with huE47, and/or bind to the same epitope as huE47, representative Abs useful for preparing EFNA4 antibody-drug conjugates of the invention include antibodies comprising at least one heavy chain variable region and at least one light chain variable region, wherein the at least one heavy chain variable region comprises three CDRs defined by SEQ ID NOs: 41, 45, and 49. Additional Abs include antibodies comprising at least one heavy chain variable region and at least one light chain variable region, wherein the at least one light chain variable region comprises three CDRs defined as SEQ ID NOs: 55, 59, and 61. Additional Abs include antibodies comprising (a) a heavy chain variable region comprising three CDRs set forth as SEQ ID NOs: 41, 45, and 49; and (b) a light chain variable region comprising three CDRs set forth as SEQ ID NOs: 55, 59, and 61.

In other EFNA4 antibody-drug conjugates of the invention, the Ab comprises a heavy chain variable region having an amino acid sequence that is at least 90% identical to SEQ ID NO: 39 and a light chain variable having an amino acid sequence that is at least 90% identical to SEQ ID NO: 53, for example, a heavy chain variable region set forth as SEQ ID NO: 39 and a light chain variable region set forth as SEQ ID NO: 53.

In some aspects of the invention, EFNA4 antibody-drug conjugates comprise an Ab comprising a IgG1 heavy chain constant region, a kappa light chain constant region, or a IgG1 heavy chain constant region and a kappa light chain constant region. For example, Abs useful for preparing EFNA4 antibody-drug conjugates of the invention include antibodies comprising a heavy chain set forth as SEQ ID NO: 25, a light chain set forth as SEQ ID NO: 37, or a heavy chain set forth as SEQ ID NO: 25 and a light chain set forth as SEQ ID NO: 37. Additional examples include antibodies comprising a heavy chain set forth as SEQ ID NO: 51, a light chain set forth as SEQ ID NO: 63, or a heavy chain set forth as SEQ ID NO: 51 and a light chain set forth as SEQ ID NO: 63.

In other aspects of the invention, an EFNA4 antibody-drug conjugate of the invention comprises an antibody having a heavy chain variable region set forth as SEQ ID NO: 13 or 39. In other aspects of the invention, an EFNA4 antibody-drug conjugate of the invention comprises an antibody having light chain variable region set forth as SEQ ID NO: 27 or 53.

In particular aspects of the invention, the Ab is a huE5 or hu15 antibody, or an antibody that competes for binding to human EFNA4 with huE5 or huE15, and/or an antibody that binds to the same epitope as a huE5 or huE15 antibody. For example, the Ab may compete for binding to human EFNA4 with, and/or bind the same epitope as, an antibody comprising (a) a heavy chain variable region set forth as SEQ ID NO: 5 and a light chain variable region set forth as SEQ ID NO: 7; or (b) a heavy chain variable region set forth as SEQ ID NO: 9 and a light chain variable region set forth as SEQ ID NO: 11.

In another aspect of the invention, the Ab is a humanized antibody such as huE5, huE15, huE22 or hu47 antibody, Any of the EFNA4 antibody-drug conjugates disclosed herein may be prepared with a linker comprising 4-(4'acetylphenoxy)butanoic acid (AcBut).

Any of the EFNA4 antibody drug conjugates disclosed herein may be prepared with a calicheamicin drug, including N-acetyl derivatives of calicheamicin, such as N-acetyl-γ-calicheamicin and N-acetyl-γ-calicheamicin dimethyl hydrazide (CM).

Any of the EFNA4 antibody-drug conjugates disclosed herein may have a drug-to-antibody ratio (DAR) from 1 to 12. In a particular aspect of the invention, an EFNA4 antibody-drug conjugate of the formula Ab-(L-D) comprises (a) an antibody, or antigen-binding fragment thereof, Ab, comprising a heavy chain set forth as SEQ ID NO: 25 and a light chain set forth as SEQ ID NO: 37; and (b) a linker-drug moiety, L-D, wherein L is a linker, and D is a drug, wherein the linker is 4-(4'acetylphenoxy)butanoic acid (AcBut), and wherein the drug is N-acetyl-γ-calicheamicin dimethyl hydrazide (CM).

In another aspect of the invention, an EFNA4 antibody-drug conjugate of the formula Ab-(L-D) comprises (a) an antibody, or antigen-binding fragment thereof, Ab, comprising a heavy chain set forth as SEQ ID NO: 51 and a light chain set forth as SEQ ID NO: 63; and (b) a linker-drug moiety, L-D, wherein L is a linker, and D is a drug, wherein the linker is 4-(4'acetylphenoxy)butanoic acid (AcBut), and wherein the drug is N-acetyl-γ-calicheamicin dimethyl hydrazide (CM).

The present invention provides for compositions comprising a plurality of antibody-drug conjugate disclosed herein and optionally a pharmaceutical carrier, wherein the composition has an average DAR within a range of 1 to 12. In a particular aspect of the invention, the composition may have an average DAR within the range of 3 to 5. In another aspect of the invention, the composition may have an average DAR within the range of 3 to 4. In another aspect of the invention, the composition may have an average DAR within the range of 4 to 5. In another aspect of the invention, the composition may have an average DAR of about 4.

The present invention further provides for a composition comprising a plurality of an antibody-drug conjugate disclosed herein and optionally a pharmaceutical carrier, wherein the composition has at least 50% antibody-drug conjugates having a DAR from 3 to 5. In another aspect of the invention, the composition has at least 60% antibody-drug conjugates having a DAR from 3 to 5. In another aspect of the invention, the composition has at least 70% antibody-drug conjugates having a DAR from 3 to 5. In another aspect of the invention, the composition has at least 75% antibody-drug conjugates having a DAR from 3 to 5. In another aspect of the invention, the composition has about 70% to 80% antibody-drug conjugates having a DAR from 3 to 5.

The present invention further provides for an EFNA4 antibody-drug conjugate that is generally of the formula: Ab-(L-D), wherein Ab is an antibody, or antigen-binding fragment thereof, that binds to EFNA4, or an EFNA4-binding fragment thereof; and L-D is a linker-drug moiety, wherein L is vc or mc, and D is a drug.

The present invention further provides for an EFNA4 antibody-drug conjugate that is generally of the formula: Ab-(L-D), wherein Ab is an antibody, or antigen-binding fragment thereof, that binds to EFNA4, or an EFNA4-binding fragment thereof; and L-D is a linker-drug moiety, wherein L is a linker, and D is 0101 or 8261.

The present invention further provides methods for preparing an EFNA4 antibody-drug conjugate disclosed herein. For example, a process for producing an antibody-drug conjugate can include the steps of (a) linking the linker to the drug moiety; (b) conjugating the linker-drug moiety to the antibody; and (c) purifying the antibody-drug conjugate.

Another aspect of the invention includes methods of making, methods of preparing, methods of synthesis, methods of conjugation, and methods of purification of the antibody-drug conjugates disclosed herein, and the intermediates for the preparation, synthesis, and conjugation of the antibody-drug conjugates disclosed herein.

Further provided are pharmaceutical compositions comprising an EFNA4 antibody-drug conjugate disclosed herein and a pharmaceutically acceptable carrier.

In other aspects, are provided methods of treating an EFNA associated disorder by administering a therapeutically effective amount of a composition comprising an EFNA4 antibody-drug conjugate disclosed herein. Representative EFNA associated disorders include hyperproliferative disorders, such as neoplastic disorders, such as solid tumors (e.g., breast cancer, ovarian cancer, colorectal cancer, liver cancer, lung cancer, etc.) and hematologic malignancies (e.g., leukemia, etc.). Also provided are uses of the disclosed EFNA4 antibody-drug conjugates for the manufacture of a medicament for treating an EFNA associated disorder in a subject. Also provided are EFNA4 antibody-drug conjugates for use in the treatment of an EFNA associated disorder.

In other aspects, the present invention provides for methods of treating an EFNA associated disorder in a subject by administering a therapeutically effective amount of a composition comprising an EFNA4 antibody-drug conjugate disclosed herein and a chemotherapeutic agent.

Another aspect of the invention includes methods of treating a disorder characterized by the overexpression of EFNA4 in a patient with an antibody-drug conjugate disclosed herein. In other aspects, the present invention provides for methods of treating cancer characterized by the overexpression of EFNA4 in a patient with an antibody-drug conjugate disclosed herein.

In still other aspects, the present invention provides a method of reducing tumor initiating cells in a tumor cell population. For example, the method can comprise contacting a tumor cell population, wherein the population comprises tumor initiating cells and tumor cells other than tumor initiating cells, with an EFNA4 antibody-drug conjugate; whereby the frequency of tumor initiating cells in the tumor cell population is reduced. The contacting step may be performed in vitro or in vivo.

Another aspect of the invention includes diagnostic and therapeutic uses for the compounds and compositions disclosed herein.

Other aspects of the invention include articles of manufacture, i.e. kits, comprising an antibody-drug conjugate disclosed herein, a container, and a package insert or label indicating a treatment.

These and other aspects of the invention will be appreciated by a review of the application as a whole.

BRIEF DESCRIPTION OF THE DRAWINGS

FIG. 1 provides an alignment of human EFNA4 a, b and c isoform sequences showing amino acid differences (SEQ ID NOS: 2-4).

FIG. 2 provides the genetic arrangement and the heavy and light chain CDR sequences (derived from an analysis of the VBASE2 database) of EFNA4 antibodies.

FIG. 19 shows the efficacy of huE15, huE22 and huE47 conjugated to the microtubule inhibitors (MTIs) vc0101 and mc8261 in the BR22 TNBC PDX.

FIG. 20 shows the efficacy of huE15, huE22 and huE47 conjugated to the MTI vc0101 in the BR31 TNBC PDX.

FIG. 30 shows a further comparison of analytical HICs for purified huE22-AcBut-CM ADCs generated from a ratio of CM to huE22 Ab of 4 m/m and 6 m/m.

DETAILED DESCRIPTION OF THE INVENTION

Figure 3A:
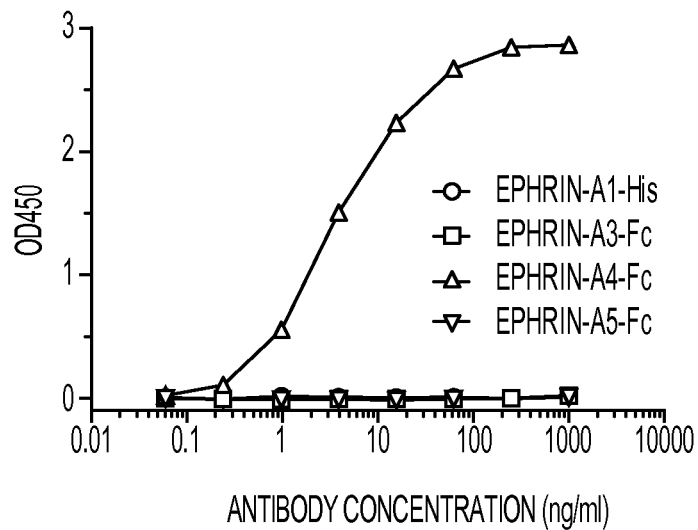
FIGS. 3A and 3B provide binding data for huE22 and huE47 antibodies, respectively, to illustrate binding specificity for EFNA4.

The present invention provides antibody-drug conjugates that bind to ephrin-A ligands (or EFNA), such as EFNA4. The invention also provides processes for preparing the conjugates using EFNA4 antibodies, linkers, and drugs. The antibody-drug conjugates of the invention are useful for the preparation and manufacture of compositions, such as medicaments that may be used in the diagnosis, prophylaxis, and/or treatment of hyperproliferative disorders characterized by EFNA4 expression. In some aspects of the invention, the disclosed antibody-drug conjugates may reduce the frequency of tumor initiating cells (TIC), which encompass both tumor perpetuating cells (TPC) and highly proliferative tumor progenitor cells (TProg).

I. EFNA Physiology

PCT International Publication No. WO2012/118547 describes that, as with all cell surface receptor-ligand interactions, engagement of the ephrin receptor (EPH) by an ephrin ligand (EFN) ultimately results in the activation of intracellular signaling cascades. Although receptor-ligand interactions may take place between molecules on the surface of the same cell (cis interactions), it is generally thought that cis interactions do not lead to the triggering of signaling cascades, or that cis interactions may actually antagonize signaling cascades initiated by trans interactions (e.g., between receptors and ligands on separate cells). One aspect of EPH-EFN trans interactions is the capacity for the triggering of two signaling cascades upon receptor-ligand engagement—a forward signaling cascade in the cell expressing the EPH, and a reverse signaling cascade in the cell expressing the EFN. The activation of two separate signaling cascades may reflect cell sorting and cell positioning processes that EPH and EFN have evolved to co-ordinate in animal embryonic development.

EPH-EFN signaling frequently activates cell-signaling pathways that regulate cytoskeletal dynamics and lead to modulation of the adhesive and repulsive interactions between different types of cells. Generally, EPH and EFN proteins are found at much higher levels during embryogenesis versus those observed in adult tissues, although continued low-level expression in the adult may reflect roles for these molecules in the normal function of tissues such as the adult gut, which has a well-defined architecture arising from the migration of differentiating cells from their source at the tissue stem cell in the crypt to their final location at the surface of the villi facing the intestinal lumen. Since EPH were first identified in hepatocellular carcinomas, and EPH and EFN expression is typically limited in adults, reactivation of the expression of EFN and/or EPH in human cancers may be linked to the dedifferentiation of the cancer cells and/or the ability of these cancer cells to invade surrounding normal tissue and to migrate from the site of the primary tumor to distant locations. Other studies have suggested that EPH-EFN interactions also have a role in neoangiogenesis.

Consistent with findings that EPH-EFN interactions in non-lymphoid tissues regulate cellular interactions by generating adhesive or repulsive forces between cells through integrin and cytoskeleton rearrangements, EPH and EFN molecules found on lymphoid cells have been shown to mediate cell adhesion to extracellular matrix components, chemotaxis and cell migration. For example, EFNA1, (which binds to the EPHA2 receptor and comprises, for example, an amino sequence as in Genbank accession NM_004428) engagement on primary CD4 and CD8 T cells has been found to stimulate cell migration and enhance chemotaxis. Like EFNA1, EFNA4 is expressed on primary CD4 T cells but, due to the promiscuity of the EPH-EFN interaction, it is unclear if EFNA4 engagement has similar effects on these cells. However, it has been demonstrated that mature human B-lymphocytes express EFNA4 and secrete it upon activation. Further EFNA4, unlike any other EFN or EPH molecule, is also consistently expressed on or by B cells of chronic lymphocytic leukemia (CLL) patients. Interestingly, the expression of EFNA4 isoforms as measured by Q-PCR may be correlated with the clinical manifestation of the disorder. Also, B cells from CLL patients known to have increased expression of EFNA4 showed impairment in transendothelial migration potential compared to B cells from healthy individuals. Evidently, engagement of EFNA4 reduced the ability of CLL cells to adhere to extracellular matrix molecules and reduced their chemotactic response to CCL1. Together these reports suggest a role for EFNA4 in B and T cell trafficking and, when viewed in combination with the intracellular signaling data discussed above, make EFNA, and EFNA4 in particular, very intriguing targets for the development of anti-cancer therapeutics.

In addition, the expression of EFNA4 is elevated in various cancer stem cell populations. Along with concomitant upregulation of several EPHA receptors in the bulk tumor, this raises the possibility that EFNA4 mediated ligand-receptor interactions may be triggering cell signaling cascades linked to tumor proliferation, neoangiogenesis and/or tumor metastasis. While not wishing to be bound by any particular theory, It is believed that EFNA4 antibodies and EFNA4 antibody-drug conjugates of the present invention act, at least in part, by either reducing or eliminating tumor initiating cell (TIC) frequency thereby interfering with tumor propagation or survival in a different manner than traditional standard of care (SOC) therapeutic regimens (e.g. doxorubicin and irinotecan), or through immunotherapeutic signaling or delivering a payload able to kill EFNA4 expressing cells. See Examples 8 and 9.

Representative EFNA4 protein orthologs include, but are not limited to, human (NP_005218, NP_872631 or NP_872632), mouse (NP_031936), chimpanzee (XP_001153095, XP_001152971, XP_524893, and XP_001152916) and rat (NP_001101162). The transcribed human EFNA4 gene includes at minimum 5817 bp from chromosome 1.

Three human EFNA4 mRNA transcript variants and encoded proteins are shown in Table 1, each of which arises from alternative splicing of the transcribed RNA: (1) a 1276 base pair variant (NM_005227; EFNA4 transcript variant 1; SEQ ID NO: 1) which encodes a 201 amino acid proprotein (NP_005218; EFNA4 isoform a; SEQ ID NO: 2); (2) a 1110 base pair variant (NM_182689; EFNA4 transcript variant 2) which encodes a 207 amino acid proprotein (NP_872631; EFNA4 isoform b; SEQ ID NO: 3); and (3) a 1111 base pair variant (NM_182690; EFNA4 transcript variant 3) which encodes a 193 amino acid proprotein (NP_872632; EFNA4 isoform c; SEQ ID NO: 4).

TABLE 1

Human EFNA4 mRNA transcript variants and encoded proteins.

| SEQ ID NO | Sequence |
| --- | --- |
| 1 | CTTCCCTCTTCACTTTGTACCTTTCTCTCCTCGACTGTGAAGCGGGCCGGGACCT<br>GCCAGGCCAGACCAAACCGGACCTCGGGGGCGATGCGGCTGCTGCCCCTGCTG<br>CGGACTGTCCTCTGGGCCGCGTTCCTCGGCTCCCCTCTGCGCGGGGGCTCCAG<br>CCTCCGCCACGTAGTCTACTGGAACTCCAGTAACCCCAGGTTGCTTCGAGGAGA<br>CGCCGTGGTGGAGCTGGGCCTCAACGATTACCTAGACATTGTCTGCCCCCACTA |

TABLE 1-continued

Human EFNA4 mRNA transcript variants and encoded proteins.

| SEQ ID NO | Sequence |
|---|---|
| | CGAAGGCCCAGGGCCCCCTGAGGGCCCCGAGACGTTTGCTTTGTACATGGTGG<br>ACTGGCCAGGCTATGAGTCCTGCCAGGCAGAGGGCCCCCGGGCCTACAAGCGC<br>TGGGTGTGCTCCCTGCCCTTTGGCCATGTTCAATTCTCAGAGAAGATTCAGCGCT<br>TCACACCCTTCTCCCTCGGCTTTGAGTTCTTACCTGGAGAGACTTACTACTACATC<br>TCGGTGCCCACTCCAGAGAGTTCTGGCCAGTGCTTGAGGCTCCAGGTGTCTGTC<br>TGCTGCAAGGAGAGGAAGTCTGAGTCAGCCCATCCTGTTGGGAGCCCTGGAGA<br>GAGTGGCACATCAGGGTGGCGAGGGGGGGACACTCCCAGCCCCCTCTGTCTCT<br>TGCTATTACTGCTGCTTCTGATTCTTCGTCTTCTGCGAATTCTGTGAGCCAAGCAG<br>ACCTTCCCTCTCATCCCAAGGAGCCAGAGTCCTCCCAAGATCCCCTGGAGGAGG<br>AGGGATCCCTGCTGCCTGCACTGGGGGTGCCAATTCAGACCGACAAGATGGAG<br>CATTGATGGGGAGATCAGAGGGTCTGAGGTGACTCTTGCAGGAGCCTGTCCCC<br>TCATCACAGGCTAAAGAAGAGCAGTAGACAGCCCTGGACACTCTGAAGCAGAGG<br>CAAGACAAACACAGGCGCTTTGCAGGCTGCTCTGAGGGTCTCAGCCCATCCCCC<br>AGGAGGACTGGGATTTGGTATGATCAAATCCTCAAGCCAGCTGGGGGCCCAGGC<br>TGAAGACCTGGGGACAGGTCGATTGCTGGACCAGGGCAAAGAAGAAGCCCTGC<br>CATCTGTGCCCTGTGGGCCTTTTCCCTGGGGCAGCACCTTGCCCTCCCCAGGGG<br>ATCACTCACTTGTCTTCTATGAAGACGGACTCTTCATGAGGTTGAATTTCATGCCA<br>GTTTGTATTTTTATAAGTATCTAGACCAAACCTTCAATAAACCACTCATCTTTTTGT<br>TGCCCTCCCCAAAAAAAAAAAAAAAAAAAAA |
| 2 | MRLLPLLRTVLWAAFLGSPLRGGSSLRHVVYWNSSNPRLLRGDAVVELGLNDYLDIV<br>CPHYEGPGPPEGPETFALYMVDWPGYESCQAEGPRAYKRWVCSLPFGHVQFSEKI<br>QRFTPFSLGFEFLPGETYYYISVPTPESSGQCLRLQVSVCCKERKSESAHPVGSPGE<br>SGTSGWRGGDTPSPLCLLLLLLLLILRLLRIL |
| 3 | MRLLPLLRTVLWAAFLGSPLRGGSSLRHVVYWNSSNPRLLRGDAVVELGLNDYLDIV<br>CPHYEGPGPPEGPETFALYMVDWPGYESCQAEGPRAYKRWVCSLPFGHVQFSEKI<br>QRFTPFSLGFEFLPGETYYYISVPTPESSGQCLRLQVSVCCKERRARVLPRSPGGGG<br>IPAACTGGANSDRQDGALMGEIRGSEVTLAGACPLITG |
| 4 | MRLLPLLRTVLWAAFLGSPLRGGSSLRHVVYWNSSNPRLLRGDAVVELGLNDYLDIV<br>CPHYEGPGPPEGPETFALYMVDWPGYESCQAEGPRAYKRWVCSLPFGHVQFSEKI<br>QRFTPFSLGFEFLPGETYYYISVPTPESSGQCLRLQVSVCCKERNLPSHPKEPESSQ<br>DPLEEEGSLLPALGVPIQTDKMEH |

It will be appreciated that each of the human EFNA4 proteins include a predicted signal or leader sequence comprising amino acids 1-25 of SEQ ID NO: 2 which is clipped off to provide the mature form of the protein (i.e. 168-182 aa in length). This signal peptide targets the polypeptide to the cell surface/secretory pathway. The term "signal sequence," also called signal peptide, leader peptide, refers to a segment of about 15 to 30 amino acids at the N terminus of a protein that enables the protein to be secreted (pass through a cell membrane). The signal sequence is removed as the protein is secreted. Due to the alternative splicing of the mRNA with consequent effects upon the protein coding sequences, the protein isoforms are processed differently by the cell. Isoform a is membrane localized and anchored to the cell surface by a glycosylphosphatidylinositol (GPI) linkage, whereas isoforms b and c lack the GPI-anchor signal sequence and therefore are expected to be secreted by the cell. An alignment of the three protein isoforms of human EFNA4 is shown in FIG. 1. As previously indicated, unless otherwise indicated by direct reference or contextual necessity the term EFNA4 shall be directed to isoform a of human EFNA4 and immunoreactive equivalents. It will further be appreciated that the term may also refer to a derivative or fragment of a native or variant form of EFNA4 that contains an epitope to which an antibody or immunoreactive fragment can specifically bind.

II. EFNA4 Antibody-Drug Conjugates

The present invention provides antibody-drug conjugates of the formula Ab-(L-D), wherein (a) Ab is an antibody, or antigen-binding fragment thereof, that binds to EFNA4, and (b) L-D is a linker-drug moiety, wherein L is a linker, and D is a drug. In contrast to the TKIs developed to inhibit Eph receptor signaling, antibody-drug conjugates (ADCs), such as anti-EFNA4 ADCs, can target specific surface molecules and the cells expressing them regardless of their signaling function, as long as the molecules efficiently internalize. Also provided are methods of preparing and manufacturing such antibody-drug conjugates, and use of the same in clinical applications. "Antibody-drug conjugate" or "ADC" refers to antibodies, or antigen-binding fragments thereof, including antibody derivatives that bind to EFNA4 and are conjugated to a drug such as a cytotoxic, cytostatic, and/or therapeutic agent, as described further herein below. For example, a cytotoxic agent can be linked or conjugated to an anti-EFNA4 antibody as described herein for targeted local delivery of the cytotoxic agent to tumors (e.g., EFNA4 expressing tumor).

As used herein, the term "EFNA4" includes variants, isoforms, homologs, orthologs and paralogs. EFNA4 is also known in the art as ephrin-A4, ephrin-A4 ligand, EPH-related receptor tyrosine kinase ligand 4, Ligand Of Eph-Related Kinase 4, EFL4, EPLG4 and LERK4. In some aspects of the invention, antibodies and antibody-drug conjugates cross-react with EFNA4 from species other than human, such as EFNA4 of mouse, rat, or primate, as well as different forms of EFNA4 (e.g., glycosylated EFNA4). In other aspects, the antibodies and antibody-drug conjugates may be completely specific for human EFNA4 and may not exhibit species or other types of cross-reactivity. As used herein the term EFNA4 refers to naturally occurring human EFNA4 unless contextually dictated otherwise. Therefore, an "EFNA4 antibody", "anti-EFNA4 antibody", "ephrin-A4 antibody" or "ephrin-A4 ligand antibody" or other similar designation, means any antibody (as defined herein) that associates, binds or reacts with the EFNA4 type ligand or isoform, or fragment or derivative thereof. Further, an "EFNA4 antibody-drug conjugate", "anti-EFNA4 antibody-drug conjugate", "ephrin-A4 antibody-drug conjugate" or "ephrin-A4 ligand antibody-drug conjugate" means any antibody-drug conjugate or ADC (as defined herein) that associates, binds or reacts with the EFNA4 type ligand or isoform, or fragment or derivative thereof.

"Linker (L)" describes the direct or indirect linkage of the antibody to the drug. Attachment of a linker to an antibody can be accomplished in a variety of ways, such as through surface lysines, reductive-coupling to oxidized carbohydrates, and through cysteine residues liberated by reducing interchain disulfide linkages. A variety of ADC linkage systems are known in the art, including hydrazone-, disulfide- and peptide-based linkages.

"Drug (D)" is any substance having biological or detectable activity, for example, therapeutic agents, detectable labels, binding agents, etc., and prodrugs, which are metabolized to an active agent in vivo. The terms drug, payload and compound are used interchangeably.

"L-D" is a linker-drug moiety resulting from a drug (D) linked to a linker (L).

Additional scientific and technical terms used in connection with the present invention, unless indicated otherwise herein, shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art.

In particular aspects of the invention, an EFNA4 antibody-drug conjugate of the formula Ab-(L-D) includes (a) an antibody (Ab), or antigen-binding fragment thereof, including a heavy chain variable region set forth as SEQ ID NO: 13 and a light chain variable region set forth as SEQ ID NO: 27; and (b) a linker-drug moiety (L-D), wherein L is a linker, and D is a drug, wherein the linker is 4-(4'acetylphenoxy)butanoic acid (AcBut), and wherein the drug is N-acetyl-γ-calicheamicin dimethyl hydrazide (CM). In other aspects of the invention, an EFNA4 antibody-drug conjugate of the formula Ab-(L-D) includes (a) an antibody (Ab), or antigen-binding fragment thereof, having a heavy chain variable region set forth as SEQ ID NO: 39 and a light chain variable region set forth as SEQ ID NO: 53; and (b) a linker-drug moiety (L-D), wherein L is a linker, and D is a drug, wherein the linker is 4-(4'acetylphenoxy)butanoic acid (AcBut), and wherein the drug is N-acetyl-γ-calicheamicin dimethyl hydrazide (CM).

In particular aspects of the present invention, an EFNA4 antibody-drug conjugate of the formula Ab-(L-D) includes (a) an antibody (Ab), or antigen-binding fragment thereof, including a heavy chain set forth as SEQ ID NO: 25 and a light chain set forth as SEQ ID NO: 37; and (b) a linker-drug moiety (L-D), wherein L is a linker, and D is a drug, wherein the linker is 4-(4'acetylphenoxy)butanoic acid (AcBut), and wherein the drug is N-acetyl-γ-calicheamicin dimethyl hydrazide (CM). In other aspects of the invention, an EFNA4 antibody-drug conjugate of the formula Ab-(L-D) includes (a) an antibody (Ab), or antigen-binding fragment thereof, having a heavy chain set forth as SEQ ID NO: 51 and a light chain set forth as SEQ ID NO: 63; and (b) a linker-drug moiety (L-D), wherein L is a linker, and D is a drug, wherein the linker is 4-(4'acetylphenoxy)butanoic acid (AcBut), and wherein the drug is N-acetyl-γ-calicheamicin dimethyl hydrazide (CM).

The present invention further provides antibody-drug conjugates that have an optimized average DAR and narrow DAR distribution. See further description below in section IIC Drugs. The average DAR and DAR distribution can have an effect on the clinical efficacy of an ADC, in particular, an effect on both potency and potential toxicity of the ADC, and can have a significant effect on properties, such as stability and aggregation of the ADC.

The DAR (drug-to-antibody ratio) or drug loading, indicating the number of drug molecules conjugated per antibody, may be from 1 to 12. Compositions, batches, and/or formulations of a plurality of antibody-drug conjugates may be characterized by an average DAR. DAR and average DAR can be determined by various conventional means such as UV spectroscopy, mass spectroscopy, ELISA assay, radiometric methods, hydrophobic interaction chromatography (HIC), electrophoresis and HPLC.

The DAR distribution provides the percent or fraction of various ADC species, e.g. DAR 1 to 12, that may be present in a composition, batch, and/or formulation of ADCs. The DAR distribution of a composition, batch, and/or formulation of ADCs may be determined by methods known in the art, such as capillary iso-electric focusing (cIEF). The DAR distribution of a composition, batch, and/or formulation of ADCs may be characterized as a highly heterogeneous mixture with a broad DAR distribution, generally containing a broad range of ADC species with DAR 1 to 12. The DAR distribution of a composition, batch, and/or formulation of ADCs may be characterized as a highly homogeneous mixture with a narrow DAR distribution, generally containing a narrow range of ADC species having a particular DAR, such as DAR 3 to 5.

In particular aspects of the present invention, the improved conjugation and purification conditions disclosed herein provide anti-EFNA4 ADCs with an optimized average DAR in the range of about 3 to 5, preferably about 4, and a narrow DAR distribution, for example, less heterogeneity, in which species with a DAR from 3 to 5 (which are the most desired) make up at least 60%, or at least 70%, or about 70% to 80%, or preferably about 75% to 80% of the total anti-EFNA4 ADC. See FIG. 9.

In particular aspects of the invention, during conjugation and purification, it is beneficial to eliminate ADCs having a high DAR (DAR>5) which are more hydrophobic and demonstrate faster clearance, which may contribute to higher toxicity and lower the therapeutic index (TI). In other aspects of the invention, it is beneficial to eliminate ADCs having a low DAR (DAR<2) which contribute little to efficacy, however, provide an increase in the amounts of unconjugated antibody which may compete with the ADC for the target antigen, such as EFNA4, and lead to a lower TI. In another aspect of the invention, it is beneficial to eliminate ADCs having a high DAR (DAR>5) and ADCs having a low DAR (DAR<2).

In particular aspects of the invention, the CM to huE22 ratio used in the preparation of a conjugation reaction mixture may be 4-5 to 1, compared to higher ratios, to generate anti-EFNA4 ADCs having an optimized DAR and eliminate higher DAR species.

In other aspects of the invention, high agitation and vigorous mixing is conducted during the addition of the linker-drug moiety (AcBut-CM), for example, as achieved in part by addition of the linker-drug moiety into the middle portion of the mixing vortex, which is helpful in achieving low amounts of unconjugated antibody, which is an improvement over prior methods.

In other aspects of the invention, the incubation time of the reaction may be reduced to 2-5 minutes, compared to 60-90 minutes, to provide low aggregates and increase stability of anti-EFNA4 ADCs. In another aspect of the invention, the amount of ethanol (EtOH) in the reaction mixture may be reduced to 6-8%, compared to 9%, to provide low aggregates and increase stability of anti-EFNA4 ADCs.

In particular aspects of the invention, during purification, the elution gradient may be optimized to provide a narrow DAR distribution for anti-EFNA4 ADCs.

Figure 6:
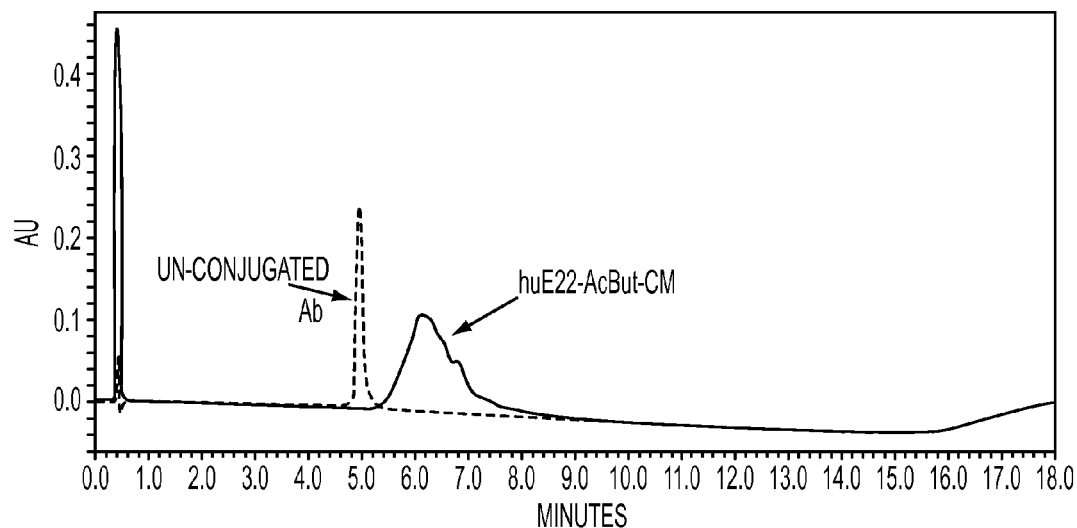
FIG. 6 provides an UPLC-HIC analysis of purified huE22-AcBut-CM on TSKgel Butyl-NPR for the presence of unconjugated antibody.

In particular aspects of the invention, purified anti-EFNA4 ADCs may have no unconjugated antibodies (free antibodies) present, see FIG. 6. In other aspects of the invention, the purified anti-EFNA4 ADCs may be monomeric ADCs, and the aggregates and dimers are absent, see FIG. 7. In other aspects of the invention, the purified anti-EFNA4 ADCs may have no free drug present, see FIG. 8. In further aspects of the invention, the purified anti-EFNA4 ADCs may be monomeric ADCs and have no free drug present.

IIA. EFNA4 Antibodies

For preparation of EFNA4 antibody-drug conjugates of the invention, the antibody, or antigen-binding fragment thereof, can be any antibody, or antigen-binding fragment thereof, that specifically binds to EFNA4. The antibodies the present invention are further disclosed and characterized in PCT International Publication No. WO2012/118547, which is incorporated herein by reference in its entirety. The antibody, or antigen-binding fragment thereof, may be isolated, purified, or derivatized for use in preparation of EFNA antibody-drug conjugates.

An "antibody" or "Ab" is an immunoglobulin molecule capable of recognizing and binding to a specific target or antigen, such as a carbohydrate, polynucleotide, lipid, polypeptide, etc., through at least one antigen recognition site, located in the variable region of the immunoglobulin molecule. As used herein, the term "antibody" can encompass any type of antibody, including but not limited to monoclonal antibodies, polyclonal antibodies, "antigen-binding fragments" (or portion), such as Fab, Fab', F(ab')$_2$, Fd, Fv, Fc, etc., of intact antibodies that retain the ability to specifically bind to a given antigen (e.g. EFNA4), an isolated complementarity determining region (CDR), bispecific antibodies, heteroconjugate antibodies, mutants thereof, fusion proteins having an antibody, or antigen-binding fragment thereof, (e.g., a domain antibody), single chain (ScFv) and single domain antibodies (e.g., shark and camelid antibodies), maxibodies, minibodies, intrabodies, diabodies, triabodies, tetrabodies, v-NAR and bis-scFv (see, e.g., Holliger and Hudson, 2005, Nature Biotechnology 23(9): 1126-1136), humanized antibodies, chimeric antibodies and any other modified configuration of the immunoglobulin molecule that includes an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). In some aspects of the invention, the antibody, or antigen-binding fragment thereof, of the disclosed EFNA4 antibody-drug conjugates is a chimeric, humanized, or a recombinant human antibody, or EFNA4-binding fragment thereof.

An antibody, an antibody-drug conjugate, or a polypeptide that "specifically binds" or "preferentially binds" (used interchangeably herein) to a target or antigen (e.g., EFNA4 protein) is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target or antigen if it binds with greater affinity, avidity, more readily, and/or with greater duration than it binds to other substances. For example, an antibody that specifically or preferentially binds to an EFNA4 epitope is an antibody that binds this epitope with greater affinity, avidity, more readily, and/or with greater duration than it binds to other EFNA4 epitopes or non-EFNA4 epitopes.

The term "binding affinity" or "$K_D$" as used herein, is intended to refer to the equilibrium dissociation constant of a particular antigen-antibody interaction. The $K_D$ is the ratio of the rate of dissociation, also called the "off-rate" or "$k_d$", to the rate of association, or "on-rate" or "$k_a$". Thus, $K_D$ equals $k_d/k_a$ and is expressed as a molar concentration (M). It follows that the smaller the $K_D$, the stronger the binding affinity. Therefore, a $K_D$ of 1 µM indicates weak binding affinity compared to a $K_D$ of 1 nM. $K_D$ values for antibodies can be determined using methods well established in the art. One method for determining the $K_D$ of an antibody is by using surface plasmon resonance, typically using a biosensor system such as a Biacore® system.

Specific binding of the disclosed EFNA4 antibody-drug conjugates refers to a preferential binding of an antibody to human EFNA4 antigen in a heterogeneous sample having multiple different antigens. Typically, specific binding occurs if the binding affinity is at least about $10^{-7}$ M or higher, such as at least about $10^{-8}$ M or higher, including at least about $10^{-9}$ M or higher, at least about $10^{-11}$ M or higher, or at least about $10^{-12}$ M or higher. For example, specific binding of an antibody of the invention to a human EFNA4 antigen includes binding in the range of at least about $1 \times 10^{-7}$ M to about $1 \times 10^{-12}$ M, such as within the range of about $1 \times 10^{-8}$ M to about $1 \times 10^{-12}$ M, or within the range of about $1 \times 10^{-8}$ M to about $1 \times 10^{-11}$ M, or within the range of about $1 \times 10^{-8}$ M to about $1 \times 10^{-10}$ M, or within the range of about $1 \times 10^{-9}$ M to about $1 \times 10^{-10}$ M. Specific binding also refers to selective targeting of an EFNA4 antibody, or antigen-binding fragment thereof, to EFNA4-expressing cells following administration of the antibody to a subject.

As used herein, "epitope" includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. An epitope may be 'linear' or 'conformational.' In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another. Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, i.e. the antibodies compete for binding to the antigen. A high throughput process for 'binning' antibodies based upon their cross-competition is described in PCT International Publication No. WO 03/48731. As used herein, the term 'binning' refers to a method to group antibodies based on their antigen binding characteristics and competition with each other.

An isolated antibody that specifically binds EFNA4 may, however, have cross-reactivity to other antigens, such as EFNA4 molecules from other species (i.e. an ortholog) or with more than one isoform of EFNA4. An "isolated antibody", as used herein, refers to an antibody that is substantially free of other antibodies having different antigenic specificities (e.g., an isolated antibody that specifically binds EFNA4 is substantially free of antibodies that specifically bind antigens other than EFNA4). Moreover, an isolated antibody may be substantially free of other cellular material and/or chemicals. It is also understood that by reading this definition, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

In some aspects of the invention, an EFNA4 antibody-drug conjugate includes an antibody that competes for binding to human EFNA4 with, and/or binds the same epitope as, an antibody, or antigen-binding fragment thereof, having (a) a heavy chain variable region set forth as SEQ ID NO: 13 and a light chain variable region set forth as SEQ ID NO: 27; or (b) a heavy chain variable region set forth as SEQ ID NO: 39 and a light chain variable region set forth as SEQ ID NO: 53.

The term "compete", as used herein with regard to an antibody, means that a first antibody, or an antigen-binding fragment thereof, binds to an epitope in a manner sufficiently similar to the binding of a second antibody, or an antigen-binding fragment thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

Native or naturally occurring antibodies, and native immunoglobulins are typically heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains. The term "variable" refers to the fact that certain portions of the variable domains differ extensively in sequence among antibodies.

Antibodies and the above-noted antibody domains may be described as "polypeptides", "oligopeptides", "peptides" and "proteins", i.e., chains of amino acids of any length, preferably, relatively short (e.g., 10-100 amino acids). The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains. Amino acids may be referred to herein by either their commonly known three letter symbols or by the one-letter symbols recommended by the IUPAC-IUB Biochemical.

A "constant region" of an antibody refers to the constant region of the antibody light chain or the constant region of the antibody heavy chain, either alone or in combination. The constant regions of chimeric and humanized EFNA4 antibodies may be derived from constant regions of any one of IgA, IgD, IgE, IgG, IgM, any isotypes thereof (e.g., IgG1, IgG2, IgG3, or IgG4 isotypes of IgG), as well as subclasses and mutated versions thereof. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy chain constant regions that correspond to the different classes of immunoglobulins are called alpha, delta, epsilon, gamma, and mu, respectively. The subunit structures and three-dimensional configurations of different classes of immunoglobulins are well known.

The constant domains are not involved directly in binding an antibody to an antigen, but exhibit various effector functions, such as Fc receptor (FcR) binding, participation of the antibody in antibody-dependent cellular toxicity, opsonization, initiation of complement dependent cytotoxicity, and mast cell degranulation. As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally having two constant regions, CH2 and CH3.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, Ann. Rev. Immunol., 9:457-92, 1991; Capel et al., Immunomethods, 4:25-34, 1994; and de Haas et al., J. Lab. Clin. Med., 126: 330-41, 1995. "FcR" also includes the neonatal receptor, FcRn, which is responsible for the transfer of maternal IgGs to the fetus (Guyer et al., J. Immunol., 117:587-593 (1976); and Kim et al., European J. Immunol., 24:2429-2434 (1994)).

In some aspects of the invention, the antibody, or antigen-binding fragment thereof, of the disclosed EFNA4 antibody-drug conjugates includes an IgG1 heavy chain constant region, for example a huE22 heavy chain set forth as SEQ ID NO: 25 or a huE47 heavy chain set forth as SEQ ID NO: 51. In other aspects, the antibody, or antigen-binding fragment thereof, of the disclosed EFNA4 antibody-drug conjugates includes a kappa light chain constant region, for example a huE22 light chain set forth as SEQ ID NO: 37 or a huE47 light chain set forth as SEQ ID NO: 63. In particular aspects of the invention, an EFNA4 antibody-drug conjugate can include an IgG1 heavy chain constant region and a kappa light chain constant region, for example, a heavy chain set forth as SEQ ID NO: 25 and a light chain set forth as SEQ ID NO: 37, or as another example, a heavy chain set forth as SEQ ID NO: 51 and a light chain set forth as SEQ ID NO: 63.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-Lazikani et al., J. Molec. Biol. 273: 927-948 (1997)). As used herein, a CDR may refer to CDRs defined by either approach or by a combination of both approaches.

A CDR of a variable domain are amino acid residues within the variable region that are identified in accordance with the definitions of the Kabat, Chothia, the accumulation of both Kabat and Chothia, VBASE2, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, (1989). The CDR positions may also be derived from an analysis of the VBASE2 database. (See, e.g. Retter et al., Nucleic Acids Res. 33(Database Issue):D671-D674, 2005.

Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, (1996). In another approach, referred to herein as the "conformational definition" of CDRs, the positions of the CDRs may be identified as the residues that make enthalpic contributions to antigen binding. See, e.g., Makabe et al., Journal of Biological Chemistry, 283:1156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For EFNA4 antibody-drug conjugates described herein, CDRs may be defined in accordance with any of Kabat, Chothia, extended, VBASE2, AbM, contact, and/or conformational definitions.

In other aspects of the invention, the EFNA4 antibody, or antigen-binding fragment thereof, includes one or more CDR(s) of the antibody (such as one, two, three, four, five, or all six CDRs).

For the instant invention, the CDRs set forth in Table 2 below (SEQ ID NOS: 5-64) were derived using Kabat and Chothia approaches and the CDRS set forth in FIG. 2 were derived from an analysis of the VBASE2 database. Accordingly, antibodies having CDRs defined by all such nomenclature are expressly included within the scope of the instant invention. More broadly, the term "variable region CDR amino acid residue" includes amino acids in a CDR as identified using any sequence or structure based method as set forth above.

In some aspects of the invention, an EFNA4 antibody-drug conjugate includes an antibody, or antigen-binding fragment thereof, having CDRs of a huE22 antibody. For example, an EFNA4 antibody-drug conjugate may include an antibody, or antigen-binding fragment thereof, including at least one heavy chain variable region and at least one light chain variable region, wherein the at least one heavy chain variable region has three CDRs set forth as SEQ ID NOs: 15, 19, and 23. In some aspects of the invention, an EFNA4 antibody-drug conjugate includes an antibody, or antigen-binding fragment thereof, having at least one heavy chain variable region and at least one light chain variable region, wherein the at least one light chain variable region has three CDRs set forth as SEQ ID NOs: 29, 33, and 35. An EFNA4 antibody-drug conjugate of the invention can also include an antibody, or antigen-binding fragment thereof, including (a) a heavy chain variable region having three CDRs set forth as SEQ ID NOs: 15, 19, and 23; and (b) a light chain variable region having three CDRs set forth as SEQ ID NOs: 29, 33, and 35.

In still other aspects of the invention, an EFNA4 antibody-drug conjugate includes an antibody, or antigen-binding fragment thereof, having one or more huE22 CDRs defined according to Chothia or derived from an analysis of the VBASE2 database. For example, an EFNA4 antibody-drug conjugate can include an antibody, or antigen-binding fragment thereof, having at least one heavy chain variable region and at least one light chain variable region, wherein the at least one heavy chain variable region includes three huE22 CDRs defined by Chothia (see Table 2) or three huE22 CDRs derived from an analysis of the VBASE2 database (see FIG. 2). As another example, an EFNA4 antibody-drug conjugate can include an antibody, or antigen-binding fragment thereof, having at least one heavy chain variable region and at least one light chain variable region, wherein the at least one light chain variable region includes three huE22 CDRs defined by Chothia (see Table 2) or three huE22 CDRs derived from an analysis of the VBASE2 database (see FIG. 2). In some aspects of the invention, an EFNA4 antibody-drug conjugate of the invention can include an antibody, or antigen-binding fragment thereof, having (a) a heavy chain variable region having three huE22 CDRs defined according to Chothia (see Table 2); and (b) a light chain variable region having three huE22 CDRs defined according to Chothia (see Table 2). In some aspects of the invention, an EFNA4 antibody-drug conjugate of the invention can include an antibody, or antigen-binding fragment thereof, having (a) a heavy chain variable region including three huE22 CDRs derived from an analysis of the VBASE2 database (see FIG. 2); and (b) a light chain variable region including three huE22 CDRs derived from an analysis of the VBASE2 database (see FIG. 2).

In other aspects of the invention, an EFNA4 antibody-drug conjugate includes an antibody, or antigen-binding fragment thereof, having CDRs of a huE47 antibody. For example, an EFNA4 antibody-drug conjugate may include an antibody, or antigen-binding fragment thereof, having at least one heavy chain variable region and at least one light chain variable region, wherein the at least one heavy chain variable region includes three CDRs set forth as SEQ ID NOs: 41, 45, and 49. In some aspects of the invention, an EFNA4 antibody-drug conjugate includes an antibody, or antigen-binding fragment thereof, having at least one heavy chain variable region and at least one light chain variable region, wherein the at least one light chain variable region includes three CDRs set forth as SEQ ID NOs: 55, 59, and 61. An EFNA4 antibody-drug conjugate of the invention can also include (a) a heavy chain variable region having three CDRs set forth as SEQ ID NOs: 41, 45, and 49; and (b) a light chain variable region having three CDRs set forth as SEQ ID NOs: 55, 59, and 61.

In still other aspects of the invention, an EFNA4 antibody-drug conjugate includes an antibody, or antigen-binding fragment thereof, having one or more huE47 CDRs defined according to Chothia or derived from an analysis of the VBASE2 database. For example, an EFNA4 antibody-drug conjugate can include an antibody, or antigen-binding fragment thereof, having at least one heavy chain variable region and at least one light chain variable region, wherein the at least one heavy chain variable region includes three huE47 CDRs defined by Chothia (see Table 2) or three huE47 CDRs derived from an analysis of the VBASE2 database (see FIG. 2). As another example, an EFNA4 antibody-drug conjugate can include an antibody, or antigen-binding fragment thereof, having at least one heavy chain variable region and at least one light chain variable region, wherein the at least one light chain variable region includes three huE47 CDRs defined by Chothia (see Table 2) or three huE47 CDRs derived from an analysis of the VBASE2 database (see FIG. 2). In some aspects of the invention, an EFNA4 antibody-drug conjugate of the invention can include an antibody, or antigen-binding fragment thereof, having (a) a heavy chain variable region including three huE47 CDRs defined according to Chothia (see Table 2); and (b) a light chain variable region including three huE47 CDRs defined according to Chothia (see Table 2). In some aspects of the invention, an EFNA4 antibody-drug conjugate of the invention can include an antibody, or antigen-binding fragment thereof, having (a) a heavy chain variable region having three huE47 CDRs derived from an analysis of the VBASE2 database (see FIG. 2); and (b) a light chain variable region having three huE47 CDRs derived from an analysis of the VBASE2 database (see FIG. 2).

In some aspects of the invention, antibodies used to prepare EFNA4 antibody-drug conjugates of the invention will be monoclonal antibodies. The term "monoclonal antibody" or "mAb" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256:495-497, 1975, or may be made by recombinant DNA methods such as described in U.S. Pat. No. 4,816,567. The monoclonal antibodies may also be isolated from phage libraries generated using the techniques described in McCafferty et al., Nature 348:552-554, 1990, for example.

In some aspects of the invention, antibodies used to prepare antibody-drug conjugates of the invention will be monovalent, i.e., having one antigen binding site per molecule (e.g., IgG or Fab). In some instances, a monovalent antibody can have more than one antigen binding sites, but the binding sites are from different antigens. In some aspects of the invention, the antibody, or antigen-binding fragment thereof, of an antibody-drug conjugate of the invention may include a "bivalent antibody", i.e., having two antigen binding sites per molecule (e.g., IgG). In some instances, the two binding sites have the same antigen specificities. Alternatively, bivalent antibodies may be bispecific. A "bispecific," "dual-specific" or "bifunctional" antibody is a hybrid antibody having two different antigen binding sites. The two antigen binding sites of a bispecific antibody bind to two different epitopes, which may reside on the same or different protein targets.

The term "chimeric antibody" is intended to refer to antibodies in which part or all of the variable region sequences are derived from one species and the constant region sequences are derived from another species, such as an antibody in which the variable region sequences are derived from a mouse antibody and the constant region sequences are derived from a human antibody.

As used herein, "humanized" or "CDR grafted" antibody refers to forms of non-human (e.g. murine) antibodies that are chimeric immunoglobulins, immunoglobulin chains, or fragments thereof (such as Fv, Fab, Fab', F(ab')$_2$ or other antigen binding subsequences of antibodies) that contain minimal sequence derived from a non-human immunoglobulin. Preferably, humanized antibodies are human immunoglobulins (recipient antibody) in which residues from one or more complementary determining regions (CDRs) of the recipient are replaced by residues from one or more CDRs of a non-human species (donor antibody) such as mouse, rat, or rabbit having the desired specificity, affinity, and capacity.

In some instances, Fv framework region (FR) residues of the human immunoglobulin are replaced by corresponding non-human residues. Furthermore, the humanized antibody may include residues that are found neither in the recipient antibody nor in the imported CDR or framework sequences, but are included to further refine and optimize antibody performance. In general, the humanized antibody will include substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will include at least a portion of an immunoglobulin constant region or domain (Fc), typically that of a human immunoglobulin. In some aspects of the invention the antibodies have Fc regions modified as described in PCT International Publication No. WO 99/58572. Other forms of humanized antibodies have one or more CDRs (CDR L1, CDR L2, CDR L3, CDR H1, CDR H2, or CDR H3) which may be altered with respect to the original antibody, which are also termed one or more CDRs "derived from" one or more CDRs from the original antibody.

Humanization can be essentially performed following the method of Winter and co-workers (Jones et al. Nature 321: 522-525 (1986); Riechmann et al. Nature 332:323-327 (1988); Verhoeyen et al. Science 239:1534-1536 (1988)), by substituting rodent or mutant rodent CDRs or CDR sequences for the corresponding sequences of a human antibody. See also U.S. Pat. Nos. 5,225,539; 5,585,089; 5,693,761; 5,693,762; 5,859,205; which are incorporated herein by reference in its entirety. In some instances, residues within the framework regions of one or more variable regions of the human immunoglobulin are replaced by corresponding non-human residues (see, for example, U.S. Pat. Nos. 5,585,089; 5,693,761; 5,693,762; and 6,180,370). Furthermore, humanized antibodies may include residues that are not found in the recipient antibody or in the donor antibody. These modifications are made to further refine antibody performance (e.g., to obtain desired affinity). In general, the humanized antibody will include substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will include at least a portion of an immunoglobulin constant region (Fc), typically that of a human immunoglobulin. For further details see Jones et al. Nature 321:522-525 (1986); Riechmann et al. Nature 332:323-327 (1988); and Presta Curr. Op. Struct. Biol. 2:593-596 (1992); which are incorporated herein by reference in its entirety. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225, 539; 5,585,089; 5,693,761; 5,693,762; 5,859,205. See also U.S. Pat. No. 6,180,370, and PCT International Publication No. WO 01/27160, where humanized antibodies and techniques for producing humanized antibodies having improved affinity for a predetermined antigen are disclosed.

"Recombinant human antibody" or "fully human antibody" refers to those antibodies having an amino acid sequence corresponding to that of an antibody produced by a human and/or which has been made using any of the techniques for making human antibodies known to those skilled in the art or disclosed herein. This definition of a human antibody includes antibodies having at least one human heavy chain polypeptide or at least one human light chain polypeptide. One such example is an antibody having murine light chain and human heavy chain polypeptides. Human antibodies can be produced using various techniques known in the art. For example, a human antibody is selected from a phage library, where that phage library expresses human antibodies (Vaughan et al., Nature Biotechnology, 14:309-314, (1996); Sheets et al., Proc. Natl. Acad. Sci. (USA) 95:6157-6162, (1998); Hoogenboom and Winter, J. Mol. Biol., 227:381-388, (1992); Marks et al., J. Mol. Biol., 222:581-597, (1991)). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al. Monoclonal Antibodies and Cancer Therapy, Alan R. Liss, p. 77, (1985); Boerner et al., J. Immunol., 147 (1):86-95, (1991); and U.S. Pat. No. 5,750,373.

Antibodies of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50 (1999) and Fellouse, F. A., et al, J. Mol. Biol., 373(4):924-40 (2007)). Additional guidance may be found in Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual, Cold Spring Harbor Laboratory Press, Cold Spring Harbor, N.Y. (1998); and Coligan et al., Short Protocols in Protein Science, Wiley, John & Sons, Inc. (2003). Representative methods are also described in Examples 1-3 herein below.

In general, for the production of hybridoma cell lines, the route and schedule of immunization of the host animal are generally in keeping with established and conventional techniques for antibody stimulation and production. It is contemplated that any mammalian subject including humans or antibody producing cells therefrom can be manipulated to serve as the basis for production of mammalian, including human and hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., Nature 256:495-497, 1975 or as modified by Buck, D. W., et al., In Vitro, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the EFNA4 monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay). Hybridomas that may be used as source of antibodies encompass all derivatives, progeny cells of the parent hybridomas that produce monoclonal antibodies specific for EFNA4, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with a human EFNA4, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups, can yield a population of antibodies (e.g., monoclonal antibodies).

If desired, the EFNA4 antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., J. Immunol. Methods 329:112-124, 2008; U.S. Pat. No. 7,314,622.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

The term "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

Alternatively, the polynucleotide sequence may be used for genetic manipulation to "humanize" the antibody or to improve the affinity, or other characteristics of the antibody. For example, the constant region may be engineered to more nearly resemble human constant regions to avoid immune response if the antibody is used in clinical trials and treatments in humans. It may be desirable to genetically manipulate the antibody sequence to obtain greater affinity to EFNA4 and greater efficacy in inhibiting EFNA4.

There are four general steps that may be used to humanize a monoclonal antibody: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

Humanized antibodies may be prepared using any one of a variety of methods including veneering, grafting of complementarity determining regions (CDRs), grafting of abbreviated CDRs, grafting of specificity determining regions (SDRs), and Frankenstein assembly, as described below. Humanized antibodies also include superhumanized antibodies, in which one or more changes have been introduced in the CDRs. For example, human residues may be substituted for non-human residues in the CDRs. These general approaches may be combined with standard mutagenesis and synthesis techniques to produce an anti-EFNA4 antibody of any desired sequence.

Veneering is based on the concept of reducing potentially immunogenic amino acid sequences in a rodent or other non-human antibody by resurfacing the solvent accessible exterior of the antibody with human amino acid sequences. Thus, veneered antibodies appear less foreign to human cells than the unmodified non-human antibody. See Padlan (1991) *Mol. Immunol.* 28:489-98. A non-human antibody is veneered by identifying exposed exterior framework region residues in the non-human antibody, which are different from those at the same positions in framework regions of a human antibody, and replacement of the identified residues with amino acids that typically occupy these same positions in human antibodies.

Grafting of CDRs is performed by replacing one or more CDRs of an acceptor antibody (e.g., a human antibody or other antibody having desired framework residues) with CDRs of a donor antibody (e.g., a non-human antibody). Acceptor antibodies may be selected based on similarity of framework residues between a candidate acceptor antibody and a donor antibody. For example, according to the Frankenstein approach, human framework regions are identified as having substantial sequence homology to each framework region of the relevant non-human antibody, and CDRs of the non-human antibody are grafted onto the composite of the different human framework regions. A related method also useful for preparation of antibodies of the invention is described in U.S. Patent Application Publication No. 2003/0040606.

Grafting of abbreviated CDRs is a related approach. Abbreviated CDRs include the specificity-determining residues and adjacent amino acids, including those at positions 27d-34, 50-55 and 89-96 in the light chain, and at positions 31-35b, 50-58, and 95-101 in the heavy chain (numbering convention of (Kabat et al. (1987)). See (Padlan et al. (1995) *FASEB J.* 9: 133-9). Grafting of specificity-determining residues (SDRs) is premised on the understanding that the binding specificity and affinity of an antibody combining site is determined by the most highly variable residues within each of the complementarity determining regions (CDRs). Analysis of the three-dimensional structures of antibody-antigen complexes, combined with analysis of the available amino acid sequence data may be used to model sequence variability based on structural dissimilarity of amino acid residues that occur at each position within the CDR. SDRs are identified as minimally immunogenic polypeptide sequences consisting of contact residues. See Padlan et al. (1995) *FASEB J.* 9: 133-139.

In general, human acceptor frameworks are selected on the basis that they are substantially similar to the framework regions of the donor antibodies, or which are most similar to the consensus sequence of the variable region subfamily. Following grafting, additional changes may be made in the donor and/or acceptor sequences to optimize antibody binding, functionality, codon usage, expression levels, etc, including introduction of non-human residues into the framework regions. See e.g., PCT International Publication No. WO 91/09967.

For grafting of CDRs onto a heavy chain variable framework region, useful framework sequences may be derived from a DP-21 (VH7), DP-54 (VH3-07), DP-47 (VH3-23), DP-53 (VH-74), DP-49 (VH3-30), DP-48 (VH3-13), DP-75, DP-8(VH1-2), DP-25, VI-2b and VI-3 (VH1-03), DP-15 and V1-8 (VH1-08), DP-14 and V1-18 (VH1-18), DP-5 and V1-24P (VH1-24), DP-4 (VH1-45), DP-7 (VH1-46), DP-10, DA-6 and YAC-7 (VH1-69), DP-88 (VH1-e), DP-3 and DA-8 (VH1-f). For grafting of CDRs onto a light chain variable framework region, useful framework sequences may be derived from a DPK24 subgroup IV germ line clone, a Will subgroup (DPK23, DPK22, DPK20, DPK21), or a VκI subgroup germ line clone (DPK9, DPK1, O2, DPK7).

Antigen-binding fragments or antibody fragments can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody or antibody fragment could be produced by an automated polypeptide synthesizer employing the solid phase method. See also, U.S. Pat. Nos. 5,807,715; 4,816,567; and 6,331,415.

In other aspects of the invention, the EFNA4 antibody-drug conjugates include an antibody, or antigen-binding fragment thereof, having a huE5, huE15, huE22, or huE47 heavy chain and/or light chain variable region, or a variable region substantially similar to a huE5, huE15, huE22, or huE47 heavy chain or light chain variable region.

As applied to polypeptides, the term "substantial identity" or "substantial similarity" means that two amino acid sequences, when optimally aligned, such as by the programs GAP or BESTFIT using default gap weights as supplied with the programs, share at least 70%, 75% or 80% sequence identity, preferably at least 90% or 95% sequence identity, and more preferably at least 97%, 98% or 99% sequence identity. In some substantially similar amino acid sequences, residue positions that are not identical differ by conservative amino acid substitutions.

Substantially similar polypeptides also include conservatively substituted variants in which one or more residues have been conservatively substituted with a functionally similar residue. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

A further indication that two proteins are substantially identical is that they share an overall three-dimensional structure, or are biologically functional equivalents.

In some aspects of the invention, an antibody-drug conjugate, which binds to EFNA4, including an antibody, or antigen-binding fragment thereof, having a heavy chain variable region set forth as any one of SEQ ID NOs: 5, SEQ ID NO: 9, SEQ ID NO: 13 and SEQ ID NO: 39 and/or a light chain variable region set forth as any one of SEQ ID NOs: 7, SEQ ID NO: 11, SEQ ID NO: 27 and SEQ ID NO: 53. For example, an EFNA4 antibody-drug conjugate of the invention can include an antibody, or antigen-binding fragment thereof, having a heavy chain variable region having an amino acid sequence that is at least 90% identical to SEQ ID NO: 13 and a light chain variable region having an amino acid sequence that is at least 90% identical to SEQ ID NO: 27; or an antibody, or antigen-binding fragment thereof, having a heavy chain variable region set forth as SEQ ID NO: 13 and a light chain variable region having an amino acid sequence set forth as SEQ ID NO: 27. As another example, an EFNA4 antibody-drug conjugate of the invention can include an antibody, or antigen-binding fragment thereof, having a heavy chain variable region having an amino acid sequence that is at least 90% identical to SEQ ID NO: 39 and a light chain variable region having an amino acid sequence that is at least 90% identical to SEQ ID NO: 53; or an antibody, or antigen-binding fragment thereof, having a heavy chain variable region set forth as SEQ ID NO: 39 and a light chain variable region having an amino acid sequence set forth as SEQ ID NO: 53.

To express the EFNA4 antibodies of the present invention, DNA fragments encoding VH and VL regions can first be obtained using any of the methods described above. As known in the art, "polynucleotide," "nucleic acid/nucleotide," and "oligonucleotide" are used interchangeably herein, and include polymeric forms of nucleotides of any length, either deoxyribonucleotides or ribonucleotides, analogs thereof, or any substrate that can be incorporated into a chain by DNA or RNA polymerase. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, DNA, cDNA, genomic DNA, recombinant polynucleotides, branched polynucleotides, plasmids, vectors, isolated DNA of any sequence, isolated RNA of any sequence, nucleic acid probes, and primers. Polynucleotides may be naturally-occurring, synthetic, recombinant or any combination thereof. A polynucleotide may include modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, features wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

Representative DNAs encoding anti-EFNA4 antibody heavy chain and light chain variable regions are set forth as SEQ ID NOs: 6 (huE5 VH DNA), 8 (huE5 VL DNA), 10 (huE15 VH DNA), 12 (huE15 VL DNA), 14 (huE22 VH DNA), 28 (huE22 VL DNA), 40 (huE47 VH DNA), and 54 (huE47 VL DNA). Representative DNAs encoding anti-EFNA antibody heavy chains and light chains are set forth as SEQ ID NO: 26 (huE22 HC), SEQ ID NO: 28 (huE22 LC), SEQ ID NO: 52 (huE47 HC), and SEQ ID NO: 64 (huE47 LC). See Table 2 herein below. The CDRs of the huE5 and huE15 antibodies are indicated by underlining in Table 2. The CDRs of the huE22 and huE47 antibodies are set forth as separate sequences and sequence identifiers in Table 2 (defined by Kabat or Chothia) or in FIG. 2 (derived from an analysis of the VBASE2 database).

Various modifications, e.g. mutations, substitutions, deletions, and/or additions can also be introduced into the huE5, huE15, huE22, and huE47 DNA sequences using standard methods known to those of skill in the art. For example, mutagenesis can be carried out using standard methods, such as PCR-mediated mutagenesis, in which the mutated nucleotides are incorporated into the PCR primers such that the PCR product contains the desired mutations or site-directed mutagenesis.

Accordingly, based upon the disclosure of the instant application, one skilled in the art would readily recognize the sequences of DNAs substantially similar huE5, huE15, huE22, and huE47 DNAs. The term "substantial similarity" or "substantial sequence similarity," when referring to a nucleic acid or fragment thereof, means that when optimally aligned with appropriate nucleotide insertions or deletions with another nucleic acid (or its complementary strand), there is nucleotide sequence identity in at least about 85%, preferably at least about 90%, and more preferably at least about 95%, 96%, 97%, 98% or 99% of the nucleotide bases, as measured by any well-known algorithm of sequence identity, such as FASTA, BLAST or Gap.

The term "percent sequence identity" in the context of nucleic acid sequences means the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, Methods Enzymol. 183:63-98 (1990); Pearson, Methods Mol. Biol. 132:185-219 (2000); Pearson, Methods Enzymol. 266:227-258 (1996); Pearson, J. Mol. Biol. 276:71-84 (1998); which are incorporated herein by reference in its entirety). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, which is incorporated herein by reference in its entirety.

A further indication that two nucleic acid sequences are substantially identical is that proteins encoded by the nucleic acids are substantially identical, share an overall three-dimensional structure, or are biologically functional equivalents. These terms are defined further herein below. Nucleic acid molecules that do not hybridize to each other under stringent conditions are still substantially identical if the corresponding proteins are substantially identical. This may occur, for example, when two nucleotide sequences comprise conservatively substituted variants as permitted by the genetic code.

Conservatively substituted variants are nucleic acid sequences having degenerate codon substitutions wherein the third position of one or more selected (or all) codons is substituted with mixed-base and/or deoxyinosine residues. See Batzer et al. (1991) Nucleic Acids Res. 19:5081; Ohtsuka et al. (1985) J. Biol. Chem. 260:2605-2608; and Rossolini et al. (1994) Mol. Cell Probes 8:91-98.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. As another example, the cysteine may be canonical.

The antibodies may also be modified, e.g. in the variable domains of the heavy and/or light chains, e.g., to alter a binding property of the antibody. For example, a mutation may be made in one or more of the CDR regions to increase or decrease the $K_D$ of the antibody for EFNA4, to increase or decrease $k_{off}$, or to alter the binding specificity of the antibody. Techniques in site-directed mutagenesis are well-known in the art. See, e.g., Sambrook et al. and Ausubel et al., supra.

A modification or mutation may also be made in a framework region or constant region to increase the half-life of an EFNA4 antibody. See, e.g. PCT International Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. According to the invention, a single antibody may have mutations in any one or more of the CDRs or framework regions of the variable domain or in the constant region.

In a process known as "germlining", certain amino acids in the VH and VL sequences can be mutated to match those found naturally in germline VH and VL sequences. In particular, the amino acid sequences of the framework regions in the VH and VL sequences can be mutated to match the germline sequences to reduce the risk of immunogenicity when the antibody is administered. As used herein, the term "germline" refers to the nucleotide sequences and amino acid sequences of the antibody genes and gene segments as they are passed from parents to offspring via the germ cells. This germline sequence is distinguished from the nucleotide sequences encoding antibodies in mature B cells which have been altered by recombination and hypermutation events during the course of B cell maturation. An antibody that "utilizes" a particular germline has a nucleotide or amino acid sequence that most closely aligns with that germline nucleotide sequence or with the amino acid sequence that it specifies. Such antibodies frequently are mutated compared with the germline sequence. Germline DNA sequences for human VH and VL genes are known in the art (see e.g., the "Vbase" human germline sequence database; see also Kabat, E. A., et al., 1991, Sequences of Proteins of Immunological Interest, Fifth Edition, U.S. Department of Health and Human Services, NIH Publication No. 91-3242; Tomlinson et al., J. Mol. Biol. 227:776-798, 1992; and Cox et al., Eur. J. Immunol. 24:827-836, 1994.

Another type of amino acid substitution that may be made is to remove potential proteolytic sites in the antibody. Such sites may occur in a CDR or framework region of a variable domain or in the constant region of an antibody. Substitution of cysteine residues and removal of proteolytic sites may decrease the risk of heterogeneity in the antibody product and thus increase its homogeneity. Another type of amino acid substitution is to eliminate asparagine-glycine pairs, which form potential deamidation sites, by altering one or both of the residues. In another example, the C-terminal lysine of the heavy chain of an EFNA4 antibody of the invention can be cleaved. In various aspects of the invention, the heavy and light chains of the EFNA4 antibodies may optionally include a signal sequence.

Once DNA fragments encoding the VH and VL segments of the present invention are obtained, these DNA fragments can be further manipulated by standard recombinant DNA techniques, for example to convert the variable region genes to full-length antibody chain genes, to Fab fragment genes, or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG2 constant region. The IgG constant region sequence can be any of the various alleles or allotypes known to occur among different individuals, such as Gm(1), Gm(2), Gm(3), and Gm(17). These allotypes represent naturally occurring amino acid substitution in the IgG1 constant regions. For a Fab fragment heavy chain gene, the VH-encoding DNA can be operatively linked to another DNA molecule encoding only the heavy chain CH1 constant region. The CH1 heavy chain constant region may be derived from any of the heavy chain genes.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. The kappa constant region may be any of the various alleles known to occur among different individuals, such as Inv(1), Inv(2), and Inv(3). The lambda constant region may be derived from any of the three lambda genes.

To create a scFv gene, the VH- and VL-encoding DNA fragments are operatively linked to another fragment encoding a flexible linker such that the VH and VL sequences can be expressed as a contiguous single-chain protein, with the VL and VH regions joined by the flexible linker (See e.g., Bird et al., 1988, Science 242:423-426; Huston et al., 1988, Proc. Natl. Acad. Sci. USA 85:5879-5883; McCafferty et al., 1990, Nature 348:552-554. The single chain antibody may be monovalent, if only a single VH and VL are used, bivalent, if two VH and VL are used, or polyvalent, if more than two VH and VL are used. Bispecific or polyvalent antibodies may be generated that bind specifically to EFNA4 and to another molecule.

In another aspect of the invention, a fusion antibody or immunoadhesin may be made that includes all or a portion of an EFNA4 antibody of the invention linked to another polypeptide. In another aspect, only the variable domains of the EFNA4 antibody are linked to the polypeptide. In another aspect, the VH domain of an EFNA4 antibody is linked to a first polypeptide, while the VL domain of an EFNA4 antibody is linked to a second polypeptide that associates with the first polypeptide in a manner such that the VH and VL domains can interact with one another to form an antigen binding site. In another aspect, the VH domain is separated from the VL domain by a linker such that the VH and VL domains can interact with one another. The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bispecific antibody.

Other modified antibodies may be prepared using EFNA4 antibody encoding nucleic acid molecules. For instance, "Kappa bodies" (Ill et al., Protein Eng. 10:949-57, 1997), "Minibodies" (Martin et al., EMBO J., 13:5303-9, 1994), "Diabodies" (Holliger et al., Proc. Natl. Acad. Sci. USA 90:6444-6448, 1993), or "Janusins" (Traunecker et al., EMBO J. 10:3655-3659, 1991 and Traunecker et al., Int. J. Cancer (Suppl.) 7:51-52, 1992) may be prepared using standard molecular biological techniques following the teachings of the specification.

Bispecific antibodies or antigen binding fragments can be produced by a variety of methods including fusion of hybridomas or linking of Fab' fragments. See, e.g., Songsivilai & Lachmann, Clin. Exp. Immunol. 79:315-321, 1990, Kostelny et al., J. Immunol. 148:1547-1553, 1992. In addition, bispecific antibodies may be formed as "diabodies" or "Janusins." In some aspects of the invention, a bispecific antibody binds to two different epitopes of EFNA4. In other aspects, modified antibodies described above are prepared using one or more of the variable domains or CDR regions from the EFNA4 antibodies provided herein.

For use in preparation of antibody-drug conjugates, EFNA4 antibodies described herein may be substantially pure, i.e., at least 50% pure (i.e., free from contaminants), more preferably, at least 90% pure, more preferably, at least 95% pure, yet more preferably, at least 98% pure, and most preferably, at least 99% pure.

Table 2 provides the amino acid (protein) sequences and associated nucleic acid (DNA) sequences of humanized anti-EFNA4 antibodies of the present invention. The CDRs of huE5 VH, huE5 VL, huE15 VH, and huE15 VL, as defined by Kabat, are underlined. The CDRs of huE22 VH, huE22 VL, huE47 VH, and huE47 VL, as defined by Kabat and by Chothia, are set forth as separate sequences.

TABLE 2

Sequences of humanized anti-EFNA4 antibodies.

| SEQ ID NO | Description | Sequences |
|---|---|---|
| 5 | huE5 VH Protein | EVQLVESGGGLVQPGGSLRLSCAASGFTVT<u>TYGVD</u>WVRQAPGK GLEWLGVIWGG<u>GSTNYNSALKS</u>RFTISRDNSKNTLYLQMNSLRA EDTAVYYCAS<u>DWAYW</u>GQGTLVTVSS |
| 6 | huE5 VH DNA | GAGGTGCAGCTGGTGGAGTCTGGGGGAGGCTTGGTCCAGCCT GGGGGGTCCCTGAGACTCTCCTGTGCAGCCTCTGGATTCACC GTCACTACTTATGGTGTGGACTGGGTCCGCCAAGCTCCAGGG AAGGGGCTGGAGTGGTTAGGTGTAATATGGGGTGGTGGAAGC ACAAATTATAATAGCGCTTTGAAGAGCCGATTCACCATCTCCAG AGACAACTCCAAGAACACCCTGTATCTGCAAATGAACAGTCTG AGAGCCGAGGACACGGCCGTGTATTACTGTGCCAGTGATTGG GCTTACTGGGGCCAAGGGACTCTGGTCACTGTCTCTTC |
| 7 | huE5 VL Protein | DIQMTQSPSSLSASVGDRVTITCR<u>ASQNVGTNVA</u>WFQQKPGKAP KSLIHS<u>ASYRYS</u>GVPSRFSGSGSGTDFTLTISSLQPEDFATYYC<u>Q QYKRYPYT</u>FGGGTKLEIK |
| 8 | huE5 VL DNA | GACATCCAGATGACCCAGTCTCCATCTTCCCTGTCTGCATCTG TAGGAGACAGAGTCACCATCACTTGTCGGGCGAGTCAGAATG TGGGTACAAATGTAGCCTGGTTTCAGCAGAAACCAGGGAAAG CCCCTAAGTCCCTGATCCATTCGGCATCCTACCGTTACAGTGG GGTCCCATCAAGGTTCAGCGGCAGTGGATCTGGGACAGATTT CACTCTCACCATCAGCAGCCTGCAGCCTGAAGATTTTGCAACT TACTATTGTCAGCAATATAAGAGGTATCCGTACACGTTCGGAG GGGGGACCAAGCTGGAAATAAAAC |
| 9 | huE15 VH Protein | EVQLVESGGGLVKPGGSLRLSCAASGFTFS<u>TYGMS</u>WVRQAPGK GLEWVAT<u>ISSGGTYTYYPDSVKG</u>RFKISRDNAKNSLYLQMNSLRA EDTAVYYCTR<u>HDPNDGYYFLFAYW</u>GQGTLVTVSS |
| 10 | huE15 VH DNA | GAGGTGCAACTGGTGGAGTCTGGGGGAGGCCTGGTCAAGCC TGGGGGGTCCCTGAGACTCTCCTGTGCAGCCTCTGGATTCAC CTTCAGTACCTATGGCATGAGCTGGGTCCGCCAGGCTCCAGG GAAGGGGCTGGAGTGGGTCGCAACCATTAGTAGTGGTGGTAC TTACACATACTACCCAGACTCAGTGAAGGGCCGATTCAAAATC TCCAGAGACAACGCCAAGAACTCACTGTATCTGCAAATGAACA GCCTGAGAGCCGAGGACACGGCTGTGTATTACTGTACAAGAC ATGACCCCAATGATGGTTACTACTTCCTGTTTGCTTACTGGGG CCAGGGGACTCTGGTCACTGTCTCTTC |
| 11 | huE15 VL Protein | EIVLTQSPGTLSLSPGERATLSC<u>KASQSVGNNVA</u>WYQQKPGQAP RLLIY<u>YASNRYT</u>GIPDRFSGSGSGTDFTLTISRLEPEDFAVYYC<u>QQ HYSSPLT</u>FGAGTKLEIK |
| 12 | huE15 VL DNA | GAAATTGTGTTGACGCAGTCTCCAGGCACCCTGTCTTTGTCTC CAGGGGAAAGAGCCACCCTCTCCTGCAAGGCCAGTCAGAGTG TTGGCAACAATGTAGCTTGGTACCAGCAGAAACCTGGCCAGG CTCCCAGGCTCCTCATCTACTATGCATCCAATAGGTATACAGG CATCCCAGACAGGTTCAGTGGCAGTGGGTCTGGGACAGACTT CACTCTCACCATCAGCAGACTGGAGCCTGAAGATTTTGCAGTG TATTACTGTCAACAGCATTATAGCTCTCCGCTCACGTTCGGTG CTGGGACCAAGCTGGAGATCAAAC |

TABLE 2 -continued

Sequences of humanized anti-EFNA4 antibodies.

| SEQ ID NO | Description | Sequences |
|---|---|---|
| 13 | huE22 VH Protein | QVQLVQSGAEVKKPGASVKVSCKASGYTFTGYYIHWVRQAPGQ GLEWMGWIYPGNFNTKYNERFKGRVTMTTDTSTSTAYMELRSLR SDDTAVYYCAREDGSPYYAMDYWGQGTSVTVSS |
| 14 | huE22 VH DNA | CAGGTTCAGCTGGTGCAGTCTGGAGCTGAGGTGAAGAAGCCT GGGGCCTCAGTGAAGGTCTCCTGCAAGGCTTCTGGTTACACC TTTACCGGCTATTACATCCACTGGGTGCGACAGGCCCCTGGA CAAGGGCTTGAGTGGATGGGATGGATCTACCCTGGCAATTTTA ACACAAAATATAACGAGCGGTTCAAGGGCAGAGTCACCATGAC CACAGACACATCCACGAGCACAGCCTACATGGAGCTGAGGAG CCTGAGATCTGACGACACGGCCGTGTATTACTGTGCGAGAGA GGATGGTAGCCCCTACTATGCTATGGACTACTGGGGTCAAGG AACCTCAGTCACCGTCTCCTCA |
| 15 | huE22 VH CDR1 Protein-Kabat | GYYIH |
| 16 | huE22 VH CDR1 Protein-Chothia | GYTFTGY |
| 17 | huE22 VH CDR1 DNA-Kabat | GGCTATTACATCCAC |
| 18 | huE22 VH CDR1 DNA-Chothia | GGTTACACCTTTACCGGCTAT |
| 19 | huE22 VH CDR2 Protein-Kabat | WIYPGNFNTKYNERFKG |
| 20 | huE22 VH CDR2 Protein-Chothia | YPGNFN |
| 21 | huE22 VH CDR2 DNA-Kabat | TGGATCTACCCTGGCAATTTTAACACAAAATATAACGAGCGGTT CAAGGGC |
| 22 | huE22 VH CDR2 DNA-Chothia | TACCCTGGCAATTTTAAC |
| 23 | huE22 VH CDR3 Protein-Kabat and Chothia | EDGSPYYAMDY |
| 24 | huE22 VH CDR3 DNA-Kabat and Chothia | GAGGATGGTAGCCCCTACTATGCTATGGACTAC |
| 25 | huE22 HC Protein-HuIgG1 | QVQLVQSGAEVKKPGASVKVSCKASGYTFTGYYIHWVRQAPGQ GLEWMGWIYPGNFNTKYNERFKGRVTMTTDTSTSTAYMELRSLR SDDTAVYYCAREDGSPYYAMDYWGQGTSVTVSSASTKGPSVFP LAPSSKSTSGGTAALGCLVKDYFPEPVTVSWNSGALTSGVHTFP AVLQSSGLYSLSSVVTVPSSSLGTQTYICNVNHKPSNTKVDKKVE PKSCDKTHTCPPCPAPELLGGPSVFLFPPKPKDTLMISRTPEVTC VVVDVSHEDPEVKFNWYVDGVEVHNAKTKPREEQYNSTYRVVS VLTVLHQDWLNGKEYKCKVSNKALPAPIEKTISKAKGQPREPQVY TLPPSRDELTKNQVSLTCLVKGFYPSDIAVEWESNGQPENNYKTT PPVLDSDGSFFLYSKLTVDKSRWQQGNVFSCSVMHEALHNHYT QKSLSLSPG |
| 26 | huE22 HC DNA | CAGGTTCAGCTGGTGCAGTCTGGAGCTGAGGTGAAGAAGCCT GGGGCCTCAGTGAAGGTCTCCTGCAAGGCTTCTGGTTACACC TTTACCGGCTATTACATCCACTGGGTGCGACAGGCCCCTGGA CAAGGGCTTGAGTGGATGGGATGGATCTACCCTGGCAATTTTA ACACAAAATATAACGAGCGGTTCAAGGGCAGAGTCACCATGAC CACAGACACATCCACGAGCACAGCCTACATGGAGCTGAGGAG CCTGAGATCTGACGACACGGCCGTGTATTACTGTGCGAGAGA GGATGGTAGCCCCTACTATGCTATGGACTACTGGGGTCAAGG AACCTCAGTCACCGTCTCCTCAGCCTCCACCAAGGGCCCATC GGTCTTCCCCCTGGCGCCCTCGAGCAAGAGCACCTCTGGGGG CACAGCGGCCCTGGGCTGCCTGGTCAAGGACTACTTCCCCGA GCCGGTGACGGTGTCGTGGAACTCAGGCGCCCTGACCAGCG GCGTGCACACCTTCCCGGCTGTCCTACAGTCCTCAGGACTCTA CTCCCTCAGCAGCGTGGTGACCGTGCCCTCCAGCAGCTTGGG CACCCAGACCTACATCTGCAACGTGAATCACAAGCCCAGCAAC ACCAAGGTGGACAAGAAAGTTGAGCCCAAATCTTGTGACAAAA CTCACACATGCCCACCGTGCCCAGCACCTGAACTCCTGGGGG GACCGTCAGTCTTCCTCTTCCCCCCAAAACCCAAGGACACCCT |

TABLE 2 -continued

Sequences of humanized anti-EFNA4 antibodies.

| SEQ ID NO | Description | Sequences |
|---|---|---|
| | | CATGATCTCCCGGACCCCTGAGGTCACATGCGTGGTGGTGGA<br>CGTGAGCCACGAAGACCCTGAGGTCAAGTTCAACTGGTACGT<br>GGACGGCGTGGAGGTGCATAATGCCAAGACAAAGCCGCGGG<br>AGGAGCAGTACAACAGCACGTACCGTGTGGTCAGCGTCCTCA<br>CCGTCCTGCACCAGGACTGGCTGAATGGCAAGGAGTACAAGT<br>GCAAGGTCTCCAACAAAGCCCTCCCAGCCCCCATCGAGAAAA<br>CCATCTCCAAAGCCAAAGGGCAGCCCCGAGAACCACAGGTGT<br>ACACCCTGCCCCCATCCCGGGATGAGCTGACCAAGAACCAGG<br>TCAGCCTGACCTGCCTGGTCAAAGGCTTCTATCCCAGCGACAT<br>CGCCGTGGAGTGGGAGAGCAATGGGCAGCCGGAGAACAACT<br>ACAAGACCACGCCTCCCGTGCTGGACTCCGACGGCTCCTTCT<br>TCCTCTACAGCAAGCTCACCGTGGACAAGAGCAGGTGGCAGC<br>AGGGGAACGTCTTCTCATGCTCCGTGATGCATGAGGCTCTGC<br>ACAACCACTACACGCAGAAGAGCCTCTCCCTGTCTCCGGGT |
| 27 | huE22 VL Protein | DIVMTQTPLSLSVTPGQPASISCRSSQSLVHSNGNTFLYWYLQKP<br>GQSPQLLIYRVSNRFSGVPDRFSGSGSGTDFTLKISRVEAEDVGV<br>YYCFQATHVPWTFGGGTKVEIK |
| 28 | huE22 VL DNA | GATATTGTGATGACCCAGACTCCACTCTCTCTGTCCGTCACCC<br>CTGGACAGCCGGCCTCCATCTCCTGCCGGTCTAGTCAGAGCC<br>TCGTGCATAGTAATGGAAACACCTTTTTGTATTGGTACCTGCAG<br>AAGCCAGGCCAGTCTCCACAGCTCCTAATCTATAGAGTTTCCA<br>ACCGGTTCTCTGGAGTGCCAGATAGGTTCAGTGGCAGCGGGT<br>CAGGGACAGATTTCACACTGAAAATCAGCCGGGTGGAGGCTG<br>AGGATGTTGGGGTTTATTACTGCTTTCAAGCTACACATGTTCC<br>GTGGACGTTCGGTGGAGGCACCAAAGTGGAAATCAAA |
| 29 | huE22 VL CDR1 Protein-Kabat | RSSQSLVHSNGNTFLY |
| 30 | huE22 VL CDR1 Protein-Chothia | QSLVHSNGNTF |
| 31 | huE22 VL CDR1 DNA-Kabat | CGGTCTAGTCAGAGCCTCGTGCATAGTAATGGAAACACCTTTT<br>TGTAT |
| 32 | huE22 VL CDR1 DNA-Chothia | CAGAGCCTCGTGCATAGTAATGGAAACACCTTT |
| 33 | huE22 VL CDR2 Protein-Kabat and Chothia | RVSNRFS |
| 34 | huE22 VL CDR2 DNA-Kabat and Chothia | AGAGTTTCCAACCGGTTCTCT |
| 35 | huE22 VL CDR3 Protein-Kabat and Chothia | FQATHVPWT |
| 36 | huE22 VL CDR3 DNA-Kabat and Chothia | CAAGCTACACATGTTCCGTGGACG |
| 37 | huE22 LC Protein-Kappa | DIVMTQTPLSLSVTPGQPASISCRSSQSLVHSNGNTFLYWYLQKP<br>GQSPQLLIYRVSNRFSGVPDRFSGSGSGTDFTLKISRVEAEDVGV<br>YYCFQATHVPWTFGGGTKVEIKRTVAAPSVFIFPPSDEQLKSGTA<br>SVVCLLNNFYPREAKVQWKVDNALQSGNSQESVTEQDSKDSTY<br>SLSSTLTLSKADYEKHKVYACEVTHQGLSSPVTKSFNRGEC |
| 38 | huE22 LC DNA | GATATTGTGATGACCCAGACTCCACTCTCTCTGTCCGTCACCC<br>CTGGACAGCCGGCCTCCATCTCCTGCCGGTCTAGTCAGAGCC<br>TCGTGCATAGTAATGGAAACACCTTTTTGTATTGGTACCTGCAG<br>AAGCCAGGCCAGTCTCCACAGCTCCTAATCTATAGAGTTTCCA<br>ACCGGTTCTCTGGAGTGCCAGATAGGTTCAGTGGCAGCGGGT<br>CAGGGACAGATTTCACACTGAAAATCAGCCGGGTGGAGGCTG<br>AGGATGTTGGGGTTTATTACTGCTTTCAAGCTACACATGTTCC<br>GTGGACGTTCGGTGGAGGCACCAAAGTGGAAATCAAACGGAC<br>TGTGGCTGCACCAAGTGTCTTCATCTTCCCGCCATCTGATGAG<br>CAGTTGAAATCTGGAACTGCCTCTGTTGTGTGCCTGCTGAATA<br>ACTTCTATCCCAGAGAGGCCAAAGTACAGTGGAAGGTGGATAA<br>CGCCCTCCAATCGGGTAACTCCCAGGAGAGTGTCACAGAGCA<br>GGACAGCAAGGACAGCACCTACAGCCTCAGCAGCACCCTGAC |

TABLE 2 -continued

Sequences of humanized anti-EFNA4 antibodies.

| SEQ ID NO | Description | Sequences |
|---|---|---|
| | | GCTGAGCAAAGCAGACTACGAGAAACACAAAGTCTACGCCTG CGAAGTCACCCATCAGGGCCTGAGCTCGCCCGTCACAAAGAG CTTCAACAGGGGAGAGTGT |
| 39 | huE47 VH Protein | QVQLVQSGAEVKKPGASVKVSCKASGYTFTYFYMNWVRQAPGQ GLEWVGQINPNNGGTAYAQKFQGRVTMTRDTSTSTVYMELSSL RSEDTAVYYCARWVGTHYFDYWGQGTTLTVSS |
| 40 | huE47 VH DNA | CAGGTGCAGCTGGTGCAGTCTGGGGCTGAGGTGAAGAAGCCT GGGGCCTCAGTGAAGGTTTCCTGCAAGGCATCTGGATACACC TTCACTTACTTCTATATGAACTGGGTGCGACAGGCCCCTGGAC AAGGGCTTGAGTGGGTGGGACAAATCAACCCTAATAATGGTG GCACAGCCTACGCACAGAAGTTCCAGGGCAGAGTCACCATGA CCAGGGACACGTCCACGAGCACAGTCTACATGGAGCTGAGCA GCCTGAGATCTGAGGACACGGCCGTGTATTACTGTGCAGAT GGGTCGGGACTCACTACTTTGACTACTGGGGCCAAGGCACCA CTCTCACAGTCTCCTCC |
| 41 | huE47 VH CDR1 Protein-Kabat | YFYMN |
| 42 | huE47 VH CDR1 Protein-Chothia | GYTFTYF |
| 43 | huE47 VH CDR1 DNA-Kabat | TACTTCTATATGAAC |
| 44 | huE47 VH CDR1 DNA-Chothia | GGATACACCTTCACTTACTTC |
| 45 | huE47 VH CDR2 Protein-Kabat | QINPNNGGTAYAQKFQG |
| 46 | huE47 VH CDR2 Protein-Chothia | NPNNGGT |
| 47 | huE47 VH CDR2 DNA-Kabat | CAAATCAACCCTAATAATGGTGGCACAGCCTACGCACAGAAGT TCCAGGGC |
| 48 | huE47 VH CDR2 DNA-Chothia | AACCCTAATAATGGTGGCACA |
| 49 | huE47 VH CDR3 Protein-Kabat and Chothia | WVGTHYFDY |
| 50 | huE47 VH CDR3 DNA-Kabat and Chothia | TGGGTCGGGACTCACTACTTTGACTAC |
| 51 | huE47 HC Protein-Human IGg1 | QVQLVQSGAEVKKPGASVKVSCKASGYTFTYFYMNWVRQAPGQ GLEWVGQINPNNGGTAYAQKFQGRVTMTRDTSTSTVYMELSSL RSEDTAVYYCARWVGTHYFDYWGQGTTLTVSSASTKGPSVFPL APSSKSTSGGTAALGCLVKDYFPEPVTVSWNSGALTSGVHTFPA VLQSSGLYSLSSVVTVPSSSLGTQTYICNVNHKPSNTKVDKKVEP KSCDKTHTCPPCPAPELLGGPSVFLFPPKPKDTLMISRTPEVTCV VVDVSHEDPEVKFNWYVDGVEVHNAKTKPREEQYNSTYRVVSV LTVLHQDWLNGKEYKCKVSNKALPAPIEKTISKAKGQPREPQVYT LPPSRDELTKNQVSLTCLVKGFYPSDIAVEWESNGQPENNYKTTP PVLDSDGSFFLYSKLTVDKSRWQQGNVFSCSVMHEALHNHYTQ KSLSLSPG |
| 52 | huE47 HC DNA | CAGGTGCAGCTGGTGCAGTCTGGGGCTGAGGTGAAGAAGCCT GGGGCCTCAGTGAAGGTTTCCTGCAAGGCATCTGGATACACC TTCACTTACTTCTATATGAACTGGGTGCGACAGGCCCCTGGAC AAGGGCTTGAGTGGGTGGGACAAATCAACCCTAATAATGGTG GCACAGCCTACGCACAGAAGTTCCAGGGCAGAGTCACCATGA CCAGGGACACGTCCACGAGCACAGTCTACATGGAGCTGAGCA GCCTGAGATCTGAGGACACGGCCGTGTATTACTGTGCAGAT GGGTCGGGACTCACTACTTTGACTACTGGGGCCAAGGCACCA CTCTCACAGTCTCCTCCGCCTCCACCAAGGGCCCATCGGTCTT CCCCCTGGCGCCCTCGAGCAAGAGCACCTCTGGGGGCACAG CGGCCCTGGGCTGCCTGGTCAAGGACTACTTCCCCGAGCCGG TGACGGTGTCGTGGAACTCAGGCGCCCTGACCAGCGGCGTG CACACCTTCCCGGCTGTCCTACAGTCCTCAGGACTCTACTCCC |

TABLE 2 -continued

Sequences of humanized anti-EFNA4 antibodies.

| SEQ ID NO | Description | Sequences |
|---|---|---|
| | | TCAGCAGCGTGGTGACCGTGCCCTCCAGCAGCTTGGGCACCC AGACCTACATCTGCAACGTGAATCACAAGCCCAGCAACACCAA GGTGGACAAGAAAGTTGAGCCCAAATCTTGTGACAAAACTCAC ACATGCCCACCGTGCCCAGCACCTGAACTCCTGGGGGGACCG TCAGTCTTCCTCTTCCCCCCAAAACCCAAGGACACCCTCATGA TCTCCCGGACCCCTGAGGTCACATGCGTGGTGGTGGACGTGA GCCACGAAGACCCTGAGGTCAAGTTCAACTGGTACGTGGACG GCGTGGAGGTGCATAATGCCAAGACAAAGCCGCGGGAGGAG CAGTACAACAGCACGTACCGTGTGGTCAGCGTCCTCACCGTC CTGCACCAGGACTGGCTGAATGGCAAGGAGTACAAGTGCAAG GTCTCCAACAAAGCCCTCCCAGCCCCCATCGAGAAAACCATCT CCAAAGCCAAAGGGCAGCCCCGAGAACCACAGGTGTACACCC TGCCCCCATCCCGGGATGAGCTGACCAAGAACCAGGTCAGCC TGACCTGCCTGGTCAAAGGCTTCTATCCCAGCGACATCGCCGT GGAGTGGGAGAGCAATGGGCAGCCGGAGAACAACTACAAGAC CACGCCTCCCGTGCTGGACTCCGACGGCTCCTTCTTCCTCTAC AGCAAGCTCACCGTGGACAAGAGCAGGTGGCAGCAGGGGAA CGTCTTCTCATGCTCCGTGATGCATGAGGCTCTGCACAACCAC TACACGCAGAAGAGCCTCTCCCTGTCTCCGGGT |
| 53 | huE47 VL Protein | EIVLTQSPATLSLSPGERATLSCRASQSVSSSSYTYIHWYQQKPG QAPRLLINFASNLESGIPARFSGSGSGTDFTLTISSLEPEDFAVYY CQHSWEIPPTFGGGTKLEIK |
| 54 | huE47 VL DNA | GAAATTGTGTTGACACAGTCTCCAGCCACCCTGTCTTTGTCTC CAGGGGAAAGAGCCACCCTCTCCTGCAGGGCCAGTCAGAGTG TTAGCAGCTCTAGCTATACTTACATTCACTGGTACCAACAGAAA CCTGGCCAGGCTCCCAGGCTCCTCATCAATTTTGCATCCAACT TGGAAAGTGGCATCCCAGCCAGGTTCAGTGGCAGTGGGTCTG GGACAGACTTCACTCTCACCATCAGCAGCCTAGAGCCTGAAGA TTTTGCAGTTTATTACTGTCAGCACAGTTGGGAGATTCCTCCGA CGTTCGGTGGAGGCACCAAGCTGGAAATCAAA |
| 55 | huE47 VL CDR1 Protein-Kabat | RASQSVSSSSYTYIH |
| 56 | huE47 VL CDR1 Protein-Chothia | SSSYTYIH |
| 57 | huE47 VL CDR1 DNA-Kabat | AGGGCCAGTCAGAGTGTTAGCAGCTCTAGCTATACTTACATTC AC |
| 58 | huE47 VL CDR1 DNA-Chothia | AGCTCTAGCTATACTTACATTCAC |
| 59 | huE47 VL CDR2 Protein-Kabat and Chothia | FASNLES |
| 60 | huE47 VL CDR2 DNA-Kabat and Chothia | TTTGCATCCAACTTGGAAAGT |
| 61 | huE47 VL CDR3 Protein-Kabat and Chothia | QHSWEIPPT |
| 62 | huE47 VL CDR3 DNA-Kabat and Chothia | CAGCACAGTTGGGAGATTCCTCCGACG |
| 63 | huE47 LC Protein-Human Kappa | EIVLTQSPATLSLSPGERATLSCRASQSVSSSSYTYIHWYQQKPG QAPRLLINFASNLESGIPARFSGSGSGTDFTLTISSLEPEDFAVYY CQHSWEIPPTFGGGTKLEIKRTVAAPSVFIFPPSDEQLKSGTASVV CLLNNFYPREAKVQWKVDNALQSGNSQESVTEQDSKDSTYSLSS TLTLSKADYEKHKVYACEVTHQGLSSPVTKSFNRGEC |
| 64 | huE47 LC DNA | GAAATTGTGTTGACACAGTCTCCAGCCACCCTGTCTTTGTCTC CAGGGGAAAGAGCCACCCTCTCCTGCAGGGCCAGTCAGAGTG TTAGCAGCTCTAGCTATACTTACATTCACTGGTACCAACAGAAA CCTGGCCAGGCTCCCAGGCTCCTCATCAATTTTGCATCCAACT TGGAAAGTGGCATCCCAGCCAGGTTCAGTGGCAGTGGGTCTG GGACAGACTTCACTCTCACCATCAGCAGCCTAGAGCCTGAAGA |

TABLE 2 -continued

Sequences of humanized anti-EFNA4 antibodies.

| SEQ ID NO | Description | Sequences |
|---|---|---|
| | | TTTTGCAGTTTATTACTGTCAGCACAGTTGGGAGATTCCTCCGA<br>CGTTCGGTGGAGGCACCAAGCTGGAAATCAAACGGACTGTGG<br>CTGCACCAAGTGTCTTCATCTTCCCGCCATCTGATGAGCAGTT<br>GAAATCTGGAACTGCCTCTGTTGTGTGCCTGCTGAATAACTTC<br>TATCCCAGAGAGGCCAAAGTACAGTGGAAGGTGGATAACGCC<br>CTCCAATCGGGTAACTCCCAGGAGAGTGTCACAGAGCAGGAC<br>AGCAAGGACAGCACCTACAGCCTCAGCAGCACCCTGACGCTG<br>AGCAAAGCAGACTACGAGAAACACAAAGTCTACGCCTGCGAA<br>GTCACCCATCAGGGCCTGAGCTCGCCCGTCACAAAGAGCTTC<br>AACAGGGGAGAGTGT |

II.B. Linkers

Anti-EFNA4 antibody-drug conjugates of the present invention can be prepared using a linker to link or conjugate a drug to an anti-EFNA4 antibody. In particular aspects of the invention, the linker of EFNA4 antibody-drug conjugates of the invention includes, but is not limited to, 4-(4'acetylphenoxy)butanoic acid (AcBut).

The linker molecule may be stable (non-cleavable) or hydrolysable (cleavable), whereby it is released following cellular entry. The major mechanisms by which the drug is cleaved from the antibody include hydrolysis in the acidic pH of the lysosomes (hydrazones, acetals, and cis-aconitate-like amides), peptide cleavage by lysosomal enzymes (the cathepsins and other lysosomal enzymes), and reduction of disulfides. As a result of these varying mechanisms for cleavage, mechanisms of linking the drug to the antibody also vary widely and any suitable linker can be used.

An example of a suitable conjugation procedure relies on the conjugation of hydrazides and other nucleophiles to the aldehydes generated by oxidation of the carbohydrates that naturally occur on antibodies. Hydrazone-containing conjugates can be made with introduced carbonyl groups that provide the desired drug-release properties. Conjugates can also be made with a linker that has a disulfide at one end, an alkyl chain in the middle, and a hydrazine derivative at the other end. The anthracyclines are one example of cytotoxins that can be conjugated to antibodies using this technology.

Linkers containing functional groups other than hydrazones have the potential to be cleaved in the acidic milieu of the lysosomes. For example, conjugates can be made from thiol-reactive linkers that contain a site other than a hydrazone that is cleavable intracellularly, such as esters, amides, and acetals/ketals. Camptothecin is one cytotoxic agent that can be conjugated using these linkers. Ketals made from a 5 to 7-member ring ketone and that has one of the oxygens attached to the cytotoxic agent and the other to a linker for antibody attachment also can be used. The anthracyclines are also an example of a suitable cytotoxin for use with these linkers.

Another example of a class of pH sensitive linkers are the cis-aconitates, which have a carboxylic acid juxtaposed to an amide bond. The carboxylic acid accelerates amide hydrolysis in the acidic lysosomes. Linkers that achieve a similar type of hydrolysis rate acceleration with several other types of structures can also be used. The maytansinoids are an example of a cytotoxin that can be conjugated with linkers attached at C-9.

Another potential release method for drug conjugates is the enzymatic hydrolysis of peptides by the lysosomal enzymes. In one example, a peptide is attached via an amide bond to para-aminobenzyl alcohol and then a carbamate or carbonate is made between the benzyl alcohol and the cytotoxic agent. Cleavage of the peptide leads to the collapse, or self-immolation, of the aminobenzyl carbamate or carbonate. The cytotoxic agents exemplified with this strategy include anthracyclines, taxanes, mitomycin C, and the auristatins. In one example, a phenol can also be released by collapse of the linker instead of the carbamate. In another variation, disulfide reduction is used to initiate the collapse of a para-mercaptobenzyl carbamate or carbonate.

Many of the cytotoxic agents conjugated to antibodies have little, if any, solubility in water and that can limit drug loading on the conjugate due to aggregation of the conjugate. One approach to overcoming this is to add solubilizing groups to the linker. Conjugates made with a linker consisting of PEG and a dipeptide can been used, including those having a PEG di-acid, thiol-acid, or maleimide-acid attached to the antibody, a dipeptide spacer, and an amide bond to the amine of an anthracycline or a duocarmycin analogue. Another example is a conjugate prepared with a PEG-containing linker disulfide bonded to a cytotoxic agent and amide bonded to an antibody. Approaches that incorporate PEG groups may be beneficial in overcoming aggregation and limits in drug loading.

In some aspects of the invention, the linkers for the preparation of the antibody-drug conjugates of the present invention include linkers having the formula:

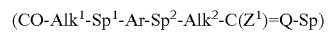

(CO-Alk$^1$-Sp$^1$-Ar-Sp$^2$-Alk$^2$-C(Z$^1$)=Q-Sp)

wherein

Alk$^1$ and Alk$^2$ are independently a bond or branched or unbranched (C$_1$-C$_{10}$) alkylene chain;

Sp$^1$ is a bond, —S—, —O—, —CONH—, —NHCO—, —NR'—, —N(CH$_2$CH$_2$)$_2$N—, or —X—Ar'—Y—(CH$_2$)$_n$—Z wherein X, Y, and Z are independently a bond, —NR'—, —S—, or —O—, with the proviso that when n=0, then at least one of Y and Z must be a bond and Ar' is 1,2-, 1,3-, or 1,4-phenylene optionally substituted with one, two, or three groups of (C$_1$-C$_5$) alkyl, (C$_1$-C$_4$) alkoxy, (C$_1$-C$_4$) thioalkoxy, halogen, nitro, —COOR', —CONHR', —(CH$_2$)$_n$COOR', —S(CH$_2$)$_n$COOR', —O(CH$_2$)$_n$CONHR', or —S(CH$_2$)$_n$CONHR', with the proviso that when Alk' is a bond, Sp$^1$ is a bond;

n is an integer from 0 to 5;

R' is a branched or unbranched (C$_1$-C$_5$) chain optionally substituted by one or two groups of —OH, (C$_1$-C$_4$) alkoxy, (C$_1$-C$_4$) thioalkoxy, halogen, nitro, (C$_1$-C$_3$) dialkylamino, or (C$_1$-C$_3$) trialkylammonium —A$^-$ where A$^-$ is a pharmaceutically acceptable anion completing a salt;

Ar is 1,2-, 1,3-, or 1,4-phenylene optionally substituted with one, two, or three groups of ($C_1$-$C_6$) alkyl, ($C_1$-$C_5$) alkoxy, ($C_1$-$C_4$) thioalkoxy, halogen, nitro, —COOR', —CONHR', —O($CH_2$)$_n$COOR', —S($CH_2$)$_n$COOR', —O($CH_2$)$_n$CONHR', or —S($CH_2$)$_n$CONHR' wherein n and R' are as hereinbefore defined or a 1,2-, 1,3-, 1,4-, 1,5-, 1,6-, 1,7-, 1,8-, 2,3-, 2,6-, or 2,7-naphthylidene or

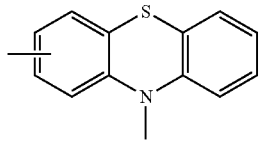

with each naphthylidene or phenothiazine optionally substituted with one, two, three, or four groups of ($C_1$-$C_6$) alkyl, ($C_1$-$C_5$) alkoxy, ($C_1$-$C_4$) thioalkoxy, halogen, nitro, —COOR', —CONHR', —O($CH_2$)$_n$COOR', —S($CH_2$)$_n$COOR', or —S($CH_2$)$_n$CONHR' wherein n and R' are as defined above, with the proviso that when Ar is phenothiazine, $Sp^1$ is a bond only connected to nitrogen;

$Sp^2$ is a bond, —S—, or —O—, with the proviso that when $Alk^2$ is a bond, $Sp^2$ is a bond, $Z^1$ is H, ($C_1$-$C_5$) alkyl, or phenyl optionally substituted with one, two, or three groups of ($C_1$-$C_5$) alkyl, ($C_1$-$C_5$) alkoxy, ($C_1$-$C_4$) thioalkoxy, halogen, nitro, —COOR', —ONHR', —O($CH_2$)$_n$COOR', —S($CH_2$)$_n$COOR', —O($CH_2$)$_n$CONHR', or —S($CH_2$)$_n$CONHR' wherein n and R' are as defined above;

Sp is a straight or branched-chain divalent or trivalent ($C_1$-$C_{18}$) radical, divalent or trivalent aryl or heteroaryl radical, divalent or trivalent ($C_3$-$C_{18}$) cycloalkyl or heterocycloalkyl radical, divalent or trivalent aryl- or heteroaryl-aryl ($C_1$-$C_{18}$) radical, divalent or trivalent cycloalkyl- or heterocycloalkyl-alkyl ($C_1$-$C_{18}$) radical or divalent or trivalent ($C_2$-$C_{18}$) unsaturated alkyl radical, wherein heteroaryl is preferably furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl and wherein if Sp is a trivalent radical, Sp may be additionally substituted by lower ($C_1$-$C_5$) dialkylamino, lower ($C_1$-$C_5$) alkoxy, hydroxy, or lower ($C_1$-$C_5$) alkylthio groups; and Q is =NHNCO—, =NHNCS—, =NHNCONH—, =NHNCSNH—, or =NHO—.

Preferably, $Alk^1$ is a branched or unbranched ($C_1$-$C_{10}$) alkylene chain; Sp' is a bond, —S—, —O—, —CONH—, —NHCO—, or —NR' wherein R' is as hereinbefore defined, with the proviso that when Alk' is a bond, $Sp^1$ is a bond;

Ar is 1,2-, 1,3-, or 1,4-phenylene optionally substituted with one, two, or three groups of ($C_1$-$C_6$) alkyl, ($C_1$-$C_5$) alkoxy, ($C_1$-$C_4$) thioalkoxy, halogen, nitro, —COOR', —CONHR', —O($CH_2$)$_n$COOR', —S($CH_2$)$_n$COOR', —O($CH_2$)$_n$CONHR', or —S($CH_2$)$_n$CONHR' wherein n and R' are as hereinbefore defined, or Ar is a 1,2-, 1,3-, 1,4-, 1,5-, 1,6-, 1,7-, 1,8-, 2,3-, 2,6-, or 2,7-naphthylidene each optionally substituted with one, two, three, or four groups of ($C_1$-$C_6$) alkyl, ($C_1$-$C_5$) alkoxy, ($C_1$-$C_4$) thioalkoxy, halogen, nitro, —COOR', —CONHR', —O($CH_2$)$_n$COOR', —S($CH_2$)$_n$COOR', —O($CH_2$)$_n$CONHR', or —S($CH_2$)$_n$CONHR'.

$Z^1$ is ($C_1$-$C_5$) alkyl, or phenyl optionally substituted with one, two, or three groups of ($C_1$-$C_5$) alkyl, ($C_1$-$C_4$) alkoxy, ($C_1$-$C_4$) thioalkoxy, halogen, nitro, —COOR', —CONHR', —O($CH_2$)$_n$COOR', —S($CH_2$)$_n$COOR', —O($CH_2$)$_n$CONHR', or —S($CH_2$)$_n$CONHR'; $Alk^2$ and $Sp^2$ are together a bond; and Sp and Q are as immediately defined above.

U.S. Pat. No. 5,773,001, which is incorporated herein by reference in its entirety, discloses linkers that may be used with nucleophilic drugs, particularly hydrazides and related nucleophiles, prepared from the calicheamicins. These linkers are especially useful in those cases where better activity is obtained when the linkage formed between the drug and the linker is hydrolysable. These linkers contain two functional groups, including (1) a group for reaction with an antibody (e.g., carboxylic acid), and (2) a carbonyl group (e.g., an aldehyde or a ketone) for reaction with a drug. The carbonyl groups may react with a hydrazide group on the drug to form a hydrazone linkage. This linkage is cleavable hydrolysable, allowing for release of the therapeutic agent from the conjugate after binding to the target cells. In some aspects of the invention, the hydrolysable linker used is 4-(4-acetylphenoxy)butanoic acid (AcBut). In other aspects of the invention, antibody-drug conjugates can be prepared using (3-Acetylphenyl)acetic acid (AcPAc) or 4-mercapto-4-methyl-pentanoic acid (Amide) as the linker molecule.

N-hydroxysuccinimide (OSu) esters or other comparably activated esters can be used to generate the activated hydrolyzable linker-drug moiety. Examples of other suitable activating esters include NHS (N-hydroxysuccinimide), sulfo-NHS (sulfonated NHS), PFP (pentafluorophenyl), TFP (tetrafluorophenyl), and DNP (dinitrophenyl).

In some aspects of the invention, the antibody-drug conjugates are prepared by reacting calicheamicin or derivatives thereof, the AcBut linker and an anti-EFNA4 antibody of the present invention. See e.g., U.S. Pat. No. 5,773,001. The AcBut linker produces conjugates that are substantially stable in circulation, releasing an estimated 2% of the calicheamicin per day when assayed at 37° C. in human plasma in vitro. The conjugates release the calicheamicin in the acidic lysosomes.

In some aspects of the invention, the AcBut-CM moiety can be generated using methods and processes described in the art, such as PCT International Publication No. WO 08/147,765 and in U.S. Pat. No. 8,273,862, which are incorporated herein by reference in their entirety.

In some aspects of the invention, the AcBut-CM moiety can be generated using an improved synthesis process, as described in U.S. Provisional Application No. 61/899,682, which is incorporated herein by reference in its entirety. The method for synthesizing a linker intermediate (compound 10) is described as follows:

Scheme 1

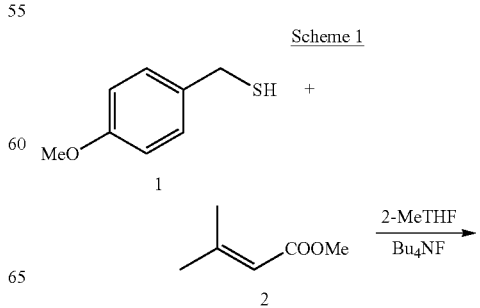

-continued

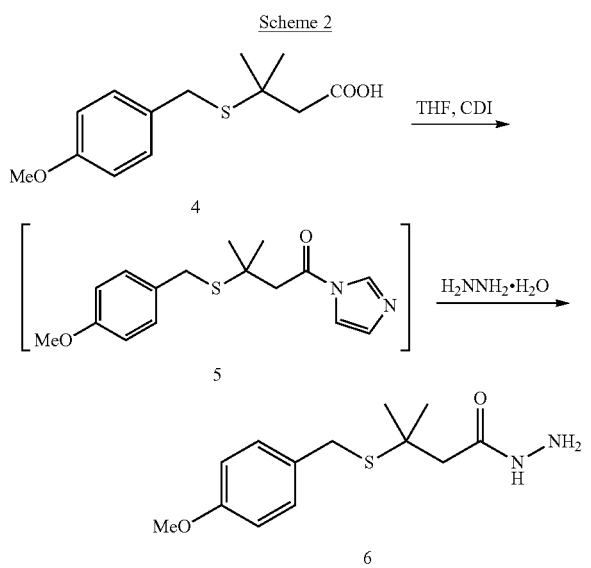

In Scheme 1, compound 1 and compound 2 are reacted in 2-methyltetrahydrofuran (2-MeTHF) and tetrabutylammonium fluoride (Bu₄NF). A solution of calcium chloride dihydrate in water is added, and the lower aqueous phase removed after stirring. To the upper organic phase is added methanol and 3 equiv. of NaOH in water. The reaction mixture is stirred until complete consumption of the intermediate ester 3 is observed. The reaction is cooled to 15° C. and 2-methyltetrahydrofuran is added followed by water. Concentrated HCl is added slowly, maintaining the reaction in the range 15-30° C. Acid 4 is yielded from the organic layer.

Scheme 2

In Scheme 2, compound 4 is charged with a suitable organic solvent such as tetrahydrofuran (THF) and an azole activating agent, such as carbonyl diimidazole (CDI), forming intermediate 5. Other azole activating agents may be used, for example thiocarbonyl diimidazole; carbonyl bis-pyrazole wherein each pyrazole optionally substituted with from one to three (C₁-C₆) alkyl groups; carbonyl bis-1,2,3-triazole; carbonyl bis-benzotriazole, and carbonyl bis-1,2,4-triazole, which would thereby form intermediate compounds analogous to compound 5 but comprising a different azole moiety other than imidazolyl. Intermediate 5 is reacted with hydrazine, preferably an aqueous source of hydrazine such as hydrazine monohydrate, yielding intermediate 6. Intermediate 6 is described in PCT International Publication No. WO 08/147,765, which is incorporated herein by reference in its entirety.

Scheme 3

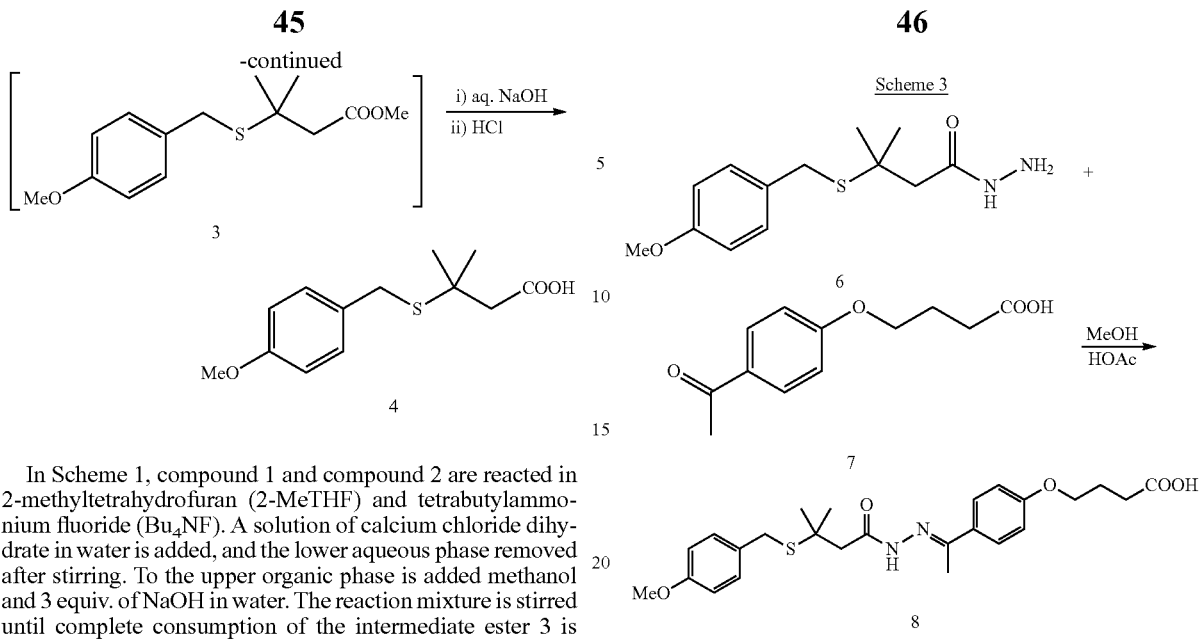

In Scheme 3, intermediate 6 is reacted with intermediate 7 in an inert (non-reactive) solvent (such as methanol (MeOH)), optionally with an acidic catalyst (such as acetic acid (HOAc)) to yield intermediate 8.

Scheme 4

In Scheme 4, intermediate 8 is deprotected by using a strong acid optionally under heat, such as trifluoroacetic acid (TFA) under heat, to form intermediate 9. Other strong acids may be used instead of trifluoroacetic acid, for example sulfuric acid.

Scheme 5

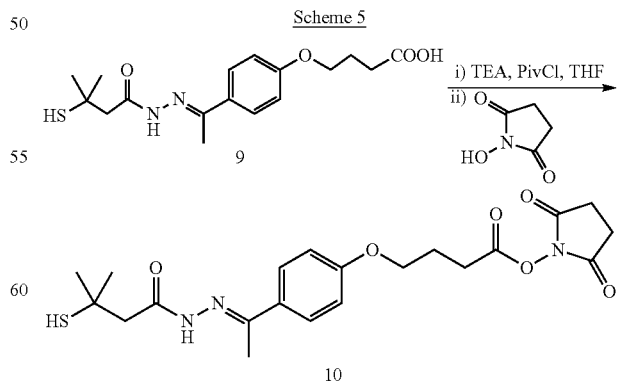

In Scheme 5, intermediate 9 is converted to linker intermediate 10. Intermediate 9 can be converted to a linker intermediate 10 as is described in the art, such as in U.S. Pat. No.

8,273,862, which is incorporated herein by reference in its entirety. Preferably, however, as depicted in Scheme 5, intermediate 9 is reacted with a tertiary amine base such as triethylamine (TEA) and with trimethylacetyl chloride (PivCl) in the presence of an inert solvent such as tetrahydrofuran. Subsequently, N-hydroxysuccinimide (OSu) is introduced to provide the linker intermediate 10.

The process for synthesizing linker intermediate 10 described herein above provides improvements over those processes described in PCT International Publication No. WO 08/147,765 and in U.S. Pat. No. 8,273,862, because the process described herein above avoids using methylene chloride and the safety measures taken therewith, and offers better yields of linker intermediate 10.

Subsequent to synthesis of linker intermediate 10, linker intermediate 10 may be conjugated to a calicheamicin molecule as is described in the prior art, for example in U.S. Pat. No. 8,273,862. Preferably, however the linker intermediate 10 is combined with a calicheamicin in the presence of a carbodiimide, which improves the yield of the resulting calicheamicin derivative. Examples of carbodiimides that can be used include, but are not limited to, 1-ethyl-3-(3-dimethylaminopropyl)carbodiimide (EDC); N,N'-dicyclohexyl carbodiimide (DCC); N,N'-diisopropyl carbodiimide (DIC); N-cylcohexyl-N'-(2-morpholinoethyl)carbodiimide; N-cylcohexyl-N'-[2-(4-methylmorpholin-4-ium-4-yl)ethyl]carbodiimide tosylate; N-cylcohexyl-N'-[4-(diethylmethylammonio)cyclohexyl]carbodiimide tosylate; N,N'-bis(2,2-dimethyl-1,3-dioxolan-4-yl)methyl]carbodiimide; and N-benzyl-N'-isopropylcarbodiimide.

The calicheamicin derivative resulting from the conjugation of linker intermediate 10 to calicheamicin can be purified and isolated prior to reaction with a monoclonal antibody (e.g. anti-EFNA4 antibody). The purification and isolation may take place as is described previously in U.S. Pat. No. 8,273,862. Or the purification may take place by using a reversed phase high performance liquid chromatography purification protocol. The reversed phase high performance liquid chromatography purification protocol for purification of 10 may comprise elution with phases comprising aqueous and organic mixtures, which phases range in pH from about 4 to about 6. For example, a mobile phase consisting of 55% 20 mM sodium acetate, pH 5 and 45% acetonitrile is an aqueous/organic mobile phase that can be used for the reversed phase high performance liquid chromatography purification. The purification with reversed phase high performance liquid chromatography purification protocol may be followed by a solid phase extraction protocol.

In other aspects of the invention, the linker can be a dipeptide linker, such as a valine-citrulline (val-cit), a phenylalanine-lysine (phe-lys) linker, or maleimidocapronic-valine-citruline-p-aminobenzyloxycarbonyl (vc) linker. In another aspect, the linker is Sulfosuccinimidyl-4-[N-maleimidomethyl]cyclohexane-1-carboxylate (smcc). Sulfo-smcc conjugation occurs via a maleimide group which reacts with sulfhydryls (thiols, —SH), while its Sulfo-NHS ester is reactive toward primary amines (as found in Lysine and the protein or peptide N-terminus). Further, the linker may be maleimidocaproyl (mc).

Representative linkers useful for conjugation of radioisotopes include diethylenetriamine pentaacetate (DTPA)-isothiocyanate, succinimidyl 6-hydrazinium nicotinate hydrochloride (SHNH), and hexamethylpropylene amine oxime (HMPAO) (Bakker et al. (1990) *J. Nucl. Med.* 31: 1501-1509, Chattopadhyay et al. (2001) *Nucl. Med. Biol.* 28: 741-744, Dewanjee et al. (1994) *J. Nucl. Med.* 35: 1054-63, Krenning et al. (1989) Lancet 1: 242-244, Sagiuchi et al. (2001) *Ann. Nucl. Med.* 15: 267-270); U.S. Pat. No. 6,024, 938). Alternatively, a targeting molecule may be derivatized so that a radioisotope may be bound directly to it (Yoo et al. (1997) *J. Nucl. Med.* 38: 294-300). Iodination methods are also known in the art, and representative protocols may be found, for example, in Krenning et al. (1989) *Lancet* 1:242-244 and in Bakker et al. (1990) *J. Nucl. Med.* 31:1501-1509.

II.C. Drugs

Drugs useful in preparation of the disclosed EFNA4 antibody-drug conjugates include any substance having biological or detectable activity, for example, therapeutic agents, detectable labels, binding agents, etc., and prodrugs, which are metabolized to an active agent in vivo. A drug may also be a drug derivative, wherein a drug has been functionalized to enable conjugation with an antibody of the invention. In accordance with the disclosed methods, the drugs are used to prepare an antibody-drug conjugates of the formula Ab-(L-D), wherein (a) Ab is an antibody, or antigen-binding fragment thereof, that binds to EFNA4, and (b) L-D is a linker-drug moiety, wherein L is a linker, and D is a drug. The drug-to-antibody ratio (DAR) or drug loading, indicating the number of drug (D) molecules conjugated per antibody, may be from DAR 1 to 12. Thus, in aspects of the invention, an EFNA4 antibody-drug conjugate may have a DAR of 1, a DAR of 2, a DAR of 3, a DAR of 4, a DAR of 5, a DAR of 6, a DAR of 7, a DAR of 8, a DAR of 9, a DAR of 10, a DAR of 11 or a DAR of 12. Thus, in aspects of the invention, an EFNA4 antibody-drug conjugate may include one drug molecule, or 2 drug molecules, or 3 drug molecules, or 4 drug molecules, or 5 drug molecules, or 6 drug molecules, or 7 drug molecules, or 8 drug molecules, or 9 drug molecules, or 10 drug molecules, or 11 drug molecules, or 12 drug molecules. DAR can be determined by various conventional means such as UV spectroscopy, mass spectroscopy, ELISA assay, radiometric methods, hydrophobic interaction chromatography (HIC), electrophoresis and HPLC.

Compositions, batches and/or formulations of antibody-drug conjugate (ADC), of the formula Ab-(L-D), may include a plurality of antibodies conjugated with a varying number of drug molecules, from DAR 1 to 12.

In particular aspects of the invention, a composition, batch, and/or formulation of antibody-drug conjugates may be characterized by an average DAR in the range of about 1 to about 12, for example, an average DAR in the range of about 2 to about 4, or an average DAR in the range of about 3 to about 5, or an average DAR in the range of about 4 to about 6, or an average DAR in the range of about 5 to about 7, or an average DAR in the range of about 6 to about 8, or an average DAR in the range of about 7 to about 9, or an average DAR in the range of about 8 to about 10, or an average DAR in the range of about 9 to about 11. In some aspects the compositions, batches and/or formulations of antibody-drug conjugate may have an average DAR of about 1, or an average DAR of about 2, an average DAR of about 3, or an average DAR of about 4, or an average DAR of about 5, or an average DAR of about 6, or an average DAR of about 7, or an average DAR of about 8, or an average DAR of about 9, or an average DAR of about 10, or an average DAR of about 11. As used in the foregoing ranges of average DAR, the term "about" means+/−0.5%.

Moreover, a composition, batch, and/or formulation of antibody-drug conjugates may be characterized by a preferred range of average DAR, e.g., an average DAR in the range of about 3 to about 5, an average DAR in the range of about 3 to about 4, or an average DAR in the range of about 4 to about 5. Further, a composition, batch, and/or formulation of antibody-drug conjugates may be characterized by a preferred range of average DAR, e.g., an average DAR in the range of 3 to 5, an average DAR in the range of 3 to 4, or an average DAR in the range of 4 to 5.

In some aspects of the invention, a composition, batch, and/or formulation of antibody-drug conjugates may be characterized by an average DAR of about 3.0, or an average DAR of 3.0, or an average DAR of 3.1, or an average DAR of 3.2, or an average DAR of 3.3, or an average DAR of 3.4, or an average DAR of 3.5, or an average DAR of 3.6, or an average DAR of 3.7, or an average DAR of 3.8, or an average DAR of 3.9. In another aspect of the invention, a composition, batch, and/or formulation of antibody-drug conjugates may be characterized by an average DAR of about 4.0, or an average DAR of 4.0, or an average DAR of 4.1, or an average DAR of 4.2, or an average DAR of 4.3, or an average DAR of 4.4, or an average DAR of 4.5, or an average DAR of 4.6, or an average DAR of 4.7, or an average DAR of 4.8, or an average DAR of 4.9, or an average DAR of 5.0.

In another aspect of the invention, a composition, batch, and/or formulation of antibody-drug conjugates may be characterized by an average DAR of 12 or less, an average DAR of 11 or less, an average DAR of 10 or less, an average DAR of 9 or less, an average DAR of 8 or less, an average DAR of 7 or less, an average DAR of 6 or less, an average DAR of 5 or less, an average DAR of 4 or less, an average DAR of 3 or less, an average DAR of 2 or less or an average DAR of 1 or less.

In other aspects of the invention, a composition, batch, and/or formulation of antibody-drug conjugates may be characterized by an average DAR of 11.5 or less, an average DAR of 10.5 or less, an average DAR of 9.5 or less, an average DAR of 8.5 or less, an average DAR of 7.5 or less, an average DAR of 6.5 or less, an average DAR of 5.5 or less, an average DAR of 4.5 or less, an average DAR of 3.5 or less, an average DAR of 2.5 or less, an average DAR of 1.5 or less.

Compositions, batches and/or formulations of ADCs of the formula Ab-(L-D), may be characterized by a DAR distribution. The DAR distribution provides the percent or fraction of various ADC species, e.g. DAR 1 to 12, that may be present in a composition, batch, and/or formulation of ADCs. The DAR distribution of a composition, batch, and/or formulation of ADCs may be determined by methods known in the art, such as capillary iso-electric focusing (cIEF).

In one aspect of the invention, the DAR distribution of a composition, batch, and/or formulation of ADCs, of the formula Ab-(L-D), may be characterized as a highly heterogeneous mixture of ADCs with a broad DAR distribution, generally containing a broad range of ADC species with DAR 1 to 12.

In another aspect of the invention, the DAR distribution of a composition, batch, and/or formulation of ADCs may be characterized as a highly homogeneous mixture with a narrow DAR distribution, generally containing a narrow range of ADC species having a particular DAR, such as DAR 3 to 5.

In particular aspects of the invention, a composition, batch, and/or formulation of antibody-drug conjugates may be characterized by having at least 50% antibody-drug conjugates having a DAR from 3 to 5, or at least 55% antibody-drug conjugates having a DAR from 3 to 5, or at least 60% antibody-drug conjugates having a DAR from 3 to 5, or at least 65% antibody-drug conjugates having a DAR from 3 to 5, or at least 70% antibody-drug conjugates having a DAR from 3 to 5, or at least 75% antibody-drug conjugates having a DAR from 3 to 5, or at least 80% antibody-drug conjugates having a DAR from 3 to 5, or at least 85% antibody-drug conjugates having a DAR from 3 to 5, or at least 90% antibody-drug conjugates having a DAR from 3 to 5, or at least 95% antibody-drug conjugates having a DAR from 3 to 5.

In another aspects of the invention, a composition, batch, and/or formulation of antibody-drug conjugates may be characterized by having 50% to 60% antibody-drug conjugates having a DAR from 3 to 5, or 60% to 70% antibody-drug conjugates having a DAR from 3 to 5, or 70% to 80% antibody-drug conjugates having a DAR from 3 to 5, or 80% to 90% antibody-drug conjugates having a DAR from 3 to 5, or 90% to 100% antibody-drug conjugates having a DAR from 3 to 5. In another aspects of the invention, a composition, batch, and/or formulation of antibody-drug conjugates may be characterized by having about 50%, or about 55%, or about 60%, or about 65%, or about 70%, or about 75%, or about 80%, or about 85%, or about 90%, or about 95%, or about 100% antibody-drug conjugates having a DAR from 3 to 5.

For example, a therapeutic agent is an agent that exerts a cytotoxic, cytostatic, and/or immunomodulatory effect on cancer cells or activated immune cells. Examples of therapeutic agents include cytotoxic agents, chemotherapeutic agents, cytostatic agents, and immunomodulatory agents. Chemotherapeutic agents are chemical compounds useful in the treatment of cancer.

Therapeutic agents are compositions that may be used to treat or prevent a disorder in a subject in need thereof. Therapeutic agents useful in the invention include anti-cancer agents, i.e., agents having anti-cancer activity in EFNA4-expressing cells such as cancer cells from breast cancer, such as triple-negative breast cancer (TNBC); ovarian cancer; colorectal cancer; leukemias, such as chronic lymphocytic leukemia (CLL); liver cancer, such as hepatocellular carcinoma (HCC); and lung cancer, such as non-small cell lung cancer (NSCLC) and small cell lung cancer (SCLC).

Representative therapeutic agents include cytotoxins, cytotoxic agents, and cytostatic agents. A cytotoxic effect refers to the depletion, elimination and/or the killing of a target cell(s). A cytotoxic agent refers to an agent that has a cytotoxic and/or cytostatic effect on a cell. A cytostatic effect refers to the inhibition of cell proliferation. A cytostatic agent refers to an agent that has a cytostatic effect on a cell, thereby inhibiting the growth and/or expansion of a specific subset of cells.

Additional representative therapeutic agents include radioisotopes, chemotherapeutic agents, immunomodulatory agents, anti-angiogenic agents, anti-proliferative agents, pro-apoptotic agents, and cytolytic enzymes (e.g., RNAses). An agent may also include a therapeutic nucleic acid, such as a gene encoding an immunomodulatory agent, an anti-angiogenic agent, an anti-proliferative agent, or a pro-apoptotic agent. These drug descriptors are not mutually exclusive, and thus a therapeutic agent may be described using one or more of the above-noted terms. For example, selected radioisotopes are also cytotoxins. Therapeutic agents may be prepared as pharmaceutically acceptable salts, acids or derivatives of any of the above. Generally, conjugates having a radioisotope as the drug are referred to as radioimmunoconjugates and those having a chemotherapeutic agent as the drug are referred to as chemoimmunoconjugates.

Examples of a cytotoxic agents include, but are not limited to an anthracycline, an auristatin, CC-1065, a dolastatin, a duocarmycin, an enediyne, a geldanamycin, a maytansine, a puromycin, a taxane, a vinca alkaloid, SN-38, tubulysin, hemiasterlin, and stereoisomers, isosteres, analogs or derivatives thereof. Plant toxins, other bioactive proteins, enzymes (i.e., ADEPT), radioisotopes, photosensitizers (i.e., for photodynamic therapy) can also be used.

The anthracyclines are derived from bacteria *Strepomyces* and have been used to treat a wide range of cancers, such as leukemias, lymphomas, breast, uterine, ovarian, and lung cancers. Exemplary anthracyclines include, but are not limited to, daunorubicin, doxorubicin (i.e., adriamycin), epirubicin, idarubicin, valrubicin, and mitoxantrone.

Dolastatins and their peptidic analogs and derivatives, auristatins, are highly potent antimitotic agents that have been shown to have anticancer and antifungal activity. See, e.g., U.S. Pat. No. 5,663,149 and Pettit et al., *Antimicrob. Agents Chemother.* 42:2961-2965, (1998). Exemplary dolastatins and auristatins include, but are not limited to, dolastatin 10, auristatin E, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB). and other novel In some aspects of the invention, auristatins described in PCT International Publication No. WO 2013/072813, which is incorporated herein by reference in its entirety, and methods of producing those auristatins are used herein.

For example, the auristatin 0101, (2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide), having the following structure:

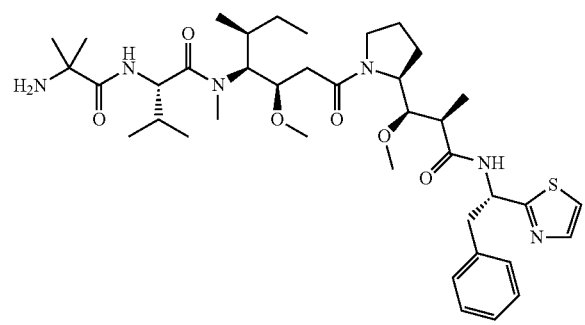 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)C(C)(C)N)C(C)C]

Additionally, the auristatin 8261, 2-Methylalanyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide, having the following structure:

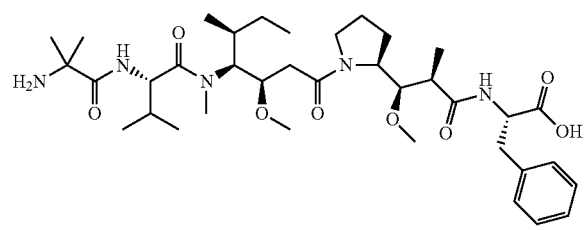 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)C(C)(C)N)C(C)C]

Duocarmycin and CC-1065 are DNA alkylating agents with cytotoxic potency. See Boger and Johnson, *PNAS* 92:3642-3649, 1995. Exemplary dolastatins and auristatins include, but are not limited to, (+)-docarmycin A and (+)-duocarmycin SA, and (+)-CC-1065.

Enediynes are a class of anti-tumor bacterial products characterized by either nine- and ten-membered rings or the presence of a cyclic system of conjugated triple-double-triple bonds. Exemplary enediynes include, but are not limited to, calicheamicin, esperamicin, and dynemicin. Calicheamicin is an enediyne antibiotic that was originally isolated as a natural product from the soil organism *Micromonospora echinospora* ssp. calichensis (Zein et al. Science 27; 240(4856): 1198-1201, 1988); it generates double-strand DNA breaks and subsequently induces apoptosis in target cells (Zein et al. Science 27; 240(4856):1198-1201, 1988; Nicolaou et al. Chem. Biol. September; 1(1):57-66, 1994; Prokop et al. Oncogene 22:9107-9120, 2003).

In some aspects of the invention, the cytotoxic agent is an antibiotic, such as calicheamicin, also called the LL-E33288 complex, for example, β-calicheamicin, γ-calicheamicin or N-acetyl-γ-calicheamicin (gamma-calicheamicin ($\gamma_1$)). Examples of calicheamicins suitable for use in the present invention are disclosed, for example, in U.S. Pat. Nos. 4,671,958 4,970,198, 5,053,394, 5,037,651, 5,079,233 and 5,108,912, which are incorporated herein by reference in its entirety. These compounds contain a methyltrisulfide that may be reacted with appropriate thiols to form disulfides, at the same time introducing a functional group such as a hydrazide or other functional group that is useful for conjugating calicheamicin to an anti-EFNA4 antibody. Disulfide analogs of calicheamicin can also be used, for example, analogs described in U.S. Pat. Nos. 5,606,040 and 5,770,710, which are incorporated herein by reference in its entirety. In some aspects of the invention, the disulfide analog is N-acetyl-γ-calicheamicin dimethyl hydrazide (hereinafter "CM").

Geldanamycins are benzoquinone ansamycin antibiotic that bind to Hsp90 (Heat Shock Protein 90) and have been used antitumor drugs. Exemplary geldanamycins include, but are not limited to, 17-AAG (17-N-Allylamino-17-Demethoxygeldanamycin) and 17-DMAG (17-Dimethylaminoethylamino-17-demethoxygeldanamycin).

Maytansines or their derivatives maytansinoids inhibit cell proliferation by inhibiting the microtubules formation during mitosis through inhibition of polymerization of tubulin. See Remillard et al., Science 189:1002-1005, 1975. Exemplary maytansines and maytansinoids include, but are not limited to, mertansine (DM1) and its derivatives as well as ansamitocin.

Taxanes are diterpenes that act as anti-tubulin agents or mitotic inhibitors. Exemplary taxanes include, but are not limited to, paclitaxel (e.g., TAXOL®) and docetaxel (TAXOTERE®).

Vinca alkyloids are also anti-tubulin agents. Exemplary vinca alkyloids include, but are not limited to, vincristine, vinblastine, vindesine, and vinorelbine.

In some aspects of the invention, the agent is an immunomodulating agent. Examples of an immunomodulating agent include, but are not limited to, gancyclovier, etanercept, tacrolimus, sirolimus, voclosporin, cyclosporine, rapamycin, cyclophosphamide, azathioprine, mycophenolgate mofetil, methotrextrate, glucocorticoid and its analogs, cytokines, xanthines, stem cell growth factors, lymphotoxins, tumor necrosis factor (TNF), hematopoietic factors, interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S 1 factor," erythropoietin and thrombopoietin, or a combination thereof.

Immunomodulatory agents useful in the invention also include anti-hormones that block hormone action on tumors and immunosuppressive agents that suppress cytokine production, down-regulate self-antigen expression, or mask MHC antigens. Representative anti-hormones include anti-estrogens including, for example, tamoxifen, raloxifene, aromatase inhibiting 4(5)-imidazoles, 4-hydroxytamoxifen, trioxifene, keoxifene, LY 117018, onapnstone, and toremifene; and anti-androgens such as flutamide, nilutamide, bicalutamide, leuprolide, and goserelin; and anti-adrenal agents. Representative immunosuppressive agents include 2-amino-6-aryl-5-substituted pyrimidines, azathioprine, cyclophosphamide, bromocryptine, danazol, dapsone, glutaraldehyde, anti-idiotypic antibodies for MHC antigens and MHC fragments, cyclosporin A, steroids such as glucocorticosteroids, cytokine or cytokine receptor antagonists (e.g., anti-interferon antibodies, anti-IL10 antibodies, anti-TNFα antibodies, anti-IL2 antibodies), streptokinase, TGFβ, rapamycin, T-cell receptor, T-cell receptor fragments, and T cell receptor antibodies.

In some aspects of the invention, the drug is a therapeutic protein including, but is not limited to, a toxin, a hormone, an enzyme, and a growth factor.

Examples of a toxin protein (or polypeptide) include, but are not limited to, dipththeria (e.g., diphtheria A chain), Pseudomonas exotoxin and endotoxin, ricin (e.g., ricin A chain), abrin (e.g., abrin A chain), modeccin (e.g., modeccin A chain), alpha-sarcin, *Aleurites fordii* proteins, dianthin proteins, ribonuclease (RNase), DNase I, Staphylococcal enterotoxin-A, pokeweed antiviral protein, gelonin, diphtherin toxin, *Phytolaca americana* proteins (PAPI, PAPII, and PAP-S), *momordica charantia* inhibitor, curcin, crotin, sapaonaria officinalis inhibitor, mitogellin, restrictocin, phenomycin, enomycin, tricothecenes, inhibitor cystine knot (ICK) peptides (e.g., ceratotoxins), and conotoxin (e.g., KIIIA or SmIIIa).

Examples of hormones include, but are not limited to, estrogens, androgens, progestins and corticosteroids.

In some aspects of the invention, the cytotoxic agent can be made using a liposome or biocompatible polymer. The anti-EFNA4 antibodies as described herein can be conjugated to the biocompatible polymer to increase serum half-life and bioactivity, and/or to extend in vivo half-lives. Examples of biocompatible polymers include water-soluble polymer, such as polyethylene glycol (PEG) or its derivatives thereof and zwitterion-containing biocompatible polymers (e.g., a phosphorylcholine containing polymer).

In some aspects of the invention, the drug is an oligonucleotide, such as anti-sense oligonucleotides.

Additional drugs useful in the invention include anti-angiogenic agents that inhibit blood vessel formation, for example, farnesyltransferase inhibitors, COX-2 inhibitors, VEGF inhibitors, bFGF inhibitors, steroid sulphatase inhibitors (e.g., 2-methoxyoestradiol bis-sulphamate (2-MeOE2bisMATE)), interleukin-24, thrombospondin, metallospondin proteins, class I interferons, interleukin 12, protamine, angiostatin, laminin, endostatin, and prolactin fragments.

Anti-proliferative agents and pro-apoptotic agents include activators of PPAR-gamma (e.g., cyclopentenone prostaglandins (cyPGs)), retinoids, triterpinoids (e.g., cycloartane, lupane, ursane, oleanane, friedelane, dammarane, cucurbitacin, and limonoid triterpenoids), inhibitors of EGF receptor (e.g., HER4), rampamycin, CALCITRIOL® (1,25-dihydroxycholecalciferol (vitamin D)), aromatase inhibitors (FEMARA® (letrozone)), telomerase inhibitors, iron chelators (e.g., 3-aminopyridine-2-carboxaldehyde thiosemicarbazone (Triapine)), apoptin (viral protein 3-VP3 from chicken aneamia virus), inhibitors of Bcl-2 and Bcl-X(L), TNF-alpha, FAS ligand, TNF-related apoptosis-inducing ligand (TRAIL/Apo2L), activators of TNF-alpha/FAS ligand/TNF-related apoptosis-inducing ligand (TRAIL/Apo2L) signaling, and inhibitors of PI3K-Akt survival pathway signaling (e.g., UCN-01 and geldanamycin).

Representative chemotherapeutic agents include alkylating agents such as thiotepa and cyclosphosphamide; alkyl sulfonates such as busulfan, improsulfan and piposulfan; aziidines such as benzodopa, carboquone, meturedopa, and uredopa; ethylenimines and methylamelamines including altretamine, triethylenemelamine, triethylenephosphoramide, triethylenethiophosphoramide and trimethylolomelamine; nitrogen mustards such as chlorambucil, chlornaphazine, cholophosphamide, estramustine, ifosfamide, mechiorethamine, mechiorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-EU; androgens such as calusterone, dromostanolone propionate, epitiostanol, mepitiostane, testolactone; anti-adrenal such as aminoglutethimide, mitotane, trilostane; folic acid replenisher such as frolinic acid; aceglatone; aldophosphamide glycoside; arninolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triazi quone; 2,2',2'-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g. paclitaxel (TAXOL®, Bristol-Myers Squibb Oncology of Princeton, N.J.) and doxetaxel (TAXOTERE®, Rhone-Poulenc Rorer of Antony, France); chiorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; and capecitabine.

Additional therapeutic agents that may be used in accordance with the present invention include photosensitizing agents, such as U.S. Publication No. 20020197262 and U.S. Pat. No. 5,952,329, which are incorporated herein by reference in its entirety, for photodynamic therapy; magnetic particles for thermotherapy, such as U.S. Publication No. 20030032995, which is incorporated herein by reference in its entirety; binding agents, such as peptides, ligands, cell adhesion ligands, etc., and prodrugs such as phosphate-containing prodrugs, thiophosphate-containing prodrugs, sulfate containing prodrugs, peptide containing prodrugs, β-lactamcontaining prodrugs, substituted phenoxyacetamide-containing prodrugs or substituted phenylacetamide-containing prodrugs, 5-fluorocytosine and other 5-fluorouridine prodrugs that may be converted to the more active cytotoxic free drug.

For diagnostic methods using anti-EFNA4 antibodies, a drug may include a detectable label used to detect the presence of EFNA4-expressing cells in vitro or in vivo. Radioisotopes that are detectable in vivo, such as those labels that are detectable using scintigraphy, magnetic resonance imaging, or ultrasound, may be used in clinical diagnostic applications. Useful scintigraphic labels include positron emitters and γ-emitters. Representative contrast agents for magnetic source imaging are paramagnetic or superparamagnetic ions (e.g., iron, copper, manganese, chromium, erbium, europium, dysprosium, holmium and gadolinium), iron oxide particles, and water soluble contrast agents. For ultrasonic detection, gases or liquids may be entrapped in porous inorganic particles that are released as microbubble contrast agents. For in vitro detection, useful detectable labels include fluorophores, detectable epitopes or binding agents, and radioactive labels.

Thus, in some aspects of the invention, the drug is an imaging agent (e.g., a fluorophore or a PET (Positron Emission Tomography) label, SPECT (Single-Photon Emission Computed Tomorgraphy) label), or MRI (Magnetic Resonance Imaging) label.

The term "label" when used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable. Radionuclides that can serve as detectable labels include, for example, I-131, I-123, I-125, Y-90, Re-188, Re-186, At-211, Cu-67, Bi-212, and Pd-109. The label might also be a non-detectable entity such as a toxin.

Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine (TAMRA) (e.g., 5,-TAMRA), tetramethylrhodamine (TMR), and sulforhodamine (SR) (e.g., SR101).

Therapeutic or diagnostic radioisotopes or other labels (e.g., PET or SPECT labels) can be incorporated in the agent for conjugation to the anti-EFNA4 antibodies as described herein. The isotope may be directly bound to the antibody, for example, at a cysteine residue present in the antibody, or a chelator may be used to mediate the binding of the antibody and the radioisotope. Radioisotopes suitable for radiotherapy include but are not limited to α-emitters, β-emitters, and auger electrons. For diagnostic applications, useful radioisotopes include positron emitters and γ-emitters. An anti-EFNA4 antibody of the invention may further be iodinated, for example, on a tyrosine residue of the antibody, to facilitate detection or therapeutic effect of the antibody.

Examples of a radioisotope or other labels include, but are not limited to, $^3H$, $^{11}C$, $^{13}N$, $^{14}C$, $^{15}N$, $^{15}O$, $^{35}S$, $^{18}F$, $^{32}P$, $^{33}P$, $^{47}Sc$, $^{51}Cr$, $^{57}Co$, $^{58}Co$, $^{59}Fe$, $^{62}Cu$, $^{64}Cu$, $^{67}Cu$, $^{67}Ga$, $^{68}Ga$, $^{75}Se$, $^{76}Br$, $^{77}Br$, $^{86}Y$, $^{89}Zr$, $^{90}Y$, $^{94}Tc$, $^{95}Ru$, $^{97}Ru$, $^{99}Tc$, $^{103}Ru$, $^{105}Rh$, $^{105}Ru$, $^{107}Hg$, $^{109}Pd$, $^{111}Ag$, $^{111}In$, $^{113}In$, $^{121}Te$, $^{122}Te$, $^{123}I$, $^{124}I$, $^{125}I$, $^{125}Te$, $^{126}I$, $^{131}I$, $^{131}In$, $^{133}I$, $^{142}Pr$, $^{143}Pr$, $^{153}Pb$, $^{153}Sm$, $^{161}Tb$, $^{165}Tm$, $^{166}Dy$, $^{166}H$, $^{167}Tm$, $^{168}Tm$, $^{169}Yb$, $^{177}Lu$, $^{186}Re$, $^{188}Re$, $^{189}Re$, $^{197}Pt$, $^{198}Au$, $^{199}Au$, $^{201}Tl$, $^{203}Hg$, $^{211}At$, $^{212}Bi$, $^{212}Pb$, $^{213}Bi$, $^{223}Ra$, $^{224}Ac$, and $^{225}Ac$.

II.D. Methods of Preparing EFNA4 Antibody-Drug Conjugates

Also provided are methods for preparing antibody-drug conjugates of the present invention. For example, a process for producing an EFNA4 antibody-drug conjugate as disclosed herein can include (a) linking the linker to the drug moiety; (b) conjugating the linker-drug moiety to the antibody; and (c) purifying the antibody-drug conjugate.

In one example, an antibody-drug conjugate of the formula Ab(L-D) may be prepared by (a) adding the linker-drug moiety (e.g. AcBut-CM) to the anti-EFNA4 antibody, or antigen-binding fragment thereof, wherein the concentration of antibody may range from 1 to 25 mg/ml and the linker-drug moiety is at a molar ratio ranging from about 1-15 to 1 of the anti-EFNA4 antibody; (b) incubating the linker-drug moiety and anti-EFNA4 antibody in a non-nucleophilic, protein-compatible, buffered solution having a pH in a range from about 7 to 9 to produce an monomeric antibody-drug conjugate, wherein the solution further compromises (i) a suitable organic cosolvent, and (ii) an additive having at least one $C_6$-$C_{18}$ carboxylic acid or its salt, and wherein the incubation is conducted at a temperature ranging from about 0° C. to about 45° C., for a period of time ranging from about 1 minute to about 24 hours; and (c) subjecting the conjugate produced in step (b) to a chromatographic separation process to separate antibody-drug conjugates with a DAR from 1 to 12; and provides low conjugated fraction (LCF) of below 10% from unconjugated anti-EFNA4 antibody, linker-drug moiety, and aggregated conjugates.

In some aspects of the invention, the linker-drug moiety is added to the anti-EFNA4 antibody wherein the antibody has a concentration of about 0.01 to about 1 mg/ml, or wherein the antibody has a concentration of about 1 to about 2 mg/ml, or wherein the antibody has a concentration of about 2 to about 3 mg/ml, or wherein the antibody has a concentration of about 3 to about 4 mg/ml, or wherein the antibody has a concentration of about 4 to about 5 mg/ml, or wherein the antibody has a concentration of about 5 to about 6 mg/, or wherein the antibody has a concentration of about 6 to about 7 mg/ml, or wherein the antibody has a concentration of about 7 to about 8 mg/ml, or wherein the antibody has a concentration of about 8 to about 9 mg/ml, or wherein the antibody has a concentration of about 9 to about 10 mg/ml, or wherein the antibody has a concentration of about 10 to about 11 mg/ml, or wherein the antibody has a concentration of about 11 to about 12 mg/ml, or wherein the antibody has a concentration of about 12 to about 13 mg/ml, or wherein the antibody has a concentration of about 13 to about 14 mg/ml, or wherein the antibody has a concentration of about 14 to about 15 mg/ml, or wherein the antibody has a concentration of about 15 to about 16 mg/ml, or wherein the antibody has a concentration of about 16 to about 17 mg/ml, or wherein the antibody has a concentration of about 17 to about 18 mg/ml, or wherein the antibody has a concentration of about 18 to about 19 mg/ml, or wherein the antibody has a concentration of about 19 to about 20 mg/ml, or wherein the antibody has a concentration of about 20 to about 21 mg/ml, or wherein the antibody has a concentration of about 21 to about 22 mg/ml, or wherein the antibody has a concentration of about 22 to about 23 mg/ml, or wherein the antibody has a concentration of about 23 to about 24 mg/ml, or wherein the antibody has a concentration of about 24 to about 25 mg/ml, or wherein the antibody has a concentration of about 10 mg/ml, or wherein the antibody has a concentration of less than 10 mg/ml, As used in the foregoing ranges of antibody, the term "about" means+/−0.5 mg/ml.

In some aspects of the invention, the linker-drug moiety is added to the anti-EFNA4 antibody wherein the linker-drug moiety to anti-EFNA4 antibody is a molar ratio of 2-3 to 1, or a molar ratio of 3-4 to 1, or a molar ratio of 4-5 to 1, or a molar ratio of 5-6 to 1, or a molar ratio of 6-7 to 1, or a molar ratio of 7-8 to 1, or a molar ratio of 8-9 to 1, or a molar ratio of 9-10 to 1, or a molar ratio of 10-11 to 1, or a molar ratio of 11-12 to 1, or a molar ratio of 12-13 to 1, or a molar ratio of 13-14 to 1, or a molar ratio of 14-15 to 1. In some aspects of the invention, the linker-drug moiety is added to the anti-EFNA4 antibody at a molar ratio of about 4-4.5 to 1 to thereby decrease undesirable higher DAR antibody-drug conjugates. For example, the linker-drug moiety is added to the anti-EFNA4 antibody at a molar ratio of 4-4.5 to 1. Other ranges of linker-drug moiety to antibody may also be used to reduce unconjugated antibody, low DAR and high DAR antibody-drug conjugates.

In some aspects of the invention, the linker-drug moiety is added to the anti-EFNA4 antibody wherein the drug is about 2% to about 3% by weight of the anti-EFNA4 antibody, or wherein the drug is about 3% to about 4% by weight of the anti-EFNA4 antibody, or wherein the drug is about 4% to about 5% by weight of the anti-EFNA4 antibody, or wherein the drug is about 5% to about 6% by weight of the anti-EFNA4 antibody, or wherein the drug is about 6% to about 7% by weight of the anti-EFNA4 antibody, or wherein the drug is about 7% to about 8% by weight of the anti-EFNA4 antibody, or wherein the drug is about 8% to about 9% by weight of the anti-EFNA4 antibody, or wherein the drug is about 9% to about 10% by weight of the anti-EFNA4 antibody, or wherein the drug is about 10% to about 11% by weight of the anti-EFNA4 antibody. As used in the foregoing ranges of linker-drug moiety to antibody (5 by weight), the term "about" means+/−0.5%.

In some aspects of the invention, the linker-drug moiety is added to the anti-EFNA4 antibody wherein the drug is 2% to 3% by weight of the anti-EFNA4 antibody, or wherein the drug is 3% to 4% by weight of the anti-EFNA4 antibody, or wherein the drug is 4% to 5% by weight of the anti-EFNA4 antibody, or wherein the drug is 5% to 6% by weight of the anti-EFNA4 antibody, or wherein the drug is 6% to 7% by weight of the anti-EFNA4 antibody, or wherein the drug is 7% to 8% by weight of the anti-EFNA4 antibody, or wherein the drug is 8% to 9% by weight of the anti-EFNA4 antibody, or wherein the drug is 9% to 10% by weight of the anti-EFNA4 antibody, or wherein the drug is 10% to 11% by weight of the anti-EFNA4 antibody.

In some aspects of the invention, the incubation described in step (b)(ii) above is conducted at a temperature ranging from about 0° C. to about 5° C., or at temperature ranging from about 0° C. to about 4° C., or at temperature ranging from about 5° C. to about 10° C., or at temperature ranging from about 10° C. to about 15° C., or at temperature ranging from about 15° C. to about 20° C., or at temperature ranging from about 20° C. to about 25° C., or at temperature ranging from about 25° C. to about 30° C., or at temperature ranging from about 30° C. to about 35° C., or at temperature ranging from about 35° C. to about 40° C., or at temperature ranging from about 40° C. to about 45° C. As used in the foregoing temperature ranges, the term "about" means+/−1° C.

In some aspects of the invention, the incubation described in step (b)(ii) above is allowed to proceed for a time sufficient for completion of at least about 50% of the conjugation reaction, for example, at least about 60% complete, at least about 70% complete, at least about 80% complete, at least about 90% complete, at least about 95% complete, or at least about 99% complete. Thus, the reaction may be allowed to proceed for at least about 1 minute to about 5 minutes. Longer times are also permissible so long as aggregation of the conjugate remains at an acceptable level. In some aspects of the invention, the reaction is mostly complete by about 1 minute, which short duration is an improvement over prior methods.

In some aspects of the invention, in step (c) above, the antibody-conjugate of step (b) above is subjected to a chromatographic separation process to select compositions, batches and/or formulations of antibody-drug conjugates with an average DAR in the range of about 1 to about 12, for example, an average DAR in the range of about 2 to about 4, or an average DAR in the range of about 3 to about 5, or an average DAR in the range of about 4 to about 6, or an average DAR in the range of about 5 to about 7, or an average DAR in the range of about 6 to about 8, or an average DAR in the range of about 7 to about 9, or an average DAR in the range of about 8 to about 10, or an average DAR in the range of about 9 to about 11. In some aspects the compositions, batches and/or formulations of antibody-drug conjugate may have an average DAR of about 1, or an average DAR of about 2, an average DAR of about 3, or an average DAR of about 4, or an average DAR of about 5, or an average DAR of about 6, or an average DAR of about 7, or an average DAR of about 8, or an average DAR of about 9, or an average DAR of about 10, or an average DAR of about 11. As used in the foregoing ranges of average DAR, the term "about" means+/−0.5%.

In some aspects the compositions, batches, and/or formulations of antibody-drug conjugates may have an average DAR in the range of about 3 to about 5, an average DAR in the range of about 3 to about 4, or an average DAR in the range of about 4 to about 5.

In some aspects the compositions, batches and/or formulations of antibody-drug conjugate may have an average DAR in the range of 3 to 5, or an average DAR in the range of 3 to 4, or an average DAR in the range of 4 to 5.

In some aspects, the antibody-drug conjugate has an average DAR of about 3.0, or an average DAR of 3.0, or an average DAR of 3.1, or an average DAR of 3.2, or an average DAR of 3.3, or an average DAR of 3.4, or an average DAR of 3.5, or an average DAR of 3.6, or an average DAR of 3.7, or an average DAR of 3.8, or an average DAR of 3.9. In another aspect of the invention, a composition, batch, and/or formulation of antibody-drug conjugates may be characterized by an average DAR of about 4.0, or an average DAR of 4.0, or an average DAR of 4, or an average DAR of 4.1, or an average DAR of 4.2, or an average DAR of 4.3, or an average DAR of 4.4, or an average DAR of 4.5, or an average DAR of 4.6, or an average DAR of 4.7, or an average DAR of 4.8, or an average DAR of 4.9, or an average DAR of 5.0.

In another aspect of the invention, a composition, batch, and/or formulation of antibody-drug conjugates may be characterized by an average DAR of 12 or less, an average DAR of 11 or less, an average DAR of 10 or less, an average DAR of 9 or less, an average DAR of 8 or less, an average DAR of 7 or less, an average DAR of 6 or less, an average DAR of 5 or less, an average DAR of 4 or less, an average DAR of 3 or less, an average DAR of 2 or less or an average DAR of 1 or less.

In other aspects of the invention, a composition, batch, and/or formulation of antibody-drug conjugates may be characterized by an average DAR of 11.5 or less, an average DAR of 10.5 or less, an average DAR of 9.5 or less, an average DAR of 8.5 or less, an average DAR of 7.5 or less, an average DAR of 6.5 or less, an average DAR of 5.5 or less, an average DAR of 4.5 or less, an average DAR of 3.5 or less, an average DAR of 2.5 or less, an average DAR of 1.5 or less.

In some aspects of the invention, in step (c) above, the antibody-conjugate of step (b) above is subjected to a chromatographic separation process to select antibody-drug conjugates with a loading in the range of about 2% to about 10% by weight drug, for example, loading in the range of about 2% to about 4% by weight drug, or loading in the range of about 3% to about 5% by weight drug, or loading in the range of about 4% to about 6% by weight drug, or loading in the range of about 5% to about 7% by weight drug, or loading in the range of about 6% to about 8% by weight drug, or loading in the range of about 7% to about 9% by weight drug, or loading in the range of about 8% to about 10% by weight drug. As used in the foregoing ranges of drug loading, the term "about" means+/−0.5%.

In some aspects of the invention, in step (c) above, the antibody-drug conjugate of step (b) above is subjected to a chromatographic separation to select antibody-drug conjugates with low conjugated fraction (LCF) of below about 10%, for example, less than 10%, or less than about 9%, or less than 9%, or less than about 8%, or less than 8%, or less than about 7%, or less than 7%, or less than about 6%, or less than 6%, or less than about 5%, or less than 5%, or less than about 4%, or less than 4%, or less than about 3%, or less than 3%, or less than about 2%, or less than 2%, or less than about 1%, or less than 1%, or 0%. In some aspects of the invention, it is contemplated that an LCF above 0%, but below 10% is desirable. In the foregoing description of LCF, the term "about" means+/−0.5% of the indicated percentages. In some aspects of the invention, high agitation and vigorous mixing is conducted during the addition of the linker-drug moiety, for example, as achieved in part by addition of the linker-drug moiety into the middle portion of the mixing vortex, which is helpful in achieving low unconjugated fraction, which is an improvement over prior methods.

In the context of the present invention, a monomeric antibody-drug conjugate refers to a single antibody linked or conjugated to any number of drug molecules without significant aggregation of the antibodies. The percentage of antibody in a given population having unconjugated or significantly under-conjugated antibody is referred to as the low conjugate fraction (LCF). The monomeric form of the conjugates as opposed to the aggregated form has significant therapeutic value, and minimizing the LCF and substantially reducing aggregation results in the utilization of the antibody starting material in a therapeutically meaningful manner by preventing the LCF from competing with the more highly conjugated fraction (HCF).

The hydrophobic nature of many drugs, including calicheamicins, may result in aggregation of antibody-drug conjugates. To produce monomeric antibody-drug conjugates with higher drug conjugates (reduced LCF) and decreased aggregation, the conjugation reaction may be performed in a non-nucleophilic, protein-compatible, buffered solution containing (i) ethanol as a cosolvent and (ii) an additive having at least one $C_6$-$C_{18}$ carboxylic acid or its salt. Other protein-compatible organic cosolvents such as ethylene glycol, propylene glycol, DMF and DMSO may also be used. Some or all of the organic cosolvent is used to transfer the drug into the conjugation mixture. Useful $C_6$-$C_{18}$ carboxylic acids include decanoic acid, octanoic acid or caprylic acid, or its salts. In one aspects of the invention of the invention, the carboxylic acid is decanoic acid, or the corresponding salts, such as sodium decanoate. Representative amounts of an additive having at least one $C_6$-$C_{18}$ carboxylic acid or its salt range from 20 mM to 100 mM, such as from 30 mM to 90 mM, or about 40 mM to 80 mM, or about 40 mM to 50 mM. The concentration of the $C_6$-$C_{18}$ carboxylic acid or its salt may be increased to 150-300 mM and the cosolvent dropped to 1% to 10%. Useful buffers for the preparation of antibody-drug conjugates using N-hydroxysuccinimide (OSu) esters or other comparably activated esters include phosphate-buffered saline (PBS) and N-2-hydroxyethyl piperazine-N'-2-ethanesulfonic acid (HEPES buffer). The buffered solution used in conjugation reactions should substantially lack free amines and nucleophiles. As another approach, the conjugation reactions may be performed in a non-nucleophilic, protein-compatible, buffered solution containing t-butanol without the additional additives. See e.g., U.S. Pat. Nos. 5,712,374 and 5,714,586, which are incorporated herein by reference in its entirety. Additional methods for conjugation and calicheamicin-containing conjugates are described in U.S. Pat. Nos. 5,739,116 and 5,877,296, which are incorporated herein by reference in its entirety.

Optimal reaction conditions for formation of a conjugate may be empirically determined by variation of reaction variables such as temperature, pH, linker-calicheamicin moiety input, and additive concentration. Conditions suitable for conjugation of other drugs may be determined by those skilled in the art without undue experimentation.

Other methods for preparing antibody-drug conjugates have been described in various publications. For example, chemical modification can be made in the antibodies either through lysine side chain amines or through cysteine sulfhydryl groups activated by reducing interchain disulfide bonds for the conjugation reaction to occur. See, e.g., Tanaka et al., FEBS Letters 579:2092-2096, 2005, and Gentle et al., Bioconjugate Chem. 15:658-663, 2004. Reactive cysteine residues engineered at specific sites of antibodies for specific drug conjugation with defined stoichiometry have also been described. See, e.g., Junutula et al., Nature Biotechnology, 26:925-932, 2008. Conjugation using an acyl donor glutamine-containing tag or an endogenous glutamine made reactive (i.e., the ability to form a covalent bond as an acyl donor) by polypeptide engineering in the presence of transglutaminase and an amine (e.g., a cytotoxic agent having or attached to a reactive amine) is also described in PCT International Publication No. WO 2012/059882.

To further increase the number of drug molecules per antibody-drug conjugate, the drug may be conjugated to polyethylene glycol (PEG), including straight or branched polyethylene glycol polymers and monomers. A PEG monomer is of the formula: —$(CH_2CH_2O)$—. Drugs and/or peptide analogs may be bound to PEG directly or indirectly, i.e. through appropriate spacer groups such as sugars. A PEG-antibody-drug composition may also include additional lipophilic and/or hydrophilic moieties to facilitate drug stability and delivery to a target site in vivo. Representative methods for preparing PEG-containing compositions may be found in U.S. Pat. Nos. 6,461,603; 6,309,633; and 5,648,095, among other places.

For example, to increase the amount of calicheamicin in antibody-calicheamicin conjugates, the antibody is conjugated to PEG prior to conjugation with calicheamicin, for example, using PEG-SPA, PEG-SBA, or PEG-bis-maleimide. Antibody-drug conjugates prepared using PEG may show reduced binding affinity for the target antigen, but are still effective as a result of increased drug load.

Following conjugation, the chromatographic separation of step (c) above, the conjugates may be separated from unconjugated reactants and/or aggregated forms of the conjugates by conventional methods. This can include processes such as size exclusion chromatography (SEC), ultrafiltration/diafiltration, ion exchange chromatography (IEC), chromatofocusing (CF) HPLC, FPLC, or Sephacryl S-200 chromatography. The chromatographic separation may also be accomplished by hydrophobic interaction chromatography (HIC), which offers some advantages over SEC including (1) a capability to efficiently reduce LCF content as well as aggregate; (2)

accommodation of large reaction volumes; and (3) minimal dilution of the product. Suitable HIC media includes Phenyl Sepharose 6 Fast Flow chromatographic medium, Butyl Sepharose 4 Fast Flow chromatographic medium, Octyl Sepharose 4 Fast Flow chromatographic medium, Toyopearl Ether-650M chromatographic medium, Macro-Prep methyl HIC medium or Macro-Prep t-Butyl HIC medium.

In some aspects of the invention, the chromatographic separation is performed using Butyl Sepharose 4 Fast Flow chromatographic medium. When using the customized gradient as described in Example 6, higher DAR species that remain bound to the column are removed, which is an improvement over prior methods.

In some aspects the purification process, may include a centrifuge cell removal step, optionally a Protein A affinity capture step followed by one or two orthogonal chromatographic polishing steps, a virus filtration step, and a tangential flow filtration step for concentration and formulation.

A typical anti-EFNA4-ActBut-CM antibody-drug conjugate preparation contains predominantly (~95%) conjugated antibody containing 3-5 moles CM per mole antibody, for example, 3-4 moles CM per antibody, or 4-5 moles CM per antibody. In in vivo studies, EFNA4 antibody-drug conjugates prepared with this molar range for drug loading are highly efficacious with minimal toxicity.

The EFNA4-ActBut-CM antibody-drug conjugate has been reproducibly prepared at the laboratory scale (10-200 mg). DAR or drug loading, which is expressed as pg CM/mg monoclonal antibody, is determined by dividing the CM concentration (μg/mL) by the antibody concentration (mg/mL). These values are determined by measuring the UV absorbance of the conjugate solution at 280 nm (antibody) and 310 nm (calicheamicin). It is important to note that this is an average drug loading and that the actual drug loading is a quasi-gaussian distribution centered on the average drug loading value, i.e., some of the antibody is loaded higher than average and some of the antibody is loaded lower than the average. As compared to known antibody-calicheamicin conjugates (e.g., CMC-676 and CMC-544), the DAR distribution is very narrow, and 3 to 5 DAR species (which are the most desired) make up ~75% of the total. Unconjugated antibody (low conjugated fraction or LCF) can be measured using analytical HIC-HPLC (hydrophobic interaction high-performance liquid chromatography). This value is a measure of CM distribution on the antibody and does not generally affect the amount of CM dosed. Unconjugated CM, which can be measured using ELISA, refers to the amount of CM that is not conjugated to the antibody and is expressed in terms of percent of total CM. Drug-loading assays do not differentiate between unconjugated and conjugated CM. The amount of unconjugated CM is undetectable or negligible when using drug-loading assays, and therefore these assays effectively measure the amount of conjugated CM.

Analytical methods can be used to assay for release and stability testing of humanized EFNA4-AcBut-CM antibody-drug conjugates. The conjugates can be evaluated for identity (IEF), strength (total protein and total CM loading), purity (unconjugated CM, low conjugated antibody, aggregate content and SDS-PAGE Reduced), and immunoaffinity (antigen binding ELISA). Additional assays known to those of skill in the art can be used. Using these assays, batch-to-batch consistency can be maintained in commercial manufacture.

III. Functional Assays for Characterization of EFNA Antibody-Drug Conjugates

The present invention further discloses in vitro and in vivo assays to characterize activities of an EFNA4 antibody-drug conjugate, including EFNA binding activity, cellular internalization following binding to EFNA4 antigen presented on a cell surface, and targeting to EFNA4-expressing cells in a subject. In some aspects of the invention, EFNA4 antibody-drug conjugates are characterized by the neutralizing or depleting aspects of the antibody, or antigen-binding fragment thereof. In some aspects of the invention, EFNA4 antibody-drug conjugates are characterized by unexpected efficacy of a particular drug as compared to lack of efficacy of an alternate drug. In some aspects of the invention, EFNA4 antibody-drug conjugates are characterized as outperforming a standard-of-care therapeutic agent having a same mode of action as the drug.

Techniques for detecting binding of EFNA4 antibody-drug conjugates to an EFNA4 antigen, or other EFNA antigen, are known in the art, including for example, BIACORE® assays. Additional representative techniques include centrifugation, affinity chromatography and other immunochemical methods. See e.g., Manson (1992) Immunochemical Protocols, Humana Press, Totowa, N.J., United States of America; Ishikawa (1999) Ultrasensitive and Rapid Enzyme Immunoassay, Elsevier, Amsterdam/New York. Antigen binding assays may be performed using isolated EFNA4 antigen or EFNA4-expressing cells.

The binding specificity of EFNA4 antibody-drug conjugates may be further described by definition of a binding epitope, i.e., identification of residues, including nonadjacent residues that participate in antigen binding, and/or definition of residues that influence antigen binding.

Internalization of EFNA4 antibody-drug conjugates by EFNA-expressing cells may be assayed by observing the amount of antibodies or conjugates bound to the surface of the EFNA-expressing cells over time. Selected EFNA ligands or their isoforms may be present in a soluble form, and at least some EFNA4 likely remains associated with the cell surface thereby allowing for internalization of the antibodies disclosed herein. Accordingly, anti-EFNA4 antibody-drug conjugates of the present invention may be internalized by cells that express EFNA4. For example, an anti-EFNA4 antibody-drug conjugates that binds to EFNA4 on the surface of a tumor initiating cell may be internalized by the tumor initiating cell.

Internalization of EFNA4 antibodies may be assessed using a functional assay in which cells are incubated with the EFNA4 antibody and a secondary antibody Fab fragment that is conjugated to the saporin toxin. Cell viability is then measured by any suitable method, with cellular cytotoxicity indicative of antibody internalization. See Example 5.

In some aspects of the invention, the antibody, or antigen-binding fragment thereof, of the disclosed EFNA4 antibody-drug conjugates is an "antagonist" as used in the broadest sense, i.e., any molecule that partially or fully blocks, inhibits, or neutralizes a biological activity of a native target disclosed herein or the transcription or translation thereof. The terms "inhibit" or "neutralize" as used herein with respect to bioactivity of an antibody of the invention mean the ability of the antibody to substantially antagonize, prohibit, prevent, restrain, slow, disrupt, eliminate, stop, reduce or reverse e.g. progression or severity of that which is being inhibited including, but not limited to, a biological activity. For example, in some aspects of the invention, anti-EFNA4 antibody-drug conjugate facilitate cell killing upon internalization of the antibody-drug conjugate.

More particularly, the term neutralizing antibody or neutralizing antagonist refers to an antibody or antagonist that binds to or interacts with an EFNA ligand and prevents binding or association of the ligand to its binding partner (e.g., EPHA receptor) thereby interrupting the biological response that otherwise would result from the interaction of the molecules. For EFNA4, a neutralizing antibody or antagonist will preferably diminish the ability of EFNA4 to bind to EPHA4 by at least about 20%, 30%, 40%, 50%, 60%, 70%, 80%, 85%, 90%, 95%, 97%, 99% or more. It will be appreciated that this diminished activity may be measured directly using art recognized techniques or may be measured by the impact such reduction will have on EPHA4 receptor activity.

In other aspects of the invention the anti-EFNA4 antibody-drug conjugates of the present invention may be depleting antibodies. The term depleting antibody refers to an antibody that binds to or associates with EFNA4 on or near the cell surface and induces, promotes or causes the death or elimination of the cell (e.g., by complement-dependent cytotoxicity or antibody-dependent cellular cytotoxicity). Preferably a depleting antibody will be able to remove, eliminate or kill at least 20%, 30%, 40%, 50%, 60%, 70%, 80%, 85%, 90%, 95%, 97%, or 99% of tumor perpetuating cells in a defined cell population.

Functional assays also include methods for assessing anti-cancer activity of antibody-drug conjugates, for example, an ability to destroy existing cancer cells, or to delay or prevent growth of cancer cells. Cancers targeted by antibody-drug conjugates of the invention include both primary and metastasized tumors and carcinomas of any tissue in a subject, including carcinomas and hematopoietic malignancies such as leukemias and lymphomas.

EFNA4 antibody-drug conjugates having growth inhibitory activity can eliminate EFNA-expressing cells or to prevent or reduce proliferation of EFNA-expressing cancer cells. Representative methods for rapid in vitro assessment of cell growth inhibition are described in Jones et al. (2001) J. Immunol. Methods 254:85-98.

EFNA4 antibody-drug conjugates may also include an ability to induce cell death, for example, programmed cell death characterized by nuclear DNA degradation, nuclear degeneration and condensation, loss of membrane integrity, and phagocytosis. Representative assays to assess cell are described in Hoves et al. (2003) Methods 31:127-34; Peng et al. (2002) Chin. Med. Sci. J. 17:17-21; Yasuhara et al. (2003) J. Histochem. Cytochem. 51:873-885.

For example, to assess the cytotoxicity of EFNA4 antibody-drug conjugates in vitro, EFNA4-expressing cancer cells and control cells are cultured in the presence EFNA4 antibody-drug conjugates and separately with free drug. The cytotoxicity of each agent is reported as ED50 (ng/ml), which is the amount of drug given as conjugate or as free drug that causes 50% reduction of a cell culture relative to an untreated control. The number of cells in culture is determined using a vital dye (MTS) following drug exposure.

To assess the cytotoxicity of EFNA4 antibody-drug conjugates in vivo, tumors are prepared in NOD/SCID mice by subcutaneous injection of various cancer cells. EFNA4 antibody-drug conjugates and control compounds may be administered to tumor-bearing mice, for example, by intraperitoneal injection twice a week for two weeks (q4dx4). Measurable therapeutic outcomes include inhibition of tumor cell growth. See Example 8.

Further, the present invention provides for EFNA4 antibody-drug conjugates that may deplete, silence, neutralize, eliminate or inhibit growth, propagation or survival of tumor cells, including tumor initiating cells (TIC), and/or associated neoplasia through a variety of mechanisms, including agonizing or antagonizing selected pathways or eliminating specific cells depending, for example, on the anti-EFNA4 antibody, or dosing and method of delivery. See Example 9.

As used herein, the term tumor initiating cell (TIC) encompasses both tumor perpetuating cells (TPC; i.e., cancer stem cells or CSC) and highly proliferative tumor progenitor cells (TProg), which together generally include a unique subpopulation (i.e. 0.1-40%) of a bulk tumor or mass. For the purposes of the instant disclosure the terms tumor perpetuating cells and cancer stem cells are equivalent and may be used interchangeably herein. Conversely, TPC differ from TProg in that they can completely recapitulate the composition of tumor cells existing within a tumor and have unlimited self-renewal capacity as demonstrated by serial transplantation (two or more passages through mice) of low numbers of isolated cells. As used herein, the term "tumor initiating cell" also refers to cancer stem cells of various hematologic malignancies, which are not characterized by a tumor per se.

The present invention provides EFNA4 antibody-drug conjugates that target tumor initiating cells (TIC), and especially tumor perpetuating cells (TPC), thereby facilitating the treatment, management or prevention of neoplastic disorders and hyperproliferative disorders. More specifically, specific tumor cell subpopulations express EFNA4 and likely modify localized coordination of morphogen signaling important to cancer stem cell self-renewal and cell survival. Thus, EFNA4 antibody-drug conjugates may be used to reduce the frequency of TICs upon administration to a subject. The reduction in tumor initiating cell frequency may occur as a result of a) elimination, depletion, sensitization, silencing or inhibition of tumor initiating cells; b) controlling the growth, expansion or recurrence of tumor initiating cells; c) interrupting the initiation, propagation, maintenance, or proliferation of tumor initiating cells; or d) by otherwise hindering the survival, regeneration and/or metastasis of the tumorigenic cells. In some aspects of the invention, the reduction in the frequency of tumor initiating cells occurs as a result of a change in one or more physiological pathways. The change in the pathway, whether by reduction or elimination of the tumor initiating cells or by modifying their potential (e.g., induced differentiation, niche disruption) or otherwise interfering with their ability to exert effects on the tumor environment or other cells, in turn allows for the more effective treatment of EFNA4-associated disorders by inhibiting tumorigenesis, tumor maintenance and/or metastasis and recurrence.

Among the methods that can be used to assess such a reduction in the frequency of tumor initiating cells is limiting dilution analysis either in vitro or in vivo, preferably followed by enumeration using Poisson distribution statistics or assessing the frequency of predefined definitive events such as the ability to generate tumors in vivo or not. It is also possible to determine reduction of frequency values through well-known flow cytometric or immunohistochemical means. As to all the aforementioned methods see, for example, Dylla et al., PLoS ONE 3(6):e2428, 20082 & Hoey et al, Cell Stem Cell 5:168-177, 2009, each of which is incorporated herein by reference in its entirety. Other methods compatible with the instant invention that may be used to calculate tumor initiating cell frequency, include quantifiable flow cytometric techniques and immunohistochemical staining procedures. Representative methods are described in Example 9.

Using any of the above-referenced methods it is then possible to quantify the reduction in frequency of TIC (or the TPC therein) provided by the disclosed EFNA4 antibody-drug conjugates in accordance with the teachings herein. In some instances, the EFNA4 antibody-drug conjugates of the instant invention may reduce the frequency of TIC (by a variety of mechanisms noted above, including elimination, induced differentiation, niche disruption, silencing, etc.) by 10%, 15%, 20%, 25%, 30% or even by 35%. In other aspects of the invention, the reduction in frequency of TIC may be on the order of 40%, 45%, 50%, 55%, 60% or 65%. In certain aspects of the invention, the disclosed compounds my reduce the frequency of TIC by 70%, 75%, 80%, 85%, 90% or even 95%. It will be appreciated that any reduction of the frequency of the TIC likely results in a corresponding reduction in the tumorigenicity, persistence, recurrence and aggressiveness of the neoplasia.

Amassing evidence supports the hypothesis that tumor growth, resistance to therapy, and disorder relapse are controlled by TPCs. The frequency of TPC may vary in a tumor type or between patients with the same tumor type as a product of disorder stage and/or degree of differentiation within the tumor. TPC can be identified and enriched using panels of cell surface markers that often overlap in their expression among patients with certain types of cancer. TPC are best defined by their functional ability to initiate tumors upon serial transplantation, whereas non-tumorigenic (NTG) cells are devoid of this capacity. Solid tumor cells enriched for their unique tumor initiating capacity were first identified in breast cancer; however, breast cancer includes a spectrum of malignancies. To date, the scientific community has failed to associate specific TPC identities with particular disorder subtypes, which may underlie discrepant results both across and within groups and may also increase the likelihood of failed translation to the clinic.

The present invention provides a combination of new cell surface makers that improve the enrichment of TPCs. In particular aspect, the invention provides a combination of new cell surface makers that facilitate the enrichment of triple negative breast cancer (TNBC) TPCs. The present invention further provides for the identification of EFNA4 as a novel TPC-associated therapeutic target in TNBC; the expression level of which is significantly higher than in other breast cancer subtypes and normal tissue.

The pharmacokinetics of EFNA4 antibody-drug conjugates can be evaluated and compared to the pharmacokinetics of unconjugated calicheamicin in various animals. For example, this can be done following a single intravenous bolus administration in female NOD/SCID mice, male Sprague-Dawley rats, and female cynomolgus monkeys. Pharmacokinetics of EFNA4 antibody-drug conjugates are generally characterized by low clearance, low volume of distribution, and long apparent terminal half-life in various species. The serum concentrations of unconjugated calicheamicin derivatives are expected to be below the quantification limit. The toxicity profile for these conjugates in single-dose toxicity ranging studies is expected to be similar to that obtained for other antibody-calicheamicin conjugates at comparable doses.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is a tumor cell, e.g., breast, ovarian, colorectal, liver and lung. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells.

As used herein "antibody-dependent cell-mediated cytotoxicity" or "ADCC" refers to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., PNAS (USA), 95:652-656 (1998).

"Complement dependent cytotoxicity" or "CDC" refers to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods, 202: 163-171 (1997), may be performed.

"Human effector cells" are leukocytes that express one or more FcRs and perform effector functions. The cells may express FcγRIII and carry out antigen-dependent cell-mediated cytotoxicity (ADCC) effector function. Examples of human leukocytes that mediate ADCC include but are not limited to peripheral blood mononuclear cells (PBMC), natural killer (NK) cells, monocytes, macrophages, eosinophils, and neutrophils, with PBMCs and NK cells being preferred. Antibodies that have ADCC activity are typically of the IgG1 or IgG3 isotype. Such ADCC-mediating antibodies can also be made by engineering a variable region from a non-ADCC antibody or variable region fragment to an IgG1 or IgG3 isotype constant region.

IV. Uses of EFNA Antibody-Drug Conjugates

The antibodies and the antibody drug-conjugates of the present invention are useful in various applications including, but are not limited to, therapeutic treatment methods and diagnostic treatment methods.

IV.A. In Vitro Applications

The present invention provides in vitro methods using EFNA4 antibody-drug conjugates. For example, the disclosed antibodies may be used, either alone or in combination with cytotoxic agents or other drugs to specifically bind EFNA-positive cancer cells to deplete such cells from a cell sample. Methods are also provided for inducing apoptosis and/or inhibition of cell proliferation via contacting EFNA-expressing cells with an EFNA4 antibody-drug conjugate. Representative in vitro methods are described herein above under the heading of "Functional Assays for Characterization of EFNA4 antibody-drug conjugates."

EFNA4 antibody-drug conjugates of the invention also have utility in the detection of EFNA-positive cells in vitro based on their ability to specifically bind EFNA4 antigen. A method for detecting EFNA-expressing cells may include: (a) preparing a biological sample having cells; (b) contacting an EFNA4 antibody-drug conjugates with the biological sample in vitro, wherein the drug is a detectable label; and (c) detecting binding the EFNA4 antibody-drug conjugates.

EFNA4 antibody-drug conjugates disclosed herein are also useful for reducing the frequency of tumor initiating cells in a tumor sample. For example, the method can include the steps contacting in vitro a tumor cell population, wherein the population comprises tumor initiating cells and tumor cells other than tumor initiating cells, with an EFNA4 antibody-drug conjugate; whereby the percentage of tumor initiating cells in the cell population is reduced. As used herein, the term "tumor initiating cell" also refers to cancer stem cells of various hematologic malignancies, which are not characterized by a tumor per se. Representative tumor samples include any biological or clinical sample which contains tumor cells, for example, a tissue sample, a biopsy, a blood sample, plasma, saliva, urine, seminal fluid, etc. Representative methods are described in Example 9.

IV.B. Therapeutic Applications

EFNA4 associated disorders include but are not limited to as breast cancer, such as triple-negative breast cancer (TNBC); ovarian cancer; colorectal cancer; leukemias, such as chronic lymphocytic leukemia (CLL); liver cancer, such as hepatocellular carcinoma (HCC); and lung cancer, such as non-small cell lung cancer (NSCLC) and small cell lung cancer (SCLC).

The phrase "effective amount", "effective dosage" or as used herein refers to an amount of a drug, compound or pharmaceutical composition necessary to achieve any one or more beneficial or desired therapeutic results. For prophylactic use, beneficial or desired results include eliminating or reducing the risk, lessening the severity, or delaying the outset of the disorder, including biochemical, histological and/or behavioral symptoms of the disorder, its complications and intermediate pathological phenotypes presenting during development of the disorder. For therapeutic use, beneficial or desired results include clinical results such as reducing incidence or amelioration of one or more symptoms of various EFNA4 associated disorders decreasing the dose of other medications required to treat the disorder, enhancing the effect of another medication, and/or delaying the progression of the EFNA4 associated disorder of patients.

In one aspect, the invention provides a method for treating a disorder associated with EFNA4 expression in a subject. The invention also provides an antibody-drug conjugate, or a pharmaceutical composition, as described herein, for use in a method for treating a disorder associated with EFNA4 expression in a subject. The invention further provides the use of an antibody-drug conjugate, or a pharmaceutical composition, as described herein, in the manufacture of a medicament for treating a disorder associated with EFNA4 expression in a subject.

In some aspects of the invention, the method of treating a disorder associated with EFNA4 expression in a subject includes administering to the subject in need thereof an effective amount of a composition (e.g., pharmaceutical composition) having the EFNA4 antibody-drug conjugates as described herein. The disorders associated with EFNA4 expression include, but are not limited to, abnormal EFNA4 expression, altered or aberrant EFNA4 expression, EFNA4 overexpression, and a proliferative disorder (e.g., cancer).

In one aspect of the invention, the disorder is cancer, including, but not limited to, mesothelioma, hepatobilliary (hepatic and billiary duct), hepatocellular carcinoma, a primary or secondary CNS tumor, a primary or secondary brain tumor, lung cancer (NSCLC and SCLC), bone cancer, pancreatic cancer, skin cancer, cancer of the head or neck, melanoma, ovarian cancer, colon cancer, rectal cancer, cancer of the anal region, stomach cancer, gastrointestinal (gastric, colorectal, and duodenal), breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the cancers disclosed herein.

In a particular aspect of the invention, cancers suitable for targeting using anti-EFNA4 antibody-drug conjugates include EFNA4-expressing primary and metastatic cancers, such as breast cancer, including triple-negative breast cancer (TNBC); ovarian cancer; colorectal cancer; leukemias, such as chronic lymphocytic leukemia (CLL); liver cancer, such as hepatocellular carcinoma (HCC); and lung cancer, such as non-small cell lung cancer (NSCLC) and small cell lung cancer (SCLC). In some aspects of the invention, provided is a method of inhibiting tumor growth or progression in a subject who has a EFNA4 expressing tumor, including administering to the subject in need thereof an effective amount of a composition having the EFNA4 antibody-drug conjugates as described herein. In other aspects of the invention, provided is a method of inhibiting metastasis of EFNA4 expressing cancer cells in a subject, including administering to the subject in need thereof an effective amount of a composition having the EFNA4 antibody-drug conjugates as described herein. In other aspects of the invention, provided is a method of inducing regression of a EFNA4 expressing tumor regression in a subject, including administering to the subject in need thereof an effective amount of a composition having the EFNA4 antibody-drug conjugates as described herein. In other aspects, the invention provides an antibody-drug conjugate, or a pharmaceutical composition, as described herein, for use in a method as described above. In other aspects the invention provides the use of an antibody-drug conjugate, or a pharmaceutical composition, as described herein, in the manufacture of a medicament for use in the methods described above.

Thus, patients to be treated with EFNA4 antibody-drug conjugates of the invention may be selected based on biomarker expression, including but not limited to mRNA (qPCR) of bulk tumor samples and elevated expression of EFNA4 antigen which results in a patient population selected for enriched target expression rather than tumor origin or histology. Target expression can be measured as a function of the number of cells staining combined with the intensity of the cells staining. For example, classification of high expression of EFNA4 includes those patients with greater than 30% (i.e., 40%, 50% or 60%) of the cells tested by immunohistochemical staining positive for EFNA4 at a level of 3+ (on a scale of 1 to 4), while moderate expression of the EFNA4 can include those patients with greater than 20% of the cell cells staining at 1+ to 2+. Target expression can also be measured by detecting EFNA expression on tumor initiating cells (TIC) as described herein.

The expression of EFNA4 in TNBC is specific as it is higher than in other breast cancer subtypes and normal tissues. In general, tumors with lower expression levels of EFNA4 exhibited the Claudin-low TNBC molecular signature, which suggests the potential translational relevance of that classification for patient selection strategies. The present invention provides for selecting patients having an increased expression of EFNA4 and treating the patients with an EFNA4 ADC disclosed herein. Further, copy number gain of EFNA4 and mRNA levels in breast cancer, ovarian cancer and hepatocellular carcinoma may be relevant to determine genetic basis for overexpression of EFNA4 and used in patient selection strategies. The present invention further provides for selecting patients having an increase in copy number of EFNA4 and treating the patients with an EFNA4 ADC disclosed herein. The present invention further provides for selecting patients having an increase in mRNA levels of EFNA4 and treating the patients with an EFNA4 ADC disclosed herein.

Biomarkers other than expression of EFNA4 can be also used for patient selection, including characterization of the tumor based on multi-drug resistance (MDR), for example. Nearly 50% of human cancers are either completely resistant to chemotherapy or respond only transiently, after which they are no longer affected by commonly used anticancer drugs. This phenomenon is referred to as MDR and is inherently expressed by some tumor types, while others acquire MDR after exposure to chemotherapy treatment. The drug efflux pump P-glycoprotein mediates a majority of the MDR associated with cytotoxic chemotherapeutics. Phenotypic and functional analysis of MDR mechanisms present in cancer patient tumor specimens can be conducted in order to relate specific MDR mechanism(s) with resistance to chemotherapy in specific tumor types.

The present invention provides that TNBC TPC are significantly enriched among $ESA^+CD46^+CD324^+$ cells, but not in the $CD324^-$ counterparts. The present invention further provides the use of ESA and/or CD46 and/or CD324 as markers for selecting patients and treating the patients with an EFNA4 ADC disclosed herein. The present invention further provides the use of ESA and/or CD46 and/or CD324 as markers for selecting TNBC patients and treating the patients with an EFNA4 ADC disclosed herein.

Cancer growth or abnormal proliferation refers to any one of a number of indices that suggest change within cells to a more developed cancer form or disorder state. Inhibition of growth of cancer cells or cells of a non-neoplastic proliferative disorder may be assayed by methods known in the art, such as delayed tumor growth and inhibition of metastasis. Other indices for measuring inhibition of cancer growth include a decrease in cancer cell survival, a decrease in tumor volume or morphology (for example, as determined using computed tomographic (CT), sonography, or other imaging method), destruction of tumor vasculature, improved performance in delayed hypersensitivity skin test, an increase in the activity of cytolytic T-lymphocytes, and a decrease in levels of tumor-specific antigens.

Desired outcomes of the disclosed therapeutic methods are generally quantifiable measures as compared to a control or baseline measurement. As used herein, relative terms such as "improve," "increase," or "reduce" indicate values relative to a control, such as a measurement in the same individual prior to initiation of treatment described herein, or a measurement in a control individual (or multiple control individuals) in the absence of the treatment described herein. A representative control individual is an individual afflicted with the same form of hyperproliferative disorder as the individual being treated, who is about the same age as the individual being treated (to ensure that the stages of the disorder in the treated individual and the control individual are comparable.

Changes or improvements in response to therapy are generally statistically significant. As used herein, the term "significance" or "significant" relates to a statistical analysis of the probability that there is a non-random association between two or more entities. To determine whether or not a relationship is "significant" or has "significance," statistical manipulations of the data can be "p-value." Those p-values that fall below a user-defined cut-off point are regarded as significant. A p-value less than or equal to 0.1, less than 0.05, less than 0.01, less than 0.005, or less than 0.001 may be regarded as significant.

As described herein above under the heading "III. Functional Assays for Characterization of EFNA Antibody-Drug Conjugates," the present invention also provides methods for targeting tumor initiating cells. More particularly, EFNA4 antibody-drug conjugates of the invention may deplete, silence, neutralize, eliminate or inhibit growth, propagation or survival of tumor cells, including tumor initiating cells.

Thus, EFNA4 antibody-drug conjugates disclosed herein are also useful for reducing the frequency of tumor initiating cells in a tumor sample. For example, the method can include the steps contacting a tumor cell population, wherein the population comprises tumor initiating cells and tumor cells other than tumor initiating cells, with an EFNA4 antibody-drug conjugate; whereby the percentage of tumor initiating cells in the cell population is reduced. As used herein, the term "tumor initiating cell" also refers to cancer stem cells of various hematologic malignancies, which are not characterized by a tumor per se. The contacting step may be performed in vitro, wherein the tumor cell population is contained in a biological sample, as described herein above. Alternatively, the contacting step may be performed in vivo as occurs following administration of an EFNA4 antibody-drug conjugate to a subject.

IV.C. In Vivo Detection and Diagnosis

In another aspect, provided is a method of detecting, diagnosing, and/or monitoring a disorder associated with EFNA4 expression. For example, the EFNA4 antibodies as described herein can be labeled with a detectable moiety such as an imaging agent and an enzyme-substrate label. The antibodies as described herein can also be used for in vivo diagnostic assays, such as in vivo imaging (e.g., PET or SPECT), or a staining reagent.

Following administration of an EFNA4 antibody-drug conjugate to a subject, wherein the drug is a detectable label, and after a time sufficient for binding, the biodistribution of EFNA4-expressing cells bound by the antibody may be visualized. The disclosed diagnostic methods may be used in combination with treatment methods. In addition, EFNA4 antibody-drug conjugates of the invention may be administered for the dual purpose of detection and therapy.

Representative non-invasive detection methods include scintigraphy (e.g., SPECT (Single Photon Emission Computed Tomography), PET (Positron Emission Tomography), gamma camera imaging, and rectilinear scanning), magnetic resonance imaging (e.g., convention magnetic resonance imaging, magnetization transfer imaging (MTI), proton magnetic resonance spectroscopy (MRS), diffusion-weighted imaging (DWI) and functional MR imaging (fMRI)), and ultrasound.

IV.D. Formulation

The present invention further provides pharmaceutical compositions including any of the EFNA4 antibody-drug conjugates disclosed herein and a pharmaceutically acceptable carrier. Further, the compositions can include more than one EFNA4 antibody or EFNA4 antibody-drug conjugate (e.g., a mixture of EFNA4 antibodies that recognize different epitopes of EFNA4). Other exemplary compositions include more than one EFNA4 antibody or EFNA4 antibody-drug conjugate that recognize the same epitope(s), or different species of EFNA4 antibodies or EFNA4 antibody-drug conjugate that bind to different epitopes of EFNA4 (e.g., human EFNA4).

The composition used in the present invention can further include pharmaceutically acceptable carriers, excipients, or stabilizers (Remington: The Science and practice of Pharmacy 21st Ed., 2005, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). "Pharmaceutically acceptable salt" as used herein refers to pharmaceutically acceptable organic or inorganic salts of a molecule or macromolecule. Pharmaceutically acceptable excipients are further described herein.

Various formulations of the EFNA4 antibody or the EFNA4 antibody-drug conjugate may be used for administration. In some aspects of the invention, the EFNA4 antibody or the EFNA4 antibody-drug conjugate may be administered neat. The EFNA4 antibody or the EFNA4 antibody-drug conjugate and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing, 2000.

In some aspects of the invention, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

Therapeutic formulations of the EFNA4 antibody or the EFNA4 antibody-drug conjugate used in accordance with the present invention are prepared for storage by mixing an antibody having the desired degree of purity with optional pharmaceutically acceptable carriers, excipients or stabilizers (Remington, The Science and Practice of Pharmacy 21st Ed. Mack Publishing, 2005), in the form of lyophilized formulations or aqueous solutions. Acceptable carriers, excipients, or stabilizers are nontoxic to recipients at the dosages and concentrations employed, and may include buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the EFNA4 antibody or the EFNA4 antibody-drug conjugate are prepared by methods known in the art, such as described in Eppstein, et al., Proc. Natl. Acad. Sci. USA 82:3688-3692, 1985; Hwang, et al., Proc. Natl. Acad. Sci. USA 77:4030-4034, 1980; and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition including phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 21st Ed. Mack Publishing, 2005.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The formulations to be used for in vivo administration must be sterile. This is readily accomplished by, for example, filtration through sterile filtration membranes. Therapeutic EFNA4 antibody or EFNA4 antibody-drug conjugate compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can include an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently include between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can include fat droplets between 0.1 and 1.0 µm, particularly 0.1 and 0.5 µm, and have a pH in the range of 5.5 to 8.0.

The emulsion compositions can be those prepared by mixing a EFNA4 antibody or a EFNA4 antibody-drug conjugate with INTRALIPID™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some aspects of the invention, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The invention also provides kits for use in the instant methods. Kits of the invention include one or more containers including the EFNA4 antibody or the EFNA4 antibody-drug conjugate as described herein and instructions for use in accordance with any of the methods of the invention described herein. Generally, these instructions include a description of administration of the EFNA4 antibody or the EFNA4 antibody-drug conjugate for the above described therapeutic treatments.

The instructions relating to the use of the EFNA4 antibodies or the EFNA4 antibody conjugates as described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an EFNA4 antibody or EFNA4 antibody-drug conjugate. The container may further include a second pharmaceutically active agent.

Kits may optionally provide additional components such as buffers and interpretive information. Normally, the kit includes a container and a label or package insert(s) on or associated with the container.

IV.E. Dose and Administration

For in vitro and in vivo applications, EFNA4 antibody-drug conjugates are provided or administered in an effective dosage. In a clinical context, an effective dosage of drug, compound, or pharmaceutical composition is an amount sufficient to accomplish prophylactic or therapeutic treatment either directly or indirectly. An effective dosage can be administered in one or more administrations. An effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved. For detection of EFNA-positive cells using the disclosed EFNA4 antibody-drug conjugates, a detectable amount of a composition of the invention is administered to a subject, i.e., a dose of the conjugate such that the presence of the conjugate may be determined in vitro or in vivo.

For example, when administered to a cancer-bearing subject, an effective amount includes an amount sufficient to elicit anti-cancer activity, including cancer cell cytolysis, inhibition of cancer cell proliferation, induction of cancer cell apoptosis, reduction of cancer cell antigens, delayed tumor growth, and/or inhibition of metastasis. Tumor shrinkage is well accepted as a clinical surrogate marker for efficacy. Another well accepted marker for efficacy is progression-free survival. EFNA4 antibody-drug conjugates generally demonstrate at least a 25% improvement in key efficacy parameters, such as improvement in median survival, time to tumor progression, and overall response rate.

The EFNA4 antibody or the EFNA4 antibody-drug conjugates can be administered to an individual via any suitable route. It should be understood by persons skilled in the art that the examples described herein are not intended to be limiting but to be illustrative of the techniques available. Accordingly, in some aspects of the invention, the EFNA4 antibody or the EFNA4 antibody conjugate is administered to an individual in accord with known methods, such as intravenous administration, e.g., as a bolus or by continuous infusion over a period of time, by intramuscular, intraperitoneal, intracerebrospinal, intracranial, transdermal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, the EFNA4 antibody or the EFNA4 antibody-drug conjugate can be aerosolized using a fluorocarbon formulation and a metered dose inhaler, or inhaled as a lyophilized and milled powder.

In some aspects of the invention, the EFNA4 antibody or the EFNA4 antibody-drug conjugate is administered via site-specific or targeted local delivery techniques. Examples of site-specific or targeted local delivery techniques include various implantable depot sources of the EFNA4 antibody or the EFNA4 antibody-drug conjugate or local delivery catheters, such as infusion catheters, indwelling catheters, or needle catheters, synthetic grafts, adventitial wraps, shunts and stents or other implantable devices, site specific carriers, direct injection, or direct application. See, e.g. PCT International Publication No. WO 2000/53211 and U.S. Pat. No. 5,981,568.

EFNA4 antibodies or the EFNA4 antibody-drug conjugates as described herein can be administered using any suitable method, including by injection (e.g., intraperitoneally, intravenously, subcutaneously, intramuscularly, etc.). The EFNA4 antibody or the EFNA4 antibody-drug conjugate can also be administered via inhalation, as described herein. Generally, for administration of an EFNA4 antibody and an EFNA4 antibody-drug conjugate, an initial candidate dosage can be about 2 mg/kg. For the purpose of the present invention, a typical daily dosage might range from about any of 3 µg/kg to 30 µg/kg to 300 µg/kg to 3 mg/kg, to 30 mg/kg, to 100 mg/kg or more, depending on the factors mentioned above. For example, dosage of about 1 mg/kg, about 2.5 mg/kg, about 5 mg/kg, about 10 mg/kg, and about 25 mg/kg may be used. For repeated administrations over several days or longer, depending on the disorder, the treatment is sustained until a desired suppression of symptoms occurs or until sufficient therapeutic levels are achieved, for example, to inhibit or delay tumor growth/progression or metatstasis of cancer cells. An exemplary dosing regimen includes administering an initial dose of about 2 mg/kg, followed by a weekly maintenance dose of about 1 mg/kg of the EFNA4 antibody or EFNA4 antibody-drug conjugate, or followed by a maintenance dose of about 1 mg/kg every other week. Other exemplary dosing regimen include administering increasing doses (e.g., initial dose of 1 mg/kg and gradual increase to one or more higher doses every week or longer time period). Other dosage regimens may also be useful, depending on the pattern of pharmacokinetic decay that the practitioner wishes to achieve. For example, in some aspects of the invention, dosing from one to four times a week is contemplated. In other aspects, dosing once a month or once every other month or every three months is contemplated, as well as weekly, bi-weekly and every three weeks. The progress of this therapy may be easily monitored by conventional techniques and assays. The dosing regimen (including the EFNA4 antibody or the EFNA4 antibody-drug conjugate used) can vary over time.

For the purpose of the present invention, the appropriate dosage of an EFNA4 antibody or an EFNA4 antibody-drug conjugate will depend on the EFNA4 antibody or the EFNA4 antibody-drug conjugate (or compositions thereof) employed, the type and severity of symptoms to be treated, whether the agent is administered for therapeutic purposes, previous therapy, the patient's clinical history and response to the agent, the patient's clearance rate for the administered agent, and the discretion of the attending physician. The clinician may administer an EFNA4 antibody or an EFNA4 antibody-drug conjugate until a dosage is reached that achieves the desired result and beyond. Dose and/or frequency can vary over course of treatment, but may stay constant as well. Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms, e.g., tumor growth inhibition or delay, etc. Alternatively, sustained continuous release formulations of EFNA4 antibodies or EFNA4 antibody-drug conjugates may be appropriate. Various formulations and devices for achieving sustained release are known in the art.

In some aspects of the invention, dosages for an EFNA4 antibody or an EFNA4 antibody-drug conjugate may be determined empirically in individuals who have been given one or more administration(s) of the EFNA4 antibody or the EFNA4 antibody-drug conjugate. Individuals are given incremental dosages of an EFNA4 antibody or an EFNA4 antibody-drug conjugate. To assess efficacy, an indicator of the disorder can be followed.

Administration of an EFNA4 antibody or an EFNA4 antibody-drug conjugate in accordance with the method in the present invention can be continuous or intermittent, depending, for example, upon the recipient's physiological disorder, whether the purpose of the administration is therapeutic or prophylactic, and other factors known to skilled practitioners. The administration of an EFNA4 antibody or an EFNA4 antibody-drug conjugate may be essentially continuous over a preselected period of time or may be in a series of spaced doses.

IV.F. Combination Therapies

In some aspects of the invention, the methods described herein further include a step of treating a subject with an additional form of therapy. In some aspects, the additional form of therapy is an additional anti-cancer therapy including, but not limited to, chemotherapy, radiation, surgery, hormone therapy, and/or additional immunotherapy.

The disclosed EFNA4 antibody-drug conjugates may be administered as an initial treatment, or for treatment of disorders that are unresponsive to conventional therapies. In addition, the EFNA4 antibody-drug conjugates may be used in combination with other therapies (e.g., surgical excision, radiation, additional anti-cancer drugs etc.) to thereby elicit additive or potentiated therapeutic effects and/or reduce hepatocytotoxicity of some anti-cancer agents. EFNA4 antibody-drug conjugates of the invention may be co-administered or co-formulated with additional agents, or formulated for consecutive administration with additional agents in any order.

Representative agents useful for combination therapy include any of the drugs described herein above as useful for preparation of EFNA4 antibody-drug conjugates under the subheading "Drugs." EFNA4 antibody-drug conjugates of the invention may also be used in combination with other therapeutic antibodies and antibody-drug conjugates, including anti-EFNA antibodies other than the disclosed anti-EFNA antibodies, as well as antibodies and conjugates targeting a different antigen. Representative antibodies, which may be used alone or as an antibody-drug conjugate, include anti-5T4 antibodies (e.g., A1, A2, and A3), anti-CD19 antibodies, anti-CD20 antibodies (e.g., RITUXAN®, ZEVALIN®, BEXXAR®), anti-CD22 antibodies, anti-CD33 antibodies (e.g., MYLOTARG®), anti-CD33 antibody-drug conjugates, anti-Lewis Y antibodies (e.g., Hu3S193, Mthu3S193, AGmthu3S193), anti-HER-2 antibodies (e.g., HERCEPTIN® (trastuzumab), MDX-210, OMNITARG® (pertuzumab, rhuMAb 2C4)), anti-CD52 antibodies (e.g., CAMPATH®), anti-EGFR antibodies (e.g., ERBITUX® (cetuximab), ABX-EGF (panitumumab)), anti-VEGF antibodies (e.g., AVASTIN® (bevacizumab)), anti-DNA/histone complex antibodies (e.g., ch-TNT-1/b), anti-CEA antibodies (e.g., CEA-Cide, YMB-1003) hLM609, anti-CD47 antibodies (e.g., 6H9), anti-VEGFR2 (or kinase insert domain-containing receptor, KDR) antibodies (e.g., IMC-1C11), anti-EpCAM antibodies (e.g., ING-1), anti-FAP antibodies (e.g., sibrotuzumab), anti-DR4 antibodies (e.g., TRAIL-R), anti-progesterone receptor antibodies (e.g., 2C5), anti-CA19.9 antibodies (e.g., GIVAREX®) and anti-fibrin antibodies (e.g., MH-1).

The disclosed EFNA4 antibody-drug conjugates may also be administered together with one or more combinations of cytotoxic agents as part of a treatment regimen. Useful cytotoxic preparations for this purpose include CHOPP (cyclophosphamide, doxorubicin, vincristine, prednisone and procarbazine); CHOP (cyclophosphamide, doxorubicin, vincristine, and prednisone); COP (cyclophosphamide, vincristine, prednisone); CAP-BOP (cyclophosphamide, doxorubicin, procarbazine, bleomycin, vincristine and prednisone); m-BACOD (methotrexate, bleomycin, doxorubicin, cyclophosphamide, vincristine, dexamethasone, and leucovorin; ProMACE-MOPP (prednisone, methotrexate, doxorubicin, cyclophosphamide, etoposide, leukovorin, mechloethamine, vincristine, prednisone and procarbazine); ProMACE-CytaBOM (prednisone, methotrexate, doxorubicin, cyclophosphamide, etoposide, leukovorin, cytarabine, bleomycin and vincristine); MACOP-B (methotrexate, doxorubicin, cyclophosphamide, vincristine, prednisone, bleomycin and leukovorin); MOPP (mechloethamine, vincristine, prednisone and procarbazine); ABVD (adriamycin/doxorubicin, bleomycin, vinblastine and dacarbazine); MOPP (mechloethamine, vincristine, prednisone and procarbazine) alternating with ABV (adriamycin/doxorubicin, bleomycin, vinblastine); MOPP (mechloethamine, vincristine, prednisone and procarbazin) alternating with ABVD (adriamycin/doxorubicin, bleomycin, vinblastine and dacarbazine); ChIVPP (chlorambucil, vinblastine, procarbazine, prednisone); IMVP-16 (ifosfamide, methotrexate, etoposide); MIME (methyl-gag, ifosfamide, methotrexate, etoposide); DHAP (dexamethasone, high-dose cytaribine and cisplatin); ESHAP (etoposide, methylpredisolone, HD cytarabine, and cisplatin); CEPP(B) (cyclophosphamide, etoposide, procarbazine, prednisone and bleomycin); CAMP (lomustine, mitoxantrone, cytarabine and prednisone); and CVP-1 (cyclophosphamide, vincristine and prednisone); DHAP (cisplatin, high-dose cytarabine and dexamethasone); CAP (cyclophosphamide, doxorubicin, cisplatin); PV (cisplatin, vinblastine or vindesine); CE (carboplatin, etoposide); EP (etoposide, cisplatin); MVP (mitomycin, vinblastine or vindesine, cisplatin); PFL (cisplatin, 5-fluorouracil, leucovorin); IM (ifosfamide, mitomycin); IE (ifosfamide, etoposide); IP (ifosfamide, cisplatin); MIP (mitomycin, ifosfamide, cisplatin); ICE (ifosfamide, carboplatin, etoposide); PIE (cisplatin, ifosfamide, etoposide); Viorelbine and cisplatin; Carboplatin and paclitaxel; CAV (cyclophosphamide, doxorubicin, vincristine); CAE (cyclophosphamide, doxorubicin, etoposide); CAVE (cyclophosphamide, doxorubicin, vincristine, etoposide); EP (etoposide, cisplatin); and CMCcV (cyclophosphamide, methotrexate, lomustine, vincristine).

EFNA4 antibody-drug conjugates may be used in combination with systemic anti-cancer drugs, such as epithilones (BMS-247550, Epo-906), reformulations of taxanes (Abraxane, Xyotax), microtubulin inhibitors (MST-997, TTI-237), or with targeted cytotoxins such as CMD-193 and SGN-15. Additional useful anti-cancer agents include TAXOTERE®, TARCEVA®, GEMZAR® (gemcitabine), 5-FU, AVASTIN® ERBITUX®, TROVAX®, anatumomab mafenatox, letrazole, docetaxel, and anthracyclines.

For combination therapies, an EFNA4 antibody-drug conjugate and/or one or more additional therapeutic or diagnostic agents are administered within any time frame suitable for performance of the intended therapy or diagnosis. Thus, the single agents may be administered substantially simultaneously (i.e., as a single formulation or within minutes or hours) or consecutively in any order. For example, single agent treatments may be administered within about 1 year of each other, such as within about 10, 8, 6, 4, or 2 months, or within 4, 3, 2 or 1 week(s), or within about 5, 4, 3, 2 or 1 day(s). The administration of an EFNA4 antibody-drug conjugate in combination with a second therapeutic agent preferably elicits a greater effect than administration of either alone.

In some aspects of the invention, the additional form of therapy includes administering one or more therapeutic agent in addition to the EFNA4 antibodies or the EFNA4 antibody-drug conjugates as described herein. The therapeutic agents include, but are not limited to, a second antibody (e.g., an anti-VEGF antibody, an anti-HER2 antibody, anti-CD25 antibody, and/or an anti-CD20 antibody), an angiogenesis inhibitor, a cytotoxic agent, an anti-inflammatory agent (e.g., paclitaxel, docetaxel, cisplatin, doxorubicin, prednisone, mitomycin, progesterone, tamoxifen, or fluorouracil).

In some aspects of the invention, more than one EFNA4 antibody or EFNA4 antibody-drug conjugate may be present. At least one, at least two, at least three, at least four, at least five different or more EFNA4 antibody or EFNA4 antibody-drug conjugate can be present. Generally, those EFNA4 antibodies or EFNA4 antibody-drug conjugates may have complementary activities that do not adversely affect each other. For example, one or more of the following EFNA4 antibody may be used: a first EFNA4 antibody directed to one epitope on EFNA4 and a second EFNA4 antibody directed to a different epitope on EFNA4.

The disclosed combination therapies may elicit a synergistic therapeutic effect, i.e., an effect greater than the sum of their individual effects or therapeutic outcomes. Measurable therapeutic outcomes are described herein. For example, a synergistic therapeutic effect may be an effect of at least about two-fold greater than the therapeutic effect elicited by a single agent, or the sum of the therapeutic effects elicited by the single agents of a given combination, or at least about five-fold greater, or at least about ten-fold greater, or at least about twenty-fold greater, or at least about fifty-fold greater, or at least about one hundred-fold greater. A synergistic therapeutic effect may also be observed as an increase in therapeutic effect of at least 10% compared to the therapeutic effect elicited by a single agent, or the sum of the therapeutic effects elicited by the single agents of a given combination, or at least 20%, or at least 30%, or at least 40%, or at least 50%, or at least 60%, or at least 70%, or at least 80%, or at least 90%, or at least 100%, or more. A synergistic effect is also an effect that permits reduced dosing of therapeutic agents when they are used in combination.

As used throughout the detailed description, the term "about" means a value+/−1% of the value following the term "about," unless otherwise indicated.

EXAMPLES

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

Example 1

Generation of Anti-EFNA4 Antibodies

As described in International Publication No. WO2012/118547, EFNA4 murine antibodies were produced by inoculation with hEFNA4-ECD-Fc, hEFNA4-ECD-His, whole cell BALB/c 3T3 cells over expressing EFNA4 or the plasma preps prepared as set forth herein (ECD—extracellular domain). Immunogens were all prepared using commercially available starting materials (e.g., Recombinant Human ephrin-A4 Fc Chimera, CF R&D systems #369-EA-200) and/or techniques well known to those skilled in the art.

EFNA4 murine antibodies were generated by immunizing female mice (Balb/c, CD-I, FVB) with various preparations of EFNA4 antigen. Immunogens included Fc constructs or His tagged human EFNA4, membrane fractions extracted from $10^7$ over expressing EFNA4 293 cells or whole 3T3 cells over expressing human EFNA4 on the surface. Mice were immunized via footpad route for all injections. 10 μg of EFNA4 immunogen or $1\times10^6$ cells or cell equivalents emulsified with an equal volume of TITERMAX or alum adjuvant were used for immunization. After immunization mice were euthanized, and draining lymph nodes (popliteal and inguinal, if enlarged) were dissected out and used as a source for antibody producing cells. Lymphocytes were released by mechanical disruption of the lymph nodes using a tissue grinder.

One of two fusion protocols was used. In the first electrofusion with a Genetronic device was performed followed by plating and screening of the polyclonal hybridomas with a subsequent subcloning to generate monoclonal hybridomas. In the second ectrofusion with a BTX instrument was performed followed by growth of the hybridoma library in bulk and single cell deposition of the hybridomas with a subsequent screen of the clones.

Genetronic device fusion protocol: The fusion was performed by mixing a single cell suspension of B cells with non-secreting P3x63Ag8.653 myeloma cells purchased from (ATCC CRL-1580; Kearney et al, J. Immunol. 123: 1548-1550 (1979)) at a ratio of 1:1. The cell mixture was gently pelleted by centrifugation at 800 g. After complete removal of the supernatant, the cells were treated with 2-4 mL of Pronase solution for no more than 2 minutes. Electrofusion was performed using a fusion generator, model ECM2001 (Genetronic, Inc.). Cells were plated at $2\times10^4$/well in flat bottom microtiter plates, followed by two weeks incubation in selective HAT medium (Sigma, CRL P-7185). Individual wells were then screened by ELISA and FACS for anti-human EFNA4 monoclonal IgG antibodies.

ELISA microtiter plates were coated with purified recombinant EFNA4 His fusion proteins from transfected 293 cells at 100 ng/well in carbonate buffer. Plates incubated at 4° C. overnight than blocked with 200μ/well of 3% BSA in PBS/Tween (0.05%). Supernatant from hybridoma plates were added to each well and incubated for 1-2 hours at ambient temperature. The plates were washed with PBS/Tween and then incubated with Goat anti mouse IgG, Fc Fragment Specific conjugated with horseradish proxidase (HRP) Jackson ImmunoResearch) for one hour at room temperature. After washing, the plates were developed with TMB substrate (Thermo Scientific 34028) and analyzed by spectrophotometer at OD 450.

EFNA4 secreted hybridoma from positive wells were, rescreened and subcloned by limited dilution or single cell FACS sorting. Sub cloning was performed on selected antigen-positive wells using limited dilution plating. Plates were visually inspected for the presence of single colony growth and supernatants from single colony wells then screened by antigen-specific ELISAs described above and FACS confirmation as described below. The resulting clonal populations were expanded and cryopreserved in freezing medium (90% FBS, 10% DMSO) and stored in liquid nitrogen. This fusion from mice immunized with EFNA4 yielded murine monoclonal antibodies reactive for EFNA4 using the ELISA protocol described above.

BTX instrument fusion protocol: A single cell suspension of B cells were fused with non-secreting P3x63Ag8.653 myeloma cells at a ratio of 1:1 by electrofusion. Electrofusion was performed using the Hybrimune System, model 47-0300, (BTX Harvard Apparatus). Fused cells were resuspended in hybridoma selection medium supplemented with Azaserine (Sigma #A9666) (DMEM (Cellgro cat#15-017-CM) medium containing, 15% Fetal Clone I serum (Hyclone), 10% BM Condimed (Roche Applied Sciences), 1 mM sodium pyruvate, 4 mM L-glutamine, 100 IU Penicillin-Streptomycin, 50 μM 2-mercaptoefhanol, and 100 μM hypoxanthine) and then plated in four T225 flasks at 90 ml selection medium per flask. The flasks are then placed in a humidified 37° C. incubator containing 5% $CO_2$ and 95% air for 6-7 days.

At 6-7 days of growth the library is plated at 1 cell per well in 48 Falcon 96 well U-bottom plates using the Aria I cell sorter. Briefly culture medium containing 15% Fetal Clone I serum (Hyclone), 10% BM-Condimed (Roche Applied Sciences), 1 mM sodium pyruvate, 4 mM L-glutamine, 100 IU Penecillin-Streptamycin, 50 μM 2-mercaptoethanol, and 100 μM hypoxanthine is plated at 200 ul per well in 48 Falcon 96 well U-bottom plates. Viable hybridomas are placed at 1 cell per well using the Aria I cell sorter and cultured for 10-11 days and the supernatants are assayed for antibodies reactive by FACS or ELISA for EFNA4.

Growth positive hybridomas wells secreting mouse immunoglobulins were screened for murine EFNA4 specificity using an ELISA assay similar to that described above. Briefly, 96 well plates (VWR, 610744) were coated with 1 μg/mL murine EFNA4-His in sodium carbonate buffer overnight at 4° C. The plates were washed and blocked with 2% FCS-PBS for one hour at 37° C. and used immediately or kept at 4° C. Undiluted hybridoma supernatants were incubated on the plates for one hour at RT. The plates are washed and probed with HRP labeled goat anti-mouse IgG diluted 1:10,000 in 1% BSA-PBS for one hour at RT. The plates are then incubated with substrate solution as described above and read at OD 450. The amino acid sequences and associated nucleic acid sequences (CDRs underlined) of exemplary murine antibodies E2, E5, E8, E15, E22, E31, E47, E60, E73, E76, E91 and E105 that bound human EFNA4 with high affinity are provided in International Publication No. WO2012/118547.

Binding characteristics of various murine anti-EFNA4 antibodies of the present invention are shown in Table 3. The antibodies exhibited relatively high affinities in the nanomolar range and bind to at least three different bins or epitopes on the EFNA4 protein. Most anti-EFNA4 antibodies reacted only with antigen where disulfide bonds are intact (NR), while E22 and E91 reacted with both non-reduced and reduced antigen (NR/R). E22 and E91 recognized the sequence QRFTPFSLGFE (SEQ ID NO: 137 and RLLRG-DAVVE (SEQ ID NO: 138), respectively. Further, E5, E15, E91 and E105 were cross-reactive with mouse EFNA4 and all antibodies cross-reacted with highly similar cynomolgus EFNA4. The ability of the antibodies to neutralize (i.e. block receptor ligand interaction, specifically EFNA4-EphA2) and/or internalize, along with the ability to kill cells is also provided.

sequence and its canonical structure. For the purposes of the analysis the assignment of amino acids to each of the CDR domains is in accordance with the Kabat et al. numbering. Several humanized antibody variants were made in order to generate the optimal humanized antibody with the humanized antibodies generally retaining the antigen-binding complementarity-determining regions (CDRs) from the mouse hybridoma in association with human framework regions. HuE15, huE22 and huE47 mAbs bound to EFNA4 antigen with similar affinity to their murine counterpart and huE5 bound with slightly lower affinity as measured using the Biacore system.

Molecular engineering procedures were conducted using art-recognized techniques. Total mRNA was extracted from the hybridomas according to the manufacturer's protocol (Trizol® Plus RNA Purification System, Life Technologies). A primer mix including thirty-two mouse specific 5' leader sequence primers, designed to target the complete mouse repertoire, was used in combination with 3' mouse Cγ1 primer to amplify and sequence the variable region of the antibody heavy chains. Similarly thirty-two 5' Vk leader sequence primer mix designed to amplify each of the Vk mouse families combined with a single reverse primer specific to the mouse kappa constant region were used to amplify and sequence the kappa light chain. The $V_H$ and $V_L$ transcripts were amplified from 100 ng total RNA using reverse transcriptase polymerase chain reaction (RT-PCR).

TABLE 3

| Clone | Bin | Affinity (nM) | Western Reactivity | Mouse XR | Cyno XR | Neutralizing | Internalizing | Killing |
|---|---|---|---|---|---|---|---|---|
| E2 | A | $20^F$ | NR | No | ND | No | Yes | Yes |
| E5 | B | $0.3^B$ | NR | Yes | Yes | No | Yes | Yes |
| E15 | B | $4.8^B$ | NR | Yes | Yes | ND | Yes | Yes |
| E22 | A | $3.1^B$ | NR/R | No | Yes | No | Yes | Yes |
| E31 | A | $11^B$ | NR | ND | ND | Yes | Yes | Yes |
| E47 | C | $<0.1^B$ | NR | No | Yes | Yes | Yes | Yes |
| E76 | A | $0.4^F$ | NR | ND | ND | No | Yes | ND |
| E91 | B | $0.2^B$ | NR/R | Yes | Yes | No | Yes | Yes |
| E105 | B | $16^F$ | ND | Yes | Yes | ND | Yes | Yes |

$^B$Biacore affinity;
$^F$ForteBIO in-house comparison;
ND: not determined

Example 2

Humanization of Anti-EFNA4 Antibodies

As further described in International Publication No. WO2012/118547, four of the murine antibodies from Example 1 were humanized using complementarity determining region (CDR) grafting. Human frameworks for heavy and light chains were selected based on sequence and structure similarity with respect to functional human germline genes. Structural similarity was evaluated by comparing the mouse canonical CDR structure to human candidates with the same canonical structures as described in Chothia et al. (supra).

More particularly murine antibodies E5, E15, E22 and E47 were humanized using a computer-aided CDR-grafting method (Abysis Database, UCL Business Plc.) and standard molecular engineering techniques to generate humanized antibodies E5, E15, E22 and E47, hereinafter huE5, huE15, huE22 and huE47, respectively. The human framework regions of the variable regions were selected based on their highest sequence homology to the mouse framework A total of eight RT-PCR reactions were run for each hybridoma: four for the V kappa light chain and four for the V gamma heavy chain (γ1). The QIAGEN One Step RT-PCR kit was used for amplification, (Qiagen, Inc.). The extracted PCR products were directly sequenced using specific V region primers. Nucleotide sequences were analyzed using IMGT to identify germline V, D and J gene members with the highest sequence homology. The derived sequences were compared to known germline DNA sequences of the Ig V- and J-regions derived from an analysis of the VBASE2 database (Retter et al., supra) and by alignment of $V_H$ and VL genes to the mouse germ line database.

From the nucleotide sequence information, data regarding V, D and J gene segments of the heavy and light chains of E5, E15, E22 and E47 were obtained. Based on the sequence data new primer sets specific to the leader sequence of the Ig $V_H$ and $V_K$ chain of the antibodies were designed for cloning of the recombinant monoclonal antibody. Subsequently the V-(D)-J sequences were aligned with mouse Ig germ line sequences.

Heavy chain and light chain genes of E5, E15, E22 and E47 were identified and the results are summarized in Table 4 below.

TABLE 4

| Clone | Mouse Isotype | VH | DH | JH | VL | JL |
|---|---|---|---|---|---|---|
| E5 | IgG1/K | IGHV2-6 | None | JH3 | IGKV6-15 | JK2 |
| E15 | IgG1/K | IGHV5-6 | DSP2.9 | JH3 | IGKV6-b | JK5 |
| E22 | IgG2b/K | VhJ558 | DFL16.1e | JH4 | IGKV1-110 | JK1 |
| E47 | IgG1/K | IGHV1-26 | P1inv | JH2 | IGKV21-7 | JK1 |

The obtained heavy and light chain sequences from all four clones were aligned to the functional human variable region sequences and reviewed for homology and canonical structure. The result the heavy and light chain analysis are shown below in Tables 5 and 6, respectively.

TABLE 5

| Clone | Human VH | Human DH | Human JH | % Homology to human germ line sequence | % Homology to mouse sequence |
|---|---|---|---|---|---|
| E5 | VH3-66 | IGHD2 | JH4 | 82 | 75 |
| E15 | VH3-21 | IGHD5-5 | JH4 | 88 | 88 |
| E22 | VH1-18 | IGHD5-24 | JH6 | 87 | 83 |
| E47 | VH1-46 | IGHD3-10 | JH4 | 91 | 76 |

TABLE 6

| Clone | Human VK | Human JK | % Homology to human germ line sequence | % Homology to mouse sequence |
|---|---|---|---|---|
| E5 | L1 | JK2 | 86 | 79 |
| E15 | A27 | JK4 | 89 | 76 |
| E22 | A18b | JK1 | 89 | 91 |
| E47 | L6 | JK4 | 87 | 84 |

The germ line selection and CDR grafting processes appeared to provide antibodies that generally retained their binding characteristics, there was little need to insert murine residues in most of the constructs. However, in huE15 the heavy chain residue 68 was back mutated from Thr (T) to Lys (K) to improve the antibody characteristics.

The amino acid sequences and associated nucleic acid sequence of huE5, huE15, huE22 and huE47 are shown above in Table 2 above. The amino acid sequences of the VH region for huE5, huE15, huE22 and huE47 are shown in SEQ ID NO: 5, SEQ ID NO: 9, SEQ ID NO: 13 and SEQ ID NO: 39 respectively, with the corresponding nucleic acid sequences set forth in SEQ ID NO: 6, SEQ ID NO: 10, SEQ ID NO: 14 and SEQ ID NO: 40. The amino acid sequence of the kappa VL region of huE5, huE15, huE22 and huE47 are shown in SEQ ID NO: 7, SEQ ID NO: 11, SEQ ID NO: 27 and SEQ ID NO: 53 respectively, with the corresponding nucleic acid sequences set forth in SEQ ID NO: 8, SEQ ID NO: 10, SEQ ID NO: 28 and SEQ ID NO: 54.

Example 3

Expression of Humanized Anti-EFNA4 Antibodies

The anti-EFNA4 antibodies huE5, huE15, huE22 and huE47 were expressed and isolated using art recognized techniques and described in International Publication No. WO2012/118547. To that end synthetic humanized variable DNA fragments (Integrated DNA Technologies) of both heavy chains were cloned into human IgG1 expression vector. The variable light chain fragments were cloned into human C-kappa expression vector. Antibodies were expressed by co-transfection of the heavy and the light chain into CHO cells.

More particularly, for antibody production, directional cloning of the murine and humanized variable gene PCR products into human immunoglobulin expression vectors was undertaken. All primers used in Ig gene-specific PCRs included restriction sites (AgeI and XhoI for IgH, XmaI and DraIII for IgK, which allowed direct cloning into expression vectors containing the human IgG1, and IGK constant regions, respectively. In brief, PCR products were purified with Qiaquick PCR purification kit (Qiagen, Inc.) followed by digestion with AgeI and XhoI (IgH), XmaI and DraIII (IgK), respectively. Digested PCR products were purified prior to ligation into expression vectors. Ligation reactions were performed in a total volume of 10 µL with 200 U T4-DNA Ligase (New England Biolabs), 7.5 µL of digested and purified gene-specific PCR product and 25 ng linearized vector DNA. Competent E. coli DH10B bacteria (Life Technologies) were transformed via heat shock at 42° C. with 3 µL ligation product and plated onto ampicillin plates (100 µg/mL). The AgeI-EcoRI fragment of the $V_H$ region was than inserted into the same sites of pEE6.4HuIgGI expression vector while the synthetic XmaI-DraIII Vκ insert was cloned into the XmaI-DraIII sites of—the respective pEE12.4Hu-Kappa expression vector.

Cells producing humanized antibodies were generated by transfection of HEK 293 cells with the appropriate plasmids using 293fectin. Plasmid DNA was purified with QIAprep Spin columns (Qiagen). Human embryonic kidney (HEK) 293T (ATCC No CRL-1 1268) cells were cultured in 150 mm plates (Falcon, Becton Dickinson) under standard conditions in Dulbecco's Modified Eagle's Medium (DMEM) supplemented with 10% heat inactivated FCS, 100 µg/mL streptomycin, 100 µg/mL penicillin G (all from Life Technologies).

For transient transfections, cells were grown to 80% confluency. Equal amounts of IgH and corresponding IgL chain vector DNA (12.5 µg of each vector DNA) was added to 1.5 mL Opti-MEM mixed with 50 µL HEK 293 transfection reagent in 1.5 mL opti-MEM. The mix was incubated for 30 min at room temperature and distributed evenly to the culture plate. Supernatants were harvested three days after transfection, replaced by 20 mL of fresh DMEM supplemented with 10% FBS and harvested again at day 6 after transfection. Culture supernatants were cleared from cell debris by centrifugation at 800×g for 10 min and stored at 4° C. Recombinant chimeric and humanized antibodies were purified with Protein G beads (GE Healthcare).

Example 4

Binding Properties of Anti-EFNA4 Antibodies

As described in International Publication No. WO2012/118547, binding characteristics of E15, E22 and E47 antibodies of the present invention are shown in Table 7.

TABLE 7

| Clone | Bin | mAb Isotype | Mouse Ag Affinity | Cyno Ag Binding | Hu Ag Affinity (Murine mAb) | Hu Ag Affinity (Humanized mAb) |
|---|---|---|---|---|---|---|
| E15 | B | chimHuIgG1 | 3.4 nM | + | 2.7 nM | 4.8 nM |
| E22 | A | msIgG2b | >100 nM | + | 3.1 nM | 3.8 nM |
| E47 | C | msIgG1 | >100 nM | + | <0.1 nM | <0.1 nM |

Figure 3B:
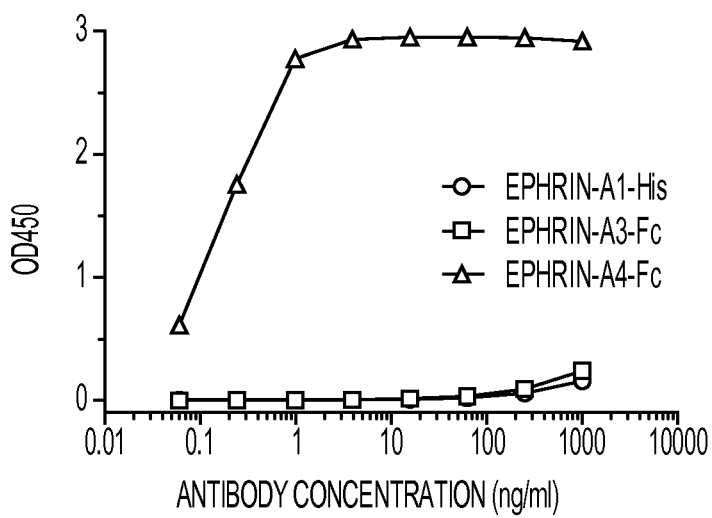

Further properties were determined using ELISA to analyze the binding specificity of anti-EFNA4 antibodies huE22 and huE47 to Ephrin-A4 (EFNA4) along with homologous family members Ephrin-A1 (EFNA1) and Ephrin-A3 (EFNA3). Antibody binding was determined by direct ELISA with Ephrin-A1-His, Ephrin-A3-huFc, Ephrin-A4-huFc and Ephrin-A5-huFc (all from R&D) coated on BioOne Microlon (Greiner) plates in PBS overnight at 4° C. Biotin-labeled huE22 and huE47 were incubated on the plate for 2.5 hours at room temperature and Streptavidin HRP was used to develop signal from biotin labeled antibody in the absence of interfering human IgG signal. The data shown in FIG. 3A demonstrates that huE22 binds to EFNA4 but not to EFNA1, EFNA3 or EFNA5. The data shown in FIG. 3B demonstrates that huE47 binds to EFNA4 but not EFNA1 or EFNA3.

Binding of humanized anti-EFNA4 antibodies huE22 and huE47 was assessed on EFNA4 expressing cells by flow cytometry. Adherent cells were dissociated using TrpLE Express (GIBCO cat #12604-021), neutralized with cell culture media and counted. Cells were plated into a U-bottom 96-well plate (BD Falcon cat #353077) with 5×10e5 cells/100 μL media/well. The plate was centrifuged at 300×g, 5 minutes, 4° C. to pellet cells and the supernatant was discarded. All reagents were kept on ice for the following steps. Each pellet was resuspended in 100 μL primary humanized anti-EFNA4 antibody (huE22 or huE47) or negative control antibody at 10 μg/mL in 3% BSA in PBS. The plate was incubated on ice for 30 minutes. The plate was centrifuged and the cell pellets were washed in 200 μL 3% BSA in PBS. Each cell pellet was resuspended in 100 μL of R-phycoerythrin (PE)-conjugated goat anti-human IgG Fc fragment (Jackson ImmunoResearch cat #109-115-098) that had been diluted 1:50 in 3% BSA in PBS. The plate was incubated on ice for 30 minutes. The plate was centrifuged and the cell pellets were washed in 200 μL 3% BSA in PBS. Each pellet was resuspended in 100 μL 3% BSA in PBS and transferred to a 5 mL polycarbonate tube (BD Falcon cat #352054) containing 250 μL 3% BSA in PBS. The samples were analyzed by flow cytometry using 5 μL 7AAD (B-D Pharmingen cat #51-68981E) per sample as a viability stain.

Antibody binding was measured in the manner described above for HEK293T parental cells, which express very low levels of EFNA4, and HEK293T-EFNA4 cells which are stable transfectants of HEK293T with a vector that enables high expression of human EFNA4. Table 8 shows mean channel fluorescence (MCF) of antibodies binding to EFNA4 expressing cell lines. The huE22 and huE47 antibodies demonstrate specificity for the EFNA4 target by strongly binding to the HEK293T-EFNA4 cells overexpressing cells but not to parental HEK293T cells.

TABLE 8

| Cell Line | Expression Level | Mean Channel Fluorescence (MCF) 10 μg/ml antibody | | |
|---|---|---|---|---|
| | | huE22 | huE47 | Non-binding control IgG |
| HEK293T parent | Low expression of EFNA4 | 7.2 | No data | 6.9 |
| HEK293T-EFNA4 | High expression of EFNA4 | 1521 | 576 | 3.3 |

Endogenous EFNA4 expressing cancer cell lines were analyzed: Breast cell lines BT-483, HCC202 and MX-1, Chronic Lymphocytic Leukemia (CLL) cell line MEC1 and mantle cell lymphoma (MCL) cell line Z138. The MCF values shown in Table 9 demonstrate the ability of anti-EFNA4 antibodies, huE22 and huE47, to bind various cancer cell lines with endogenous expression of the antigen.

TABLE 9

| Cell Line | Tumor type | Mean Channel Fluorescent (MCF) 10 μg/ml antibody | | |
|---|---|---|---|---|
| | | huE22 | huE47 | Non-binding control IgG |
| BT-483 | Breast | 17.7 | 24 | 3.1 |
| HCC202 | Breast | 13.2 | 21.9 | 15.6 |
| MX-1 | Breast | 12.8 | 21.1 | 3.6 |
| MEC1 | B-Chronic Lymphocytic Leukemia (B-CLL) | 24 | 33 | 7.2 |
| Z138 | Mantle Cell Lymphoma (MCL) | 44 | 44 | 7.4 |

Example 5

Internalization and In Vitro Cytotoxicity of Anti-EFNA4 Antibodies

The internalization of huE22 was assessed in a functional assay in which cells were incubated with the primary antibody and a secondary antibody (antigen-binding fragment, Fab) that is conjugated to the saporin toxin. Cells were seeded in 96-well plates, incubated overnight, and then exposed for four days to a dose response of huE22 or human IgG1 control antibody each with saporin-conjugated anti-human Fab fragment (Advanced Targeting Systems catalog number IT-51) at a molar ratio of 1.5:1 of secondary:primary antibodies. Cell viability was then measured with the MTS assay (Promega catalog number G5430) and the primary antibody concentration that inhibited cell viability by 50% ($IC_{50}$) relative to untreated cells was calculated by logistic non-linear regression on GraphPad Prism software.

Cytotoxicity is achieved when the primary antibody such as huE22 internalizes into the target cell and carries the saporin-conjugated Fab fragment into the cell. As shown in Table 10, huE22 conferred saporin-mediated cytotoxicity to HEK293T-EFNA4 cells with ~60-fold specificity over HEK293T parental cells, while the control primary antibody did not confer significant cytotoxicity to either cell line. Low levels of EFNA4 expressed in HEK293T-parental cells may have led to huE22 generating a lower $IC_{50}$ value than the control antibody. These results demonstrate that huE22 antibody internalized into the cells in a target-dependent manner.

TABLE 10

| | Saporin-mediated cytotoxicity | |
|---|---|---|
| | $IC_{50}$ Values (ng/mL) | |
| Cell Line | huE22 | Control IgG |
| HEK293T parent | 174 | 375 |
| HEK293T-EFNA4 | 3 | 360 |

Example 6

Conjugation and Purification
Anti-EFNA4-AcBut-CM Antibody-Drug Conjugates

A. Conjugation

Figure 4A:
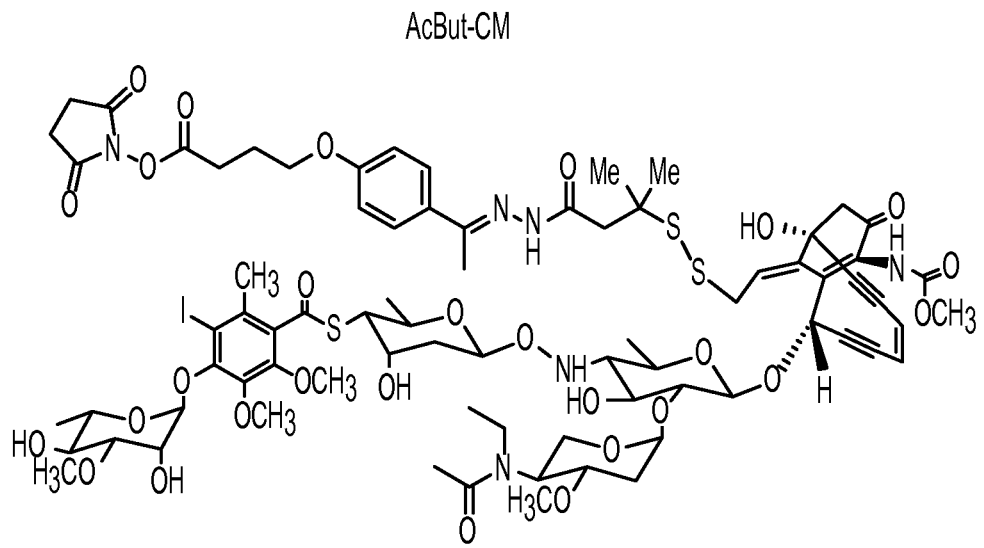
FIGS. 4A and 4B provide the structure of AcBut-CM and AcBut-CM conjugated to an antibody (X), respectively.
Figure 4B:
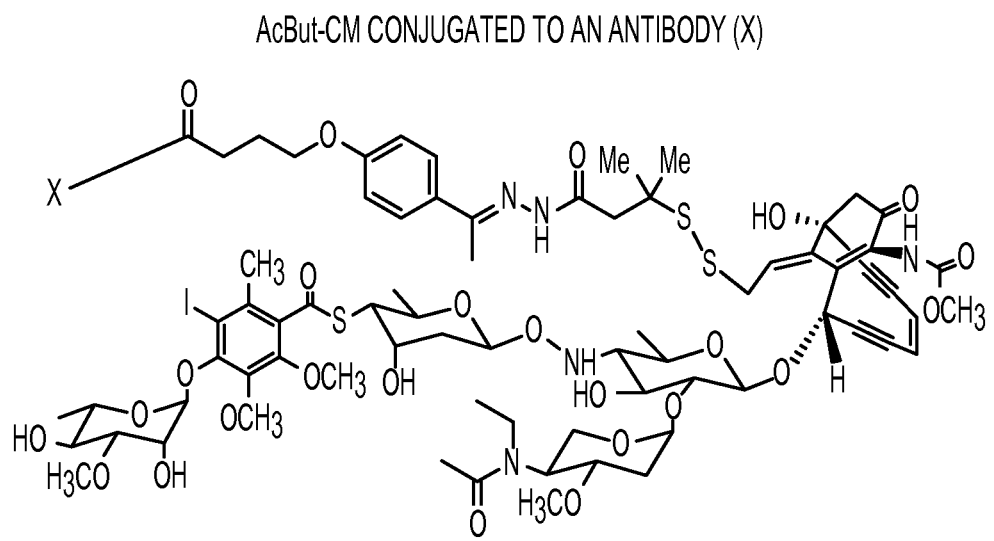

In the present invention, anti-EFNA4 antibodies huE22 and huE47 were conjugated to AcBut-N-acetyl-γ-calicheamicin dimethyl hydrazide (AcBut-CM) OSu ester, as shown in FIG. 4A, to generate huE22-AcBut-CM ADC and huE47-AcBut-CM ADC as shown in FIG. 4B, wherein X can be any antibody, such as huE22 and huE47. The AcBut-CM was conjugated to the anti-EFNA4 antibodies via lysine residues to produce anti-EFNA4-AcBut-CM ADCs having a narrow distribution of drug-to-antibody ratio (DAR), where about 70% to 80% of ADCs have a DAR between 3 and 5, and average DAR in the range of about 3 to 5.

The conjugation reaction mixture for the generation of huE22-AcBut-CM included 10 mg/ml or less of purified huE22 antibody and AcBut-CM OSu ester at a molar ratio of 4-4.5 to 1. High agitation was conducted during the addition of AcBut-CM to a mixing vortex. The reaction pH was 8.3 and the concentrations of other reaction components were as follows: 180 mM HEPES buffer, 41 mM sodium decanoate, and 8% (v/v) ethanol. The reaction was conducted at 33° C. for 5 minutes. After the conjugation reaction was completed, the reaction mixture was diluted slowly with 1.3 volumes of 1M $K_2HPO_4$ adjusted to pH 8.5 with mixing. A similar reaction mixture was used for the generation of huE47-AcBut-CM ADC.

B. Purification

Figure 5:
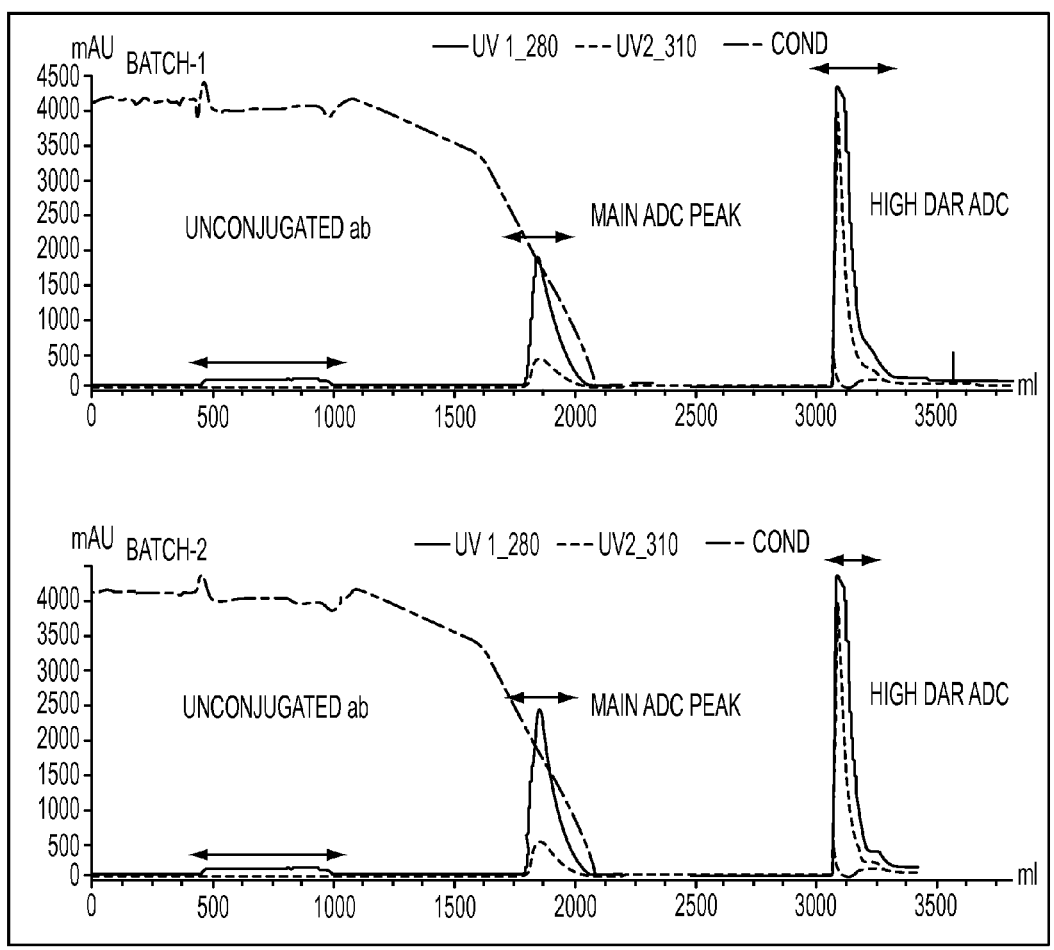
FIG. 5 provides the hydrophobic interaction chromatography (HIC) analysis of huE22-AcBut-CM.

To purify, the above diluted reaction mixture was loaded in two batches on a Butyl Sepharose-4 Fast Flow HIC column (GE Healthcare) that was previously equilibrated in five column volumes (cv) of 0.52M potassium phosphate buffer, pH 8.5, as shown in FIG. 5 (top line 280 nm and bottom line 310 nm). The protein loaded on the column was 3.5 mg/ml of bed volume. The flow rate was 15 ml/minute through the sample loading and 22 ml/minute throughout the wash and elution phase of the chromatography. This improved gradient removes higher DAR ADCs that were bound to the column.

The unbound fraction during the loading was predominantly reaction reagents and most of the unconjugated antibody, which was discarded. The column was then washed with 0.3 cv of 0.52M potassium phosphate buffer, pH 8.5, to remove any remaining reagents. A step gradient with 1 cv from 0.52M to 0.4M potassium phosphate buffer, pH 8.5 was then used to elute any loosely bound unconjugated antibody along with low loaded anti-EFNA4-AcBut-CM, if present. The main fraction was then eluted using a step gradient of 1 cv from 0.4M to 5 mM potassium phosphate buffer, pH 8.5, to provide huE22-AcBut-CM having a DAR from 3 to 5, toward the end of the gradient. If huE22-AcBut-CM conjugates with a higher DAR were present, the fraction was eluted using a gradient of 2 cv of 5 mM potassium phosphate buffer, pH 8.5, and then an elution of pure deionized water. Any huE22-AcBut-CM conjugates with a higher DAR that remained bound after the deionized water elution were eluted using 2 cv of 10 mM sodium hydroxide containing 20% ethanol.

Figure 9:
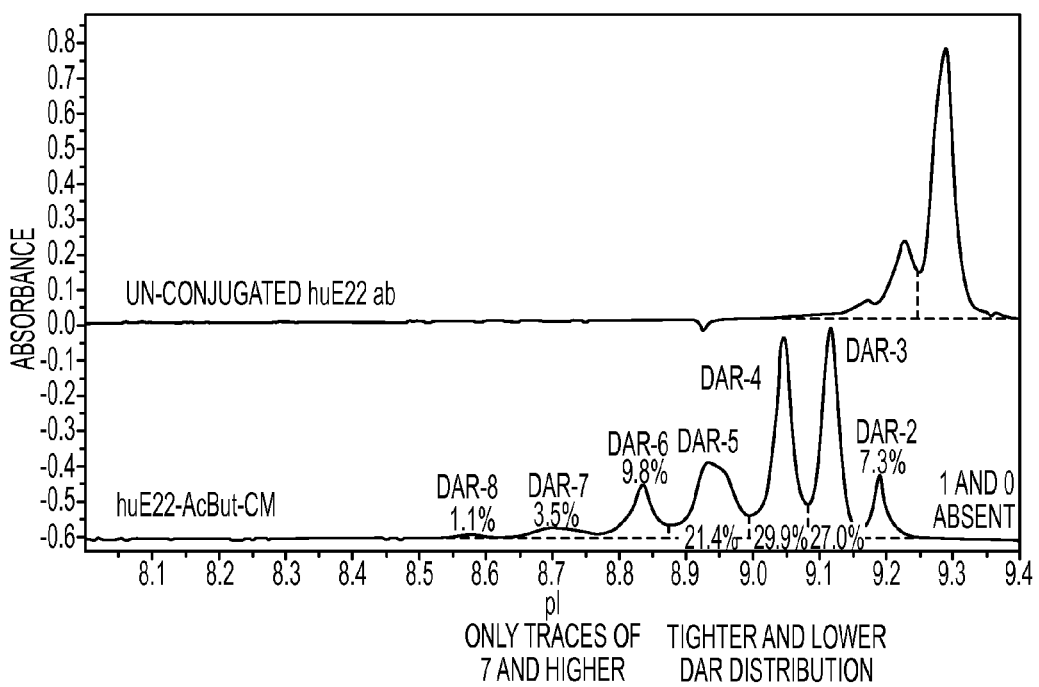
FIG. 9 provides a cIEF analysis of purified huE22-AcBut-CM on iCE280 for the DAR distribution profile.

Using capillary isoelectric focusing (cIEF; iCE280, ProteinSimple) purified batches of huE22-ActBut-CM ADCs had a narrow DAR distribution, where about 70% to 80%, preferably about 75% to 80%, of the ADCs had a DAR from 3 to 5. For example, FIG. 9 shows a purified batch of huE22-ActBut-CM ADCs had a narrow DAR distribution, where about 78% of the ADCs had a DAR from 3 to 5. The DAR is determined by UV spectroscopy, measuring absorbance at 280 nm and 310 nm.

Further, purified batches of huE22-ActBut-CM ADCs had an average DAR in the range of about 3 to about 5. For example, a purified batch of huE22-ActBut-CM ADCs had an average DAR of about 4, and more particularly the average DAR was about 4.6.

This improved conjugation and purification processes generated ADCs having a DAR that was less than 6, and in some aspects in the range of 3 to 5. Further, the processes generated a narrower distribution of loading, for example, less heterogeneity within the product. Improvements to the conjugation and purification processes further included: 1) decreasing the AcBut-CM to huE22 ratio to 4-4.5 to 1 to generate an ADC having a lower DAR, 2) conducting high agitation during addition of AcBut-CM to huE22 to generate ADCs with low amounts of unconjugated antibody (free antibody), 3) reducing incubation time to 2-5 minutes, compared to 60-90 minutes, to provide low aggregates and 4) a reduction in ethanol amount to 6-8% to provide low aggregates.

Figure 7:
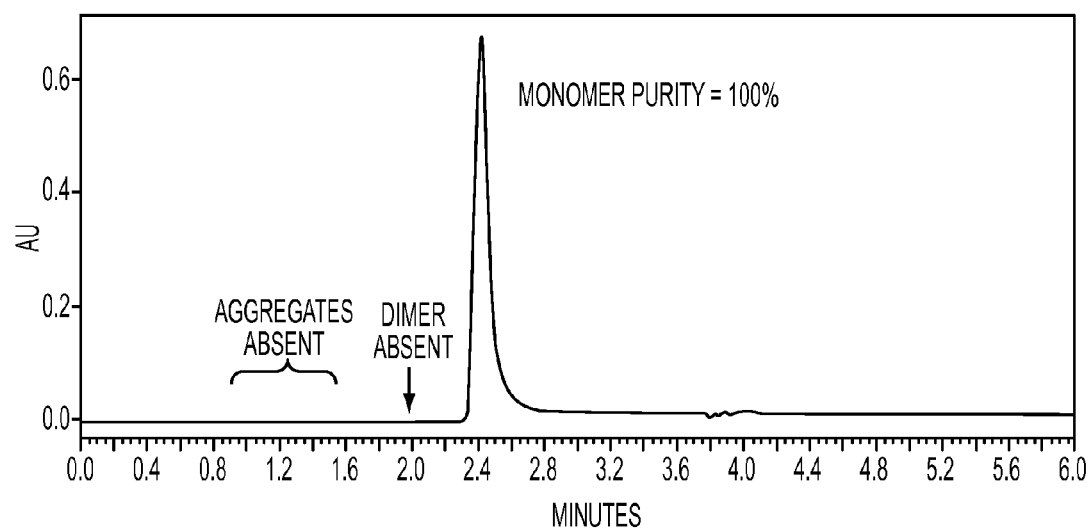
FIG. 7 provides an UPLC-SEC analysis of purified huE22-AcBut-CM on BEH200 SEC for the presence of aggregates and dimers.
Figure 8:
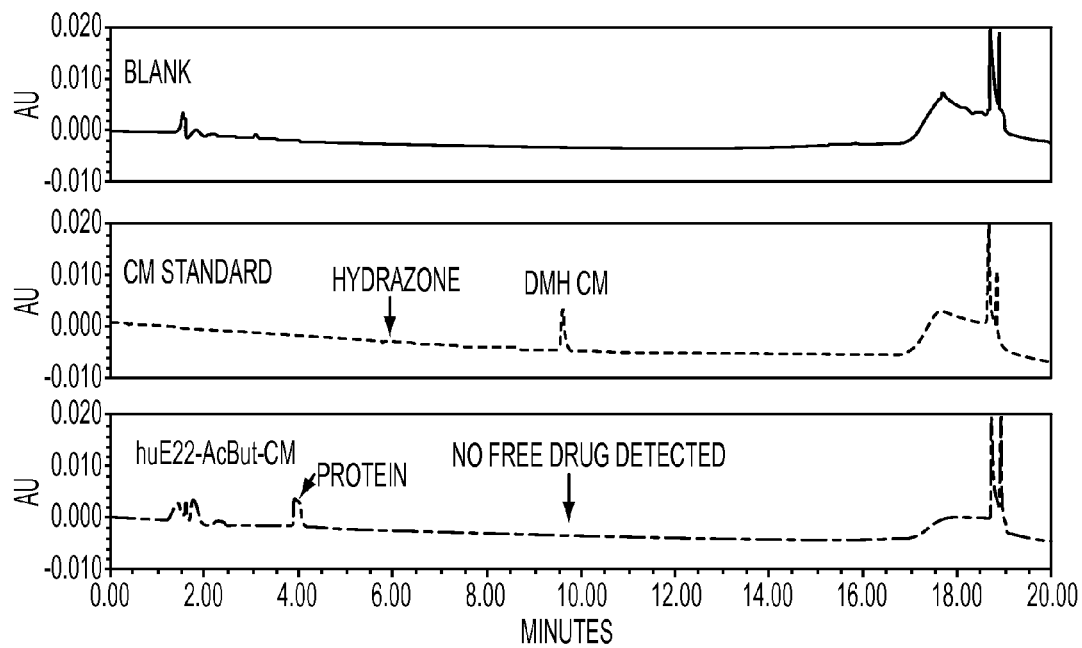
FIG. 8 provides a reverse phase analysis of purified huE22-AcBut-CM on Zorbax 300SB-CN for presence of free drug.

The purified pooled peaks from both batches were dialyzed twice against a formulated buffer to facilitate storage in a frozen state. The formulated buffer composition was 20 mM Tris, 7.5% sucrose, 0.01% polysorbate 80, 10 mM NaCl, pH 8.0. The purified huE22-AcBut-CM ADC was characterized using the following:

Hydrophobic interaction chromatography (HIC; TSKgel Butyl-NPR, Tosoh Bioscience, LLC) for the presence of unconjugated antibody, as shown in FIG. 6, no free antibody was detected in the purified huE22-AcBut-CM;

Size exclusion chromatography (SEC; Acquity UPLC BEH200 SEC, Waters) for presence of aggregates and dimer, as shown in FIG. 7, there was 100% monomer, no aggregate or dimer was detected;

Reverse phase high-performance liquid chromatography (HPLC-RP; Zorbax 300SB-CN, Agilent) for presence of free drug, as shown in FIG. 8, no free drug was detected in the purified huE22-AcBut-CM; and Capillary isoelectric focusing (cIEF; iCE280, ProteinSimple) for the drug distribution profile, as shown in FIG. 9, the desired narrow DAR distribution from 3 to 5 was about 78%, only traces of DAR 7 and higher species were present and DAR 1 and unconjugated (DAR 0) species were not detected.

Figure 10:
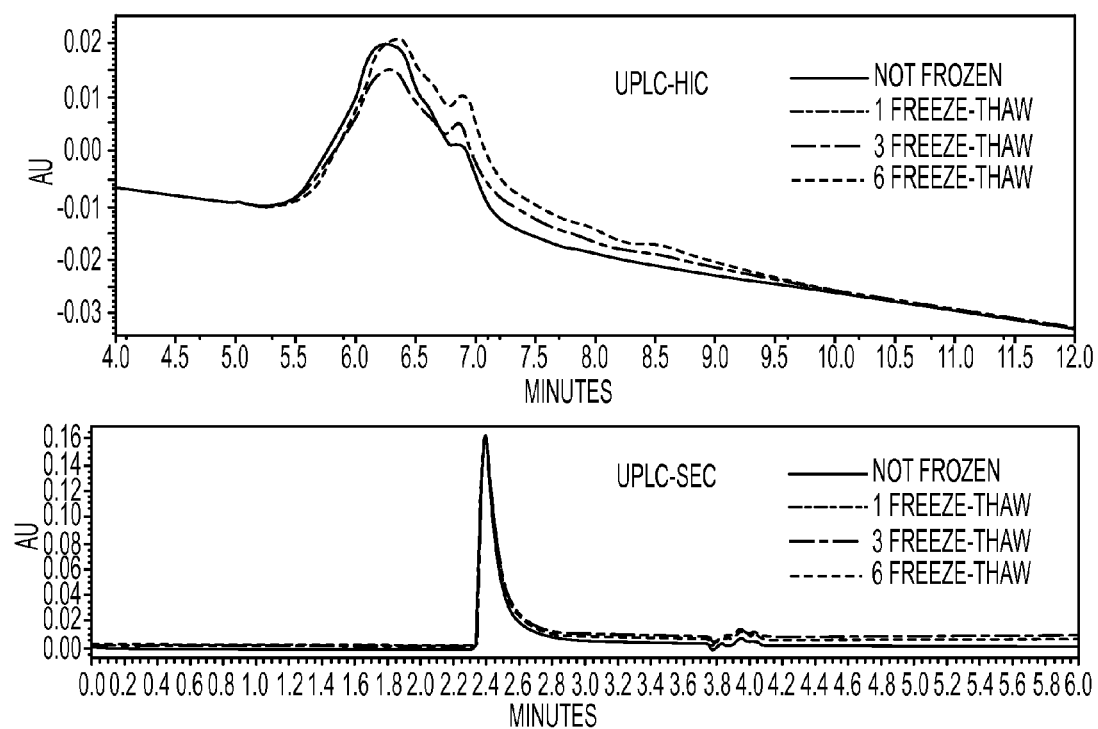
FIG. 10 provides the effect of multiple freeze-thaws on stability of huE22-AcBut-CM.

A similar purification process was used for the generation of huE47-AcBut-CM ADC. FIG. 10 and Table 11 below show the effect of freeze-thaw cycles on the stability of the purified huE22-AcBut-CM antibody-drug conjugate. No significant changes were observed on multiple freeze-thaws.

TABLE 11

| huE22-AcBut-CM Antibody-Drug Conjugate | | | |
|---|---|---|---|
| Conditions | % Free Antibody | % Monomer | Free Drug |
| T = 0 (not frozen) | 0.2 | 100 | n/a |
| Freeze Thaw (−70° C.) #1 | 0.1 | 100 | None detected |
| Freeze Thaw (−70° C.) #3 | 0.1 | 100 | None detected |
| Freeze Thaw (−70° C.) #6 | 0.1 | 100 | None detected |

Figure 29:
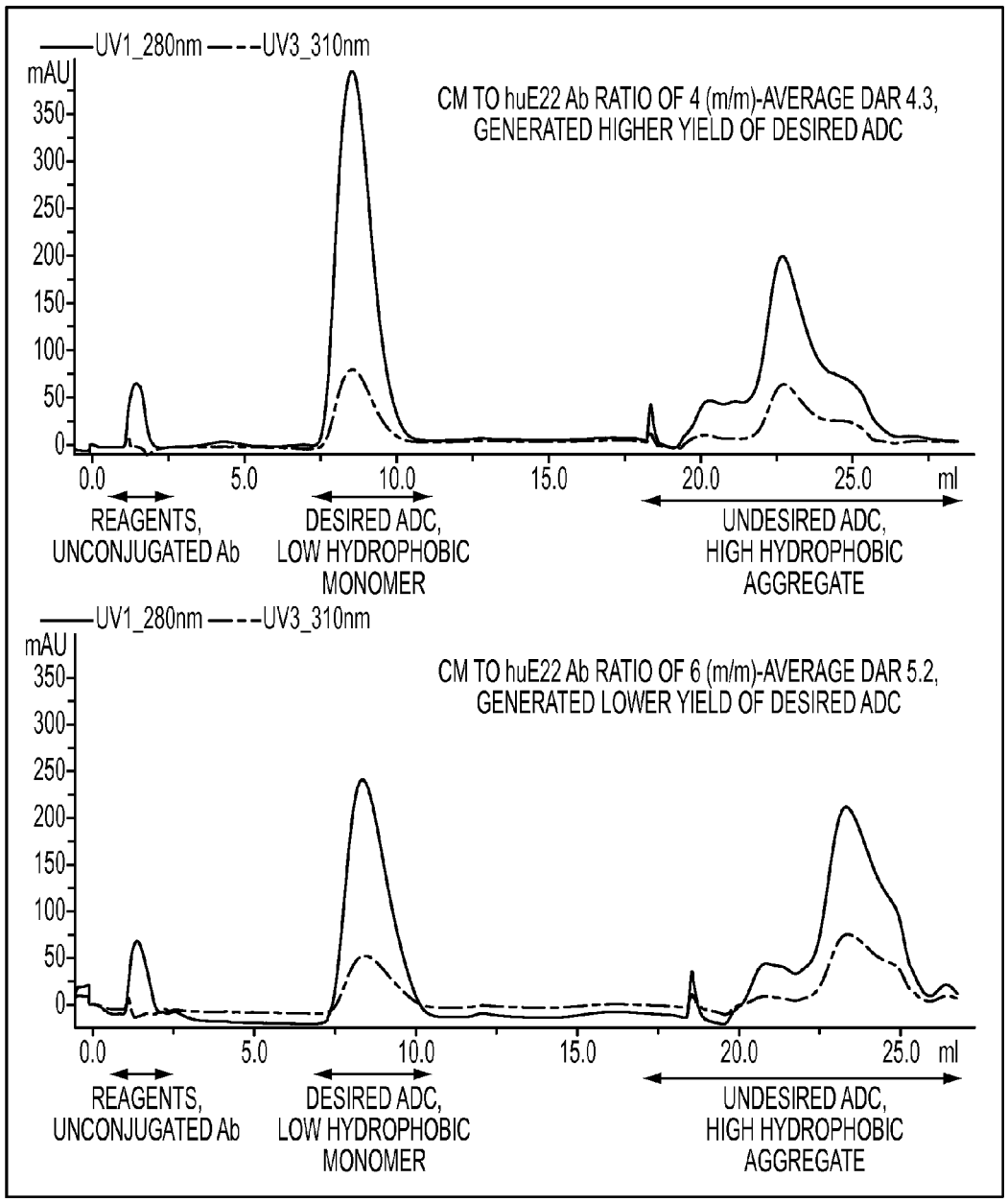
FIG. 29 shows a comparison of analytical HICs for purified huE22-AcBut-CM ADCs generated from a ratio of CM to huE22 Ab of 4 m/m and 6 m/m.

FIG. 29 shows a comparison of analytical HICs for purified ADC (2 mg) generated from a ratio of CM to huE22 Ab of 4 m/m and 6 m/m (top line 280 nm and bottom line 310 nm). The CM to huE22 Ab ratio of 4 m/m generated ADCs having an average DAR of 4.3 (top panel) and the CM to huE22 Ab ratio of 6 m/m generated ADCs having an average DAR of 5.2 (bottom panel). The ADCs generated using 4 m/m had a higher yield of desired ADCs, characterized as low hydrophobic monomers, and a lower yield of undesired ADCs, characterized as highly hydrophobic aggregates. FIG. 30 shows a further analytical HIC for purified ADCs generated from a ratio of CM to huE22 Ab of 4 m/m (top line) and 6 m/m (bottom line). In particular, the ADCs generated using 6 m/m (5.2 DAR preparation) had an increased presence of highly hydrophobic species and aggregation, which was lower in the 4 m/m (4.3 DAR preparation) generated ADCs.

Example 7

In Vitro Binding and Cytotoxicity of Anti-EFNA4-AcBut-CM ADCs

A. Binding Assays

The binding constants of huE22 for human and cynomolgus monkey EFNA4 proteins were determined by surface plasmon resonance (SPR) using BIAcore 2000 (GE Healthcare) using recombinant EFNA4 extracellular domain that was fused to a histidine tag to facilitate purification. The results indicated high affinity of huE22 for both human and cynomolgus monkey EFNA4, see Table 12. The cynomolgus monkey EFNA4 protein sequence is highly homologous to human EFNA4 protein sequence, with 98% identity overall and 98% identity in the extracellular domain. In contrast, no huE22 binding to rat antigen was detected, and in separate studies no binding to mouse antigen was detected. The lack of huE22 binding to rat or mouse EFNA4 is likely explained by a non-conserved residue in the rat and mouse EFNA4 sequences within the defined huE22 epitope.

The binding constants of huE22-AcBut-CM ADC for human and cynomolgus monkey EFNA4 were determined in the same binding study as huE22. As shown in Table 12, the ADC and unconjugated mAb (huE22) had comparable binding constants to both human and cynomolgus monkey antigen.

TABLE 12

Binding constants of huE22 mAb and huE22-AcBut-CM ADC.

|  | Antigen Species | kon (M-1s-1) | koff (s-1) | Kd (nM) |
|---|---|---|---|---|
| huE22 mAb | Human | 1.9E+06 | 3.3E−03 | 1.7 |
|  | Cynomolgus monkey | 3.8E+06 | 7.8E−03 | 2.1 |
|  | Rat | No binding detected at 400 nM antigen | | |
| huE22-AcBut-CM ADC | Human | 2.6E+06 | 6.1E−03 | 2.3 |
|  | Cynomolgus monkey | 4.2E+06 | 1.1E−02 | 2.7 |
|  | Rat | No binding detected at 400 nM antigen | | |

Cell binding and internalization of huE22 and huE22-AcBut-CM ADC were analyzed. Parental HEK293T cells (EFNA4 negative) and HEK293T-EFNA4 (engineered to express high levels of human EFNA4) were used. huE22 and huE22-AcBut-CM ADC demonstrated specific binding to cells that expressed the EFNA4 antigen. Further, the unconjugated huE22 and the huE22-AcBut-CM ADC exhibited comparable binding to HEK293T-EFNA4 cells, and neither antibody bound to parental HEK293T cells, see Table 13. Together with the SPR results in Table 12 (above), these data indicate that the bioconjugation process did not alter the binding characteristics of huE22.

B. Cytotoxicity Assay

Figure 21:
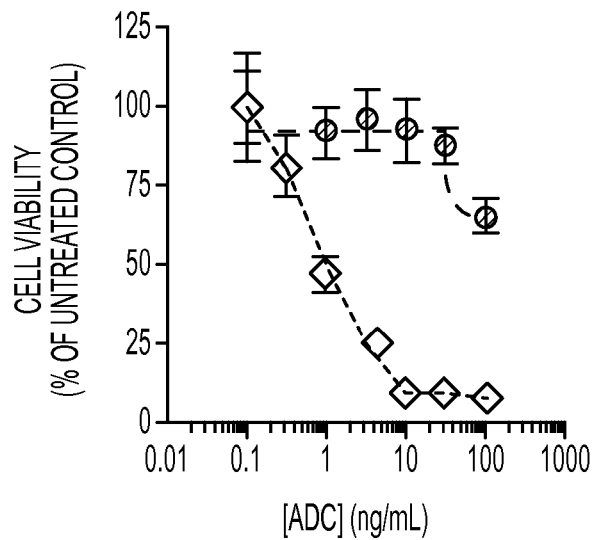
FIG. 21 shows the in vitro cytotoxicity of huE22-AcBut-CM in EFNA4-expressing 293T cells (open diamonds) versus control-AcBut-CM ADC (diagonal-hatched circles).

Once the huE22-AcBut-CM ADC is internalized into the cell, the release of calicheamicin elicits cytotoxicity. Internalizing antibodies typically traffic to the lysosomal compartment for degradation. A direct cytotoxicity assay was used to analyze cytotoxic response of huE22-AcBut-CM. HEK293T-EFNA4 overexpressing cells and the HEK293T parental (EFNA4 negative) cells were plated into a clear flat-bottom tissue culture plate (BD Falcon cat #353072) at 500 cells per 180 μL of cell culture media per well. The cells were incubated overnight at 37° C. in a 5% CO2 incubator. On the following day the huE22-AcBut-CM and the negative non-binding control hIgG1-AcBut-CM ADC were added to the cells as a 10 point concentration curve starting with 1 μg/mL with half-log dilutions in cell culture media in triplicate. The plate was incubated in a 37° C., 5% CO2 incubator for 96 hours. Cell viability was then measured with the MTS assay (Promega CellTiter 96 Aqueous Non-Radioactive Cell Proliferation Assay cat #G5430) according to the manufacturer's instructions. 40 μL of the combined MTS reagent was added to each well. The plate was incubated in a 37° C., 5% CO2 incubator for 1.5 hours. The concentration that inhibited cell viability by 50% ($IC_{50}$) relative to untreated cells was calculated by logistic non-linear regression on GraphPad Prism software, as show in Table 14. FIG. 21 shows HEK293T-EFNA4 cells exposed to various concentrations of huE22-AcBut-CM (open diamonds) or hIgG-AcBut control ADC (diagonal-hatched circles), and cell viability was measured and normalized to that of the untreated cells.

As shown in Table 14 and FIG. 21, huE22-AcBut-CM elicited a dose-dependent cytotoxic response in vitro against EFNA4 target-expressing cells and inhibited cell growth in a target- and concentration dependent manner. When HEK293T-EFNA4 cells were exposed to huE22-AcBut-CM, a concentration of 1 ng/mL ADC inhibited cell growth by 50% ($IC_{50}$), in contrast, the control ADC was >150-fold less active. The data demonstrates the potent and specific cytotoxic activity of huE22-AcBut-CM. The control ADC and huE22-AcBut-CM ADC did not elicit cytotoxicity against HEK293T parental cells that lack EFNA4 expression, which demonstrated specificity and antigen dependence.

TABLE 13

Cell binding of huE22 and huE22-AcBut-CM ADC.

|  |  | Concentration | | | |
|---|---|---|---|---|---|
| Cell Line | Test Article | 0.3 μg/mL | 1.0 μg/mL | 3.0 μg/mL | 10.0 μg/mL |
| HEK293T parental | huE22-AcBut-CM ADC | 6.8 | 6.1 | 8.2 | 13.4 |
|  | huE22 mAb | 8.3 | 6.8 | 6.1 | 14.5 |
| HEK293T-EFNA4 | huE22-AcBut-CM ADC | 446 | 621 | 728 | 863 |
|  | huE22 mAb | 446 | 606 | 739 | 856 |

TABLE 14

Anti-EFNA4-AcBut-CM Cytotoxicity

| Cell Line | IC$_{50}$ Values (ng/mL) | |
|---|---|---|
| | huE22-AcBut-CM | Control-AcBut-CM |
| HEK293T parental | 650 | 100 |
| HEK293T-EFNA4 | 1 | 157 |

Example 8

In Vivo Efficacy of Anti-EFNA4 Antibody-Drug Conjugates

The effects of anti-EFNA4 huE22-AcBut-CM and huE47-AcBut-CM, prepared according the conjugation and purification processes described in Example 6, were further evaluated on the in vivo growth of human tumor patient-derived xenografts (PDX). Primary tumor resection samples were procured from clinical sites following Institutional Review Board for the Protection of Human Subjects approval and in accordance with HIPAA regulations.

The expression of the target EFNA4 in each model was measured in two ways: reverse transcriptase polymerase chain reaction (RT-PCR) using mRNA extracts and ELISA using protein extracts. Table 15 shows the normalized mRNA and protein levels of EFNA4 in the panel of tumor models. EFNA4 was detected in all models tested, in other words both measurements exceeded those from the tumor model MDA-MB-231.

TABLE 15

| Type Tumor | Tumor Model | EFNA4 RT-PCR (normalized signal) | EFNA4 ELISA (ng EFNA4/ mg protein) |
|---|---|---|---|
| Breast cancer (TNBC) | BR5 | 1.58 | 1.80 |
| | BR13 | 0.45 | 1.00 |
| | BR22 | 1.01 | 1.91 |
| | BR31 | 0.48 | 1.02 |
| | 144580A1 | 3.86 | 1.74 |
| | MDA-MB-231 | 0.19 | 0.25 |
| Ovarian cancer | OV44 | 2.10 | 1.39 |
| | OV45 | 3.39 | 3.64 |
| | OV55 | 1.45 | 0.42 |
| | OV63 | 2.40 | 0.49 |
| Lung | LU86 | 0.85 | 0.45 |
| | LU80 | ND | ND |
| Colorectal | CR5 | ND | ND |

ND = Not Determined.

Tumor fragments were stored and shipped in Hypothermasol (Biolife Solutions) on ice and were embedded in Matrigel (BD) containing a proprietary mix of growth factors and implanted subcutaneously into the mammary fatpad of female NOD/SCID mice within 24 hours of resection. Mice were monitored for health status daily and for tumor growth initially by visual inspection twice per week. Once the tumors were palpable, measurements of tumor volume began to track tumor growth and estimate cell doubling time. Tumor volume was estimated using the equation $V=(A*B^2)/2$ where A is the long axis and B is the short axis. When tumor reached a volume of 500 mm$^3$ to 1,500 mm$^3$, they were harvested for study and for re-transplant. Depending on the line, mechanical and/or chemical dissociation can be used to separate the individual cells for passaging. Live cells were inoculated into naïve animals with 10,000 to 50,000 cells per animals.

For efficacy studies, tumors were harvested from passaging studies and cells were dissociated into single cell suspension. Preparations were counted for live cells using Trypan blue exclusion and 10,000 to 50,000 cells were inoculated per mouse in Matrigel. To account for differential growth rates of PDX, at least 25% more animals were started to allow for minimal tumor volume variance at randomization. Tumor growth was initially followed by palpability with measurements beginning once tumor volumes reached about 30 mm$^3$. Studies were randomized based on tumor size once a cohort of tumor-bearing mice reached 140-180 mm$^3$; groups ranged from 6-10 mice. Animals were dosed by intraperitoneal injection twice a week for two weeks (Q4dx4) with ADC at various dose levels, once a week for two weeks (Q7dx2) with doxorubicin at 1.5 mg/kg (maximum tolerated dose) or once a week for two weeks with cisplatin at 5 mg/kg. Study groups were followed until individual mice or entire group tumor measurements reached 1200 mm$^3$ when sacrifice was indicated in accordance with IACUC protocol. For selected dosing studies, pharmacokinetic submandibular bleeds were performed at 2 or 6 hours, 36 hours and 72 hours. A volume of 10 µL of blood was immediately pipetted into 90 µL of HBS-P (GE Healthcare). Samples were stored at −80 C prior to analysis. For each tumor measurement the tumor volume±standard error of the mean (SEM) is provided. GT=Group Terminated due to large tumor size. ND=Not enough animals remaining to make significant measurement with SEM. All studies included a PBS vehicle and a control antibody-drug conjugate having a non-binding hIgG1 antibody conjugated to the same linker-payload being analyzed and with comparable drug-to-antibody ratio (DAR) and DAR distribution.

A. Breast Cancer

Tables 16-20 and FIGS. 11-14 provide data which demonstrate the efficacy of huE22-AcBut-CM and huE47-AcBut-CM in various triple-negative breast cancer (TNBC) PDX tumor models. The results obtained were unexpected because huE22-AcBut-CM demonstrated superior efficacy in all TNBC PDX models compared to the treatment with doxorubicin standard-of-care (SOC) which has a similar mechanism of action to calicheamicin (DNA damaging agent).

Figure 11:
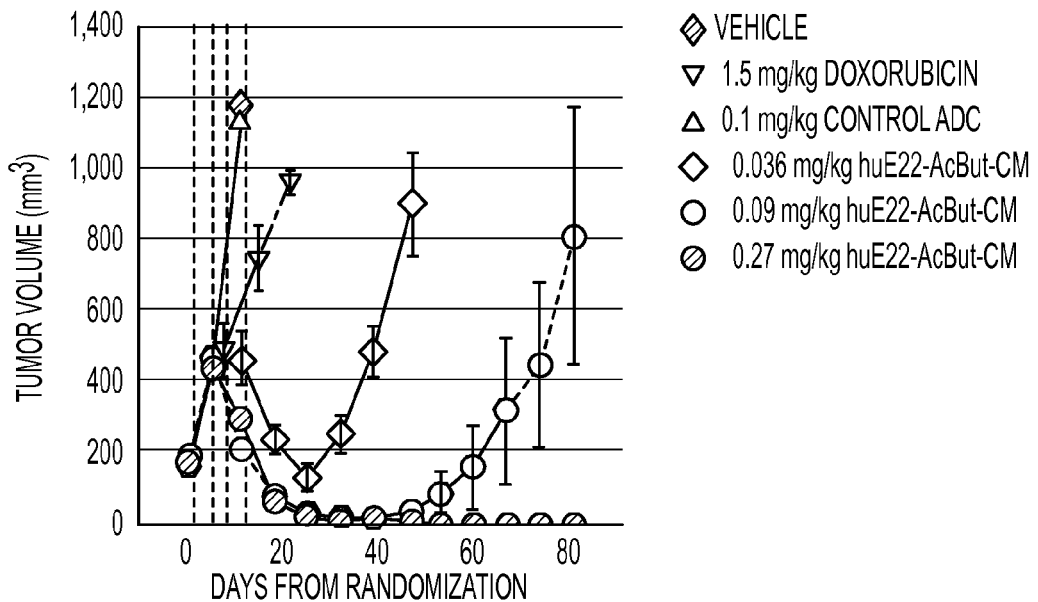
FIG. 11 shows the efficacy of huE22-AcBut-CM in the Breast-5 (BR5) triple-negative breast cancer (TNBC) PDX.

Table 16 and FIG. 11 show the efficacy of huE22-AcBut-CM in the Breast-5 (BR5) triple-negative breast cancer (TNBC) PDX. Sustained regressions for more than 80 days were achieved with 0.27 mg/kg huE22-AcBut-CM, and dose levels as low as 0.036 mg/kg elicited anti-tumor activity. In contrast, neither the control ADC nor doxorubicin standard-of-care (SOC) impacted tumor growth.

TABLE 16

Efficacy of huE22-AcBut-CM in BR5 TNBC PDX

| Day | Vehicle | Doxorubicin | 0.1 mg/kg Control-AcBut-CM | 0.036 mg/kg huE22-AcBut-CM | 0.09 mg/kg huE22-AcBut-CM | 0.27 mg/kg huE22-AcBut-CM |
|---|---|---|---|---|---|---|
| 0 | 178 ± 18 | 166 ± 18 | 191 ± 41 | 173 ± 24 | 161 ± 21 | 174 ± 23 |
| 7 | 468 ± 87 | 494 ± 70 | 472 ± 31 | 461 ± 36 | 441 ± 57 | 428 ± 46 |

TABLE 16-continued

Efficacy of huE22-AcBut-CM in BR5 TNBC PDX

| Day | Vehicle | Doxorubicin | 0.1 mg/kg Control-AcBut-CM | 0.036 mg/kg huE22-AcBut-CM | 0.09 mg/kg huE22-AcBut-CM | 0.27 mg/kg huE22-AcBut-CM |
|---|---|---|---|---|---|---|
| 11 | 1138 ± 41 | 752 ± 92 | 1176 ± 9 | 467 ± 75 | 209 ± 42 | 290 ± 42 |
| 18 | GT | 966 ± 32 | GT | 239 ± 40 | 83 ± 25 | 69 ± 7 |
| 25 | GT | GT | GT | 137 ± 27 | 30 ± 8 | 34 ± 6 |
| 32 | GT | GT | GT | 254 ± 53 | 15 ± 10 | 3 ± 3 |
| 39 | GT | GT | GT | 485 ± 73 | 14 ± 9 | 0 ± 0 |
| 47 | GT | GT | GT | 903 ± 145 | 32 ± 25 | 0 ± 0 |
| 53 | GT | GT | GT | GT | 82 ± 66 | 0 ± 0 |
| 60 | GT | GT | GT | GT | 159 ± 118 | 0 ± 0 |
| 67 | GT | GT | GT | GT | 318 ± 209 | 0 ± 0 |
| 74 | GT | GT | GT | GT | 452 ± 234 | 0 ± 0 |
| 81 | GT | GT | GT | GT | 811 ± 362 | 0 ± 0 |
| 89 | GT | GT | GT | GT | GT | 0 ± 0 |
| 95 | GT | GT | GT | GT | GT | 0 ± 0 |
| 102 | GT | GT | GT | GT | GT | 0 ± 0 |
| 109 | GT | GT | GT | GT | GT | 0 ± 0 |
| 116 | GT | GT | GT | GT | GT | 0 ± 0 |
| 123 | GT | GT | GT | GT | GT | 0 ± 0 |
| 130 | GT | GT | GT | GT | GT | 0 ± 0 |
| 137 | GT | GT | GT | GT | GT | 0 ± 0 |
| 144 | GT | GT | GT | GT | GT | 0 ± 0 |
| 152 | GT | GT | GT | GT | GT | 0 ± 0 |
| 155 | GT | GT | GT | GT | GT | 0 ± 0 |
| 168 | GT | GT | GT | GT | GT | 0 ± 0 |
| 172 | GT | GT | GT | GT | GT | 0 ± 0 |

Figure 12:
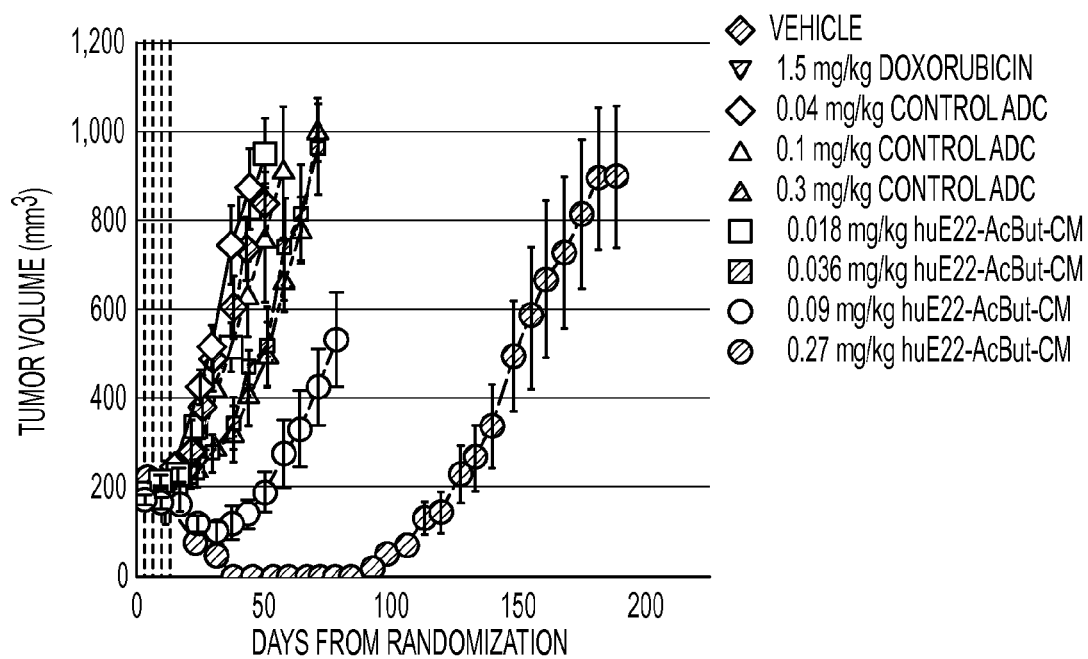
FIG. 12 shows the efficacy of huE22-AcBut-CM in the Breast-13 (BR13) TNBC PDX.

Table 17 and FIG. 12 show the efficacy of huE22-AcBut-CM and huE47-AcBut-CM in the Breast-13 (BR13) TNBC PDX. For huE22-AcBut-CM, the 0.27 mg/kg dose level produced regressions for 90 days after which the tumors regrew. Further, the 0.09 mg/kg dose level delayed tumor growth for ~40 days. In contrast, neither the control ADC nor doxorubicin SOC impacted tumor growth.

Figure 13:
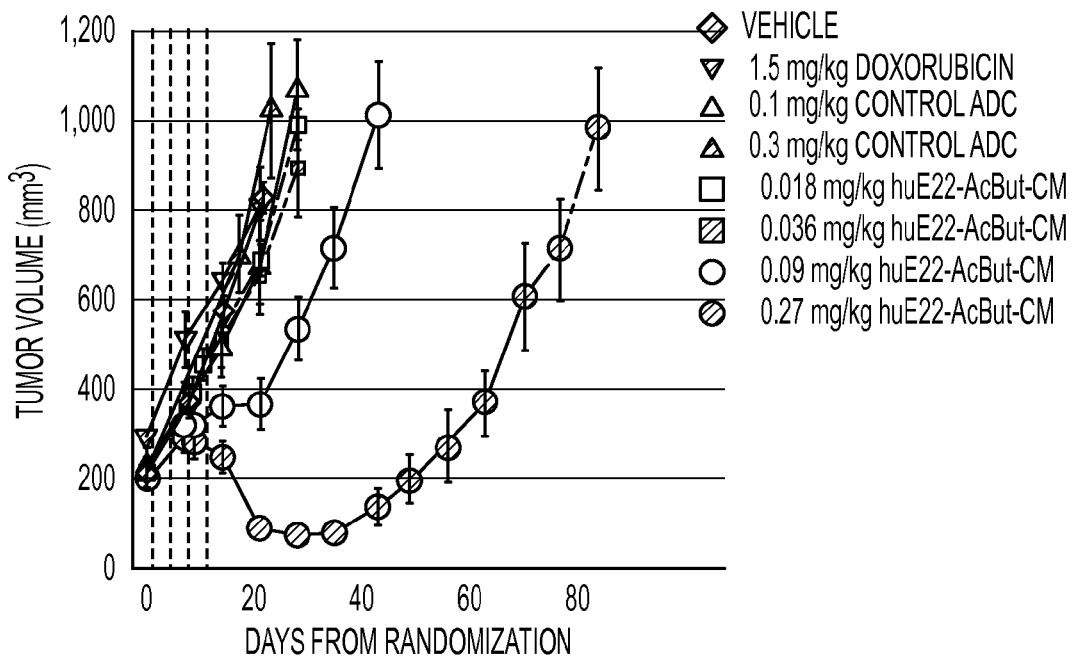
FIG. 13 shows the efficacy of huE22-AcBut-CM in the Breast-22 (BR22) PDX.

Table 18 and FIG. 13 show the efficacy of huE22-AcBut-CM and huE47-AcBut-CM in the Breast-22 (BR22) PDX, a less sensitive tumor model of TNBC. For huE22-AcBut-CM, the 0.27 mg/kg dose level delayed tumor growth for ~40 days but did not produce any complete regressions. Further, dose levels below 0.27 mg/kg had minimal effect. Neither the control ADC nor doxorubicin SOC impacted tumor growth.

TABLE 17

Efficacy of huE22-AcBut-CM and huE47-AcBut-CM in BR13 TNBC PDX

| Day | Vehicle | Doxorubicin | 0.3 mg/kg Control-AcBut-CM | 0.036 mg/kg huE22-AcBut-CM | 0.09 mg/kg huE22-AcBut-CM | 0.27 mg/kg huE22-AcBut-CM | 0.1 mg/kg huE47-AcBut-CM | 0.3 mg/kg huE47-AcBut-CM |
|---|---|---|---|---|---|---|---|---|
| 0 | 161 ± 15 | 167 ± 13 | 154 ± 11 | 156 ± 13 | 156 ± 10 | 155 ± 14 | 19 ± 25 | 172 ± 26 |
| 7 | 180 ± 15 | 178 ± 20 | 171 ± 20 | 176 ± 20 | 145 ± 14 | 144 ± 15 | 251 ± 42 | 242 ± 37 |
| 14 | 239 ± 27 | 227 ± 25 | 183 ± 12 | 184 ± 24 | 156 ± 21 | 91 ± 14 | 261 ± 42 | 238 ± 38 |
| 22 | 382 ± 52 | 322 ± 38 | 237 ± 24 | 232 ± 32 | 112 ± 20 | 35 ± 5 | 264 ± 47 | 92 ± 18 |
| 28 | 484 ± 72 | 326 ± 34 | 287 ± 28 | 279 ± 47 | 98 ± 23 | 17 ± 4 | 439 ± 86 | 34 ± 7 |
| 36 | 600 ± 98 | GT | 315 ± 30 | 341 ± 42 | 116 ± 32 | 4 ± 1 | 509 ± 105 | 41 ± 21 |
| 42 | 735 ± 106 | GT | 402 ± 19 | 471 ± 68 | 138 ± 34 | 3 ± 1 | 546 ± 121 | 46 ± 15 |
| 49 | 841 ± 106 | GT | 493 ± 38 | 516 ± 91 | 188 ± 46 | 1 ± 1 | 698 ± 144 | 79 ± 27 |
| 56 | GT | GT | 659 ± 41 | 738 ± 109 | 274 ± 75 | 6 ± 2 | 713 ± 132 | 155 ± 57 |
| 63 | GT | GT | 779 ± 33 | 814 ± 110 | 328 ± 86 | 7 ± 3 | 960 ± 192 | 135 ± 51 |
| 70 | GT | GT | 991 ± 71 | 959 ± 103 | 425 ± 93 | 13 ± 4 | GT | 167 ± 56 |
| 77 | GT | GT | GT | GT | 531 ± 116 | 13 ± 7 | GT | 132 ± 46 |
| 84 | GT | GT | GT | GT | 667 ± 133 | 30 ± 13 | GT | 151 ± 50 |
| 91 | GT | GT | GT | GT | 830 ± 146 | 40 ± 15 | GT | 198 ± 62 |
| 98 | GT | GT | GT | GT | GT | 79 ± 33 | GT | 559 ± 186 |
| 105 | GT | GT | GT | GT | GT | 99 ± 36 | GT | 788 ± 257 |
| 112 | GT | GT | GT | GT | GT | 147 ± 53 | GT | 744 ± 217 |
| 119 | GT | GT | GT | GT | GT | 198 ± 65 | GT | 1030 ± 349 |
| 126 | GT | GT | GT | GT | GT | 290 ± 97 | GT | GT |
| 133 | GT | GT | GT | GT | GT | 332 ± 113 | GT | GT |
| 140 | GT | GT | GT | GT | GT | 522 ± 156 | GT | GT |
| 144 | GT | GT | GT | GT | GT | 573 ± 144 | GT | GT |
| 150 | GT | GT | GT | GT | GT | 709 ± 248 | GT | GT |

TABLE 18

Efficacy of huE22-AcBut-CM and huE47-AcBut-CM in BR22 TNBC PDX

| Day | Vehicle | Doxorubicin | 0.1 mg/kg Control-AcBut-CM | 0.036 mg/kg huE22-AcBut-CM | 0.09 mg/kg huE22-AcBut-CM | 0.27 mg/kg huE22-AcBut-CM | 0.3 mg/kg huE47-AcBut-CM |
|---|---|---|---|---|---|---|---|
| 0 | 195 ± 17 | 244 ± 17 | 208 ± 23 | 207 ± 17 | 217 ± 17 | 202 ± 16 | 194 ± 17 |
| 7 | 376 ± 43 | 416 ± 61 | 354 ± 35 | 358 ± 41 | 324 ± 52 | 292 ± 32 | 438 ± 36 |
| 9 | 401 ± 42 | — | 376 ± 23 | 366 ± 37 | 319 ± 63 | 281 ± 28 | 522 ± 48 |
| 14 | 564 ± 54 | 553 ± 39 | 494 ± 24 | 511 ± 60 | 364 ± 45 | 248 ± 31 | 468 ± 58 |
| 21 | 819 ± 97 | 729 ± 91 | 677 ± 52 | 649 ± 83 | 368 ± 58 | 92 ± 15 | 557 ± 80 |
| 28 | GT | GT | 1054 ± 122 | 891 ± 106 | 535 ± 70 | 77 ± 21 | 855 ± 112 |
| 35 | GT | GT | GT | GT | 715 ± 90 | 81 ± 24 | 1145 ± 165 |
| 43 | GT | GT | GT | GT | 1007 ± 115 | 140 ± 41 | GT |
| 49 | GT | GT | GT | GT | GT | 199 ± 53 | GT |
| 56 | GT | GT | GT | GT | GT | 274 ± 78 | GT |
| 63 | GT | GT | GT | GT | GT | 370 ± 73 | GT |
| 70 | GT | GT | GT | GT | GT | 605 ± 120 | GT |
| 77 | GT | GT | GT | GT | GT | 711 ± 110 | GT |
| 84 | GT | GT | GT | GT | GT | 981 ± 135 | GT |

FIG. 19 shows the efficacy of huE15, huE22 and huE47 conjugated to various microtubule inhibitors (MTIs) in the BR22PDX, such as vc0101 and mc8261. The data demonstrates that the MTI ADCs did not significantly impact tumor growth. Therefore, it was unexpected that huE22-AcBut-CM and huE47-AcBut-CM demonstrated increased efficacy in the same BR22 PDX model.

Figure 14:
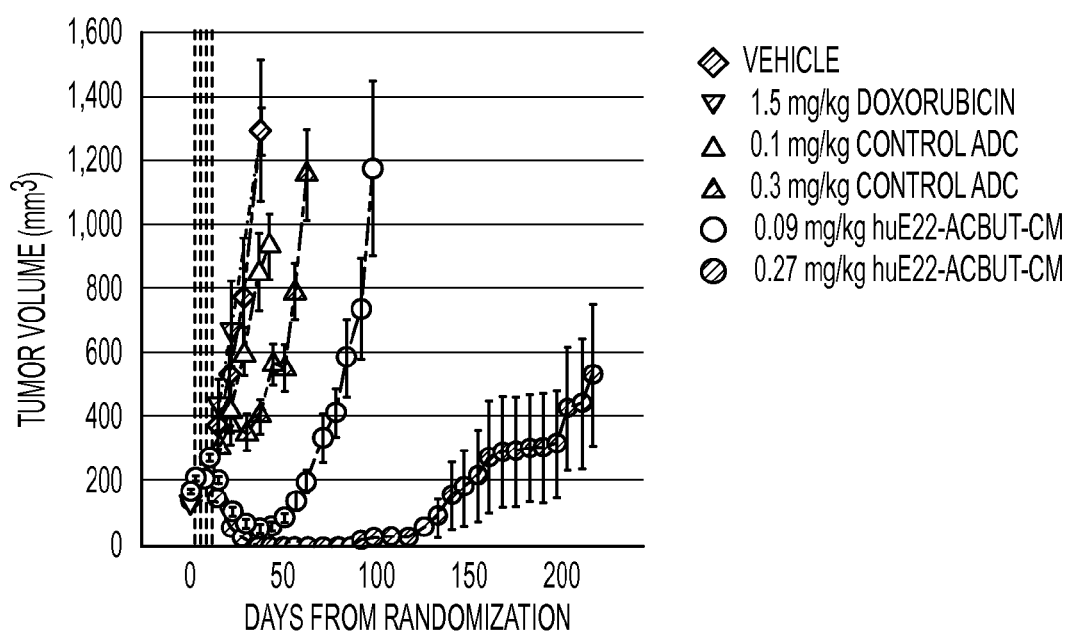
FIG. 14 shows the efficacy of huE22-AcBut-CM in the Breast-31 (BR31) TNBC PDX.

Table 19 and FIG. 14 show the efficacy of huE22-AcBut-CM in the Breast-31 (BR31) TNBC PDX. The 0.27 mg/kg dose level produced regressions for ~120 days, after which the tumors regrew in some animals. The 0.09 mg/kg dose level regressed tumors for ~50 days, after which the tumors regrew. In contrast, neither the control ADC nor doxorubicin SOC impacted tumor growth.

TABLE 19

Efficacy of huE22-AcBut-CM in BR31 TNBC PDX

| Day | Vehicle | Doxorubicin | 0.3 mg/kg Control-AcBut-CM | 0.09 mg/kg huE22-AcBut-CM | 0.27 mg/kg huE22-AcBut-CM | 0.1 mg/kg huE47-AcBut-CM | 0.3 mg/kg huE47-AcBut-CM |
|---|---|---|---|---|---|---|---|
| 0 | 159 ± 10 | 160 ± 11 | 163 ± 23 | 165 ± 6 | 149 ± 13 | 163 ± 6 | 147 ± 15 |
| 7 | 269 ± 17 | 304 ± 20 | 305 ± 42 | 277 ± 18 | 137 ± 11 | 283 ± 26 | 239 ± 27 |
| 14 | 425 ± 32 | 458 ± 24 | 307 ± 53 | 201 ± 11 | 59 ± 8 | 269 ± 29 | 141 ± 17 |
| 21 | 668 ± 50 | 592 ± 56 | 377 ± 58 | 103 ± 12 | 30 ± 9 | 127 ± 11 | 44 ± 11 |
| 28 | 1088 ± 93 | 759 ± 111 | 356 ± 52 | 64 ± 4 | 11 ± 7 | 126 ± 16 | 22 ± 8 |
| 36 | GT | GT | 405 ± 52 | 60 ± 11 | 17 ± 9 | 179 ± 20 | 4 ± 4 |
| 44 | GT | GT | 569 ± 64 | 57 ± 15 | 0 ± 0 | 213 ± 33 | 6 ± 6 |
| 49 | GT | GT | 557 ± 73 | 82 ± 19 | 0 ± 0 | 373 ± 39 | 11 ± 7 |
| 56 | GT | GT | 795 ± 88 | 132 ± 32 | 0 ± 0 | 750 ± 76 | 5 ± 5 |
| 63 | GT | GT | 1160 ± 142 | 206 ± 44 | 0 ± 0 | GT | 9 ± 9 |
| 71 | GT | GT | GT | 338 ± 73 | 0 ± 0 | GT | 27 ± 27 |
| 78 | GT | GT | GT | 414 ± 74 | 0 ± 0 | GT | 75 ± 64 |
| 85 | GT | GT | GT | 589 ± 121 | 12 ± 8 | GT | 63 ± 56 |
| 91 | GT | GT | GT | 741 ± 157 | 20 ± 13 | GT | 117 ± 107 |
| 98 | GT | GT | GT | 1178 ± 271 | 26 ± 17 | GT | 154 ± 137 |
| 105 | GT | GT | GT | GT | 32 ± 21 | GT | 165 ± 147 |
| 112 | GT | GT | GT | GT | 29 ± 20 | GT | 205 ± 181 |
| 119 | GT | GT | GT | GT | 58 ± 39 | GT | 210 ± 180 |
| 126 | GT | GT | GT | GT | 88 ± 58 | GT | 267 ± 209 |
| 133 | GT | GT | GT | GT | 159 ± 103 | GT | 286 ± 211 |
| 141 | GT | GT | GT | GT | 181 ± 118 | GT | 286 ± 211 |
| 147 | GT | GT | GT | GT | 219 ± 142 | GT | 286 ± 211 |
| 154 | GT | GT | GT | GT | 279 ± 176 | GT | 428 ± 302 |
| 161 | GT | GT | GT | GT | 293 ± 172 | GT | 571 ± 376 |
| 168 | GT | GT | GT | GT | 293 ± 172 | GT | 571 ± 376 |
| 175 | GT | GT | GT | GT | 306 ± 170 | GT | GT |
| 182 | GT | GT | GT | GT | 308 ± 169 | GT | GT |
| 189 | GT | GT | GT | GT | 317 ± 168 | GT | GT |
| 197 | GT | GT | GT | GT | 429 ± 192 | GT | GT |
| 204 | GT | GT | GT | GT | 445 ± 200 | GT | GT |

FIG. 20 shows the efficacy of huE15, huE22 and huE47 conjugated to the MTI vc0101 in the BR31 PDX. The data demonstrates that the MTI ADCs did not significantly impact tumor growth. Therefore, it was unexpected that huE22-AcBut-CM and huE47-AcBut-CM demonstrated increased efficacy in the same BR22 PDX model.

Table 20 shows the efficacy of huE22-AcBut-CM in the Breast-56 (BR56) TNBC PDX. In contrast, neither the control ADC nor doxorubicin SOC impacted tumor growth.

TABLE 20

Efficacy of huE22-AcBut-CM in BR56 TNBC PDX

| Day | Vehicle | Doxorubicin | 0.1 mg/kg Control-AcBut-CM | 0.036 mg/kg huE22-AcBut-CM | 0.09 mg/kg huE22-AcBut-CM | 0.27 mg/kg huE22-AcBut-CM |
|---|---|---|---|---|---|---|
| 0 | 144 ± 9 | 141 ± 13 | 140 ± 11 | 143 ± 13 | 148 ± 14 | 141 ± 12 |
| 4 | 179 ± 15 | 182 ± 11 | 181 ± 12 | 154 ± 13 | 150 ± 10 | 151 ± 14 |
| 11 | 271 ± 33 | 267 ± 31 | 270 ± 26 | 268 ± 42 | 268 ± 32 | 170 ± 21 |
| 18 | 373 ± 33 | 318 ± 32 | 408 ± 34 | 298 ± 55 | 251 ± 25 | 90 ± 10 |
| 25 | 727 ± 863 | 374 ± 50 | 644 ± 49 | 424 ± 89 | 286 ± 39 | 42 ± 13 |
| 33 | 1010 ± 88 | GT | 913 ± 84 | 431 ± 98 | 291 ± 45 | 14 ± 4 |
| 40 | GT | GT | GT | 591 ± 120 | 341 ± 47 | 0 ± 0 |
| 47 | GT | GT | GT | 635 ± 116 | 442 ± 66 | 0 ± 0 |
| 54 | GT | GT | GT | 780 ± 125 | 635 ± 94 | 11 ± 8 |
| 60 | GT | GT | GT | 896 ± 132 | 816 ± 64 | 48 ± 17 |
| 67 | GT | GT | GT | GT | GT | 75 ± 29 |
| 74 | GT | GT | GT | GT | GT | 155 ± 51 |
| 81 | GT | GT | GT | GT | GT | 207 ± 56 |
| 88 | GT | GT | GT | GT | GT | 270 ± 78 |
| 95 | GT | GT | GT | GT | GT | 363 ± 100 |
| 102 | GT | GT | GT | GT | GT | 530 ± 143 |
| 109 | GT | GT | GT | GT | GT | 714 ± 198 |

B. Ovarian Cancer

Figure 15:
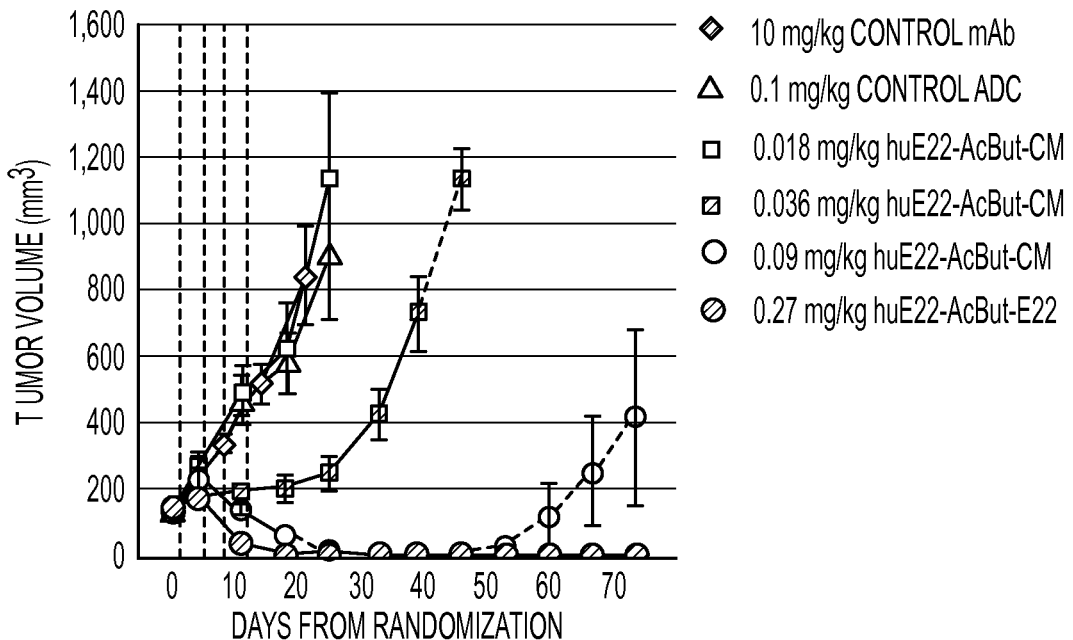
FIG. 15 shows the efficacy of huE22-AcBut-CM in the Ovarian-45 (OV45) ovarian cancer PDX.

Table 21 and FIG. 15 show the efficacy of huE22-AcBut-CM in the Ovarian-45 (OV45) ovarian cancer PDX. Sustained regressions for more than 75 days were achieved with 0.27 mg/kg. Regressions were also achieved at the 0.09 mg/kg dose level, with tumor regrowth in some animals after 50 days. The 0.036 dose level delayed tumor growth for ~25 days. In contrast the control ADC did not impact tumor growth.

TABLE 21

Efficacy of huE22-AcBut-CM in OV45 Ovarian Cancer PDX

| Day | 10 mg/kg Mouse IgG1 | 0.1 mg/kg Control-AcBut-CM | 0.036 mg/kg huE22-AcBut-CM | 0.09 mg/kg huE22-AcBut-CM | 0.27 mg/kg huE22-AcBut-CM |
|---|---|---|---|---|---|
| 0 | 157 ± 16 | 142 ± 14 | 141 ± 14 | 145 ± 15 | 153 ± 20 |
| 3 | — | 239 ± 35 | 178 ± 5 | 240 ± 41 | 177 ± 39 |
| 8 | 329 ± 32 | 470 ± 77 | 198 ± 17 | 147 ± 23 | 35 ± 5 |
| 14 | 516 ± 57 | 590 ± 101 | 206 ± 34 | 60 ± 16 | 4 ± 2 |
| 21 | 843 ± 151 | 906 ± 194 | 251 ± 53 | 15 ± 1 | 0 ± 0 |
| 33 | GT | GT | 429 ± 79 | 0 ± 0 | 0 ± 0 |
| 39 | GT | GT | 733 ± 111 | 0 ± 0 | 0 ± 0 |
| 46 | GT | GT | 1140 ± 92 | 0 ± 0 | 0 ± 0 |
| 53 | GT | GT | GT | 30 ± 30 | 0 ± 0 |
| 60 | GT | GT | GT | 118 ± 99 | 0 ± 0 |
| 67 | GT | GT | GT | 256 ± 165 | 0 ± 0 |
| 74 | GT | GT | GT | 423 ± 257 | 0 ± 0 |
| 81 | GT | GT | GT | 443 ± 252 | 0 ± 0 |
| 88 | GT | GT | GT | 743 ± 256 | 0 ± 0 |
| 96 | GT | GT | GT | 1576 ± 208 | 0 ± 0 |
| 102 | GT | GT | GT | GT | 0 ± 0 |
| 109 | GT | GT | GT | GT | 0 ± 0 |
| 116 | GT | GT | GT | GT | 0 ± 0 |
| 123 | GT | GT | GT | GT | 0 ± 0 |
| 131 | GT | GT | GT | GT | 0 ± 0 |
| 137 | GT | GT | GT | GT | 0 ± 0 |
| 141 | GT | GT | GT | GT | 0 ± 0 |
| 158 | GT | GT | GT | GT | 0 ± 0 |
| 166 | GT | GT | GT | GT | 0 ± 0 |

Figure 16:
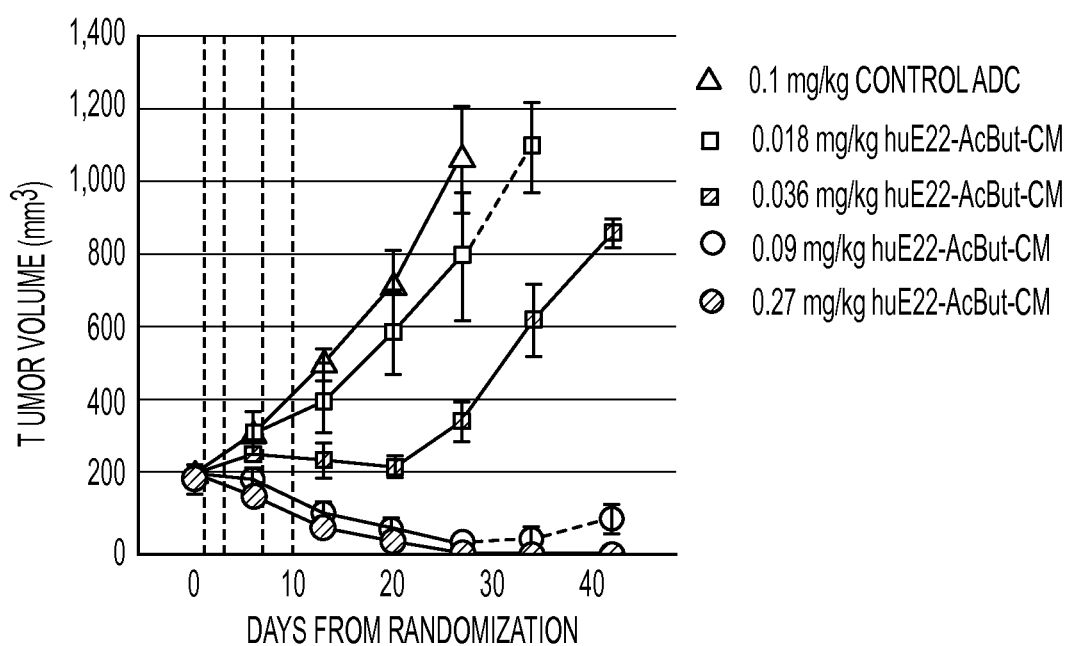
FIG. 16 shows the efficacy of huE22-AcBut-CM in the Ovarian-55 (OV55) ovarian cancer PDX.

Table 22 and FIG. 16 show the efficacy of huE22-AcBut-CM in the Ovarian-55 (OV55) ovarian cancer PDX. Tumor regressions were achieved at the 0.27 and 0.09 mg/kg dose levels, with the 0.036 dose level producing some delay in tumor growth. The control ADC did not impact tumor growth.

TABLE 22

Efficacy of huE22-AcBut-CM in OV55 Ovarian Cancer PDX

| Day | Vehicle | 0.1 mg/kg Control-AcBut-CM | 0.036 mg/kg huE22-AcBut-CM | 0.09 mg/kg huE22-AcBut-CM | 0.27 mg/kg huE22-AcBut-CM |
|---|---|---|---|---|---|
| 0 | 206 ± 41 | 216 ± 31 | 211 ± 28 | 208 ± 24 | 204 ± 28 |
| 6 | 317 ± 42 | 325 ± 57 | 262 ± 36 | 198 ± 33 | 152 ± 18 |
| 13 | 508 ± 45 | 412 ± 92 | 250 ± 46 | 109 ± 27 | 66 ± 13 |
| 20 | 717 ± 102 | 595 ± 111 | 232 ± 29 | 63 ± 14 | 35 ± 9 |
| 27 | 1064 ± 144 | 799 ± 173 | 355 ± 55 | 30 ± 9 | 5 ± 4 |
| 34 | GT | 1097 ± 123 | 630 ± 93 | 37 ± 13 | 0 ± 0 |
| 42 | GT | GT | 863 ± 41 | 94 ± 37 | 0 ± 0 |
| 48 | GT | GT | GT | 171 ± 62 | 0 ± 0 |
| 55 | GT | GT | GT | 382 ± 142 | 0 ± 0 |
| 62 | GT | GT | GT | 579 ± 209 | 4 ± 4 |
| 69 | GT | GT | GT | 980 ± 405 | 7 ± 7 |
| 76 | GT | GT | GT | GT | 11 ± 11 |
| 83 | GT | GT | GT | GT | 24 ± 24 |

TABLE 22-continued

Efficacy of huE22-AcBut-CM in OV55 Ovarian Cancer PDX

| Day | Vehicle | 0.1 mg/kg Control-AcBut-CM | 0.036 mg/kg huE22-AcBut-CM | 0.09 mg/kg huE22-AcBut-CM | 0.27 mg/kg huE22-AcBut-CM |
|---|---|---|---|---|---|
| 90 | GT | GT | GT | GT | 35 ± 35 |
| 97 | GT | GT | GT | GT | 78 ± 78 |
| 105 | GT | GT | GT | GT | 107 ± 107 |
| 108 | GT | GT | GT | GT | 99 ± 99 |
| 121 | GT | GT | GT | GT | 157 ± 157 |
| 125 | GT | GT | GT | GT | 253 ± 253 |
| 132 | GT | GT | GT | GT | 253 ± 253 |

Figure 17:
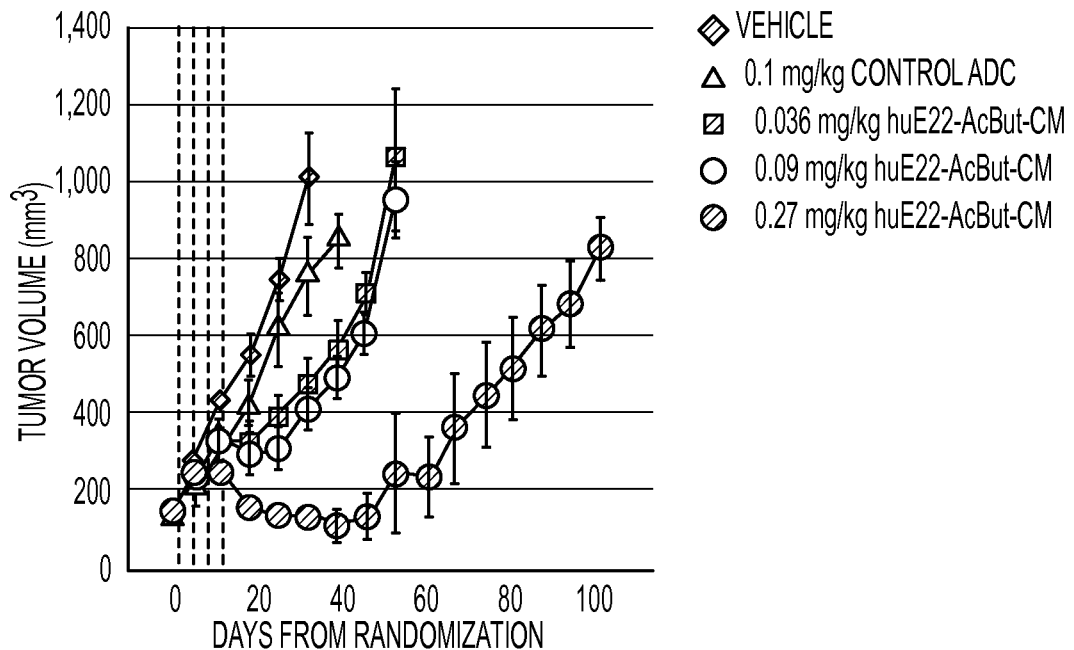
FIG. 17 shows the efficacy of huE22-AcBut-CM in the Ovarian-44 (OV44) ovarian cancer PDX.

Table 23 and FIG. 17 show the efficacy of huE22-AcBut-CM in the Ovarian-44 (OV44) ovarian cancer PDX, a less sensitive tumor model of ovarian cancer. The 0.27 mg/kg dose level delayed tumor growth for ~50 days but did not regress the tumors. Dose levels below 0.27 mg/kg had minimal effect. The control ADC did not impact tumor growth.

TABLE 23

Efficacy of huE22-AcBut-CM in OV44 Ovarian Cancer PDX

| Day | Vehicle | 0.1 mg/kg Control-AcBut-CM | 0.036 mg/kg huE22-AcBut-CM | 0.09 mg/kg huE22-AcBut-CM | 0.27 mg/kg huE22-AcBut-CM |
|---|---|---|---|---|---|
| 0 | 141 ± 14 | 138 ± 18 | 140 ± 9 | 148 ± 16 | 152 ± 17 |
| 5 | 286 ± 58 | 215 ± 30 | 269 ± 33 | 236 ± 20 | 249 ± 35 |
| 11 | 442 ± 27 | 347 ± 59 | 331 ± 45 | 328 ± 39 | 250 ± 30 |
| 18 | 555 ± 14 | 417 ± 72 | 328 ± 53 | 299 ± 29 | 162 ± 24 |
| 25 | 747 ± 35 | 621 ± 94 | 397 ± 59 | 313 ± 39 | 142 ± 21 |
| 32 | 1010 ± 120 | 760 ± 104 | 478 ± 69 | 414 ± 50 | 137 ± 33 |
| 39 | GT | 851 ± 68 | 567 ± 79 | 497 ± 44 | 114 ± 43 |
| 46 | GT | GT | 708 ± 61 | 610 ± 28 | 140 ± 59 |
| 53 | GT | GT | 1060 ± 182 | 957 ± 99 | 249 ± 152 |
| 61 | GT | GT | GT | GT | 242 ± 102 |
| 67 | GT | GT | GT | GT | 367 ± 143 |
| 74 | GT | GT | GT | GT | 452 ± 140 |
| 81 | GT | GT | GT | GT | 521 ± 130 |
| 88 | GT | GT | GT | GT | 619 ± 120 |
| 95 | GT | GT | GT | GT | 686 ± 111 |
| 102 | GT | GT | GT | GT | 830 ± 82 |

Figure 18:
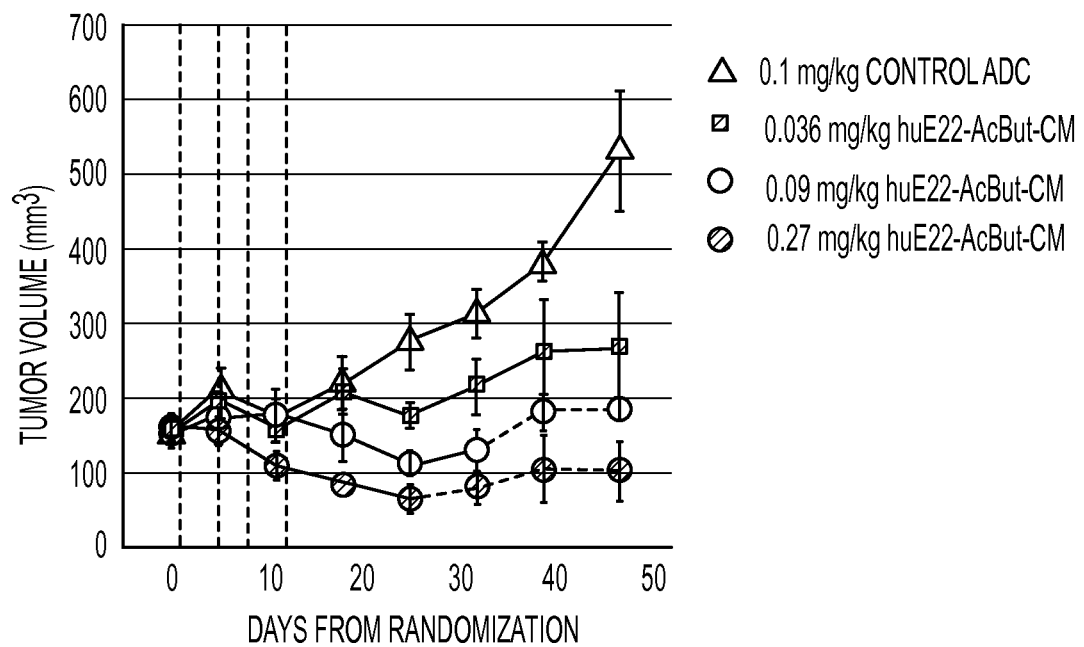
FIG. 18 shows the efficacy of huE22-AcBut-CM in the Ovarian-63 (OV63) ovarian cancer PDX.

Table 24 and FIG. 18 show the efficacy of huE22-AcBut-CM in the Ovarian-63 (OV63) ovarian cancer PDX, a less sensitive model of ovarian cancer. Transient tumor regressions were achieved at 0.27 mg/kg and delays in tumor growth achieved at 0.036 and 0.09 mg/kg.

TABLE 24

Efficacy of huE22-AcBut-CM in OV63 Ovarian Cancer PDX

| Day | Vehicle | 5.0 mg/kg Cisplatin | 0.1 mg/kg Control-AcBut-CM | 0.036 mg/kg huE22-AcBut-CM | 0.09 mg/kg huE22-AcBut-CM | 0.27 mg/kg huE22-AcBut-CM |
|---|---|---|---|---|---|---|
| 0 | 160 ± 22 | 153 ± 22 | 155 ± 18 | 153 ± 21 | 156 ± 16 | 165 ± 16 |
| 5 | 152 ± 10 | 146 ± 27 | 212 ± 30 | 197 ± 25 | 176 ± 30 | 158 ± 15 |
| 11 | 171 ± 23 | — | 178 ± 23 | 160 ± 16 | 180 ± 38 | 112 ± 19 |
| 18 | 207 ± 16 | 198 ± 29 | 221 ± 40 | 209 ± 33 | 152 ± 36 | 86 ± 15 |
| 25 | 218 ± 37 | 205 ± 36 | 277 ± 36 | 178 ± 17 | 112 ± 17 | 67 ± 18 |
| 32 | 207 ± 17 | 238 ± 49 | 316 ± 32 | 219 ± 37 | 132 ± 29 | 83 ± 22 |
| 39 | 216 ± 10 | 221 ± 40 | 381 ± 21 | 264 ± 72 | 184 ± 24 | 106 ± 44 |
| 47 | 249 ± 29 | 243 ± 42 | 533 ± 80 | 271 ± 73 | 186 ± 16 | 104 ± 40 |
| 53 | 317 ± 59 | 265 ± 63 | 504 ± 79 | 322 ± 108 | 188 ± 31 | 78 ± 30 |
| 60 | 317 ± 63 | 296 ± 80 | 643 ± 116 | 326 ± 110 | 179 ± 28 | 60 ± 43 |
| 67 | 446 ± 123 | 265 ± 82 | 805 ± 165 | 417 ± 141 | 184 ± 27 | 69 ± 38 |
| 74 | ND | ND | 840 ± 187 | 456 ± 190 | 209 ± 46 | 73 ± 45 |
| 81 | ND | ND | GT | 498 ± 188 | 241 ± 66 | 65 ± 39 |
| 88 | ND | ND | GT | 530 ± 191 | 251 ± 3 | 64 ± 26 |

Table 25 shows the efficacy of huE22-AcBut-CM in the Ovarian-39 (OV39) ovarian cancer PDX.

TABLE 25

Efficacy of huE22-AcBut-CM in OV39 Ovarian Cancer PDX

| Day | Vehicle | Doxorubicin | 0.1 mg/kg Control-AcBut-CM | 0.036 mg/kg huE22-AcBut-CM | 0.09 mg/kg huE22-AcBut-CM | 0.27 mg/kg huE22-AcBut-CM |
|---|---|---|---|---|---|---|
| 0 | 177 ± 32 | 186 ± 33 | 163 ± 23 | 165 ± 29 | 173 ± 18 | 169 ± 21 |
| 7 | 413 ± 103 | 282 ± 50 | 413 ± 74 | 448 ± 78 | 355 ± 48 | 378 ± 56 |
| 14 | 806 ± 333 | 171 ± 32 | 650 ± 118 | 814 ± 112 | 554 ± 80 | 320 ± 73 |
| 17 | 1101 ± 502 | 122 ± 24 | 822 ± 153 | 1050 ± 159 | 609 ± 94 | 252 ± 62 |
| 21 | 1305 ± 453 | 106 ± 19 | 891 ± 143 | 1265 ± 146 | 628 ± 97 | 147 ± 28 |
| 24 | 1436 ± 427 | 83 ± 11 | 1096 ± 170 | 1356 ± 185 | 614 ± 95 | 118 ± 28 |
| 28 | GT | 118 ± 17 | 1245 ± 154 | GT | 779 ± 123 | 98 ± 25 |
| 35 | GT | 361 ± 40 | GT | GT | 934 ± 99 | 67 ± 18 |
| 42 | GT | 712 ± 97 | GT | GT | GT | 72 ± 23 |
| 49 | GT | 966 ± 85 | GT | GT | GT | 170 ± 96 |
| 56 | GT | GT | GT | GT | GT | 446 ± 337 |
| 63 | GT | GT | GT | GT | GT | 940 ± 675 |
| 70 | GT | GT | GT | GT | GT | 1194 ± 422 |

C. Small-Cell Lung Cancer (SCLC) and Colorectal Cancer

Several additional efficacy studies were performed in models of small-cell lung cancer (SCLC), LU80 and LU86 PDXs, and colorectal cancer (CRC), CR5 PDX, with data shown in Tables 26-28. The results obtained were unexpected because huE22-ActBut-CM demonstrated superior efficacy in the SCLC and CRC PDX models compared to the treatment with doxorubicin standard-of-care (SOC) which has a similar mechanism of action to calicheamicin (DNA damaging agent).

TABLE 26

Efficacy of huE22-AcBut-CM in LU80 SCLC PDX

| Day | Vehicle | 5.0 mg/kg Cisplatin + 24mg/kg Etoposide | 0.1 mg/kg Control-AcBut-CM | 0.018 mg/kg huE22-AcBut-CM | 0.036 mg/kg huE22-AcBut-CM | 0.09 mg/kg huE22-AcBut-CM | 0.27 mg/kg huE22-AcBut-CM |
|---|---|---|---|---|---|---|---|
| 0 | 165 ± 27 | 190 ± 8 | 188 ± 19 | 158 ± 29 | 177 ± 19 | 161 ± 18 | 158 ± 20 |
| 7 | 500 ± 64 | 89 ± 11 | 312 ± 17 | 511 ± 37 | 527 ± 64 | 384 ± 40 | 208 ± 36 |
| 14 | 824 ± 137 | 163 ± 31 | 754 ± 41 | 630 ± 79 | 452 ± 75 | 217 ± 31 | 80 ± 10 |
| 21 | 985 ± 116 | 325 ± 68 | 1026 ± 61 | 638 ± 58 | 464 ± 67 | 134 ± 20 | 49 ± 8 |
| 28 | GT | 616 ± 67 | GT | 647 ± 96 | 439 ± 75 | 83 ± 24 | 7 ± 5 |
| 35 | GT | 979 ± 135 | GT | 1324 ± 208 | 883 ± 174 | 112 ± 31 | 0 ± 0 |
| 42 | GT | GT | GT | GT | GT | 126 ± 38 | 0 ± 0 |
| 49 | GT | GT | GT | GT | GT | 330 ± 120 | 0 ± 0 |
| 56 | GT | GT | GT | GT | GT | 686 ± 249 | 46 ± 31 |
| 63 | GT | GT | GT | GT | GT | 979 ± 216 | 105 ± 52 |
| 70 | GT | GT | GT | GT | GT | GT | 227 ± 89 |
| 77 | GT | GT | GT | GT | GT | GT | 376 ± 145 |
| 84 | GT | GT | GT | GT | GT | GT | 621 ± 209 |
| 91 | GT | GT | GT | GT | GT | GT | 703 ± 225 |

TABLE 27

Efficacy of huE22-AcBut-CM and huE47-AcBut-CM in LU86 SCLC PDX

| Day | Vehicle | 5.0 mg/kg Cisplatin + 24 mg/kg Etoposide | 0.3 mg/kg Control-AcBut-CM | 0.036 mg/kg huE22-AcBut-CM | 0.09 mg/kg huE22-AcBut-CM | 0.27 mg/kg huE22-AcBut-CM | 0.1 mg/kg huE47-AcBut-CM | 0.3 mg/kg huE47-AcBut-CM |
|---|---|---|---|---|---|---|---|---|
| 0 | 147 ± 11 | 149 ± 13 | 205 ± 19 | 139 ± 9 | 143 ± 10 | 138 ± 9 | 161 ± 16 | 195 ± 17 |
| 7 | 317 ± 33 | 250 ± 24 | 282 ± 24 | 239 ± 25 | 215 ± 19 | 105 ± 12 | 234 ± 24 | 372 ± 60 |
| 14 | 672 ± 62 | 468 ± 47 | 458 ± 62 | 296 ± 33 | 66 ± 9 | 0 ± 0 | 231 ± 34 | 260 ± 65 |
| 21 | 1233 ± 83 | 946 ± 77 | 637 ± 90 | 423 ± 50 | 0 ± 0 | 0 ± 0 | 355 ± 58 | 212 ± 84 |
| 28 | GT | GT | 964 ± 130 | 557 ± 66 | 0 ± 0 | 0 ± 0 | 458 ± 79 | 304 ± 111 |
| 35 | GT | GT | GT | 808 ± 69 | 0 ± 0 | 0 ± 0 | 598 ± 94 | 433 ± 162 |
| 42 | GT | GT | GT | GT | 0 ± 0 | 0 ± 0 | 808 ± 113 | 585 ± 198 |
| 49 | GT | GT | GT | GT | 0 ± 0 | 0 ± 0 | 1015 ± 139 | 778 ± 258 |
| 56 | GT | GT | GT | GT | 0 ± 0 | 0 ± 0 | 1262 ± 198 | 1031 ± 304 |
| 63 | GT | GT | GT | GT | 28 ± 22 | 0 ± 0 | 1770 ± 293 | GT |
| 70 | GT | GT | GT | GT | 52 ± 34 | 0 ± 0 | GT | GT |
| 77 | GT | GT | GT | GT | 93 ± 60 | 0 ± 0 | GT | GT |
| 84 | GT | GT | GT | GT | 117 ± 75 | 0 ± 0 | GT | GT |
| 92 | GT | GT | GT | GT | 237 ± 124 | 6 ± 6 | GT | GT |
| 98 | GT | GT | GT | GT | 304 ± 154 | 34 ± 24 | GT | GT |
| 105 | GT | GT | GT | GT | 385 ± 179 | 56 ± 32 | GT | GT |
| 112 | GT | GT | GT | GT | 420 ± 171 | 99 ± 56 | GT | GT |
| 119 | GT | GT | GT | GT | 491 ± 163 | 171 ± 109 | GT | GT |
| 126 | GT | GT | GT | GT | 602 ± 165 | 239 ± 139 | GT | GT |
| 133 | GT | GT | GT | GT | 828 ± 213 | 370 ± 201 | GT | GT |
| 140 | GT | GT | GT | GT | GT | 429 ± 210 | GT | GT |
| 147 | GT | GT | GT | GT | GT | 469 ± 222 | GT | GT |
| 154 | GT | GT | GT | GT | GT | 599 ± 286 | GT | GT |

TABLE 28

Efficacy of huE22-AcBut-CM in CR5 Colorectal Cancer PDX

| Day | 10 mg/kg MsIgG1 | 35 mg/kg Irinotecan | 0.3 mg/kg Control-AcBut-CM | 0.1 mg/kg Control hIgG1-AcBut-CM | 0.09 mg/kg huE22-AcBut-CM | 0.27 mg/kg huE22-AcBut-CM | 0.3 mg/kg huE47-AcBut-CM |
|---|---|---|---|---|---|---|---|
| 0 | 249 ± 17 | 252 ± 15 | 141 ± 14 | 165 ± 10 | 168 ± 9 | 141 ± 9 | 141 ± 7 |
| 3 | 397 ± 35 | 395 ± 29 | 234 ± 22 | 246 ± 23 | 255 ± 15 | 210 ± 11 | 223 ± 10 |

TABLE 28-continued

Efficacy of huE22-AcBut-CM in CR5 Colorectal Cancer PDX

| Day | 10 mg/kg MsIgG1 | 35 mg/kg Irinotecan | 0.3 mg/kg Control-AcBut-CM | 0.1 mg/kg Control hIgG1-AcBut-CM | 0.09 mg/kg huE22-AcBut-CM | 0.27 mg/kg huE22-AcBut-CM | 0.3 mg/kg huE47-AcBut-CM |
|---|---|---|---|---|---|---|---|
| 7  | 344 ± 32   | 237 ± 23   | 357 ± 30   | 166 ± 23   | 154 ± 11   | 299 ± 18  | 361 ± 20   |
| 10 | 829 ± 64   | 446 ± 35   | 524 ± 49   | 502 ± 59   | 429 ± 37   | 286 ± 15  | 498 ± 25   |
| 14 | 1250 ± 107 | 448 ± 38   | 376 ± 41   | 831 ± 88   | 531 ± 35   | 93 ± 5    | 329 ± 17   |
| 21 | GT         | 396 ± 52   | 1150 ± 75  | 1406 ± 123 | 763 ± 64   | 161 ± 10  | 885 ± 51   |
| 28 | GT         | 629 ± 116  | GT         | 2372 ± 165 | 1457 ± 90  | 149 ± 17  | 1273 ± 81  |
| 35 | GT         | 1097 ± 142 | GT         | GT         | GT         | 397 ± 90  | 1724 ± 103 |
| 42 | GT         | GT         | GT         | GT         | GT         | 889 ± 171 | GT         |

The results of all in vivo efficacy studies with huE22-AcBut-CM are summarized in Tables 29 and 30. In summary, huE22-AcBut-CM strongly inhibited tumor growth in models of TNBC (non-Claudin low), ovarian cancer, SCLC and colorectal cancer. huE22-AcBut-CM outperformed standard-of-care chemotherapy (SOC) in all cases tested (TNBC and SCLC). Tumor regression was defined as reduction in mean tumor volume relative to the size at first dose.

In breast and ovarian models, tumor regression was defined as a reduction in mean tumor volume after dosing. TGI=Tumor Growth Inhibition. % TGI=[1−(Mean Tumor Volume of Treated)/(Mean Tumor Volume of Vehicle)]. In cases where tumors regressed, Time To Progression (TTP) was determined to be the number of days between the first dose and the time at which mean tumor volume significantly increased (regrew) after regression. If the tumor did not regrow during the course of the experiment, TTP is the number of days between the first dose and the end of the experiment. As described above, all animals were dosed twice a week for 4 cycles with huE22-AcBut-CM ADC, once a week for 2 cycles with doxorubicin at 1.5 mg/kg or once a week for 2 cycles with cisplatin at 5 mg/kg. ADC dose levels are listed in mg/kg according to antibody content. Animals were dosed intraperitoneally in all studies except 144580, in which they were dosed intravenously.

TABLE 29

Summary of huE22-AcBut-CM breast cancer in vivo efficacy studies

| Breast Cancer Subtype | Tumor model | 1.5 mpk Doxorubicin Regression (TTP, Days) or % TGI | EFNA4 Protein (ng/mg) | huE22-AcBut-CM Dose Level (mg/kg) | huE22-AcBut-CM Regression (TTP, Days) or % TGI |
|---|---|---|---|---|---|
| TNBC: Basal | BR5 PDX | 44% TGI | 1.8 | 0.036 | Regression (32) |
|  |  |  |  | 0.09 | Regression (53) |
|  |  |  |  | 0.27 | Regression (200) |
|  | BR22 PDX | 27% TGI | 1.91 | 0.018 | No activity |
|  |  |  |  | 0.036 | 21% TGI |
|  |  |  |  | 0.09 | 55% TGI |
|  |  |  |  | 0.27 | Regression (43) |
|  | BR31 PDX | 30% TGI | 1.02 | 0.09 | Regression (56) |
|  |  |  |  | 0.27 | Regression (91) |
|  | BR56 PDX | 49% TGI | 1.01 | 0.018 | No activity |
|  |  |  |  | 0.036 | 34% TGI |
|  |  |  |  | 0.09 | 56% TGI |
|  |  |  |  | 0.27 | Regression (60) |
| TNBC: NL | BR13 | 16% TGI | 1.00 | 0.018 | No activity |
|  |  |  |  | 0.036 | 36% TG I |
|  |  |  |  | 0.09 | Regression (42) |
|  |  |  |  | 0.27 | Regression (84) |
| TNBC: Unknown | 144580 | ND | 1.74 | 0.03 | 11% TGI |
|  |  |  |  | 0.1 | 55% TGI |
|  |  |  |  | 0.3 | Regression (53) |
| TNBC: CL | BR25 | No activity | 0.47 | 0.27 | 27% TGI |
|  | BR64 | No activity | 0.66 | 0.27 | No activity |
| HER2+ | BR17 | 66% TGI | ND | 0.27 | No Activity |

NL = Normal-like.
CL = Claudin-low.
ND = no determined.

TABLE 30

Summary of huE22-AcBut-CM ovarian cancer in vivo efficacy studies

| Ovarian Cancer Subtype | Tumor model | 5 mpk Cisplatin Regression (TTP, Days) or % TGI | EFNA4 Protein (ng/mg) | huE22-AcBut-CM Dose Level (mg/kg) | Regression (TTP, Days) or % TGI |
|---|---|---|---|---|---|
| High Grade Serous | OV39 | Regression (28) | ND | 0.036 | No activity |
| | | | | 0.09 | 45% TGI |
| | | | | 0.27 | Regression (49) |
| | OV44 PDX | Regression (60) | 1.39 | 0.036 | 53% TGI |
| | | | | 0.09 | 59% TGI |
| | | | | 0.27 | Regression (53) |
| | OV63 PDX | 35% TGI | 0.49 | 0.036 | No activity |
| | | | | 0.09 | 59% TGI |
| | | | | 0.27 | Regression (88) |
| MMMT | OV45 PDX | NA | 3.64 | 0.018 | No activity |
| | | | | 0.036 | 70% TGI |
| | | | | 0.09 | Regression (60) |
| | | | | 0.27 | Regression (200) |
| | OV55 PDX | NA | 0.42 | 0.018 | No activity |
| | | | | 0.036 | 67% TGI |
| | | | | 0.09 | Regression (42) |
| | | | | 0.27 | Regression (76) |
| | OV124 | NA | ND | 0.27 | Regression (152) |

MMMT = malignant mixed Mullerian tumor;
ND = not determined;
NA = not applicable.

Example 9

Reduction of Tumor-Initiating Cells (TIC)

To determine whether anti-EFNA4 antibody-drug conjugate treatments reduced tumor-initiating cell (TIC) frequency in tumors, tumors were pre-treated with anti-EFNA4 antibody-drug conjugate, huE22-AcBut-CM, or control hIgG antibody-drug conjugate, control-AcBut-CM, and then live human tumor cells from pre-treated dissociated tumors were implanted into naïve animals in a limit dilution analysis. Tumors from huE22-AcBut-CM or control-AcBut-CM treated tumor-bearing mice were harvested at day 12 (for BR22) and day 21 (for BR13) post-initial treatment. The day of harvest serial transplantation was chosen based on when tumors were starting to regress following huE22-AcBut-CM exposure. Tumors were dissociated and stained with anti-human ESA, anti-mouse CD45, and anti-mouse H2Kd antibodies. Three tumors per treatment group were pooled, and live human tumor cells (ESA+) were sorted by flow cytometry.

For BR22, groups of eight mice were injected with 400, 100, 50, or 20 tumor cells sorted from control-AcBut-CM treated tumors, and groups of eight mice were injected with 390, 90, 40, or 18 tumor cells sorted from huE22-AcBut-CM treated tumors. For BR13, groups of 10 mice were injected with 400, 100, 60, or 20 tumor cells sorted from control-AcBut-CM treated tumors, and groups of 10 mice were injected with 380, 160, 50, or 25 tumor cells sorted from huE22-AcBut-CM treated tumors.

Tumors in recipient mice were measured weekly and at 21 weeks post-injection, tumors that exceeded 200 mm$^3$ in recipient mice were scored as positive. Using Poisson distribution statistics, via L-Calc software (Stemcell Technologies, Vancouver, BC), injected cell doses of recipients with and without tumors at 21 weeks post-transplant were used to calculate the frequencies of TIC in each population. For both the BR22 and BR13 PDX, the data demonstrates anti-tumor efficacy using a secondary endpoint of TIC frequencies, which is independent of standard tumor volume measurements. The data further demonstrates huE22-AcBut-CM targets the more aggressive/tumorgenic TICs (or CSCs).

The number of TIC in BR22 treated tumors were reduced by about 3-fold from 1 TIC in 55 cells of control-AcBut-CM treated to 1 TIC in 147 cells of huE22-AcBut-CM treated ($p=0.019$ in two-tailed test), as show in Table 31.

TABLE 31

Tumor-initiating cell frequency in BR22 tumor model.

| Group | Pre-treatment | # Cells implanted per animal | # Animals with tumors | # Animals in group | TIC frequency | p-value |
|---|---|---|---|---|---|---|
| A1 | control-AcBut-CM | 400 | 8 | 8 | 1 in 55 | 0.019 |
| A2 | control-AcBut-CM | 100 | 6 | 8 | | |
| A3 | control-AcBut-CM | 50 | 3 | 8 | | |
| A4 | control-AcBut-CM | 20 | 6 | 8 | | |
| B1 | huE22-AcBut-CM | 390 | 7 | 8 | 1 in 147 | |
| B2 | huE22-AcBut-CM | 90 | 6 | 8 | | |
| B3 | huE22-AcBut-CM | 40 | 1 | 8 | | |
| B4 | huE22-AcBut-CM | 18 | 0 | 7 | | |

Similarly, the number of TIC in BR13 treated tumors were reduced by about 2.6-fold from 1 TIC in 75 cells of control-AcBut-CM treated to 1 TIC in 270 cells of huE22-AcBut-CM treated (p=0.0007), as shown in Table 32. In summary, mice injected with huE22-AcBut-CM treated tumor cells consistently produced less tumors than mice injected with similar number of control-AcBut-CM treated tumor cells, indicating huE22-AcBut-CM treatment reduced tumor-initiating cells (TIC).

TABLE 32

Tumor-initiating cell frequency in BR13 tumor model.

| Group | Pre-treatment | # Cells implanted per animal | # Animals with tumors | # Animals in group | TIC frequency | p-value |
|---|---|---|---|---|---|---|
| A1 | control-AcBut-CM | 400 | 10 | 10 | 1 in 75 | 0.0007 |
| A2 | control-AcBut-CM | 100 | 7 | 10 | | |
| A3 | control-AcBut-CM | 60 | 6 | 10 | | |
| A4 | control-AcBut-CM | 20 | 2 | 10 | | |
| B1 | huE22-AcBut-CM | 380 | 7 | 10 | 1 in 270 | |
| B2 | huE22-AcBut-CM | 160 | 4 | 10 | | |
| B3 | huE22-AcBut-CM | 50 | 3 | 10 | | |
| B4 | huE22-AcBut-CM | 25 | 1 | 9 | | |

Total antibody concentrations could not be determined for the total ADC incubations in human plasma due to ELISA limitations of detection for a human IgG, in human plasma containing human IgG. The mean amounts of total ADC remaining after incubation of huE22-AcBut-CM for 168 hours at 37° C. in rat, mouse, monkey, and human plasma were similar to the buffer control and similar across species at both incubation concentrations. NC=Not calculated; SD=Standard deviation.

Example 10

In Vitro Stability of the Total huE22-AcBut-CM in Plasma

Quantitation of the total ADC and total antibody, in plasma samples from pharmacokinetic studies in mice dosed with the ADC was determined using an enzyme-linked immunosorbent assay (ELISA) method. ELISA and liquid chromatography tandem mass spectrometry (LC-MS/MS) methods were also used to quantitate total ADC, total antibody and unconjugated payload from the exploratory toxicology studies in rat and monkey and in the in vitro plasma stability study with the ADC.

The in vitro stability of the huE22-AcBut-CM, prepared according the conjugation and purification processes described in Example 6, was determined by measuring the total ADC and total antibody by ELISA in Sprague Dawley rat and cynomolgus monkey plasma. huE22-AcBut-CM was incubated at concentrations of 1 and 50 μg/mL at 37° C. up to 168 hours in mouse, rat, monkey, and human plasma and the total ADC and total antibody (with the exception of human plasma) were determined using an ELISA, see Tables 33 and 34.

The mean (n=3) amounts of total antibody remaining after incubation of huE22-AcBut-CM for 168 hours at 37° C. in rat, mouse, and monkey plasma were similar to the buffer control and similar across species at both incubation concentrations. Mean (n=3) total ADC and total antibody amounts remaining after incubation of huE22-AcBut-CM in phosphate buffered saline (PBS) w/1% bovine serum albumin (BSA) for 168 hours at 37° C. were 94.5% and 90.5% respectively for the 1 μg/mL incubation and 88.3 and 98.6% respectively for the 50 μg/mL incubation, indicating the presence of minimal thermal degradation of the total ADC in plasma at biological temperatures.

TABLE 33

% total huE22 Ab remaining in mouse, rat and monkey plasma.

| Matrix | Conc. (ug/mL) | | 0 | 8 | 24 | 48 | 72 | 168 |
|---|---|---|---|---|---|---|---|---|
| Mouse | 50 | Mean | 100 | 111 | 117 | 97.1 | 96.7 | 89.9 |
| | | SD | NC | 25.4 | 16.3 | 18.1 | 20.8 | 24.0 |
| | 1 | Mean | 100 | 105 | 126 | 109 | 101 | 102 |
| | | SD | NC | 8.0 | 16.7 | 13.2 | 9.9 | 17.7 |
| Rat | 50 | Mean | 100 | 98.1 | 115 | 111 | 87.1 | 83.3 |
| | | SD | NC | 8.0 | 21.0 | 21.0 | 3.7 | 13.3 |
| | 1 | Mean | 100 | 76.8 | 89.0 | 81.4 | 79.4 | 64.6 |
| | | SD | NC | 6.6 | 7.5 | 3.2 | 5.6 | 10.5 |
| Monkey | 50 | Mean | 100 | 106 | 109 | 106 | 103 | 94.3 |
| | | SD | NC | 6.6 | 1.3 | 15.6 | 1.8 | 11.7 |
| | | Mean | 100 | 107 | 111 | 107 | 106 | 95.0 |
| | | SD | NC | 8.9 | 2.0 | 15.9 | 5.7 | 12.0 |
| Buffer | 50 | Mean | 100 | 99.5 | 113 | 111 | 92.9 | 98.6 |
| | | SD | NC | 8.7 | 5.2 | 11.2 | 10.4 | 13.5 |
| | | Mean | 100 | 86.1 | 87.5 | 91.9 | 92.1 | 90.5 |
| | | SD | NC | 16.6 | 6.6 | 17.6 | 17.7 | 1.7 |

TABLE 34

% huE22-AcBut-CM remaining in mouse, rat, monkey and human plasma

| Matrix | Conc. (ug/mL) | | 0 | 8 | 24 | 48 | 72 | 168 |
|---|---|---|---|---|---|---|---|---|
| Mouse | 50 | Mean | 100 | 100 | 104.2 | 95.2 | 84.0 | 83.0 |
| | | SD | NC | 13.7 | 11.7 | 11.3 | 10.0 | 3.6 |
| | 1 | Mean | 100 | 96.7 | 101 | 102 | 87.5 | 79.1 |
| | | SD | NC | 5.1 | 11.8 | 23.7 | 12.8 | 9.5 |
| Rat | 50 | Mean | 100 | 94.7 | 97.3 | 107.6 | 96.9 | 70.1 |
| | | SD | NC | 1.6 | 6.7 | 21.7 | 7.9 | 10.6 |
| | 1 | Mean | 100 | 95.2 | 93.0 | 86.2 | 81.0 | 69.0 |
| | | SD | NC | 4.3 | 8.6 | 9.1 | 4.2 | 7.3 |
| Monkey | 50 | Mean | 100 | 100 | 103 | 87.9 | 81.9 | 71.6 |
| | | SD | NC | 8.6 | 7.0 | 5.1 | 2.6 | 5.8 |
| | 1 | Mean | 100 | 98.3 | 99.8 | 91.0 | 90.8 | 75.1 |
| | | SD | NC | 8.7 | 13.1 | 6.5 | 5.3 | 2.5 |

TABLE 34-continued

% huE22-AcBut-CM remaining in mouse, rat, monkey and human plasma

| Matrix | Conc. (ug/mL) | | Time (hours) | | | | | |
|---|---|---|---|---|---|---|---|---|
| | | | 0 | 8 | 24 | 48 | 72 | 168 |
| Human | 50 | Mean | 100 | 101 | 105 | 93.4 | 83.5 | 82.9 |
| | | SD | NC | 15.1 | 12.0 | 13.8 | 11.5 | 3.4 |
| | 1 | Mean | 100 | 102 | 93.2 | 98.4 | 89.3 | 82.5 |
| | | SD | NC | 10.1 | 7.1 | 11.5 | 8.3 | 5.1 |
| Buffer | 50 | Mean | 100 | 90.6 | 104 | 99.7 | 93.4 | 88.3 |
| | | SD | NC | 5.2 | 9.5 | 10.6 | 13.7 | 4.4 |
| | 1 | Mean | 100 | 90.6 | 101 | 97.5 | 94.9 | 94.5 |
| | | SD | NC | 7.5 | 17.4 | 4.5 | 3.0 | 2.8 |

Example 11

Mechanism of Action

The mechanism of action of huE22-AcBut-CM was analyzed to demonstrate that it was consistent with that of calicheamicin. Phosphorylated histone variant H2A.X (y⁻H2A.X) is an established biomarker of DNA damage. To validate the assay, cancer cell lines were treated with unconjugated AcBut-CM and the y⁻H2A.X marker was evident in the cell nuclei in discrete foci, which is the typical staining pattern. Treatment with huE22-AcBut-CM resulted in DNA double-strand breaks in the target cells both in vitro and in vivo, consistent with the expected mechanism of action of a calicheamicin ADC.

HEK293T-EFNA4 or parental HEK293T cells were exposed for four hours with 0.3 μg/mL huE22-AcBut-CM, control ADC or unconjugated huE22. Cells were washed, fixed with 4% paraformaldehyde, permeabilized with 1% Triton-X100, incubated for 1 hour with anti-histone y⁻H2A.X (Millipore #05-636), washed and incubated for 30 minutes with AlexaFluor488-conjugated secondary antibody and with DAPI nucleic acid stain, and then washed and protected with mounting medium and coverslip. Cells were visualized with a Zeiss LSM510 confocal microscope and analyzed for the y⁻H2A.X biomarker of DNA damage and DNA content.

After exposure to huE22-AcBut-CM, HEK293T-EFNA4 cells exhibited discrete y⁻H2A.X foci indicative of DNA damage; in contrast no foci were observed after treatment with control ADC or unconjugated huE22 (image not shown). Furthermore, huE22-AcBut-CM did not induce foci in target-negative HEK293T cells. Thus, huE22-AcBut-CM generated DNA damage in a target-dependent and calicheamicin-dependent manner, consistent with the expected mechanism of action of the ADC.

Analogous results were obtained in a pharmacodynamics study in vivo. Mice that harbored EFNA4-expressing BR5 TNBC PDX tumors were administered one dose of 1 mg/kg huE22-AcBut-CM, and tumors were harvested after 24, 48 and 96 hours. Tumors were fixed in formalin and embedded in paraffin (FFPE). Sections were stained with 2.4 μg/mL anti-huIgG (Cell Signaling #3443-1) and 1.8 mg/mL anti-γ-H2A.X (Cell Signaling 2577S) and slides were scanned on an Aperio AT2. For digital image analysis, the region of healthy viable tissue was classified while necrotic regions and irrelevant tissues were eliminated. Individual cells within the viable region were scored based on user-defined parameters (e.g. membrane hIgG staining or intracellular y⁻H2A.X staining), and the percentage of marker-positive cells in the viable region was reported.

Figure 22:
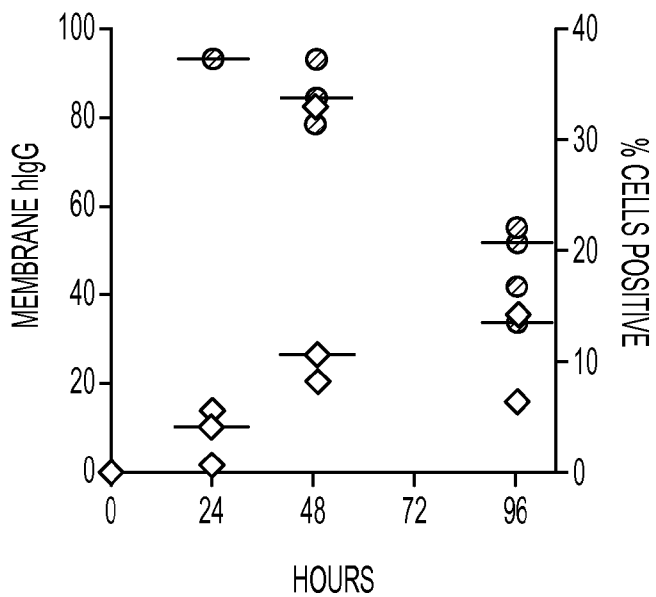
FIG. 22 shows immunohistochemistry with anti-hIgG1 antibody (diagonal-hatched circles) and anti-y$^-$-H2A.X antibody (open diamonds) of BR5 TNBC PDX tumors exposed to huE22-AcBut-CM.

As shown in FIG. 22, immunohistochemistry with anti-hIgG1 antibody (diagonal-hatched circles) demonstrated staining at the plasma membrane of nearly every tumor cell at 24 hours after the dose, and about half of the tumor cells at 96 hours. Further shown in FIG. 22, immunohistochemistry with anti-y⁻-H2A.X antibody (open diamonds) revealed nuclear staining in tumor cells; as expected, the time of peak anti-y⁻-H2A.X staining lagged behind the time of peak cell binding, since ADC internalization and payload release occurs before the calicheamicin generates DNA damage. The dashes indicate the median value per group. Together the in vitro and in vivo studies demonstrated the expected mechanism of action for anti-EFNA4-AcBut-CM ADCs.

Calicheamicin-generated DNA damage induces apoptosis, which ultimately leads to cell death (Zein et al, 1988; Nicolaou et al, 1994; Prokop et al, 2003). Apoptosis following treatment with huE22-AcBut-CM was evaluated by staining with Annexin V, which marks apoptotic cells by binding to phosphatidylserine on the cell surface (Koopman et al, 1994). HEK293T-EFNA4 or parental HEK293T were treated with huE22-AcBut-CM, control ADC or huE22 mAb and then stained with Annexin V and the viability stain 7AAD. Treatment of HEK293T-EFNA4 cells with huE22-AcBut-CM resulted in substantially higher levels of apoptotic cells, while treatment of parental HEK293T cells did not, see Table 35. Neither the control ADC nor huE22 mAb induced apoptosis to a significant degree. Thus, huE22-AcBut-CM induced apoptosis in target cells in a target- and calicheamicin-dependent manner.

TABLE 35

Apoptosis in target cells.

| | | HEK293T-EFNA4 | | | HEK293T Parental | | |
|---|---|---|---|---|---|---|---|
| Compound | Conc. (ng/mL) | % early apoptosis | % late apoptosis | % total apoptosis | % early apoptosis | % late apoptosis | % total apoptosis |
| None (vehicle) | NA | 4.9 | 1.7 | 6.6 | 1.6 | 0.7 | 2.3 |
| huE22-AcBut-CM | 1 | 22.4 | 7.8 | 30.2 | 6.0 | 1.6 | 7.6 |
| | 100 | 19.0 | 10.2 | 29.2 | 4.0 | 1.6 | 5.6 |
| | 1000 | 17.9 | 8.6 | 26.5 | 6.0 | 3.4 | 9.4 |
| Control ADC | 1 | 5.5 | 4.0 | 9.5 | 3.3 | 1.4 | 4.7 |
| | 100 | 4.5 | 2.1 | 6.6 | 3.7 | 0.9 | 4.6 |
| | 1000 | 12.0 | 5.6 | 17.6 | 7.6 | 3.9 | 11.5 |
| huE22 mAb | 1 | 4.7 | 3.1 | 7.8 | 2.7 | 1.3 | 4.0 |
| | 100 | 6.4 | 2.1 | 8.5 | 2.8 | 1.1 | 3.9 |
| | 1000 | 8.3 | 2.3 | 10.6 | 1.8 | 0.8 | 2.6 |

Example 12

Enrichment of TNBC TPC

A PDX tumor bank containing 19 breast PDX tumors was established. Based on patient pathology reports, tumor histopathology, and microarray sub-clustering using the PAM-50 (+) panel, 13 of these PDX tumor models were confirmed to originate from patients with TNBC; three of which were characterized to be of the claudin-low (CL) subtype. Breast PDX tumors were harvested, dissociated to single cell suspensions and analyzed by flow cytometry using strict doublet discrimination gating. Further, human ESA+ tumor cells were analyzed for CD46, CD324, CD24 and CD34 expression, respectively.

Upon careful phenotypic profiling for the critical cell surface marker thought to demarcate tumor perpetuating cells (I.a cancer stem cells) in breast cancer, CD24, it became apparent that all cells in PDX tumors originating from patients with TNBC uniformly express the antigen, and thus it held little utility for identifying TPC in this subtype of breast cancer. Phenotypic profiling of hundreds of cell surface antigens by flow cytometry identified a number of heterogeneously expressed antigens, including CD46 and CD324, in BR22 and BR31 PDX tumors.

Figure 23:
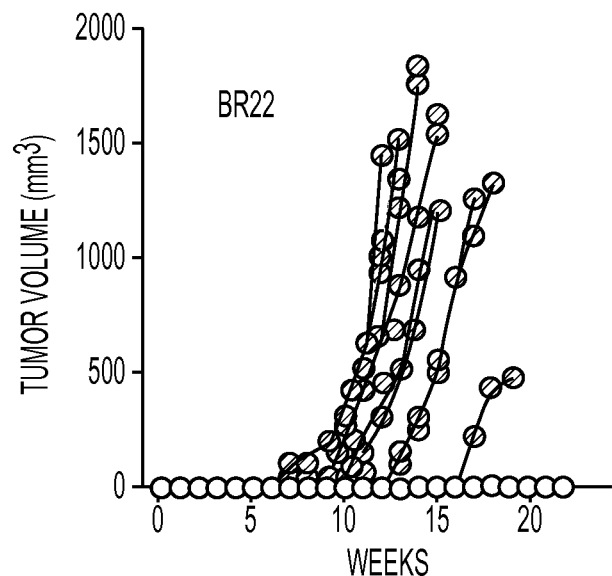
FIG. 23 shows tumor growth curves for mice implanted with ESA$^+$CD46$^+$CD324$^+$ (diagonal-hatched circles) or ESA$^+$CD46$^+$CD324$^-$ (open circles) cells isolated from dissociated BR22 TNBC PDX tumors.
Figure 24:
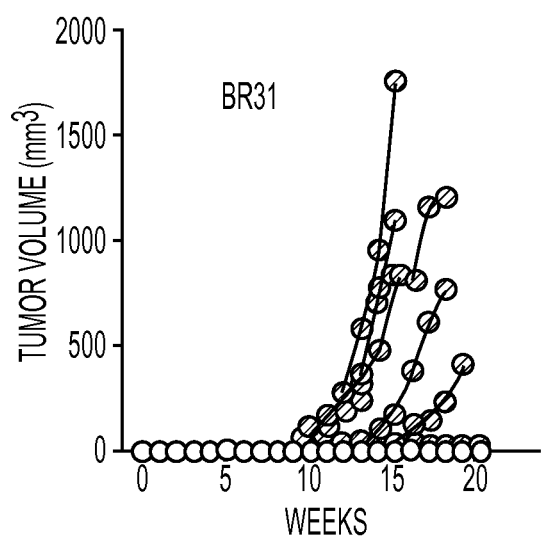
FIG. 24 shows tumor growth curves for mice implanted with ESA$^+$CD46$^+$CD324$^+$ (diagonal-hatched circles) or ESA$^+$CD46$^+$CD324$^-$ (open circles) cells isolated from dissociated BR31 TNBC PDX tumors.

Prospective TPC (i.e. ESA$^+$CD46$^+$CD324$^+$ cells) were isolated from BR22 PDX tumors by FACS and re-analyzed by flow cytometry prior to implantation. Daughter tumor(s) were similarly dissociated and analyzed to confirm cellular heterogeneity reflecting the parental tumor. Tumor growth curves for individual mice implanted with 50 ESA$^+$CD46$^+$CD324$^+$ (diagonal-hatched circles) or ESA$^+$CD46$^+$CD324$^-$ (open circles) cells isolated from dissociated BR22 and BR31 breast PDX tumors, as shown in FIGS. 23 and 24, respectively. Utilization of these markers to facilitate isolation and transplantation of single cells without or with expression of CD46 and/or CD324 into immunocompromised mice demonstrated that only ESA$^+$CD46$^+$CD324$^+$ cells, but not their CD324$^-$ counterparts, were able to efficiently perpetuate tumors replicating the phenotypic heterogeneity of their parental tumors.

Fully heterogeneous tumors were efficiently initiated with as few as 50 implanted cells, whereas TPC frequency within the CD324$^-$ subpopulation was within error of the expected false positive expectation resulting from a 1% cell impurity profile of cells isolated on a BD FACSAria, see Table 36.

TABLE 36

| PDX | # Cells | ESA+ CD46+ | | | |
|---|---|---|---|---|---|
| | | CD324+ | | CD324− | |
| BR13 | 50 | 10/20 | 50% | 2/20 | 10% |
| BR22 | 50 | 53/78 | 68% | 2/41 | 5% |
| BR31 | 50 | 13/30 | 43% | 0/15 | 0% |
| BR56 | 50 | 9/16 | 56% | 2/13 | 15% |
| BR86 | 100 | 11/20 | 55% | 0/11 | 0% |
| | 200 | 8/12 | 67% | 0/3 | 0% |
| TG+ Mice | | 104 | | 6 | |
| Mice Implanted | | 176 | | 103 | |
| | | 59% | | 6% | |
| Functional TPC Frequency | | 1:71 cells | | 1:1,000 cells | |
| TPC Enrichment Factor | | >14-fold | | | |

The demonstrated TPC frequency of 1:71 among the CD324$^+$ cell subpopulation would yield an average 1.4 functional TPC per mouse transplanted with 100 CD324$^+$ cells, whereas a 1% sort error rate would yield an average 0.014% CD324$^+$ cell contamination frequency among isolated CD324$^-$ cells, which translates to a false positive frequency of 1.4% (0.2-2.7% Range).

Further, whole transcriptome sequencing was done using the Illumina HiSeq 2000 platform (100×100 bp paired-end sequencing) using isolated ESA$^+$CD46$^+$CD324$^+$ TPC and ESA$^+$CD46$^+$CD324$^-$ NTG cells, respectively, from a number of breast PDX tumor models of various subtypes, including claudin low and non-claudin low TNBC, and the Luminal B subtype of breast cancer. Whole transcriptome sequencing was also performed using mRNA obtained from normal tissues such as heart, liver, kidney, lung, colon, skin, pancreas, and ovary. Resulting fpkm (fragments per kilobase per million) values for all samples were normalized using standard techniques and then filtered to focus on genes encoding proteins annotated to be on the cell surface. Using this filtered data set as input, the DESeq2 package within Bioconductor was used to identify genes differentially expressed in TPC versus both NTG cells and normal tissue, along with their adjusted p-values. Notably, EFNA4 was significantly elevated in TPC versus NTG cells and normal tissues, even after adjusting p-values for false discovery rate.

Example 13

EFNA4 Expression is Elevated in TNBC TPC

To further the demonstrated enrichment of TNBC TPC, whole transcriptome sequencing was performed with the Illumina HiSeq 2000 platform (100×100 bp paired-end sequencing) using isolated ESA$^+$CD46$^+$CD324$^+$ TPC and ESA$^+$CD46$^+$CD324$^-$ NTG cells from a number of breast PDX tumor models of various subtypes, including claudin low and non-claudin low TNBC, and the Luminal B subtype of breast cancer.

Whole transcriptome sequencing was also performed using mRNA obtained from a panel of normal tissues such as heart, liver, kidney, lung, colon, skin, pancreas, and ovary. Resulting FPKM (fragments per kilobase per million) values for all samples were normalized using standard techniques and then filtered to focus on genes encoding proteins annotated to be on the cell surface. Using this filtered data set as input, the DESeq2 package within Bioconductor was used to identify genes differentially expressed in TPC versus both NTG cells and normal tissue, along with their adjusted p-values. Notably, EFNA4 was significantly elevated in TPC versus NTG cells and normal tissues, even after adjusting p-values for false discovery rate.

In addition, among the 19 breast PDX tumors encompassing various subtypes (described in Example 12), EFNA4 mRNA expression as assessed in bulk breast PDX tumors or normal vital organs by microarray. EFNA4 mRNA expression was elevated an average of greater than 2.6-fold higher than normal breast or any other normal tissue assessed.

Figure 25:
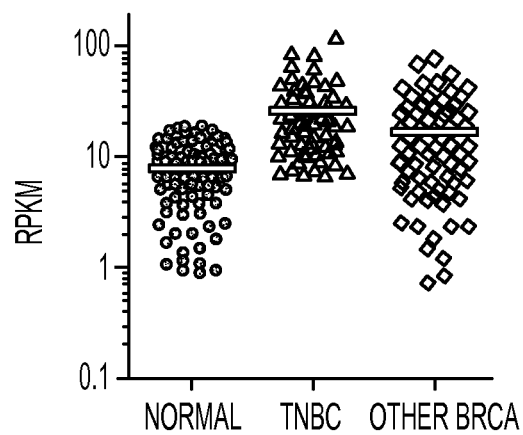
FIG. 25 shows expression of EFNA4 mRNA in normal-adjacent breast, TNBC, non-TNBC breast using TCGA data.

Further, expression of EFNA4 mRNA in normal-adjacent breast, TNBC, and non-TNBC breast tumors were assed using available The Cancer Genome Atlas (TCGA) Research Network (Weinstein J N et al. Nature Genetics 45:1113-1120, 2013) data. EFNA4 expression was generally higher in the non-Claudin low subtype of TNBC versus other breast cancer subtypes. Upon applying the PAM(50)+ gene signature to TCGA data generated from primary tumor specimens from 292 patients, elevated expression of EFNA4 in TNBC tumors (n=95) remained evident compared to normal adjacent breast (n=108), and breast tumors of the non-TNBC subtypes (n=197), as shown in FIG. 25. The horizontal lines indicate the median values.

Figure 26:
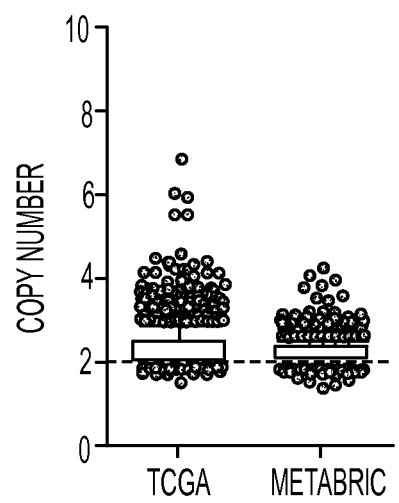
FIG. 26 shows EFNA4 copy number in breast cancer tumor samples from the TCGA and METABRIC datasets.
Figure 27:
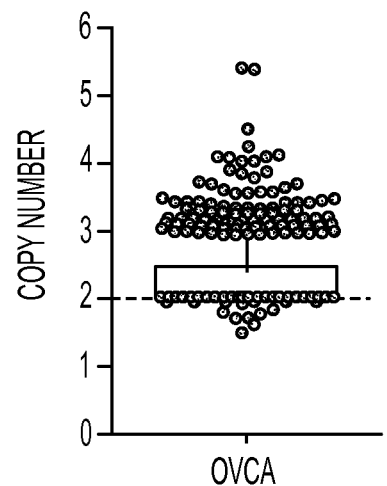
FIG. 27 shows EFNA4 copy number in ovarian cancer tumor samples from the TCGA and METABRIC datasets.

The genetic basis of overexpression of EFNA4 in breast cancer and ovarian cancer was analyzed. FIG. 26 shows the EFNA4 copy number in breast tumor samples and FIG. 27 shows the EFNA4 copy number in ovarian tumor samples from TCGA and METABRIC (Curtis, C et al. Nature April 18; 486(7403):346-352, 2012) datasets. The white box represents the th 25^th-75^th percentiles, the error bars demarcate the 10^th-90^th percentiles, and the individual dots fall below the 10^th or above the 90^th percentile. The normal copy number (n=2) is shown by the dashed line.

In some breast tumors the overexpression of EFNA4 may be a consequence of copy number gain, see FIG. 26. In TCGA breast cancer dataset 25.5% of tumor samples had notable copy number gain of EFNA4 (n≥2.5), while none had substantial copy number loss. The subset of TNBC samples had a proportional incidence of EFNA4 copy number gain. The same trend was observed in the METABRIC breast cancer dataset with n≥2.5 in 14.3% of tumor samples. Moreover, there is a strong correlation between EFNA4 mRNA level and DNA copy number (r=0.48; p<0.0001). The data suggests a potential genetic basis for the overexpression of EFNA4 in breast cancer, and particularly TNBC.

To determine whether or not elevated EFNA4 gene expression translated to an increase in protein, a panel of monoclonal antibodies was generated by traditional immunization and hybridoma approaches, and sandwich ELISA pairs were identified. Analysis of tissue protein lysates from 17 normal organs, 49 primary breast tumor specimens, and 9 TNBC PDX tumor models resulted in the observation that EFNA4 protein levels were elevated, not only in TNBC vs. normal tissues and other subtypes of breast cancer, but expression was higher in the non-claudin-low subclass of TNBC versus the claudin-low subset. These results confirm that, even at the bulk tumor level, elevated EFNA4 gene expression translates to meaningful increases in EFNA4 protein.

In ovarian cancer, the EFNA4 copy number gain (n≥2.5) was observed in a substantial fraction of TCGA samples (22.2%) whereas there were no cases of significant copy number loss, see FIG. 27. There is a strong correlation between EFNA4 mRNA level and DNA copy number (r=0.32; p<0.0001), which was similar to the observation in breast cancer. Together with the data in breast cancer, this observation suggests a potential genetic basis for EFNA4 overexpression in tumors.

Figure 28:
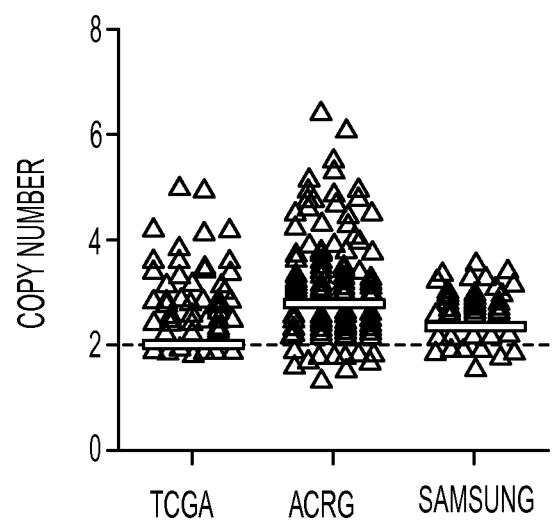
FIG. 28 shows EFNA4 copy number in hepatocellular carcinoma (HCC) tumor samples from the TCGA and METABRIC datasets.

In addition to breast and ovarian cancer, liver cancer exhibited a high frequency of EFNA4 copy number gain. FIG. 28 shows EFNA4 copy number in hepatocellular carcinoma (HCC) tumor samples from 3 datasets: Pfizer-ACRG (n=310), Pfizer-Samsung (n=272) and TCGA (n=212). Every sample is represented by a triangle, and the horizontal lines indicate the median values. The normal copy number (n=2) is shown by the dashed line. Consistently across three datasets, there was frequent EFNA4 copy number gain but no significant copy number loss; 68.4%, 37.5% and 29.7% of samples had n≥2.5 in the ACRG, Samsung and TCGA datasets respectively. In liver cancer, there was a strong correlation between EFNA4 mRNA level and DNA copy number in 3 independent datasets: TCGA correlation coefficient=0.50 (p~0); ACRG coefficient=0.56 (p~0) and Samsung coefficient=0.38 (p=3E-09). EFNA4 gain in HCC was not focal and instead occurred in the context of amplification of the chromosomal region Chr1q21-1q22, which also includes ELK4, MDM4 and PARP1. Notably, EFNA4 mRNA expression level correlated strongly with copy number in the HCC datasets, which suggested that tumors with EFNA4 gain may be more responsive to treatment with an anti-EFNA4 ADC.

Example 14

Binding Properties of Ephrin-A4

The properties of Ephrin-A4 binding to Eph receptors were further analyzed. Since anti-EFNA4 antibodies bind to Ephrin-A4 while the ligand is engaged with its Eph receptor, the affinity between these two macromolecules was determined. The affinities of commercially available Eph receptors and Ephrin-A4 were directly compared by surface plasmon resonance using a BIAcore 2000 (GE Healthcare) to determine the most relevant receptor. An anti-human antibody capture kit was used to immobilize recombinant Eph receptors on a CM5 biosensor chip. Prior to each antigen injection cycle, Eph receptors at the concentration of 2 µg/mL were captured on the surface with a contact time of 2 minutes and a flow rate of 5 µL/min. The captured antibody loading from baseline was constant at 150-260 response units. Following receptor capture and 1 min baseline, monomeric human Ephrin-A4 was flowed over the surface at concentrations of 400, 241, 145, 87, 53, 32, 19 and 12 nM for a 2 minute association phase followed by a 2 minute dissociation phase at a flow rate of 10 µL/min. Following each cycle, the anti-human capture surface was regenerated with 30 seconds contact time of 3M $MgCl_2$ at 10 µL/min.

Biacore data was processed by initially calculating an average of the response at equilibrium (Req). The Req was then plotted versus concentration (M) and the steady state affinity fit was used to calculate the affinity and theoretical Rmax. In all cases, at least 5 different analyte concentrations were used to make this calculation. All data analysis steps were completed in BiaEvaluation Software 3.1 (GE Healthcare).

Raw data and Req versus concentration curves (not shown) from the Ephrin-A4 binding to Eph receptors determined that the receptor with the highest affinity was EphA2 and the receptor with the lowest affinity was EphA10. Table 37 shows the nine Eph receptors tested for binding to Ephrin-A4 in order of decreasing affinity. The data demonstrates that the affinities for the Eph receptors to Ephrin-A4 are all lower than the anti-EFNA4 antibodies disclosed herein.

TABLE 37

| Receptor | Kd (nM) |
|---|---|
| EphA2 | 31 |
| EphA3 | 77 |
| EphA6 | 82 |
| EphA7 | 86 |
| EphB3 | 108 |
| EphA4 | 122 |
| EphB2 | 135 |
| EphA1 | 414 |
| EphA10 | 431 |

What is claimed is:

1. An antibody-drug conjugate of the formula: Ab-(L-D), wherein:
   (a) Ab is an antibody, or antigen-binding fragment thereof, that binds to EFNA4 and comprises a heavy chain variable region comprising three CDRs set forth as SEQ ID NOs: 15, 19, and 23 and a light chain variable region comprising three CDRs set forth as SEQ ID NOs: 29, 33, and 35; and
   (b) L-D is a linker-drug moiety, wherein L is a linker and D is a drug, and wherein D is a calicheamicin or calicheamicin derivative.

2. The antibody-drug conjugate of claim 1, wherein the Ab comprises a heavy chain variable region having an amino acid sequence that is at least 90% identical to SEQ ID NO: 13 and a light chain variable having an amino acid sequence that is at least 90% identical to SEQ ID NO: 27.

3. The antibody-drug conjugate of claim 2, wherein the Ab comprises a heavy chain variable region set forth as SEQ ID NO: 13 and a light chain variable region set forth as SEQ ID NO: 27.

4. The antibody-drug conjugate of claim 3, wherein the Ab comprises a IgG1 heavy chain constant region.

5. The antibody-drug conjugate of claim 4, wherein the Ab comprises a heavy chain set forth as SEQ ID NO: 25.

6. The antibody-drug conjugate of claim 3, wherein the Ab comprises a kappa light chain constant region.

7. The antibody-drug conjugate of claim 6 wherein the Ab comprises a light chain set forth as SEQ ID NO: 37.

8. The antibody-drug conjugate of claim 3, wherein the Ab comprises a heavy chain set forth as SEQ ID NO: 25 and a light chain set forth as SEQ ID NO: 37.

9. The antibody-drug conjugate of claim 1, wherein the D is an N-acetyl derivative of calicheamicin.

10. The antibody-drug conjugate of claim 9, wherein the D is N-acetyl-γ-calicheamicin.

11. The antibody-drug conjugate of claim 10, wherein the D is N-acetyl-γ-calicheamicin dimethyl hydrazide (CM).

12. The antibody-drug conjugate of claim 1, wherein the linker L comprises 4-(4'acetylphenoxy)butanoic acid (AcBut).

13. The antibody-drug conjugate of claim 1, having a DAR from 1 to 12.

14. The antibody-drug conjugate of claim 1, wherein:
  (a) the Ab comprises a heavy chain set forth as SEQ ID NO: 25 and a light chain set forth as SEQ ID NO: 37; and
  (b) the L is 4-(4'acetylphenoxy)butanoic acid (AcBut), and the D is N-acetyl-γ-calicheamicin dimethyl hydrazide (CM).

15. A composition comprising a plurality of an antibody-drug conjugate of claim 1, and optionally a pharmaceutical carrier, wherein the composition has an average DAR within a range of 1 to 12.

16. The composition of claim 15, wherein the composition has an average DAR within the range of 3 to 5.

17. The composition of claim 16, wherein the composition has an average DAR within the range of 3 to 4.

18. The composition of claim 16, wherein the composition has an average DAR within the range of 4 to 5.

19. The composition of claim 15, wherein the composition has an average DAR of about 4.

20. A composition comprising a plurality of an antibody-drug conjugate of claim 1, and optionally a pharmaceutical carrier, wherein the composition has at least 50% antibody-drug conjugates having a DAR from 3 to 5.

21. The composition of claim 20, wherein the composition has at least 60% antibody-drug conjugates having a DAR from 3 to 5.

22. The composition of claim 21, wherein the composition has at least 70% antibody-drug conjugates having a DAR from 3 to 5.

23. The composition of claim 22, wherein the composition has at least 75% antibody-drug conjugates having a DAR from 3 to 5.

24. The composition of claim 22, wherein the composition has about 70% to 80% antibody-drug conjugates having a DAR from 3 to 5.

25. A process for producing an antibody-drug conjugate of any claim 1 comprising:
  (a) linking the L to the D to provide the L-D moiety;
  (b) conjugating the linker-drug moiety to the antibody; and
  (c) purifying the antibody-drug conjugate.

26. A pharmaceutical composition comprising the antibody-drug conjugate of claim 1 and a pharmaceutically acceptable carrier.

27. A process for producing the composition of claim 15 comprising:
  (a) preparing the antibody-drug conjugate; and
  (b) purifying the composition having an average DAR within a range of 1 to 12.

* * * * *

SEQUENCE LISTING

<160> NUMBER OF SEQ ID NOS: 138

<210> SEQ ID NO 1
<211> LENGTH: 1276
<212> TYPE: DNA
<213> ORGANISM: Homo sapiens

<400> SEQUENCE: 1

```
cttccctctt cactttgtac ctttctctcc tcgactgtga agcgggccgg gacctgccag    60
gccagaccaa accggacctc gggggcgatg cggctgctgc ccctgctgcg gactgtcctc   120
tgggccgcgt tcctcggctc ccctctgcgc gggggctcca gcctccgcca cgtagtctac   180
tggaactcca gtaaccccag gttgcttcga ggagacgccg tggtggagct gggcctcaac   240
gattacctag acattgtctg ccccactac gaaggcccag ggccccctga gggccccgag    300
acgtttgctt tgtacatggt ggactggcca ggctatgagt cctgccaggc agagggcccc   360
cgggcctaca gcgctgggt gtgctccctg cccttggcc atgttcaatt ctcagagaag     420
attcagcgct tcacccctt ctccctcggc tttgagttct tacctggaga gacttactac    480
tacatctcgg tgcccactcc agagagttct ggccagtgct tgaggctcca ggtgtctgtc   540
tgctgcaagg agaggaagtc tgagtcagcc catcctgttg ggagccctgg agagagtggc   600
acatcagggt ggcgaggggg ggacactccc agccccctct gtctcttgct attactgctg   660
cttctgattc ttcgtcttct gcgaattctg tgagccaagc agaccttccc tctcatccca   720
aggagccaga gtcctcccaa gatccctgg aggaggaggg atccctgctg cctgcactgg    780
gggtgccaat tcagaccgac aagatggagc attgatgggg gagatcagag ggtctgaggt   840
gactcttgca ggagcctgtc ccctcatcac aggctaaaga agagcagtag acagccctgg   900
acactctgaa gcagaggcaa gacaaacaca ggcgctttgc aggctgctct gagggtctca   960
gcccatcccc caggaggact gggatttggt atgatcaaat cctcaagcca gctggggcc   1020 caggctgaag acctggggac aggtcgattg ctggaccagg gcaaagaaga agccctgcca  1080
tctgtgccct gtgggccttt tccctggggc agcaccttgc cctccccagg ggatcactca  1140
cttgtcttct atgaagacgg actcttcatg aggttgaatt tcatgccagt ttgtatttt   1200 ataagtatct agaccaaacc ttcaataaac cactcatctt tttgttgccc tccccaaaaa  1260
aaaaaaaaaa aaaaaa                                                  1276
```

<210> SEQ ID NO 2
<211> LENGTH: 201
<212> TYPE: PRT
<213> ORGANISM: Homo sapiens

<400> SEQUENCE: 2

```
Met Arg Leu Leu Pro Leu Leu Arg Thr Val Leu Trp Ala Ala Phe Leu
1               5                   10                  15

Gly Ser Pro Leu Arg Gly Gly Ser Leu Arg His Val Val Tyr Trp
            20                  25                  30

Asn Ser Ser Asn Pro Arg Leu Leu Arg Gly Asp Ala Val Val Glu Leu
        35                  40                  45

Gly Leu Asn Asp Tyr Leu Asp Ile Val Cys Pro His Tyr Glu Gly Pro
    50                  55                  60

Gly Pro Pro Glu Gly Pro Glu Thr Phe Ala Leu Tyr Met Val Asp Trp
65                  70                  75                  80

Pro Gly Tyr Glu Ser Cys Gln Ala Glu Gly Pro Arg Ala Tyr Lys Arg
                85                  90                  95

Trp Val Cys Ser Leu Pro Phe Gly His Val Gln Phe Ser Glu Lys Ile
            100                 105                 110

Gln Arg Phe Thr Pro Phe Ser Leu Gly Phe Glu Phe Leu Pro Gly Glu
        115                 120                 125

Thr Tyr Tyr Tyr Ile Ser Val Pro Thr Pro Glu Ser Ser Gly Gln Cys
    130                 135                 140
```

Leu Arg Leu Gln Val Ser Val Cys Cys Lys Glu Arg Lys Ser Glu Ser
145                 150                 155                 160

Ala His Pro Val Gly Ser Pro Gly Glu Ser Gly Thr Ser Gly Trp Arg
                165                 170                 175

Gly Gly Asp Thr Pro Ser Pro Leu Cys Leu Leu Leu Leu Leu Leu Leu
            180                 185                 190

Leu Ile Leu Arg Leu Leu Arg Ile Leu
        195                 200

<210> SEQ ID NO 3
<211> LENGTH: 207
<212> TYPE: PRT
<213> ORGANISM: Homo sapiens

<400> SEQUENCE: 3

Met Arg Leu Leu Pro Leu Leu Arg Thr Val Leu Trp Ala Ala Phe Leu
1               5                   10                  15

Gly Ser Pro Leu Arg Gly Gly Ser Ser Leu Arg His Val Val Tyr Trp
                20                  25                  30

Asn Ser Ser Asn Pro Arg Leu Leu Arg Gly Asp Ala Val Val Glu Leu
            35                  40                  45

Gly Leu Asn Asp Tyr Leu Asp Ile Val Cys Pro His Tyr Glu Gly Pro
        50                  55                  60

Gly Pro Pro Glu Gly Pro Glu Thr Phe Ala Leu Tyr Met Val Asp Trp
65                  70                  75                  80

Pro Gly Tyr Glu Ser Cys Gln Ala Glu Gly Pro Arg Ala Tyr Lys Arg
                85                  90                  95

Trp Val Cys Ser Leu Pro Phe Gly His Val Gln Phe Ser Glu Lys Ile
            100                 105                 110

Gln Arg Phe Thr Pro Phe Ser Leu Gly Phe Glu Phe Leu Pro Gly Glu
        115                 120                 125

Thr Tyr Tyr Tyr Ile Ser Val Pro Thr Pro Glu Ser Ser Gly Gln Cys
130                 135                 140

Leu Arg Leu Gln Val Ser Val Cys Cys Lys Glu Arg Arg Ala Arg Val
145                 150                 155                 160

Leu Pro Arg Ser Pro Gly Gly Gly Gly Ile Pro Ala Ala Cys Thr Gly
                165                 170                 175

Gly Ala Asn Ser Asp Arg Gln Asp Gly Ala Leu Met Gly Glu Ile Arg
            180                 185                 190

Gly Ser Glu Val Thr Leu Ala Gly Ala Cys Pro Leu Ile Thr Gly
        195                 200                 205

<210> SEQ ID NO 4
<211> LENGTH: 193
<212> TYPE: PRT
<213> ORGANISM: Homo sapiens

<400> SEQUENCE: 4

Met Arg Leu Leu Pro Leu Leu Arg Thr Val Leu Trp Ala Ala Phe Leu
1               5                   10                  15

Gly Ser Pro Leu Arg Gly Gly Ser Ser Leu Arg His Val Val Tyr Trp
                20                  25                  30

Asn Ser Ser Asn Pro Arg Leu Leu Arg Gly Asp Ala Val Val Glu Leu
            35                  40                  45

Gly Leu Asn Asp Tyr Leu Asp Ile Val Cys Pro His Tyr Glu Gly Pro
        50                  55                  60

Gly Pro Pro Glu Gly Pro Glu Thr Phe Ala Leu Tyr Met Val Asp Trp
65                  70                  75                  80

Pro Gly Tyr Glu Ser Cys Gln Ala Glu Gly Pro Arg Ala Tyr Lys Arg
            85                  90                  95

Trp Val Cys Ser Leu Pro Phe Gly His Val Gln Phe Ser Glu Lys Ile
        100                 105                 110

Gln Arg Phe Thr Pro Phe Ser Leu Gly Phe Glu Phe Leu Pro Gly Glu
        115                 120                 125

Thr Tyr Tyr Tyr Ile Ser Val Pro Thr Pro Glu Ser Ser Gly Gln Cys
        130                 135                 140

Leu Arg Leu Gln Val Ser Val Cys Cys Lys Glu Arg Asn Leu Pro Ser
145                 150                 155                 160

His Pro Lys Glu Pro Glu Ser Ser Gln Asp Pro Leu Glu Glu Glu Gly
                165                 170                 175

Ser Leu Leu Pro Ala Leu Gly Val Pro Ile Gln Thr Asp Lys Met Glu
            180                 185                 190

His

<210> SEQ ID NO 5
<211> LENGTH: 112
<212> TYPE: PRT
<213> ORGANISM: Artificial Sequence
<220> FEATURE:
<223> OTHER INFORMATION: Synthetic peptide sequence

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Thr Thr Tyr
            20                  25                  30

Gly Val Asp Trp Val Arg Gln Ala Pro Gly Lys Gly Leu Glu Trp Leu
        35                  40                  45

Gly Val Ile Trp Gly Gly Gly Ser Thr Asn Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Ser Asp Trp Ala Tyr Trp Gly Gln Gly Thr Leu Val Thr Val Ser Ser
            100                 105                 110

<210> SEQ ID NO 6
<211> LENGTH: 335
<212> TYPE: DNA
<213> ORGANISM: Artificial Sequence
<220> FEATURE:
<223> OTHER INFORMATION: Synthetic nucleotide sequence

<400> SEQUENCE: 6
gaggtgcagc tggtggagtc tgggggaggc ttggtccagc ctggggggtc cctgagactc      60
tcctgtgcag cctctggatt caccgtcact acttatggtg tggactgggt ccgccaagct     120
ccagggaagg ggctggagtg gttaggtgta atatggggtg gtggaagcac aaattataat     180
agcgctttga agagccgatt caccatctcc agagacaact ccaagaacac cctgtatctg     240
caaatgaaca gtctgagagc cgaggacacg gccgtgtatt actgtgccag tgattgggct     300
tactggggcc aagggactct ggtcactgtc tcttc                                335

<210> SEQ ID NO 7
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 7

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Gly Thr Asn
            20                  25                  30

Val Ala Trp Phe Gln Gln Lys Pro Gly Lys Ala Pro Lys Ser Leu Ile
        35                  40                  45

His Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Arg Tyr Pro Tyr
                85                  90                  95

Thr Phe Gly Gly Gly Thr Lys Leu Glu Ile Lys
            100                 105
```

<210> SEQ ID NO 8
<211> LENGTH: 322
<212> TYPE: DNA
<213> ORGANISM: Artificial Sequence
<220> FEATURE:
<223> OTHER INFORMATION: Synthetic nucleotide sequence

<400> SEQUENCE: 8

```
gacatccaga tgacccagtc tccatcttcc ctgtctgcat ctgtaggaga cagagtcacc      60
atcacttgtc gggcgagtca gaatgtgggt acaaatgtag cctggttttca gcagaaacca    120
gggaaagccc ctaagtccct gatccattcg gcatcctacc gttacagtgg ggtcccatca    180
aggttcagcg gcagtggatc tgggacagat tcactctcca ccatcagcag cctgcagcct    240
gaagattttg caacttacta ttgtcagcaa tataagaggt atccgtacac gttcggaggg    300
gggaccaagc tggaaataaa ac                                             322
```

<210> SEQ ID NO 9
<211> LENGTH: 122
<212> TYPE: PRT
<213> ORGANISM: Artificial Sequence
<220> FEATURE:
<223> OTHER INFORMATION: Synthetic peptide sequence

<400> SEQUENCE: 9

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Gly Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Lys Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
```

85                  90                  95
Thr Arg His Asp Pro Asn Asp Gly Tyr Tyr Phe Leu Phe Ala Tyr Trp
                100                 105                 110
Gly Gln Gly Thr Leu Val Thr Val Ser Ser
        115                 120

<210> SEQ ID NO 10
<211> LENGTH: 365
<212> TYPE: DNA
<213> ORGANISM: Artificial Sequence
<220> FEATURE:
<223> OTHER INFORMATION: Synthetic nucleotide sequence

<400> SEQUENCE: 10
gaggtgcaac tggtggagtc tgggggaggc ctggtcaagc ctgggggtc cctgagactc      60 tcctgtgcag cctctggatt caccttcagt acctatggca tgagctgggt ccgccaggct    120
ccagggaagg gctggagtg gtcgcaacc attagtagtg gtggtactta cacatactac     180
ccagactcag tgaagggccg attcaaaatc tccagagaca cgccaagaa ctcactgtat     240 ctgcaaatga acagcctgag agccgaggac acggctgtgt attactgtac aagacatgac    300
cccaatgatg gttactactt cctgtttgct tactggggcc aggggactct ggtcactgtc    360
tcttc                                                                365

<210> SEQ ID NO 11
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Ser Val Gly Asn Asn
            20                  25                  30

Val Ala Trp Tyr Gln Gln Lys Pro Gly Gln Ala Pro Arg Leu Leu Ile
        35                  40                  45

Tyr Tyr Ala Ser Asn Arg Tyr Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln His Tyr Ser Ser Pro Leu
                85                  90                  95

Thr Phe Gly Ala Gly Thr Lys Leu Glu Ile Lys
            100                 105

<210> SEQ ID NO 12
<211> LENGTH: 322
<212> TYPE: DNA
<213> ORGANISM: Artificial Sequence
<220> FEATURE:
<223> OTHER INFORMATION: Synthetic nucleotide sequence

<400> SEQUENCE: 12
gaaattgtgt tgacgcagtc tccaggcacc ctgtctttgt ctccagggga aagagccacc     60
ctctcctgca aggccagtca gagtgttggc aacaatgtag cttggtacca gcagaaacct    120
ggccaggctc ccaggctcct catctactat gcatccaata ggtatacagg catcccagac    180

```
aggttcagtg gcagtgggtc tgggacagac ttcactctca ccatcagcag actggagcct    240
gaagattttg cagtgtatta ctgtcaacag cattatagct ctccgctcac gttcggtgct    300
gggaccaagc tggagatcaa ac                                             322
```

<210> SEQ ID NO 13
<211> LENGTH: 120
<212> TYPE: PRT
<213> ORGANISM: Artificial Sequence
<220> FEATURE:
<223> OTHER INFORMATION: Synthetic peptide sequence

<400> SEQUENCE: 13

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Trp Ile Tyr Pro Gly Asn Phe Asn Thr Lys Tyr Asn Glu Arg Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Asp Gly Ser Pro Tyr Tyr Ala Met Asp Tyr Trp Gly Gln
            100                 105                 110

Gly Thr Ser Val Thr Val Ser Ser
        115                 120
```

<210> SEQ ID NO 14
<211> LENGTH: 360
<212> TYPE: DNA
<213> ORGANISM: Artificial Sequence
<220> FEATURE:
<223> OTHER INFORMATION: Synthetic nucleotide sequence

<400> SEQUENCE: 14

```
caggttcagc tggtgcagtc tggagctgag gtgaagaagc ctggggcctc agtgaaggtc    60
tcctgcaagg cttctggtta cacctttacc ggctattaca tccactgggt gcgacaggcc    120
cctggacaag ggcttgagtg gatgggatgg atctaccctg gcaattttaa cacaaaatat    180
aacgagcggt tcaagggcag agtcaccatg accacagaca catccacgag cacagcctac    240
atggagctga ggagcctgag atctgacgac acggccgtgt attactgtgc gagagaggat    300
ggtagcccct actatgctat ggactactgg ggtcaaggaa cctcagtcac cgtctcctca    360
```

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 15

```
Gly Tyr Tyr Ile His
1               5
```

<210> SEQ ID NO 16
<211> LENGTH: 7
<212> TYPE: PRT

```
<213> ORGANISM: Artificial Sequence
<220> FEATURE:
<223> OTHER INFORMATION: Synthetic peptide sequence

<400> SEQUENCE: 16

Gly Tyr Thr Phe Thr Gly Tyr
1               5

<210> SEQ ID NO 17
<211> LENGTH: 15
<212> TYPE: DNA
<213> ORGANISM: Artificial Sequence
<220> FEATURE:
<223> OTHER INFORMATION: Synthetic nucleotide sequence

<400> SEQUENCE: 17
ggctattaca tccac                                                    15

<210> SEQ ID NO 18
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 18
ggttacacct ttaccggcta t                                             21

<210> SEQ ID NO 19
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 19

Trp Ile Tyr Pro Gly Asn Phe Asn Thr Lys Tyr Asn Glu Arg Phe Lys
1               5                   10                  15

Gly

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 20

Tyr Pro Gly Asn Phe Asn
1               5

<210> SEQ ID NO 21
<211> LENGTH: 51
<212> TYPE: DNA
<213> ORGANISM: Artificial Sequence
<220> FEATURE:
<223> OTHER INFORMATION: Synthetic nucleotide sequence

<400> SEQUENCE: 21
tggatctacc ctggcaattt taacacaaaa tataacgagc ggttcaaggg c             51

<210> SEQ ID NO 22
<211> LENGTH: 18
<212> TYPE: DNA
<213> ORGANISM: Artificial Sequence
<220> FEATURE:
```

<223> OTHER INFORMATION: Synthetic nucleotide sequence

<400> SEQUENCE: 22
taccctggca attttaac 18

<210> SEQ ID NO 23
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 23

Glu Asp Gly Ser Pro Tyr Tyr Ala Met Asp Tyr
1               5                   10

<210> SEQ ID NO 24
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 24
gaggatggta gcccctacta tgctatggac tac 33

<210> SEQ ID NO 25
<211> LENGTH: 449
<212> TYPE: PRT
<213> ORGANISM: Artificial Sequence
<220> FEATURE:
<223> OTHER INFORMATION: Synthetic peptide sequence

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Ile His Trp Val Arg Gln Ala Pro Gly Gln Gly Leu Glu Trp Met
            35                  40                  45

Gly Trp Ile Tyr Pro Gly Asn Phe Asn Thr Lys Tyr Asn Glu Arg Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Asp Gly Ser Pro Tyr Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

```
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly

<210> SEQ ID NO 26
<211> LENGTH: 1347
<212> TYPE: DNA
<213> ORGANISM: Artificial Sequence
<220> FEATURE:
<223> OTHER INFORMATION: Synthetic nucleotide sequence

<400> SEQUENCE: 26
caggttcagc tggtgcagtc tggagctgag gtgaagaagc ctggggcctc agtgaaggtc      60
tcctgcaagg cttctggtta cacctttacc ggctattaca tccactgggt gcgacaggcc     120
cctggacaag gcttgagtg gatgggatgg atctaccctg caattttaa cacaaaatat      180 aacgagcggt tcaagggcag agtcaccatg accacagaca catccacgag cacagcctac     240
atggagctga ggagcctgag atctgacgac acggccgtgt attactgtgc gagagaggat     300
ggtagcccct actatgctat ggactactgg ggtcaaggaa cctcagtcac cgtctcctca     360
gcctccacca aggcccatc ggtcttcccc ctggcgccct cgagcaagag cacctctggg     420
ggcacagcgg ccctgggctg cctggtcaag gactacttcc ccgagccggt gacggtgtcg     480
tggaactcag cgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
```

```
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggatgag   1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggt                                       1347
```

<210> SEQ ID NO 27
<211> LENGTH: 112
<212> TYPE: PRT
<213> ORGANISM: Artificial Sequence
<220> FEATURE:
<223> OTHER INFORMATION: Synthetic peptide sequence

<400> SEQUENCE: 27

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Phe Leu Tyr Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Val Pro Trp Thr Phe Gly Gly Gly Thr Lys Val Glu Ile Lys
            100                 105                 110
```

<210> SEQ ID NO 28
<211> LENGTH: 336
<212> TYPE: DNA
<213> ORGANISM: Artificial Sequence
<220> FEATURE:
<223> OTHER INFORMATION: Synthetic nucleotide sequence

<400> SEQUENCE: 28

```
gatattgtga tgacccagac tccactctct ctgtccgtca cccctggaca gccggcctcc     60
atctcctgcc ggtctagtca gagcctcgtg catagtaatg gaaacacctt tttgtattgg    120
tacctgcaga agccaggcca gtctccacag ctcctaatct atagagtttc aaccggttc    180 tctggagtgc cagataggtt cagtggcagc gggtcaggga cagatttcac actgaaaatc    240
agccgggtgg aggctgagga tgttggggtt tattactgct ttcaagctac acatgttccg    300
tggacgttcg gtggaggcac caaagtggaa atcaaa                              336
```

<210> SEQ ID NO 29
<211> LENGTH: 16
<212> TYPE: PRT
<213> ORGANISM: Artificial Sequence
<220> FEATURE:
<223> OTHER INFORMATION: Synthetic peptide sequence

<400> SEQUENCE: 29

Arg Ser Ser Gln Ser Leu Val His Ser Asn Gly Asn Thr Phe Leu Tyr
1               5                   10                  15

<210> SEQ ID NO 30
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 30

Gln Ser Leu Val His Ser Asn Gly Asn Thr Phe
1               5                   10

<210> SEQ ID NO 31
<211> LENGTH: 48
<212> TYPE: DNA
<213> ORGANISM: Artificial Sequence
<220> FEATURE:
<223> OTHER INFORMATION: Synthetic nucleotide sequence

<400> SEQUENCE: 31
cggtctagtc agagcctcgt gcatagtaat ggaaacacct ttttgtat                48

<210> SEQ ID NO 32
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 32
cagagcctcg tgcatagtaa tggaaacacc ttt                                33

<210> SEQ ID NO 33
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 33

Arg Val Ser Asn Arg Phe Ser
1               5

<210> SEQ ID NO 34
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 34
agagtttcca accggttctc t                                             21

<210> SEQ ID NO 35
<211> LENGTH: 9
<212> TYPE: PRT
<213> ORGANISM: Artificial Sequence

```
<220> FEATURE:
<223> OTHER INFORMATION: Synthetic peptide sequence

<400> SEQUENCE: 35

Phe Gln Ala Thr His Val Pro Trp Thr
1               5

<210> SEQ ID NO 36
<211> LENGTH: 24
<212> TYPE: DNA
<213> ORGANISM: Artificial Sequence
<220> FEATURE:
<223> OTHER INFORMATION: Synthetic nucleotide sequence

<400> SEQUENCE: 36
caagctacac atgttccgtg gacg                                            24

<210> SEQ ID NO 37
<211> LENGTH: 219
<212> TYPE: PRT
<213> ORGANISM: Artificial Sequence
<220> FEATURE:
<223> OTHER INFORMATION: Synthetic peptide sequence

<400> SEQUENCE: 37
```

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Phe Leu Tyr Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

```
<210> SEQ ID NO 38
<211> LENGTH: 657
<212> TYPE: DNA
<213> ORGANISM: Artificial Sequence
<220> FEATURE:
<223> OTHER INFORMATION: Synthetic nucleotide sequence
```

<400> SEQUENCE: 38

```
gatattgtga tgacccagac tccactctct ctgtccgtca cccctggaca gccggcctcc      60
atctcctgcc ggtctagtca gagcctcgtg catagtaatg gaaacacctt tttgtattgg     120
tacctgcaga agccaggcca gtctccacag ctcctaatct atagagtttc aaccggttc      180
tctggagtgc cagataggtt cagtggcagc gggtcaggga cagatttcac actgaaaatc     240
agccgggtgg aggctgagga tgttggggtt tattactgct ttcaagctac acatgttccg     300
tggacgttcg gtggaggcac caaagtggaa atcaaacgga ctgtggctgc accaagtgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt       657
```

<210> SEQ ID NO 39
<211> LENGTH: 118
<212> TYPE: PRT
<213> ORGANISM: Artificial Sequence
<220> FEATURE:
<223> OTHER INFORMATION: Synthetic peptide sequence

<400> SEQUENCE: 39

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Tyr Phe
            20                  25                  30
Tyr Met Asn Trp Val Arg Gln Ala Pro Gly Gln Gly Leu Glu Trp Val
        35                  40                  45
Gly Gln Ile Asn Pro Asn Asn Gly Gly Thr Ala Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Trp Val Gly Thr His Tyr Phe Asp Tyr Trp Gly Gln Gly Thr
            100                 105                 110
Thr Leu Thr Val Ser Ser
        115
```

<210> SEQ ID NO 40
<211> LENGTH: 354
<212> TYPE: DNA
<213> ORGANISM: Artificial Sequence
<220> FEATURE:
<223> OTHER INFORMATION: Synthetic nucleotide sequence

<400> SEQUENCE: 40

```
caggtgcagc tggtgcagtc tggggctgag gtgaagaagc ctggggcctc agtgaaggtt      60
tcctgcaagg catctggata caccttcact tacttctata tgaactgggt gcgacaggcc     120
cctggacaag gcttgagtg gtgggacaa tcaaccccta ataatggtgg cacagcctac      180
gcacagaagt tccagggcag agtcaccatg accaggaca cgtccacgag cacagtctac      240
atggagctga gcagcctgag atctgaggac acggccgtgt attactgtgc gagatgggtc     300
```

```
gggactcact actttgacta ctggggccaa ggcaccactc tcacagtctc ctcc      354
```

<210> SEQ ID NO 41
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 41

Tyr Phe Tyr Met Asn
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 42

Gly Tyr Thr Phe Thr Tyr Phe
1               5

<210> SEQ ID NO 43
<211> LENGTH: 15
<212> TYPE: DNA
<213> ORGANISM: Artificial Sequence
<220> FEATURE:
<223> OTHER INFORMATION: Synthetic nucleotide sequence

<400> SEQUENCE: 43

```
tacttctata tgaac                                                 15
```

<210> SEQ ID NO 44
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 44

```
ggatacacct tcacttactt c                                          21
```

<210> SEQ ID NO 45
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 45

Gln Ile Asn Pro Asn Asn Gly Gly Thr Ala Tyr Ala Gln Lys Phe Gln
1               5                   10                  15
Gly

<210> SEQ ID NO 46
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 46

Asn Pro Asn Asn Gly Gly Thr
1               5

<210> SEQ ID NO 47
<211> LENGTH: 51
<212> TYPE: DNA
<213> ORGANISM: Artificial Sequence
<220> FEATURE:
<223> OTHER INFORMATION: Synthetic nucleotide sequence

<400> SEQUENCE: 47
caaatcaacc ctaataatgg tggcacagcc tacgcacaga agttccaggg c    51

<210> SEQ ID NO 48
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 48
aaccctaata atggtggcac a    21

<210> SEQ ID NO 49
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 49

Trp Val Gly Thr His Tyr Phe Asp Tyr
1               5

<210> SEQ ID NO 50
<211> LENGTH: 27
<212> TYPE: DNA
<213> ORGANISM: Artificial Sequence
<220> FEATURE:
<223> OTHER INFORMATION: Synthetic nucleotide sequence

<400> SEQUENCE: 50
tgggtcggga ctcactactt tgactac    27

<210> SEQ ID NO 51
<211> LENGTH: 447
<212> TYPE: PRT
<213> ORGANISM: Artificial Sequence
<220> FEATURE:
<223> OTHER INFORMATION: Synthetic peptide sequence

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Phe
            20                  25                  30

Tyr Met Asn Trp Val Arg Gln Ala Pro Gly Gln Gly Leu Glu Trp Val
        35                  40                  45

Gly Gln Ile Asn Pro Asn Asn Gly Gly Thr Ala Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Val Gly Thr His Tyr Phe Asp Tyr Trp Gly Gln Gly Thr

```
            100                 105                 110
Thr Leu Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
        210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly
        435                 440                 445

<210> SEQ ID NO 52
<211> LENGTH: 1341
<212> TYPE: DNA
<213> ORGANISM: Artificial Sequence
<220> FEATURE:
<223> OTHER INFORMATION: Synthetic nucleotide sequence

<400> SEQUENCE: 52
caggtgcagc tggtgcagtc tggggctgag gtgaagaagc ctggggcctc agtgaaggtt      60
tcctgcaagg catctggata caccttcact tacttctata tgaactgggt gcgacaggcc     120
```

```
cctggacaag ggcttgagtg ggtgggacaa atcaaccccta taatggtgg cacagcctac      180 gcacagaagt tccagggcag agtcaccatg accagggaca cgtccacgag cacagtctac      240
atggagctga gcagcctgag atctgaggac acggccgtgt attactgtgc gagatgggtc      300
gggactcact actttgacta ctggggccaa ggcaccactc tcacagtctc ctccgcctcc      360
accaagggcc catcggtctt ccccctggcg ccctcgagca gagcacctc tgggggcaca       420 gcggccctgg gctgcctggt caaggactac ttccccgagc cggtgacggt gtcgtggaac      480
tcaggcgccc tgaccagcgg cgtgcacacc ttcccggctg tcctacagtc ctcaggactc      540
tactccctca gcagcgtggt gaccgtgccc tccagcagct gggcaccca gacctacatc       600 tgcaacgtga atcacaagcc cagcaacacc aaggtggaca agaaagttga gcccaaatct      660
tgtgacaaaa ctcacacatg cccaccgtgc ccagcacctg aactcctggg gggaccgtca     720
gtcttcctct tccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca aagccgcggg aggagcagta caacagcacg     900
taccgtgtgg tcagcgtcct caccgtcctg caccaggact ggctgaatgg caaggagtac     960
aagtgcaagg tctccaacaa agccctccca gcccccatcg agaaaccat ctccaaagcc      1020 aaagggcagc cccgagaacc acaggtgtac accctgcccc catcccggga tgagctgacc     1080
aagaaccagg tcagcctgac ctgcctggtc aaaggcttct atcccagcga catcgccgtg     1140
gagtgggaga gcaatgggca gccggagaac aactacaaga ccacgcctcc cgtgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacgcagaag    1320
agcctctccc tgtctccggg t                                              1341
```

<210> SEQ ID NO 53
<211> LENGTH: 111
<212> TYPE: PRT
<213> ORGANISM: Artificial Sequence
<220> FEATURE:
<223> OTHER INFORMATION: Synthetic peptide sequence

<400> SEQUENCE: 53

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Ser Tyr Thr Tyr Ile His Trp Tyr Gln Gln Lys Pro Gly Gln Ala Pro
        35                  40                  45

Arg Leu Leu Ile Asn Phe Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Trp
                85                  90                  95

Glu Ile Pro Pro Thr Phe Gly Gly Gly Thr Lys Leu Glu Ile Lys
            100                 105                 110
```

<210> SEQ ID NO 54
<211> LENGTH: 333
<212> TYPE: DNA
<213> ORGANISM: Artificial Sequence
<220> FEATURE:

<223> OTHER INFORMATION: Synthetic nucleotide sequence

<400> SEQUENCE: 54

```
gaaattgtgt tgacacagtc tccagccacc ctgtctttgt ctccagggga aagagccacc    60
ctctcctgca gggccagtca gagtgttagc agctctagct atacttacat tcactggtac   120
caacagaaac ctggccaggc tcccaggctc ctcatcaatt ttgcatccaa cttggaaagt   180
ggcatcccag ccaggttcag tggcagtggg tctgggacag acttcactct caccatcagc   240
agcctagagc ctgaagattt tgcagtttat tactgtcagc acagttggga gattcctccg   300
acgttcggtg gaggcaccaa gctggaaatc aaa                                333
```

<210> SEQ ID NO 55
<211> LENGTH: 15
<212> TYPE: PRT
<213> ORGANISM: Artificial Sequence
<220> FEATURE:
<223> OTHER INFORMATION: Synthetic peptide sequence

<400> SEQUENCE: 55

```
Arg Ala Ser Gln Ser Val Ser Ser Ser Tyr Thr Tyr Ile His
1               5                   10                  15
```

<210> SEQ ID NO 56
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 56

```
Ser Ser Ser Tyr Thr Tyr Ile His
1               5
```

<210> SEQ ID NO 57
<211> LENGTH: 45
<212> TYPE: DNA
<213> ORGANISM: Artificial Sequence
<220> FEATURE:
<223> OTHER INFORMATION: Synthetic nucleotide sequence

<400> SEQUENCE: 57

```
agggccagtc agagtgttag cagctctagc tatacttaca ttcac              45
```

<210> SEQ ID NO 58
<211> LENGTH: 24
<212> TYPE: DNA
<213> ORGANISM: Artificial Sequence
<220> FEATURE:
<223> OTHER INFORMATION: Synthetic nucleotide sequence

<400> SEQUENCE: 58

```
agctctagct atacttacat tcac                                     24
```

<210> SEQ ID NO 59
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 59

```
Phe Ala Ser Asn Leu Glu Ser
1               5
```

<210> SEQ ID NO 60
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 60
tttgcatcca acttggaaag t          21

<210> SEQ ID NO 61
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 61

Gln His Ser Trp Glu Ile Pro Pro Thr
1               5

<210> SEQ ID NO 62
<211> LENGTH: 27
<212> TYPE: DNA
<213> ORGANISM: Artificial Sequence
<220> FEATURE:
<223> OTHER INFORMATION: Synthetic nucleotide sequence

<400> SEQUENCE: 62
cagcacagtt gggagattcc tccgacg          27

<210> SEQ ID NO 63
<211> LENGTH: 218
<212> TYPE: PRT
<213> ORGANISM: Artificial Sequence
<220> FEATURE:
<223> OTHER INFORMATION: Synthetic peptide sequence

<400> SEQUENCE: 63

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Ser Tyr Thr Tyr Ile His Trp Tyr Gln Gln Lys Pro Gly Gln Ala Pro
            35                  40                  45

Arg Leu Leu Ile Asn Phe Ala Ser Asn Leu Glu Ser Gly Ile Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Trp
                85                  90                  95

Glu Ile Pro Pro Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

```
Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215
```

<210> SEQ ID NO 64
<211> LENGTH: 654
<212> TYPE: DNA
<213> ORGANISM: Artificial Sequence
<220> FEATURE:
<223> OTHER INFORMATION: Synthetic nucleotide sequence

<400> SEQUENCE: 64

```
gaaattgtgt tgacacagtc tccagccacc ctgtctttgt ctccagggga aagagccacc      60
ctctcctgca gggccagtca gagtgttagc agctctagct atacttacat tcactggtac     120
caacagaaac ctggccaggc tcccaggctc ctcatcaatt ttgcatccaa cttggaaagt     180
ggcatcccag ccaggttcag tggcagtggg tctgggacag acttcactct caccatcagc     240
agcctagagc tgaagatttt gcagtttat tactgtcagc acagttggga gattcctccg      300
acgttcggtg gaggcaccaa gctggaaatc aaacggactg tggctgcacc aagtgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca agtctacgc ctgcgaagtc     600
acccatcagg gcctgagctc gcccgtcaca aagagcttca caggggaga gtgt            654
```

<210> SEQ ID NO 65
<211> LENGTH: 8
<212> TYPE: PRT
<213> ORGANISM: Mus spretus

<400> SEQUENCE: 65

```
Gly Tyr Thr Phe Thr Asp Tyr Glu
1               5
```

<210> SEQ ID NO 66
<211> LENGTH: 8
<212> TYPE: PRT
<213> ORGANISM: Mus spretus

<400> SEQUENCE: 66

```
Gly Phe Ser Leu Thr Thr Tyr Gly
1               5
```

<210> SEQ ID NO 67
<211> LENGTH: 8
<212> TYPE: PRT
<213> ORGANISM: Mus spretus

<400> SEQUENCE: 67

```
Gly Tyr Thr Phe Thr Asn Tyr Trp
1               5
```

<210> SEQ ID NO 68
<211> LENGTH: 8
<212> TYPE: PRT

<213> ORGANISM: Mus spretus

<400> SEQUENCE: 68

Gly Phe Thr Phe Ser Thr Tyr Gly
1               5

<210> SEQ ID NO 69
<211> LENGTH: 8
<212> TYPE: PRT
<213> ORGANISM: Mus spretus

<400> SEQUENCE: 69

Gly Tyr Thr Phe Thr Gly Tyr Tyr
1               5

<210> SEQ ID NO 70
<211> LENGTH: 8
<212> TYPE: PRT
<213> ORGANISM: Mus spretus

<400> SEQUENCE: 70

Gly Tyr Thr Phe Thr Arg Asp Trp
1               5

<210> SEQ ID NO 71
<211> LENGTH: 8
<212> TYPE: PRT
<213> ORGANISM: Mus spretus

<400> SEQUENCE: 71

Gly Tyr Thr Phe Thr Tyr Phe Tyr
1               5

<210> SEQ ID NO 72
<211> LENGTH: 8
<212> TYPE: PRT
<213> ORGANISM: Mus spretus

<400> SEQUENCE: 72

Gly Tyr Ser Phe Thr Val Tyr Asn
1               5

<210> SEQ ID NO 73
<211> LENGTH: 9
<212> TYPE: PRT
<213> ORGANISM: Mus spretus

<400> SEQUENCE: 73

Gly Tyr Ser Ile Thr Ser Gly Tyr Tyr
1               5

<210> SEQ ID NO 74
<211> LENGTH: 8
<212> TYPE: PRT
<213> ORGANISM: Mus spretus

<400> SEQUENCE: 74

Gly Tyr Thr Phe Thr Gly Tyr Tyr
1               5

<210> SEQ ID NO 75
<211> LENGTH: 8
<212> TYPE: PRT
<213> ORGANISM: Mus spretus

<400> SEQUENCE: 75

Gly Tyr Thr Phe Thr Ser Tyr Trp
1               5

<210> SEQ ID NO 76
<211> LENGTH: 8
<212> TYPE: PRT
<213> ORGANISM: Mus spretus

<400> SEQUENCE: 76

Gly Ala Ser Ile Thr Ser Gly Tyr
1               5

<210> SEQ ID NO 77
<211> LENGTH: 8
<212> TYPE: PRT
<213> ORGANISM: Mus spretus

<400> SEQUENCE: 77

Phe Asp Pro Glu Thr Gly Asn Thr
1               5

<210> SEQ ID NO 78
<211> LENGTH: 7
<212> TYPE: PRT
<213> ORGANISM: Mus spretus

<400> SEQUENCE: 78

Ile Trp Gly Gly Gly Ser Thr
1               5

<210> SEQ ID NO 79
<211> LENGTH: 8
<212> TYPE: PRT
<213> ORGANISM: Mus spretus

<400> SEQUENCE: 79

Ile Asp Pro Ser Asp Ser Tyr Ile
1               5

<210> SEQ ID NO 80
<211> LENGTH: 8
<212> TYPE: PRT
<213> ORGANISM: Mus spretus

<400> SEQUENCE: 80

Ile Ser Ser Gly Gly Thr Tyr Thr
1               5

<210> SEQ ID NO 81
<211> LENGTH: 8
<212> TYPE: PRT
<213> ORGANISM: Mus spretus

<400> SEQUENCE: 81

Ile Tyr Pro Gly Asn Phe Asn Thr
1               5

<210> SEQ ID NO 82
<211> LENGTH: 8
<212> TYPE: PRT
<213> ORGANISM: Mus spretus

<400> SEQUENCE: 82

-continued

Ile His Pro Tyr Asp Ser Glu Thr
1               5

<210> SEQ ID NO 83
<211> LENGTH: 8
<212> TYPE: PRT
<213> ORGANISM: Mus spretus

<400> SEQUENCE: 83

Ile Asn Pro Asn Asn Gly Gly Thr
1               5

<210> SEQ ID NO 84
<211> LENGTH: 8
<212> TYPE: PRT
<213> ORGANISM: Mus spretus

<400> SEQUENCE: 84

Ile Asn Pro Tyr Tyr Gly Gly Thr
1               5

<210> SEQ ID NO 85
<211> LENGTH: 7
<212> TYPE: PRT
<213> ORGANISM: Mus spretus

<400> SEQUENCE: 85

Ile Ser Tyr Asp Gly Arg Asn
1               5

<210> SEQ ID NO 86
<211> LENGTH: 8
<212> TYPE: PRT
<213> ORGANISM: Mus spretus

<400> SEQUENCE: 86

Ile Tyr Pro Gly Asn Phe Asn Thr
1               5

<210> SEQ ID NO 87
<211> LENGTH: 8
<212> TYPE: PRT
<213> ORGANISM: Mus spretus

<400> SEQUENCE: 87

Ile His Pro Asn Ser Asp Thr Ile
1               5

<210> SEQ ID NO 88
<211> LENGTH: 7
<212> TYPE: PRT
<213> ORGANISM: Mus spretus

<400> SEQUENCE: 88

Ile Asn Tyr Ser Gly Asn Thr
1               5

<210> SEQ ID NO 89
<211> LENGTH: 10
<212> TYPE: PRT
<213> ORGANISM: Mus spretus

<400> SEQUENCE: 89

Ala Arg Gly Tyr Pro Ala Trp Phe Gly Tyr
1               5                   10

<210> SEQ ID NO 90
<211> LENGTH: 6
<212> TYPE: PRT
<213> ORGANISM: Mus spretus

<400> SEQUENCE: 90

Ala Ser Asp Trp Ala Tyr
1               5

<210> SEQ ID NO 91
<211> LENGTH: 11
<212> TYPE: PRT
<213> ORGANISM: Mus spretus

<400> SEQUENCE: 91

Ala Arg Glu Arg Leu Ser His Ala Met Asp Tyr
1               5                   10

<210> SEQ ID NO 92
<211> LENGTH: 15
<212> TYPE: PRT
<213> ORGANISM: Mus spretus

<400> SEQUENCE: 92

Thr Arg His Asp Pro Asn Asp Gly Tyr Tyr Phe Leu Phe Ala Tyr
1               5                   10                  15

<210> SEQ ID NO 93
<211> LENGTH: 13
<212> TYPE: PRT
<213> ORGANISM: Mus spretus

<400> SEQUENCE: 93

Ala Arg Glu Asp Gly Ser Pro Tyr Tyr Ala Met Asp Tyr
1               5                   10

<210> SEQ ID NO 94
<211> LENGTH: 17
<212> TYPE: PRT
<213> ORGANISM: Mus spretus

<400> SEQUENCE: 94

Val Thr Phe Ile Lys Thr Met Val Asp Thr Tyr Tyr Tyr Ala Met Asp
1               5                   10                  15

Tyr

<210> SEQ ID NO 95
<211> LENGTH: 11
<212> TYPE: PRT
<213> ORGANISM: Mus spretus

<400> SEQUENCE: 95

Ala Arg Trp Val Gly Thr His Tyr Phe Asp Tyr
1               5                   10

<210> SEQ ID NO 96
<211> LENGTH: 15
<212> TYPE: PRT
<213> ORGANISM: Mus spretus

<400> SEQUENCE: 96

Ala Arg Gly Gly Lys Thr Gly Thr Tyr Tyr Tyr Val Met Asp Tyr
1               5                   10                  15

```
<210> SEQ ID NO 97
<211> LENGTH: 12
<212> TYPE: PRT
<213> ORGANISM: Mus spretus

<400> SEQUENCE: 97

Ala Arg Glu Gly Tyr Gly Asp Tyr Pro Phe Asp Tyr
1               5                   10

<210> SEQ ID NO 98
<211> LENGTH: 13
<212> TYPE: PRT
<213> ORGANISM: Mus spretus

<400> SEQUENCE: 98

Ala Arg Glu Asp Gly Ser Pro Tyr Tyr Ala Met Asp Tyr
1               5                   10

<210> SEQ ID NO 99
<211> LENGTH: 11
<212> TYPE: PRT
<213> ORGANISM: Mus spretus

<400> SEQUENCE: 99

Ala Thr Pro Glu Arg Arg Arg Ala Met Asp Tyr
1               5                   10

<210> SEQ ID NO 100
<211> LENGTH: 14
<212> TYPE: PRT
<213> ORGANISM: Mus spretus

<400> SEQUENCE: 100

Ala Arg Ser Thr Met Ile Thr Thr Gly Ala Trp Phe Ala Tyr
1               5                   10

<210> SEQ ID NO 101
<211> LENGTH: 11
<212> TYPE: PRT
<213> ORGANISM: Mus spretus

<400> SEQUENCE: 101

Gln Ser Leu Ala His Thr Asn Gly Asn Thr Tyr
1               5                   10

<210> SEQ ID NO 102
<211> LENGTH: 6
<212> TYPE: PRT
<213> ORGANISM: Mus spretus

<400> SEQUENCE: 102

Gln Asn Val Gly Thr Asn
1               5

<210> SEQ ID NO 103
<211> LENGTH: 6
<212> TYPE: PRT
<213> ORGANISM: Mus spretus

<400> SEQUENCE: 103

Gln Asp Ile Lys Ser Tyr
1               5
```

```
<210> SEQ ID NO 104
<211> LENGTH: 6
<212> TYPE: PRT
<213> ORGANISM: Mus spretus

<400> SEQUENCE: 104

Gln Ser Val Gly Asn Asn
1               5

<210> SEQ ID NO 105
<211> LENGTH: 11
<212> TYPE: PRT
<213> ORGANISM: Mus spretus

<400> SEQUENCE: 105

Gln Ser Leu Val His Ser Asn Gly Asn Thr Phe
1               5                   10

<210> SEQ ID NO 106
<211> LENGTH: 11
<212> TYPE: PRT
<213> ORGANISM: Mus spretus

<400> SEQUENCE: 106

Gln Ser Leu Leu His Ser Asp Gly Lys Thr Tyr
1               5                   10

<210> SEQ ID NO 107
<211> LENGTH: 10
<212> TYPE: PRT
<213> ORGANISM: Mus spretus

<400> SEQUENCE: 107

Gln Ser Val Ser Ser Ser Tyr Thr Tyr
1               5                   10

<210> SEQ ID NO 108
<211> LENGTH: 6
<212> TYPE: PRT
<213> ORGANISM: Mus spretus

<400> SEQUENCE: 108

Glu Asn Ile Asp Ser Tyr
1               5

<210> SEQ ID NO 109
<211> LENGTH: 10
<212> TYPE: PRT
<213> ORGANISM: Mus spretus

<400> SEQUENCE: 109

Gln Ser Val Ser Ser Ser Tyr Ser Tyr
1               5                   10

<210> SEQ ID NO 110
<211> LENGTH: 11
<212> TYPE: PRT
<213> ORGANISM: Mus spretus

<400> SEQUENCE: 110

Gln Ser Leu Val His Ser Asn Gly Asn Thr Phe
1               5                   10

<210> SEQ ID NO 111
<211> LENGTH: 7
```

```
<212> TYPE: PRT
<213> ORGANISM: Mus spretus

<400> SEQUENCE: 111

Ser Ser Leu Ser Ser Tyr
1               5

<210> SEQ ID NO 112
<211> LENGTH: 6
<212> TYPE: PRT
<213> ORGANISM: Mus spretus

<400> SEQUENCE: 112

Gln Ser Val Ser Lys Asp
1               5

<210> SEQ ID NO 113
<211> LENGTH: 8
<212> TYPE: PRT
<213> ORGANISM: Mus spretus

<400> SEQUENCE: 113

Lys Val Ser Asn Met Arg Phe Ser
1               5

<210> SEQ ID NO 114
<211> LENGTH: 7
<212> TYPE: PRT
<213> ORGANISM: Mus spretus

<400> SEQUENCE: 114

Ser Ala Ser Tyr Arg Tyr Ser
1               5

<210> SEQ ID NO 115
<211> LENGTH: 7
<212> TYPE: PRT
<213> ORGANISM: Mus spretus

<400> SEQUENCE: 115

Tyr Ala Thr Ser Leu Ala Asp
1               5

<210> SEQ ID NO 116
<211> LENGTH: 7
<212> TYPE: PRT
<213> ORGANISM: Mus spretus

<400> SEQUENCE: 116

Tyr Ala Ser Asn Arg Tyr Thr
1               5

<210> SEQ ID NO 117
<211> LENGTH: 7
<212> TYPE: PRT
<213> ORGANISM: Mus spretus

<400> SEQUENCE: 117

Arg Val Ser Asn Arg Phe Ser
1               5

<210> SEQ ID NO 118
<211> LENGTH: 7
<212> TYPE: PRT
<213> ORGANISM: Mus spretus
```

```
<400> SEQUENCE: 118

Leu Val Ser Asn Leu Asp Ser
1               5

<210> SEQ ID NO 119
<211> LENGTH: 7
<212> TYPE: PRT
<213> ORGANISM: Mus spretus

<400> SEQUENCE: 119

Phe Ala Ser Asn Leu Glu Ser
1               5

<210> SEQ ID NO 120
<211> LENGTH: 7
<212> TYPE: PRT
<213> ORGANISM: Mus spretus

<400> SEQUENCE: 120

Ala Ala Thr Leu Leu Ala Asp
1               5

<210> SEQ ID NO 121
<211> LENGTH: 7
<212> TYPE: PRT
<213> ORGANISM: Mus spretus

<400> SEQUENCE: 121

Tyr Ala Ser Asn Leu Glu Ser
1               5

<210> SEQ ID NO 122
<211> LENGTH: 7
<212> TYPE: PRT
<213> ORGANISM: Mus spretus

<400> SEQUENCE: 122

Arg Val Ser Asn Arg Phe Ser
1               5

<210> SEQ ID NO 123
<211> LENGTH: 7
<212> TYPE: PRT
<213> ORGANISM: Mus spretus

<400> SEQUENCE: 123

Ser Thr Ser Phe Leu Ala Ser
1               5

<210> SEQ ID NO 124
<211> LENGTH: 7
<212> TYPE: PRT
<213> ORGANISM: Mus spretus

<400> SEQUENCE: 124

Tyr Ala Ser Asn Arg Tyr Thr
1               5

<210> SEQ ID NO 125
<211> LENGTH: 9
<212> TYPE: PRT
<213> ORGANISM: Mus spretus

<400> SEQUENCE: 125
```

Ser Gln Asp Thr His Val Pro Pro Thr
1               5

<210> SEQ ID NO 126
<211> LENGTH: 9
<212> TYPE: PRT
<213> ORGANISM: Mus spretus

<400> SEQUENCE: 126

Gln Gln Tyr Lys Arg Tyr Pro Tyr Thr
1               5

<210> SEQ ID NO 127
<211> LENGTH: 9
<212> TYPE: PRT
<213> ORGANISM: Mus spretus

<400> SEQUENCE: 127

Leu Gln His Gly Glu Ser Pro Tyr Thr
1               5

<210> SEQ ID NO 128
<211> LENGTH: 9
<212> TYPE: PRT
<213> ORGANISM: Mus spretus

<400> SEQUENCE: 128

Gln Gln His Tyr Ser Ser Pro Leu Thr
1               5

<210> SEQ ID NO 129
<211> LENGTH: 9
<212> TYPE: PRT
<213> ORGANISM: Mus spretus

<400> SEQUENCE: 129

Phe Gln Ala Thr His Val Pro Trp Thr
1               5

<210> SEQ ID NO 130
<211> LENGTH: 9
<212> TYPE: PRT
<213> ORGANISM: Mus spretus

<400> SEQUENCE: 130

Trp Gln Gly Thr His Phe Pro Gln Thr
1               5

<210> SEQ ID NO 131
<211> LENGTH: 9
<212> TYPE: PRT
<213> ORGANISM: Mus spretus

<400> SEQUENCE: 131

Gln His Ser Trp Glu Ile Pro Pro Thr
1               5

<210> SEQ ID NO 132
<211> LENGTH: 8
<212> TYPE: PRT
<213> ORGANISM: Mus spretus

<400> SEQUENCE: 132

Gln His Tyr Tyr Ser Thr Leu Thr

```
<210> SEQ ID NO 133
<211> LENGTH: 9
<212> TYPE: PRT
<213> ORGANISM: Mus spretus

<400> SEQUENCE: 133

Gln His Ser Trp Glu Ile Pro Arg Thr
1               5

<210> SEQ ID NO 134
<211> LENGTH: 9
<212> TYPE: PRT
<213> ORGANISM: Mus spretus

<400> SEQUENCE: 134

Phe Gln Ala Thr His Val Pro Trp Thr
1               5

<210> SEQ ID NO 135
<211> LENGTH: 9
<212> TYPE: PRT
<213> ORGANISM: Mus spretus

<400> SEQUENCE: 135

Gln Gln Tyr Asp Ser Ser Pro Phe Thr
1               5

<210> SEQ ID NO 136
<211> LENGTH: 9
<212> TYPE: PRT
<213> ORGANISM: Mus spretus

<400> SEQUENCE: 136

Gln Gln Asp Tyr Ser Ser Pro Leu Thr
1               5

<210> SEQ ID NO 137
<211> LENGTH: 11
<212> TYPE: PRT
<213> ORGANISM: Homo sapiens

<400> SEQUENCE: 137

Gln Arg Phe Thr Pro Phe Ser Leu Gly Phe Glu
1               5                   10

<210> SEQ ID NO 138
<211> LENGTH: 10
<212> TYPE: PRT
<213> ORGANISM: Homo sapiens

<400> SEQUENCE: 138

Arg Leu Leu Arg Gly Asp Ala Val Val Glu
1               5                   10
```